(12) United States Patent
Bacon et al.

(10) Patent No.: US 9,795,602 B2
(45) Date of Patent: *Oct. 24, 2017

(54) POLYCYCLIC-CARBAMOYLPYRIDONE COMPOUNDS AND THEIR PHARMACEUTICAL USE

(71) Applicant: Gilead Sciences, Inc., Foster City, CA (US)

(72) Inventors: Elizabeth M. Bacon, Burlingame, CA (US); Zhenhong R. Cai, Palo Alto, CA (US); Jeromy J. Cottell, Redwood City, CA (US); Mingzhe Ji, Union City, CA (US); Haolun Jin, Foster City, CA (US); Scott E. Lazerwith, Burlingame, CA (US); Philip Anthony Morganelli, Foster City, CA (US); Hyung-Jung Pyun, Fremont, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,353

(22) Filed: Nov. 11, 2016

(65) Prior Publication Data

US 2017/0119764 A1   May 4, 2017

Related U.S. Application Data

(63) Continuation of application No. 14/977,347, filed on Dec. 21, 2015, now Pat. No. 9,522,912.

(60) Provisional application No. 62/096,291, filed on Dec. 23, 2014.

(51) Int. Cl.
| A61K 31/4985 | (2006.01) |
| C07D 491/147 | (2006.01) |
| A61K 45/06 | (2006.01) |

(52) U.S. Cl.
CPC .......... *A61K 31/4985* (2013.01); *A61K 45/06* (2013.01); *C07D 491/147* (2013.01)

(58) Field of Classification Search
CPC C07D 471/04; C07D 491/147; C07D 491/20; A61K 31/4985; A61K 45/06
See application file for complete search history.

(56) References Cited

U.S. PATENT DOCUMENTS

| 5,814,639 | A | 9/1998 | Liotta et al. |
| 5,914,331 | A | 6/1999 | Liotta et al. |
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 6,043,230 | A | 3/2000 | Arimilli et al. |
| 6,620,841 | B1 | 9/2003 | Fujishita et al. |
| 6,642,245 | B1 | 11/2003 | Liotta et al. |
| 6,703,396 | B1 | 3/2004 | Liotta et al. |
| 7,176,220 | B2 | 2/2007 | Satoh et al. |
| 7,419,969 | B2 | 9/2008 | Naidu et al. |
| 7,550,463 | B2 | 6/2009 | Yoshida |
| 7,635,704 | B2 | 12/2009 | Satoh et al. |
| 7,858,788 | B2 | 12/2010 | Yoshida et al. |
| 8,129,385 | B2 | 3/2012 | Johns et al. |
| 8,148,374 | B2 | 4/2012 | Desai et al. |
| 8,188,271 | B2 | 5/2012 | Yoshida et al. |
| 8,410,103 | B2 | 4/2013 | Johns et al. |
| 8,592,397 | B2 | 11/2013 | Dahl et al. |
| 8,633,219 | B2 | 1/2014 | Matsuzaki et al. |
| 8,716,264 | B2 | 5/2014 | Dahl et al. |
| 8,716,319 | B2 | 5/2014 | Abelman et al. |
| 8,778,943 | B2 | 7/2014 | Johns et al. |
| 8,981,103 | B2 | 3/2015 | Ando et al. |
| 8,987,441 | B2 | 3/2015 | Takahashi et al. |
| 9,051,337 | B2 | 6/2015 | Johns et al. |
| 9,216,996 | B2 | 12/2015 | Jin et al. |
| 9,284,323 | B2 | 3/2016 | Babaoglu et al. |
| 2005/0054645 | A1 | 3/2005 | Miyazaki et al. |
| 2005/0137224 | A1 | 6/2005 | Shima et al. |

(Continued)

FOREIGN PATENT DOCUMENTS

| EP | 1422218 A1 | 5/2004 |
| EP | 1544199 A1 | 6/2005 |

(Continued)

OTHER PUBLICATIONS

Agrawal, A. et al. (2012) "Probing Chelation Motifs in HIV Integrase Inhibitors" Proc. Natl. Acad. Sci. U.S.A.; 109(7): 2251-2256.
AIDS treatment Guidelines—"AIDSinfo Guidelines for the Use of Antiretroviral Agents in HIV-1-Infected Adults and Adolescents," [downloaded from http://aidsinfo.nih.gov/guidelines on Mar. 15, 2013], 267 pages.
Akiyama, T. et al. (2013) "Discovery of Novel HIV Integrase Inhibitors Part 2. Selection and Evaluation of an Azabicyclic Carbamoyl Pyridone as apre-Clinical Candidate" Poster, American Chemical Society National Meeting and Exposition; Apr. 7-11; New Orleans, LA.
Andrews, C. et al.(2014) "Long-Acting Integrase Inhibitor Protects Macaques from Intrarectal Simian/Human Immunodeficiency Virus," Science 343:1151-1154.
Bisel, P. et al. (1998) "Diastereoselective .alpha.-iminoamine rearrangement: asymmetric synthesis of (R)-(−)- and (S)-(−)-2-benzyl-2-hydroxycyclohexanone" Tetrahedron: Asymmetry 9:4027-4034.

(Continued)

*Primary Examiner* — Alexander R Pagano

(57) ABSTRACT

Compounds for use in the treatment of human immunodeficiency virus (HIV) infection are disclosed. The compounds have the following Formula (Ia):

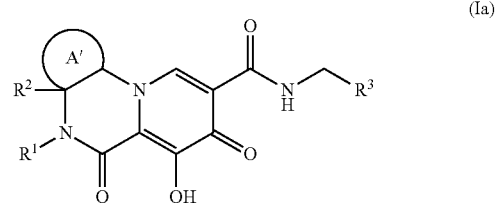

including stereoisomers and pharmaceutically acceptable salts thereof, wherein A', $R^1$, $R^2$ and $R^3$ are as defined herein. Methods associated with preparation and use of such compounds, as well as pharmaceutical compositions comprising such compounds, are also disclosed.

18 Claims, No Drawings

(56) References Cited

U.S. PATENT DOCUMENTS

| | | |
|---|---|---|
| 2007/0072831 A1 | 3/2007 | Cai et al. |
| 2008/0020010 A1 | 1/2008 | Nair et al. |
| 2008/0139579 A1 | 6/2008 | Morrissette et al. |
| 2008/0161271 A1 | 7/2008 | Yoshida et al. |
| 2008/0280945 A1 | 11/2008 | Lohani et al. |
| 2009/0036684 A1 | 2/2009 | Matsuda et al. |
| 2009/0143356 A1 | 6/2009 | Yoshida et al. |
| 2009/0253677 A1 | 10/2009 | Beaulieu et al. |
| 2009/0318702 A1 | 12/2009 | Matsuda et al. |
| 2010/0068695 A1 | 3/2010 | Kiyama et al. |
| 2011/0312951 A1 | 12/2011 | Xiao et al. |
| 2012/0022251 A1 | 1/2012 | Sumino et al. |
| 2012/0108564 A1 | 5/2012 | Miyazaki et al. |
| 2014/0011995 A1 | 1/2014 | Sumino et al. |
| 2014/0094605 A1 | 4/2014 | Yoshida et al. |
| 2014/0221355 A1 | 8/2014 | Lazerwith et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0243521 A1 | 8/2014 | Yoshida et al. |
| 2014/0256937 A1 | 9/2014 | Akiyama |
| 2015/0232479 A1 | 8/2015 | Johns et al. |
| 2016/0060272 A1 | 3/2016 | Graham et al. |

FOREIGN PATENT DOCUMENTS

| | | |
|---|---|---|
| EP | 1874117 A1 | 1/2008 |
| EP | 2412709 A1 | 2/2012 |
| EP | 2465580 A1 | 6/2012 |
| EP | 2527007 A1 | 11/2012 |
| EP | 2602260 A1 | 6/2013 |
| GB | 2345058 A | 6/2000 |
| WO | WO-03/030897 A1 | 4/2003 |
| WO | WO-03/035077 A1 | 5/2003 |
| WO | WO-2004/004657 A2 | 1/2004 |
| WO | WO-2004/024078 A2 | 3/2004 |
| WO | WO-2005/042533 A2 | 5/2005 |
| WO | WO-2005/074513 A2 | 8/2005 |
| WO | WO-2005/110414 A2 | 11/2005 |
| WO | WO-2005/112930 A1 | 12/2005 |
| WO | WO-2005/113508 A1 | 12/2005 |
| WO | WO-2005/113509 A1 | 12/2005 |
| WO | WO-2006/066414 A1 | 6/2006 |
| WO | WO-2006/116764 A1 | 11/2006 |
| WO | WO-2007/014352 A2 | 2/2007 |
| WO | WO-2007/049675 A1 | 5/2007 |
| WO | WO-2007/079260 A1 | 7/2007 |
| WO | WO-2007/089030 A1 | 8/2007 |
| WO | WO-2007/102499 A1 | 9/2007 |
| WO | WO-2007/102512 A1 | 9/2007 |
| WO | WO-2008/002959 A2 | 1/2008 |
| WO | WO-2008/033836 A2 | 3/2008 |
| WO | WO-2008/048538 A1 | 4/2008 |
| WO | WO-2009/006199 A1 | 1/2009 |
| WO | WO-2009/006203 A1 | 1/2009 |
| WO | WO-2009/036161 A1 | 3/2009 |
| WO | WO-2010/011812 A1 | 1/2010 |
| WO | WO-2010/011813 A1 | 1/2010 |
| WO | WO-2010/011814 A1 | 1/2010 |
| WO | WO-2010/011815 A1 | 1/2010 |
| WO | WO-2010/011816 A1 | 1/2010 |
| WO | WO-2010/011818 A1 | 1/2010 |
| WO | WO-2010/011819 A1 | 1/2010 |
| WO | WO-2011/094150 A1 | 8/2011 |
| WO | WO-2011/105590 A1 | 9/2011 |
| WO | WO-2011/119566 A1 | 9/2011 |
| WO | WO-2012/018065 A1 | 2/2012 |
| WO | WO-2012/151361 A1 | 11/2012 |
| WO | WO-2012/151567 A1 | 11/2012 |
| WO | WO-2013/038407 A1 | 3/2013 |
| WO | WO-2013/054862 A1 | 4/2013 |
| WO | WO-2014/008636 A1 | 1/2014 |
| WO | WO-2014/011769 A1 | 1/2014 |
| WO | WO-2014/014933 A1 | 1/2014 |
| WO | WO-2014/018449 A1 | 1/2014 |
| WO | WO-2014/022707 A1 | 2/2014 |
| WO | WO-2014/093941 A1 | 6/2014 |
| WO | WO-2014/099586 A1 | 6/2014 |
| WO | WO-2014/100077 A1 | 6/2014 |
| WO | WO-2014/100323 A1 | 6/2014 |
| WO | WO-2014/104279 A1 | 7/2014 |
| WO | WO-2014/200880 A1 | 12/2014 |
| WO | WO-2015/039348 A1 | 3/2015 |
| WO | WO-2015/048363 A1 | 4/2015 |
| WO | WO-2015/089847 A1 | 6/2015 |
| WO | WO-2015/095258 A1 | 6/2015 |

OTHER PUBLICATIONS

Brinson, C. et al. (2013) "Dolutegravir Treatment Response and Safety by Key Subgroups in Treatment Naive HIV Infected Individuals" Poster, 20th Conference on Retroviruses and Opportunistic Infections; Mar. 3-6, 2013; Atlanta, GA.

Cahn, P. et al. (2013) "Dolutegravir (DTG) is Superior to Raltegravir (RAL) in ART-Experienced, Integrase-Naive Subjects: Week 48 Results From Sailing (ING111762)" Presentation, 7.sup.th IAS Conference on HIV Pathogenesis, Treatment and Prevention;Jun. 30-Jul. 3; Kuala Lumpur, Malaysia.

Canducci, F. et al. (2013) "In vitro phenotypes to elvitegravir and dolutegravir in primary macrophages and lymphocytes of clonal recombinant viral variants selected in patients failing raltegravir", J Antimicrob Chemother., 68:2525-32.

Castagna, A. et al. (2014) "Dolutegravir in Antiretroviral-Experienced Patients With Raltegravir-and/or Elvitegravir-Resistant HIV-1: 24-Week Results of the Phase III VIKING-3 Study" Infectious Diseases Society of America Journal of InfectiousDiseases 210:354-62.

Castellino, S., et al., (2013), "Metabolism, Excretion, and Mass Balance of the HIV-1 Integrase Inhibitor Dolutegravir in Humans", Antimicrobial Agents and Chemother., 57:3536-46.

Chen, D. et al. (2003) "New C19-diterpenoid alkaloids from the roots of Aconitum transsecutum" Abstract, Huaxue Xuebao 61(6):901-906.

Chen, S. et al. (2014) "Evaluation of the effect of UGT1A1 polymorphisms on dolutegravir pharmacokinetics" Pharmacogenomics, 15(1):9-16.

Clotet, G. et al. (2014) "Once-daily dolutegravir versus darunavir plus ritonavir in antiretroviral-naive adults with HIV-1 infection (FLAMINGO) 48 week results from the randomised open-label phase 3b study", Lancet, 383:2222-31.

Cohen, J. et al. (2014) "A Bid to Thwart HIV With Shot of Long-Lasting Drug" Science 343:1067.

Cottrell, M. et al. (2013) "Clinical Pharmacokinetic, Pharmacodynamic and Drug-Interaction Profile of the Integrase Inhibitor Dolutegravir" Clin Pharmacokinet 52:981-994.

Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC.

Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC., 1-7.

Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From SPRING-2 (ING113086) and SINGLE (ING114467)"Poster No. CUPE 282, 7.sup.th IAS Conference on HIV Pathogenesis, Treatment and Prevention; Jun. 30-Jul. 3; Kuala Lumpur, Malaysia.

Deanda, F. et al. (2013) "Dolutegravir Interactions with HIV-1 Integrase-DNA: Structural Rationale for Drug Resistance and Dissociation Kinetics" PloS One 8(10): e77448 1-12.

Enright, B. et al. (2010) "Assessment of Hydroxypropyl Methylcellulose, Propylene Glycol, Polysorbate 80, and Hydroxypropyl-.beta.-Cyclodextrin for Use in Developmental and Reproductive Toxicology Studies" Birth Defects Research (Part B) 89:504-516.

European Search Report for EP application No. 13815937.1, dated Mar. 31, 2015.

(56) References Cited

OTHER PUBLICATIONS

FDA DTG Pharmacology Review—Center for Drug Evaluation and Research; DTG PharmTox Review 2013, 103 pages.
FDA_DDI Guidance for Industry—Drug Interaction Studies—Study Design, Data Analysis, Implications for Dosing, and Labeling Recommendations, 79 pages.
Feinberg, J. et al. (2013) "Once-Daily Dolutegravir (DTG) is Superior to Darunavir/Ritonavir (DRV)/f) in Antiretroviral-Naive Adults: 48 Week Results from FLAMINGO (ING114915)" Presentation, 53.sup.rd ICAAC Interscience Conference on AntimicrobialAgents and Chemotherapy; Sep. 10-13; Denver CO.
Gad, S. et al. (2006) "Nonclinical Vehicle Use in Studies by Multiple Routes in Multiple Species" International Journal of Toxicology 25:499-521.
Gao, Y. et al. (2007) "Attenuating Pregnane X Receptor (PXR Activiatin: A Molecular Modeling Approach" Xenobiotica 37(2):124-138.
Gein, V. L., et al. (1992) "Synthesis of 4-Substituted 1-Methyl-5-Aryl- and 1,5-Diaryltetrahydropyrrole-2,3-Diones and their Antiviral Action" translated from Khimik-farmatsevticheskii Zhumal; 25(12):37-40.
Gould, S. et al. (2005) "2-Hydroxypropyl-.beta.-cyclodextrin (HP-.beta.-CD): A toxicology review" Food and Chemical Toxicology 43:1451-1459.
Gouverneur, V. et al. (1998) "New Acylnitroso Compounds for the Asymmetric Oxyamination of Dienes" Tetrahedron 54:10537-10554.
Grobler, J., et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A.; 99(10):6661-6666.
Gutierrez, M., "Drug safety profile of integrase strand transfer inhibitors," Expert Opin. Drug Saf. (2014) 13(4):431-445.
Hare, S. et al. (2011) "Structural and Functional Analyses of the Second-Generation Integrase Strand Transfer Inhibitor Dolutegravir (S/GSK1349572)" Molecular Pharmacology 80(4):565-572.
Hightower, K., "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes," Antimicrobial Agents and Chemotherapy 55(10):4552-4559 (2011).
Huang, W. et al. (2014) "Impact of Raltegravir/Elvitegravir Selected Mutationson Dolutegravir Cross-Resistance" Poster 595; 21.sup.st Conference on Retroviruses and Opportunistic Infection; Mar. 3-6; Boston, MA.
Hurt, C. et al. (2013) "Characterization of Resistance to Integrase Strand Transfer Inhibitors among Clinical Specimens in the United States, 2009-2012" Poster 591; 20th Conference on Retroviruses and Opportunistic Infections; Mar. 3-6; Atlanta, GA.
Hurt, et al., (2014), "Resistance to HIV Integrase Strand Transfer Inhibitors Among Clinical Specimens in the United States, 2009-2012", Clin Infect Dis., 58:423-31.
International Preliminary Report on Patentability dated Jun. 23, 2015 for PCT/US2013/076367.
Intl. Search Report dated Mar. 12, 2014 for PCT/US2013/076367.
Johns, B. et al., (2013), "HIV Integrase Inhibitors", Successful Strategies for Discovery of Antiviral Drugs, 32(6):149-88.
Johns, B., et al., (2013), "Carbamoyl pyridone HIV-1 integrase inhibitors 3. A diastereomeric approach to chiral nonracemic tricyclic ring systems and the discovery of dolutegravir (S/GSK1349572) and (S/GSK1265744)", J. Med. Chem., 56:5901-16.
Johns, B., et al., (2010) "Discovery of S/GSK1349572: A Once Daily Next Generation Integrase Inhibitor with a Superior Resistance Profile", 17th Conference on Retroviruses and Opportunistic Infections Feb. 16-19, 2010, San Francisco, CA, USA (18 pages).
Kawasuji, T., et al. (2007) "3-Hydroxy-1,5-dihydro-pyrrol-2-one Derivatives as Advanced Inhibitors of HIV Integrase" Bioorganic & Medicinal Chemistry; 15:5487-5492.
Kawasuji, T., et al. (2012) "Carbamoyl Pyridone HIV-1 Integrase Inhibitors. 1. Molecular Design and Establishment of an Advanced Two-Metal Binding Pharmacophore" J. Med. Chem.; 55(20):8735-8744.
Kliewer, S. et al. (2002) "The Nuclear Pregnane X Receptor: A Key Regulator of Xenobiotic Metabolism" Endocrine Reviews 23(5):687-702.
Kobayashi, M. et al. (2011) "In Vitro Antiretroviral Properties of S/GSK1349572, a Next-Generation HIV Integrase Inhibitor" Antimicrob Agents and Chemother 55(2):813-21.
Krow, G. et al. (2008) "Selectfluor as a Nucleofuge in the Reactions of Azabicyclo[n. 2.1]alkane .beta.-Halocarbamic Acid Esters (n=2,3)" J. Org. Chem. 73:2122-2129.
Lepist, E. et al. (2011) "Effect of Cobicistat and Ritonavir on Proximal Renal Tubular Cell Uptake and Efflux Tansporters" Poster A1-1724; 51.sup.st Interscience Conference on Antimicrobial Agents and Chemotherapy; Sep. 17-20; Chicago, IL.
Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB; 20th Conference on Retroviruses and Opportunistic Infections; Mar. 3-6; Atlanta, GA.
Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672; 53rd Interscience Conference onAntimicrobial Agents and Chemotherapy; Sep. 10-13; Denver, CO.
Maggi, P., (2014) "The Problem of Renal Function Monitoring in Patients Treated With the Novel Antiretroviral Drugs", HIV Clinical Trials, HIV Clin Trials;15(3):87-91.
Malet, I., et al., (2014) "New raltegravir resistance pathways induce broad cross-resistance to all currently used integrase inhibitors", J Antimicrob Chemother, 69: 2118-2122.
Margolis et al. (2014) "744 and Rilpivirine as Two Drug Oral Maintenance Therapy: LAI116482 (LATTE) Week 48 Results" Presentation; 21st Conference on Retroviruses and Opportunistic Infections; Mar. 3-6; Boston, MA.
Menendez-Arias, L., Alvarez, M., "Antiretroviral therapy and drug resistance in human immunodeficiency virus type 2 infection," Antiviral Res. (2013), http://dx.doi.org/10.1016/j.antiviral.2013.12.001.
Metifiot, M. et al. (2013) "HIV Integrase Inhibitors: 20-Year Landmark and Challenges" Advances in Pharmacology 67:75-105.
Min, S. et al. (2010) "Pharmacokinetics and Safety of S/GSK1349572, a Next-Generation HIV Integrase Inhibitor, in Healthy Volunteers" Antimicrob Agents and Chemother 54(1):254-258.
Min, S. et al. (2011) "Antiviral activity, safety, and pharmacokinetics/pharmacodynamics of dolutegravir as 10-day monotherapy in HIV-1-infected adults" AIDS 25(14):1737-1745.
Nair, V. et al.(2014) "Pharmacokinetics and Dose-range Finding Toxicity of a Novel anti-HIV Active Integrase Inhibitor" Supplementary Materials.
Nichols, G. et al (2013) "Phase 3 Assessment of Dolutegravir (DTG) 50 mg Twice Daily (BID) in HIV-1—Infected Subjects With Raltegravir (RAL) and/or Elvitegravir (EVG) Resistance in VIKING-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.
Nichols, G. et al. (2012) "Antiviral Activity of Dolutegravir in Subjects With Failure on an Integrase Inhibitor-Based Regimen: Week 24 Phase 3 Results From VIKING-3" Presentation O232; 11th International Congress on Drug Therapy in HIV Infection:Nov. 11-15; Glasgow, UK.
Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.
Office Action in Pakistan patent application No. 908/2013, dated Mar. 30, 2015.
Opposition Decision in European patent application No. 02749384.0, dated Mar. 12, 2015.

(56) References Cited

OTHER PUBLICATIONS

Pace, P., et al. (2007) "Dihydroxypyrimidine-4-carboxamides as Novel Potent and Selective HIV Integrase Inhibitors" J. Med. Chem; 50:2225-2239.
Park, B. et al. (2001) "Metabolism of Fluorine-Containing Drugs" Annu. Rev. Pharmacol. Toxicol. 41:443-70.
Patel, P. et al. (2014) "Relative Bioavailability of a Paediatric Granule Formulation of the HIV Integrase Inhibitor, Dolutegravir, in Healthy Adult Subjects" Antiviral Therapy, 19:299-33.
Patel, P., et al., (2011), "Pharmacokinetics of the HIV integrase inhibitor S/GSK1349572 co-administered with acid-reducing agents and multivitamins in healthy volunteers", J Antimicrob Chemother, 66:1567-72.
PCT/US2015/067155, ISR & Written Opinion mailed Feb. 25, 2016.
Peng, C. et al. (2002) "Norditerpenoid alkaloids from the roots of Aconitum hemsleyanum Pritz. var. pengzhouense" Abstract, Chinese Chemical Letters 13(3):233-236.
Petrocchi, A., et al. (2007) "From Dihydroxypyrimidine Carboxylic Acids to Carboxamide HIV-1 Integrase Inhibitors: SAR Around the Amide Moiety" Bioorganic & Medicinal Chemistry Letters; 17:350-353.
Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB; 20th Conference on Retroviruses and Opportunistic Infections; Mar. 3-6; Atlanta, GA.
Quashie, P. et al. (2013) "Evolution of HIV integrase resistance mutations" Curr Opin Infect Dis 26:43-49.
Raffi, F. et al. (2012) "Once-daily Dolutegravir (DTG; S/GSK1349572) is Non-inferior to Raltegravir (RAL) in Antiretroviral-naive Adults. 48 Week Results from SPRING-2 (ING113086)" Presentation THLBB04; XIX International AIDS Conference; Jul. 22-27;Washington, DC.
Raffi, F. et al. (2013) "Dolutegravir is Non-Inferior to Raltegravir and Shows Durable Response Through 96 Weeks: Results From the SPRING-2 Trial" Poster TULBPE17; 7.sup.th IAS Conference on HIV Pathogenesis, Treatment and Prevention; Jun. 30-Jul. 3; Kuala Lumpur, Malaysia.
Raffi, F. et al. (2013) "Once-daily dolutegravir versus twice-daily raltegravir in antiretroviral-naive adults with HIV-1 infection (SPRING-2 study): 96 week results from a randomised, double-blind, non-inferiority trial" www.thelancet.com/infection13:927-935.
Ragan, J. et al. (1995) "Studies of the Alkylation of Chiral, Non-Racemic, Tricyclic Pyrrolidinones," Heterocycles 41:57-70.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Reviews in Antiviral Therapy Infectious Diseases, Abstract Book 12th International Workshop on Clinical Pharmacology of HIV Therapy, Apr. 13-15, 2011, Miami, Florida USA; available on [http://regist2.virology-education.com/abstractbook/2011_3.pdf].
Rhodes, M., et al., "Assessing a Theoretical Risk of Dolutegravir-Induced Developmental Immunotoxicity in Juvenile Rats,"Toxicological Sciences 130(1), 70-81 (2012).
Song, I. et al. (2010) "Lack of Interaction Between the HIV Integrase Inhibitor S/GSK1349572 and Tenofovir in Healthy Subjects" JAIDS 55(3):365-367.
Song, I. et al. (2012) "Effect of Food on the Pharmacokinetics of the Integrase Inhibitor Dolutegravir" Antimicrob Agents and Chemother 56(3):1627-1629.
Song, I. et al. (2013) "Dolutegrvir Has no Effect on the Pharmacokinetics of Methadone or Oral Contraceptives With Norgestimate and Ethinyl Estradiol" Poster 535; 20th Conference on Retroviruses and Opportunistic Infections; Mar. 3-6; Atlanta, GA.
Song, I. et al. (2013) "Pharmacokinetics (PK) and PK.sub.—Pharmacodynamic (PD) Relationship of Dolutegravir (DTG) in Integrase Inhibitor (INI)-Naive Subjects" Poster A-1573; 53rd Interscience Conference on Antimicrobial Agents and Chemotherapy;Sep. 10-13; Denver, CO.
Soriano, V., et al. (2011) "Dolutegravir (GSK/ViiV Integrase) Treatment (with 50mg Once & Twice Daily) of HIV Subjects with Raltegravir Resistance & 3-Class ART Resistance: viral suppression at Week 24 in the VIKING Study" Presentation; EACS; Oct. 12-15; Belgrade, Serbia.
Spreen, W. et al (2013) "First study of repeat dose co-administration of GSK1265744 and TMC278 long-acting parenteral nanosuspensions: pharmacokinetics, safety, and tolerability in healthy adults" Presentation; 7.sup.th IAS Conference on HIV Pathogenesis, Treatment and Prevention Jun. 30-Jul. 3; Kuala Lumpur, Malaysia.
Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation; 19th International AIDSConference; Jul. 22-27; Washington DC.
Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.
Stellbrink, H. et al. (2013) "Dolutegravir in antiretroviral-naive adults with HIV-1:96-week results from a randomized dose-ranging study" AIDS 27:1771-1778.
Summa, V., et al. (2006) "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species" J. Med. Chem; 49:6646-6649.
Summary of Product Characteristics—Annex I, Leaflet, 62 pages—EU—Triumeq [downloaded Sep. 8, 2014].
Taoda, Y. et al. (2013) "Discovery of Novel HIV Integrase Inhibitors Part 1. Molecular Design and SAR of Azabicyclic Carbamoyl Pyridone Inhibitors" Poster; 245.sup.th American Chemical Society National Meeting and Exposition; Apr. 7-11; New Orleans,LA.
Tchaparian, Eskouhie, "Drug Transporters: An Overview of Their Role in Drug Interactions; Recommended Strategies to Assess Drug Transporters froma Regulatory and Industry Perspective," FDA Guidance Compliance Regulatory Information Guidances (Feb. 14, 2013), 19 pages.
Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.
Thomson Reuters Drug New, "Coadministration of long-acting GSK-744 and rilpivirine found feasible" [downloaded on the web http://drugnews.thomson-pharma.com/ddn/article.do?id=124544] Jul. 8, 2013 8:33:31 AM on Mon Jul. 8, 2013, 1 page.
Thomson Reuters Drug News "Results from phase III trials of dolutegravir presented," Fri Jul. 5, 2013, 1 page.
Trinite, B. et al. (2013) "An HIV-1 Replication Pathway Utilizing Reverse Transcription Products That Fail to Integrate" Journal of Virology 87(23):12701-12720.
Tseng, A. et al. (2014) "Drug Interactions with Integrase Inhibitors" Pharm. D.
Van Lunzen, J. et al. (2012) "Once daily dolutegravir (S/GSK1349572) in combination therapy in antiretroviral-naive adults with HIV: planned interim 48 week results from SPRING-1, a dose-ranging, randomised, phase 2b trial" Lancet Infectious Disease12(2):111-118.
Wai, J., et al. (2007) "Dihydroxypyridopyrazine-1,6-dione HIV-1 Integrase Inhibitors" Bioorganic & Medicinal Chemistry Letters; 17:5595-5599.
Walmsley, S. et al. (2012) "Dolutegravir (DTG; S/GSK1349572)+Abacavir/Lamivudine Once Daily Statistically Superior to Tenofovir/Emtricitabine/Efavirenz: 48-Week Results—SINGLE (ING114467)" Presentation H-556b; 52nd Interscience Conference onAntimicrobial Agents and Chemotherapy; Sep. 9-12; San Francisco, CA.
Walmsley, S. et al. (2013) "Dolutegravir plus Abacavir-Lamivudine for the Treatment of HIV-1 Infection" N Engl J Med 369(19):1807-1818.

(56) References Cited

OTHER PUBLICATIONS

Wang, F. et al. (1999) "Modifications of norditerpenoid alkaloids. I. N-deethylation reactions" Abstract, Chinese Chemical Letters 10(5):375-378.

Wang, F. et al. (2005) "To seek an approach toward the chemical conversion of C19-diterpenoid alkaloids to taxoids" Tetrahedron 61(8):2149-2167.

Wang, H. et al. (2015) "An Efficient and Highly Diastereoselective Synthesis of GSK1265744, a Potent HIV Integrase Inhibitor"Org. Letters 17:564-567.

Wang, Y., et al., (2002) "Switch in asymmetric induction sense in cycloadditions using camphor-based nitroso dienop", Tetrahedron: Asymmetry 13:691-5.

Weller, S. et al. (2013) "Pharmacokinetics (PK) and Safety of Dolutegravir (DTG) in Subjects With Severe Renal Impairment and Healthy Controls" Poster A-1571; 53rd Interscience Conference on Antimicrobial Agents and Chemotherapy; Sep. 10-13; Denver,CO.

Weller, S., et al., (2013) "Bioequivalence of a Dolutegravir, Abacavir, and Lamivudine Fixed-Dose Combination Tablet and the Effect of Food", Poster A-1572; 53rd Interscience Conference on Antimicrobial Agents and Chemotherapy; Sep. 10-13, 2013; Denver, CO.

Weller, S., et al., (2014), "Bioequivalence of a Dolutegravir, Abacavir, and Lamivudine Fixed-Dose Combination Tablet and the Effect of Food", Acquir Immune Defic Syndr 66(4):393-398.

Wensing, A. et al. (2014) "Special Contribution 2014 Update of the Drug Resistance Mutations in HIV-1" IAS-USA Topics in Antiviral Medicine 22(3):642-650.

Wolkowicz, U. et al. (2014) "Structural Basis of Mos1 Transposase Inhibition by the Anti-retroviral Drug Raltegravir" ACS Chem. Biol. 9:743-751.

Wu, B. et al. (2008) "Enantioselective Desymmetrization of meso-Aziridines with TMSN.sub.3 and TMSCN Catalyzed by Discrete Yttrium Complexes" Supporting Information, Angew. Chem. Int. Ed., 64pgs.

Zhao, X. et al. (2014) "4-Amino-1-hydroxy-2-oxo-1,8-naphthyridine-Containing Compounds Having High Potency against Raltegravir-Resistant Integrase Mutants of HIV-1" J Med Chem 57:5190-5202.

Zheng, X. et al. (2008) "Rapid analysis of a Chinese herbal prescription by liquid chromatography-time-of-flight tandem mass spectrometry" Abstract, Journal of Chromatography A 1206(2:140-146).

POLYCYCLIC-CARBAMOYLPYRIDONE COMPOUNDS AND THEIR PHARMACEUTICAL USE

CROSS-REFERENCE TO RELATED APPLICATIONS

This application is a Continuation of U.S. application Ser. No. 14/977,347, filed on Dec. 21, 2015, which claims the benefit under 35 U.S.C. §119(e) of U.S. Provisional App. No. 62/096,291, filed Dec. 23, 2014, the entirety of which are incorporated herein by reference.

BACKGROUND

Field

Compounds, compositions, and methods which may be used for the treatment of human immunodeficiency virus (HIV) infection are disclosed. In particular, novel polycyclic carbamoylpyridone compounds and methods for their preparation and use as therapeutic or prophylactic agents are disclosed.

Description of Related Art

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. *N Engl. J Med.* (1998) 338:853-860; Richman, D. D. *Nature* (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes. (Panel on Antiretroviral Guidelines for Adults and Adolescents. Guidelines for the use of antiretroviral agents in HIV-1-infected adults and adolescents. Department of Health and Human Services. Available at http://aidsinfo.nih. gov/ContentFiles/AdultandAdolescentGL.pdf. Section accessed Mar. 14, 2013.) In addition, decisions regarding the treatment of HIV infected patients are complicated when the patient requires treatment for other medical conditions (Id. at E-12). Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang et al., *Drugs* (2012) 72 (9) e1-e25). Because of the proclivity of the HIV virus to mutate, there is a need for anti-HIV drugs to be effective against a range of known HIV variants (Hurt et al., *HIV/AIDS CID* (2014) 58, 423-431).

BRIEF SUMMARY

The present invention is directed to novel polycyclic carbamoylpyridone compounds, having antiviral activity, including stereoisomers and pharmaceutically acceptable salts thereof. The compounds of the invention may be used in the treatment of HIV infections, to inhibit the activity of HIV integrase and/or to reduce HIV replication. In some embodiments, compounds disclosed herein may be resistant against a range of known HIV mutants. In some embodiments, compounds disclosed herein may minimize the potential for drug-drug interactions when co-administered with other drugs.

In one embodiment, compounds having the following Formula (Ia) are provided:

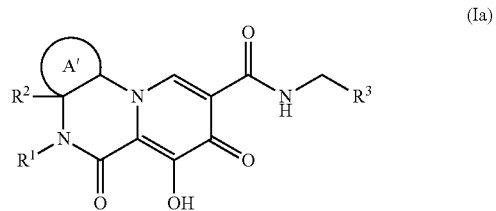

(Ia)

or a pharmaceutically acceptable salt thereof, wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;

$R^1$ is selected from the group consisting of H, $C_{1-4}$alkyl, $C_{1-4}$haloalkyl and $C_{3-6}$cycloalkyl;

$R^2$ is selected from the group consisting of hydrogen, $C_{1-3}$haloalkyl and $C_{1-3}$alkyl;

$R^3$ is selected from the group consisting of phenyl substituted with at least 3 $R^5$ groups;

each $R^5$ is independently selected from the group consisting of $C_{1-3}$alkyl and halogen.

In another embodiment, compounds having the following Formula (Ib) are provided:

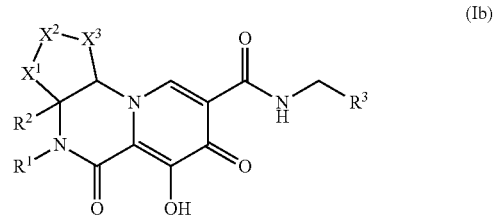

(Ib)

or a pharmaceutically acceptable salt thereof, wherein:

$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;

$R^1$ is selected from the group consisting of H, $C_{1-4}$alkyl, $C_{1-4}$haloalkyl and $C_{3-6}$cycloalkyl;

$R^2$ is selected from the group consisting of hydrogen, $C_{1-3}$haloalkyl and $C_{1-3}$alkyl;

$R^3$ is selected from the group consisting of phenyl substituted with three $R^5$ groups;

each $R^5$ is independently selected from the group consisting of $C_{1-3}$alkyl and halogen.

In another embodiment, compounds having the following Formula (Ic) are provided:

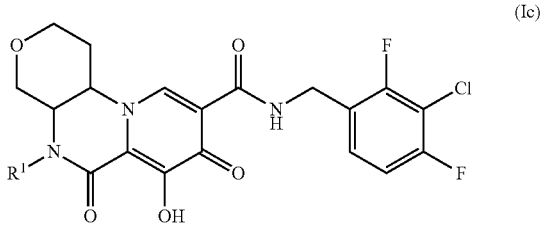

(Ic)

or a pharmaceutically acceptable salt thereof, wherein:
$R^1$ is selected from the group consisting of H, $C_{1-4}$alkyl, $C_{1-4}$haloalkyl and $C_{3-6}$cycloalkyl.

In another embodiment, compounds having the following Formula (Id) are provided:

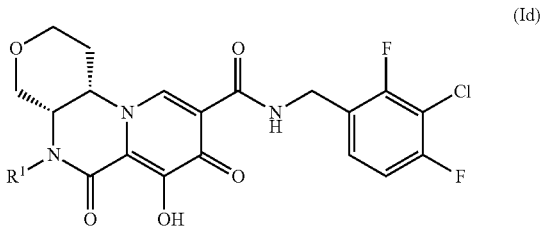

(Id)

or a pharmaceutically acceptable salt thereof, wherein:
$R^1$ is selected from the group consisting of H, $C_{1-4}$alkyl, $C_{1-4}$haloalkyl and $C_{3-6}$cycloalkyl.

In another embodiment, compounds having the following Formula (Ie) are provided:

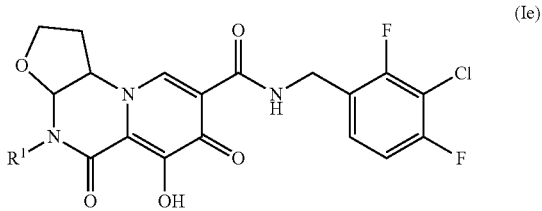

(Ie)

or a pharmaceutically acceptable salt thereof, wherein:
$R^1$ is selected from the group consisting of H, $C_{1-4}$alkyl, $C_{1-4}$haloalkyl and $C_{3-6}$cycloalkyl.

In another embodiment, compounds having the following Formula (If) are provided:

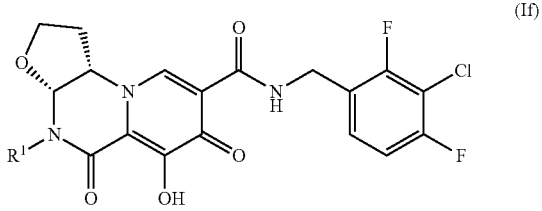

(If)

or a pharmaceutically acceptable salt thereof, wherein:
$R^1$ is selected from the group consisting of H, $C_{1-4}$alkyl, $C_{1-4}$haloalkyl and $C_{3-6}$cycloalkyl.

In another embodiment, a pharmaceutical composition is provided comprising a compound having the Formula (Ia), (Ib), (Ic), (Id), (Ie) or (If), or pharmaceutically acceptable salt thereof, and a pharmaceutically acceptable excipient.

In another embodiment, a method of treating an HIV infection in a human having or at risk of having the infection by administering to the human a therapeutically effective amount of a compound of Formula (Ia), (Ib), (Ic), (Id), (Ie) or (If), or a pharmaceutically acceptable salt thereof, or a pharmaceutical composition of a compound of Formula (Ia), (Ib), (Ic), (Id), (Ie) or (If), or a pharmaceutically acceptable salt thereof, is provided.

In another embodiment, a use of a compound of Formula (Ia), (Ib), (Ic), (Id), (Ie) or (If), or a pharmaceutically acceptable salt thereof, or a pharmaceutical composition of a compound of Formula (Ia), (Ib), (Ic), (Id), (Ie) or (If), or a pharmaceutically acceptable salt thereof, for the treatment of an HIV infection in a human having or at risk of having the infection is provided.

In another embodiment, a compound of Formula (Ia), (Ib), (Ic), (Id), (Ie) or (If), or a pharmaceutically acceptable salt thereof, or a pharmaceutical composition of a compound of Formula (Ia), (Ib), (Ic), (Id), (Ie) or (If), or a pharmaceutically acceptable salt thereof, for use in medical therapy is provided.

In another embodiment, a compound of Formula (Ia), (Ib), (Ic), (Id), (Ie) or (If), or a pharmaceutically acceptable salt thereof, or a pharmaceutical composition of a compound of Formula (Ia), (Ib), (Ic), (Id), (Ie) or (If), or a pharmaceutically acceptable salt thereof, for use in the prophylactic or therapeutic treatment of an HIV infection is provided.

In another embodiment, a method of using a compound having the Formula (Ia), (Ib), (Ic), (Id), (Ie) or (If) in therapy is provided. In particular, a method of treating the proliferation of the HIV virus, treating AIDS, or delaying the onset of AIDS or ARC symptoms in a mammal (e.g., a human) is provided, comprising administering to the mammal a compound having the Formula (Ia), (Ib), (Ic), (Id), (Ie) or (If), or a stereoisomer or a pharmaceutically acceptable salt thereof, and a pharmaceutically acceptable excipient.

In another embodiment, the use of a compound of Formula (Ia), (Ib), (Ic), (Id), (Ie) or (If) as described herein, or a pharmaceutically acceptable salt thereof, for the manufacture of a medicament for the treatment of an HIV infection in a human being having or at risk of having the infection is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula (Ia), (Ib), (Ic), (Id), (Ie) or (If) as disclosed herein or a pharmaceutically acceptable salt thereof.

In still another embodiment, a method of inhibiting the replication of HIV is disclosed. The method comprises exposing the virus to an effective amount of the compound of Formula (Ia), (Ib), (Ic), (Id), (Ie) or (If) or a salt thereof, under conditions where replication of HIV is inhibited.

In another embodiment, the use of a compound of Formula (Ia), (Ib), (Ic), (Id), (Ie) or (If) to inhibit the activity of the HIV integrase enzyme is disclosed.

In another embodiment, the use of a compound of Formula (Ia), (Ib), (Ic), (Id), (Ie) or (If) or a pharmaceutically acceptable salt thereof, to inhibit the activity of the HIV integrase enzyme is disclosed.

In another embodiment, the use of a compound of Formula (Ia), (Ib), (Ic), (Id), (Ie) or (If), or a salt thereof, to inhibit the replication of HIV is disclosed.

In another embodiment, the use of a compound of Formula (Ia), (Ib), (Ic), (Id), (Ie) or (If), or a pharmaceutically acceptable salt thereof, as a research tool, is provided.

The present invention also provides compounds of each of the Formulae herein, as well as each subgroup and embodiment thereof, including a compound selected from the group of Formula (Ia), (Ib), (Ic), (Id), (Ie) and (If), or a pharmaceutically acceptable salt thereof, or a pharmaceutical composition of a compound of Formula (Ia), (Ib), (Ic), (Id), (Ie) or (If), or a pharmaceutically acceptable salt thereof, or one of the specific compounds of the examples herein, or a pharmaceutically acceptable salt thereof for use in any of the methods of the invention as defined herein.

Other embodiments, objects, features and advantages may be set forth in the detailed description of the embodiments that follows, and in part may be apparent from the description, or may be learned by practice, of the claimed embodiments. These objects and advantages may be realized and attained by the processes and compositions particularly pointed out in the written description and claims thereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Hydroxy" or "hydroxyl" refers to the —OH radical.
"Oxo" refers to the =O substituent.

A prefix such as "$C_{u-v}$" or ($C_u$-$C_v$) indicates that the following group has from u to v carbon atoms. For example, "$C_{1-6}$alkyl" indicates that the alkyl group has from 1 to 6 carbon atoms.

"Alkyl" refers to a straight or branched hydrocarbon chain radical consisting solely of carbon and hydrogen atoms, which is saturated, having from one to twelve carbon atoms ($C_1$-$C_{12}$ alkyl), in certain embodiments one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like.

"Cycloalkyl" or "carbocyclic ring" refers to a stable non-aromatic monocyclic hydrocarbon consisting solely of carbon and hydrogen atoms, having from three to fifteen carbon atoms, in certain embodiments having from three to ten carbon atoms, and which is saturated and attached to the rest of the molecule by a single bond, or in the case of A' attached to the rest of the molecule by two single bonds. Cycloalkyls include, for example, cyclopropyl, cyclobutyl, cyclopentyl, cyclohexyl, cycloheptyl, and cyclooctyl.

"Fused" refers to any ring structure described herein which is fused to an existing ring structure in the compounds disclosed herein.

"Halo" or "halogen" refers to bromo, chloro, fluoro or iodo.

"Haloalkyl" refers to an alkyl group, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl" or "heterocyclic ring" refers to a stable saturated monocyclic 3- to 18-membered non-aromatic ring which consists of two to twelve carbon atoms and from one to six heteroatoms selected from the group consisting of nitrogen, oxygen and sulfur and attached to the rest of the molecule by a single bond, or in the case of A' attached to the rest of the molecule by two single bonds. The nitrogen, carbon or sulfur atoms in the heterocyclyl may be optionally oxidized; the nitrogen atom may be optionally quaternized. Examples of such heterocyclyl include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

The embodiments disclosed herein are also meant to encompass all pharmaceutically acceptable compounds of Formulas (Ia), (Ib), (Ic), (Id), (Ie), (If), (II), (IIa), (III), (IIIa), (25-M), (25b), (39-M) and (39) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formulas (Ia), (Ib), (Ic), (Id), (Ie), (If), (II), (IIa), (III), (IIIa), (25-M), (25b), (39-M) and

(39) for example, those incorporating a radioactive isotope, may be useful in drug and/or substrate tissue distribution studies. The radioactive isotopes tritium, i.e. $^3$H, and carbon-14, i.e. $^{14}$C, may particularly be useful for this purpose in view of their ease of incorporation and ready means of detection.

Substitution with heavier isotopes such as deuterium, i.e. $^2$H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formulas (Ia), (Ib), (Ic), (Id), (Ie), (If), (II), (IIa), (III), (IIIa), (25-M), (25b), (39-M) and (39), can generally be prepared by conventional techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., (Ia), (Ib), (Ic), (Id), (Ie), (If), (II), (IIa), (III), (IIIa), (25-M), (25b), (39-M) and (39)) or pharmaceutically acceptable salts, prodrugs, or solvates thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of compounds or pharmaceutically acceptable salts, prodrugs, or solvates thereof, when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Examples of "pharmaceutically acceptable salts" of the compounds disclosed herein include salts derived from an appropriate base, such as an alkali metal (for example, sodium), an alkaline earth metal (for example, magnesium), ammonium and NX$_4^+$ (wherein X is C$_1$-C$_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as Na$^+$ and NX$_4^+$ (wherein X is independently selected from H or a C$_1$-C$_4$ alkyl group).

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of Formula (Ia), (Ib), (Ic), (Id), (Ie), (If), (II), (IIa), (III), (IIIa), (25-M), (25b), (39-M) and (39) or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing Li$^+$, Na$^+$, and K$^+$. A less soluble metal salt can be precipitated from the solution of a more soluble salt by addition of the suitable metal compound.

In addition, salts may be formed from acid addition of certain organic and inorganic acids, e.g., HCl, HBr, H$_2$SO$_4$, H$_3$PO$_4$ or organic sulfonic acids, to basic centers, typically amines Finally, it is to be understood that the compositions herein comprise compounds disclosed herein in their unionized, as well as zwitterionic form, and combinations with stoichiometric amounts of water as in hydrates.

Often crystallizations produce a solvate of a compound of the embodiments disclosed herein. As used herein, the term "solvate" refers to an aggregate that comprises one or more molecules of a compound of the embodiments disclosed herein with one or more molecules of solvent. The solvent may be water, in which case the solvate may be a hydrate. Alternatively, the solvent may be an organic solvent. Thus, the compounds of the embodiments disclosed herein may exist as a hydrate, including a monohydrate, dihydrate, hemihydrate, sesquihydrate, trihydrate, tetrahydrate and the like, as well as the corresponding solvated forms. The compounds of the embodiments disclosed herein may be true solvates, while in other cases, a compound of the embodiments disclosed herein may merely retain adventitious water or be a mixture of water plus some adventitious solvent.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Effective amount" or "therapeutically effective amount" refers to an amount of a compound according to the embodiments disclosed herein, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the embodiments disclosed herein which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the embodiments disclosed herein, and the age, body weight, general health, sex and diet of the patient. Such a therapeutically effective amount can be determined routinely by one of ordinary skill in the art having regard to their own knowledge, the state of the art, and this disclosure.

The term "treatment" as used herein is intended to mean the administration of a compound or composition according to the present embodiments disclosed hereinto alleviate or eliminate symptoms of HIV infection and/or to reduce viral load in a patient. The term "treatment" also encompasses the administration of a compound or composition according to the present embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed hereinto prevent perinatal transmission of HIV from mother to baby, by administration to the mother before giving birth and to the child within the first days of life.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

"Dolutegravir" or DTG is:

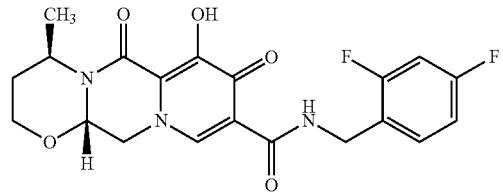 [SMILES: C[C@@H]1CCO[C@H]2Cn3cc(C(=O)NCc4ccc(F)cc4F)c(=O)c(O)c3C(=O)N12]

Compounds

As noted above, in one embodiment, compounds are provided having the following Formula (Ia):

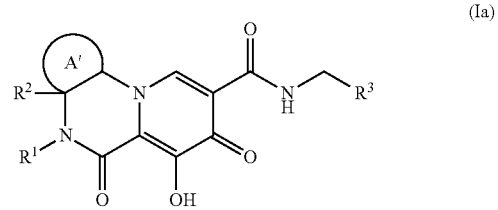

(Ia)

or a pharmaceutically acceptable salt thereof, wherein:
A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;
each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;
$R^1$ is selected from the group consisting of H, $C_{1-4}$alkyl, $C_{1-4}$haloalkyl and $C_{3-6}$cycloalkyl;
$R^2$ is selected from the group consisting of hydrogen, $C_{1-3}$haloalkyl and $C_{1-3}$alkyl;
$R^3$ is selected from the group consisting of phenyl substituted with at least 3 $R^5$ groups; and each $R^5$ is independently selected from the group consisting of $C_{1-3}$alkyl and halogen.

In another embodiment, A' is selected from the group consisting of $C_{5-6}$ monocyclic cycloalkyl and 5 to 6 membered monocyclic heterocyclyl; wherein each $C_{5-6}$ monocyclic cycloalkyl and 5 to 6 membered monocyclic heterocyclyl is optionally substituted with 1 to 5 $R^4$ groups; wherein each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring.

In another embodiment, A' is selected from the group consisting of cyclohexyl, cyclopentyl, tetrahydrofuranyl and tetrahydropyranyl; each of which is optionally substituted with one or two $R^4$ groups, wherein each $R^4$ is independently selected from the group consisting of oxo and methyl; or two $R^4$ connected to the same or adjacent carbon atoms form a spiro dioxolane or a fused cyclopropyl ring.

In another embodiment, A' is substituted with two $R^4$ groups, wherein the two $R^4$ connected to the same or adjacent carbon atoms form a spiro dioxolane or a fused cyclopropyl ring.

In another embodiment, A' is tetrahydrofuranyl

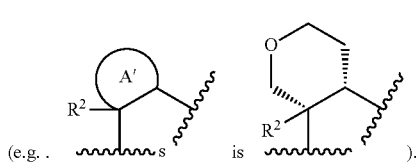

(e.g.: ).

In another embodiment, A' is tetrahydropyranyl

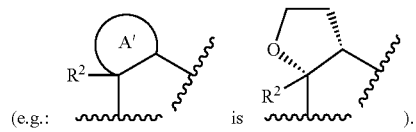

(e.g.: ).

In another embodiment, $R^2$ is selected from the group consisting of hydrogen, $C_{1-2}$haloalkyl, ethyl and methyl.

In another embodiment, $R^2$ is selected from the group consisting of hydrogen, $CHF_2$ and methyl.

In another embodiment, $R^2$ is hydrogen.

In another embodiment, $R^2$ is $C_{1-3}$haloalkyl.

In another embodiment, $R^2$ is $CHF_2$.

In another embodiment, A' is selected from the group consisting of tetrahydrofuranyl and tetrahydropyranyl and $R^2$ is hydrogen.

In another embodiment, A' is selected from the group consisting of

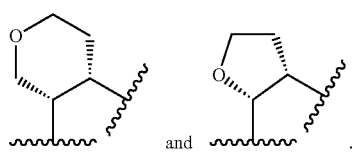 [SMILES: *[C@@H]1COCC[C@@H]1* ; *[C@@H]1OCC[C@@H]1*]

and .

In another embodiment,

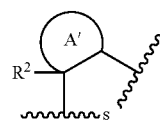

is selected from the group consisting of

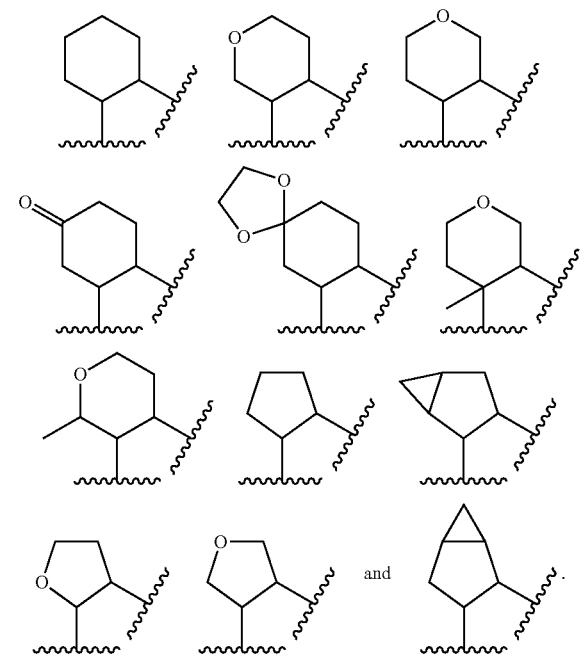

In another embodiment,

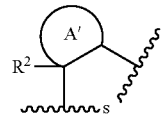

is selected from the group consisting of

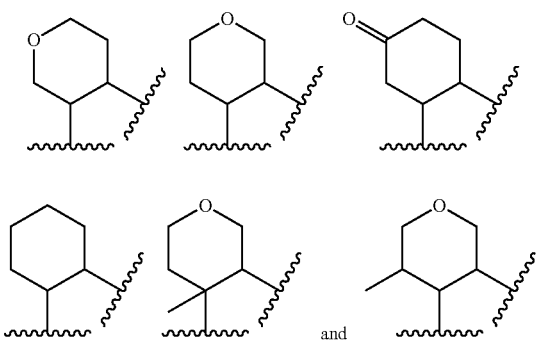

In another embodiment,
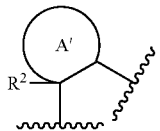
is selected from the group consisting of
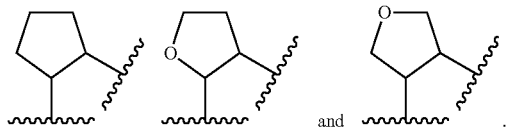
In another embodiment,
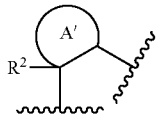
is selected from the group consisting of
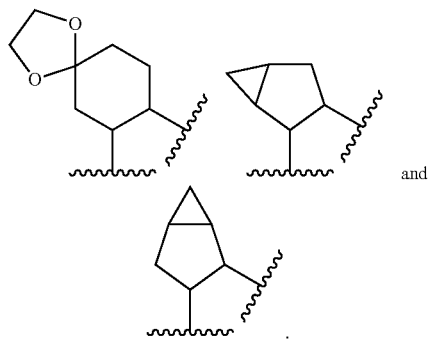
In another embodiment,
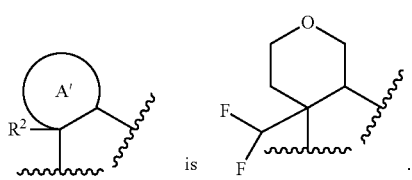
In another embodiment,
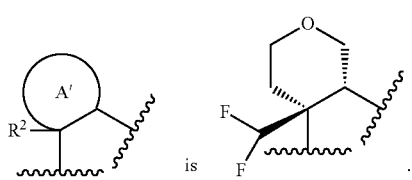
In another embodiment,
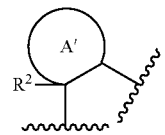
is selected from the group consisting of
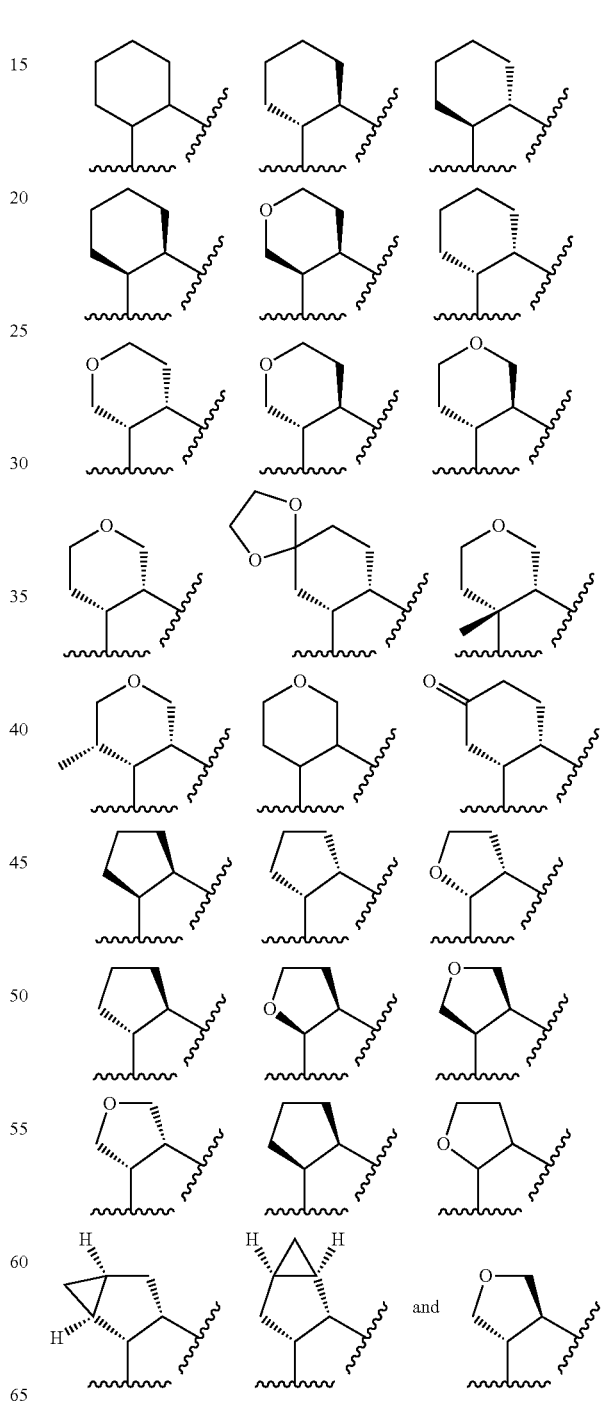

In another embodiment,

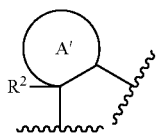

is selected from the group consisting of

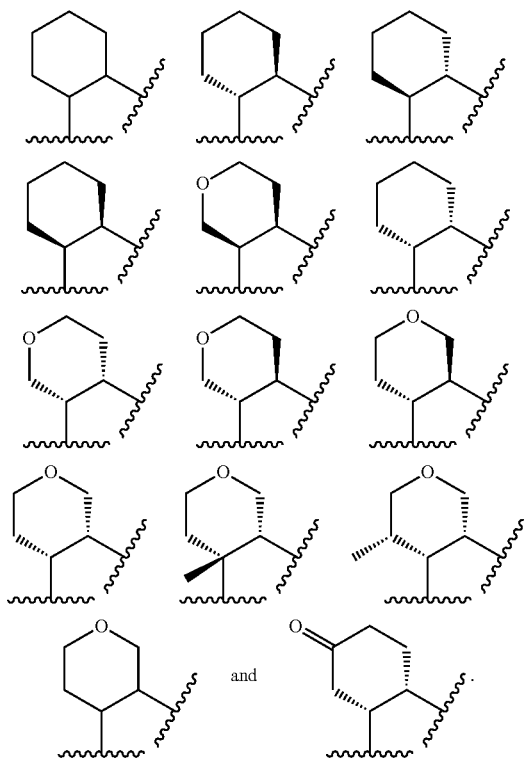

In another embodiment,

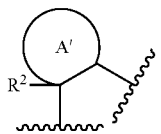

is selected from the group consisting of

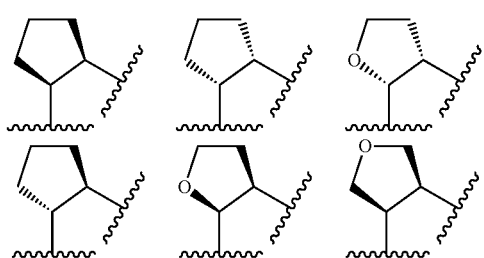

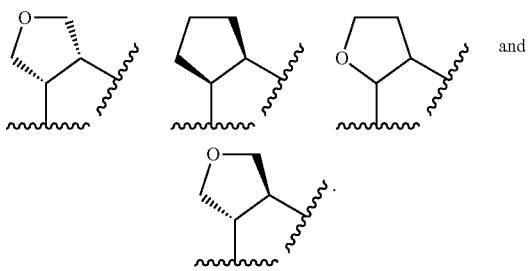

In another embodiment,

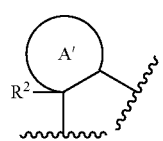

is selected from the group consisting of

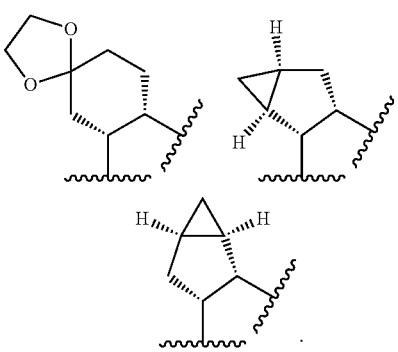

In another embodiment, $R^1$ is selected from the group consisting of $C_{1-3}$alkyl, $C_{1-2}$haloalkyl and $C_{3-4}$cycloalkyl.

In another embodiment, $R^1$ is selected from the group consisting of hydrogen, methyl, ethyl, propyl, isopropyl, $CH_2CF_3$, $CH_2CHF_2$ and cyclopropyl.

In another embodiment, $R^1$ is selected from the group consisting of $C_{1-4}$haloalkyl and $C_{3-6}$cycloalkyl.

In another embodiment, $R^1$ is selected from the group consisting of $CH_2CF_3$, $CH_2CHF_2$ and cyclopropyl.

In another embodiment $R^1$ is ethyl.

In another embodiment, $R^3$ is phenyl substituted with three $R^5$ groups, wherein each $R^5$ is independently selected from the group consisting of methyl, ethyl, and halogen.

In another embodiment, $R^3$ is selected from the group consisting of:

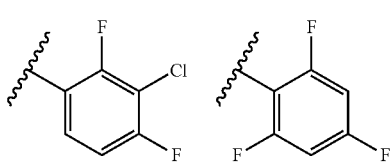

-continued

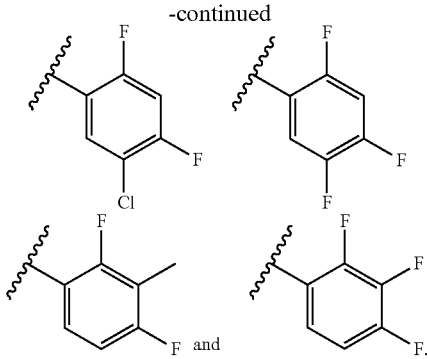

In another embodiment, $R^3$ is selected from the group consisting of:

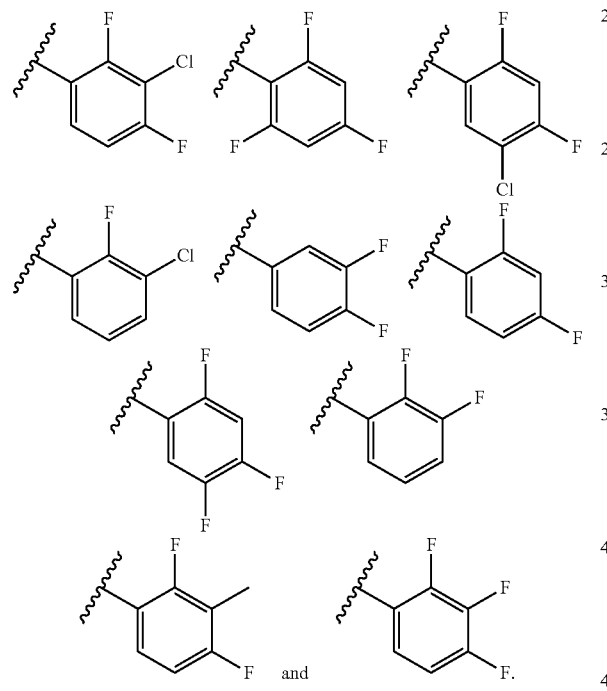

In another embodiment, $R^3$ is phenyl substituted with three $R^5$ groups, wherein each $R^5$ is independently selected from the group consisting of fluoro and chloro.

In another embodiment, $R^3$ is phenyl substituted with two fluoro groups and one chloro group.

In another embodiment, $R^3$ is:

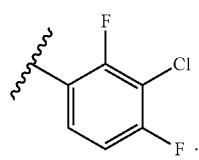 [SMILES: *c1ccc(F)c(Cl)c1F]

In another embodiment, A' is selected from the group consisting of tetrahydrofuranyl and tetrahydropyranyl, $R^2$ is hydrogen, $R^1$ is ethyl and $R^3$ is phenyl substituted with three halogens independently selected from the group consisting of fluoro and chloro.

In another embodiment, A' is selected from the group consisting of tetrahydrofuranyl and tetrahydropyranyl, $R^2$ is hydrogen, $R^1$ is ethyl and $R^3$ is phenyl substituted with two fluoro groups and one chloro group.

In another embodiment, A' is tetrahydrofuranyl, $R^2$ is hydrogen, $R^1$ is ethyl and $R^3$ is:

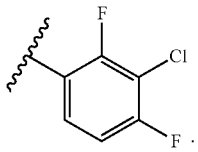 [SMILES: *c1ccc(F)c(Cl)c1F]

In another embodiment, A' is tetrahydropyranyl, $R^2$ is hydrogen, $R^1$ is ethyl and $R^3$ is:

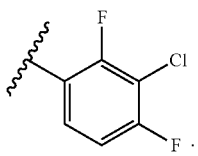 [SMILES: *c1ccc(F)c(Cl)c1F]

In one embodiment, compounds of Formula (Ia), or a pharmaceutically acceptable salt thereof, are disclosed wherein:
  A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is substituted with two $R^4$ groups, wherein the two $R^4$ are connected to the same or adjacent carbon atoms form a spiro or fused $C_{3-6}$cycloalkyl or 4 to 6 membered heterocyclyl ring;
  $R^1$ is selected from the group consisting of H, $C_{1-4}$haloalkyl and $C_{3-6}$cycloalkyl;
  $R^2$ is selected from the group consisting of hydrogen, $C_{1-3}$haloalkyl and $C_{1-3}$alkyl;
  $R^3$ is selected from the group consisting of phenyl substituted with one to three $R^5$ groups;
  and
  each $R^5$ is independently selected from the group consisting of $C_{1-3}$alkyl and halogen.

In one embodiment, compounds of Formula (Ia), or a pharmaceutically acceptable salt thereof, are disclosed wherein:
  A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;
  each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;
  $R^1$ is $C_{3-6}$cycloalkyl;
  $R^2$ is selected from the group consisting of hydrogen, $C_{1-3}$haloalkyl and $C_{1-3}$alkyl;
  $R^3$ is selected from the group consisting of phenyl substituted with one to three $R^5$ groups;
  and
  each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;

$R^1$ is $C_{1-4}$ haloalkyl;

$R^2$ is selected from the group consisting of hydrogen, $C_{1-3}$haloalkyl and $C_{1-3}$alkyl;

$R^3$ is selected from the group consisting of phenyl substituted with one to three $R^5$ groups;

and each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;

$R^1$ is selected from the group consisting of H, $C_{1-4}$haloalkyl and $C_{3-6}$cycloalkyl;

$R^2$ is $C_{1-3}$haloalkyl;

$R^3$ is selected from the group consisting of phenyl substituted with 1 to 3 $R^5$ groups;

and each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is substituted with two $R^4$ groups, wherein the two $R^4$ are connected to the same or adjacent carbon atoms form a spiro or fused $C_{3-6}$cycloalkyl or 4 to 6 membered heterocyclyl ring;

$R^1$ is selected from the group consisting of H, $C_{1-4}$haloalkyl and $C_{3-6}$cycloalkyl;

$R^2$ is selected from the group consisting of hydrogen, $C_{1-3}$haloalkyl and $C_{1-3}$alkyl;

$R^3$ is selected from the group consisting of phenyl substituted with one to three $R^5$ groups;

and each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is substituted with two $R^4$ groups, wherein the two $R^4$ are connected to the same or adjacent carbon atoms form a spiro or fused $C_{3-6}$cycloalkyl or 4 to 6 membered heterocyclyl ring;

$R^1$ is selected from the group consisting of H, $C_{1-4}$haloalkyl and $C_{3-6}$cycloalkyl;

$R^2$ is selected from the group consisting of hydrogen, $C_{1-3}$haloalkyl and $C_{1-3}$alkyl;

$R^3$ is selected from the group consisting of phenyl substituted with three $R^5$ groups;

and each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;

$R^1$ is $C_{3-6}$cycloalkyl;

$R^2$ is selected from the group consisting of hydrogen, $C_{1-3}$haloalkyl and $C_{1-3}$alkyl;

$R^3$ is selected from the group consisting of phenyl substituted with three $R^5$ groups;

and each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;

$R^1$ is $C_{1-4}$ haloalkyl;

$R^2$ is selected from the group consisting of hydrogen, $C_{1-3}$haloalkyl and $C_{1-3}$alkyl;

$R^3$ is selected from the group consisting of phenyl substituted with three $R^5$ groups;

and each $R^5$ is independently selected from the group consisting of $C_{1-3}$alkyl and halogen.

In one embodiment, compounds of Formula (Ia), or a pharmaceutically acceptable salt thereof, are disclosed wherein:

A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is optionally substituted with 1 to 5 $R^4$ groups;

each $R^4$ is independently selected from the group consisting of oxo, methyl, and ethyl; or two $R^4$ connected to the same or adjacent carbon atoms form a spiro or fused $C_{3-6}$cycloalkyl or 4 to 6 membered heterocyclyl ring;

$R^1$ is selected from the group consisting of H, $C_{1-4}$haloalkyl and $C_{3-6}$cycloalkyl;

$R^2$ is $C_{1-3}$haloalkyl;
$R^3$ is selected from the group consisting of phenyl substituted with 3 $R^5$ groups;
and
each $R^5$ is independently selected from the group consisting of $C_{1-3}$alkyl and halogen.

In one embodiment, compounds of Formula (Ia), or a pharmaceutically acceptable salt thereof, are disclosed wherein:
A' is selected from the group consisting of $C_{3-7}$ monocyclic cycloalkyl and 4 to 7 membered monocyclic heterocyclyl; wherein each $C_{3-7}$ monocyclic cycloalkyl and 4 to 7 membered monocyclic heterocyclyl is substituted with two $R^4$ groups, wherein the two $R^4$ are connected to the same or adjacent carbon atoms form a spiro or fused $C_{3-6}$cycloalkyl or 4 to 6 membered heterocyclyl ring;
$R^1$ is selected from the group consisting of H, $C_{1-4}$haloalkyl and $C_{3-6}$cycloalkyl;
$R^2$ is selected from the group consisting of hydrogen, $C_{1-3}$haloalkyl and $C_{1-3}$alkyl;
$R^3$ is selected from the group consisting of phenyl substituted with three $R^5$ groups;
and
each $R^5$ is independently selected from the group consisting of $C_{1-3}$alkyl and halogen.

In some embodiments, the compounds of Formula (Ia) is not

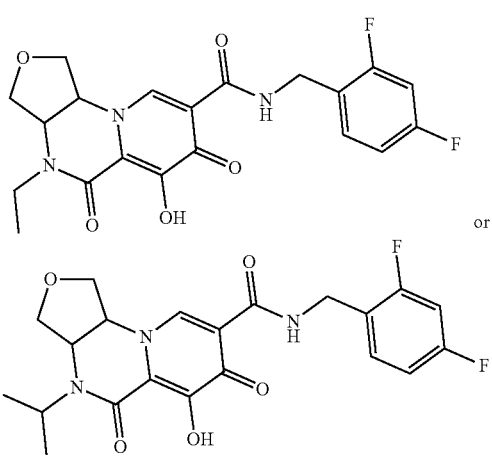

or

In another embodiment, compounds having the following Formula (Ib) are provided:

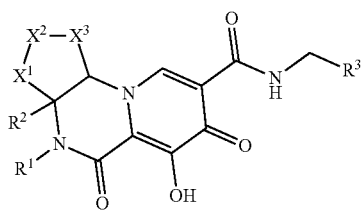

(Ib)

or a pharmaceutically acceptable salt thereof, wherein:
$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;
$R^1$ is selected from the group consisting of H, $C_{1-4}$alkyl, $C_{1-4}$haloalkyl and $C_{3-6}$cycloalkyl;
$R^2$ is selected from the group consisting of hydrogen, $C_{1-3}$haloalkyl and $C_{1-3}$alkyl;
$R^3$ is selected from the group consisting of phenyl substituted with three $R^5$ groups;
each $R^5$ is independently selected from the group consisting of $C_{1-3}$alkyl and halogen.

In another embodiment, $X^3$ is $CHR^4$; and $X^1$ and $X^2$ are each independently O, $CHR^4$ or C=O.
In another embodiment, $X^3$ is $CHR^4$; and $X^1$ and $X^2$ are each independently O or $CHR^4$.
In another embodiment, $R^4$ is H.
In another embodiment, —$X^1$—$X^2$—$X^3$— is selected from the group consisting of —$CH_2$—$CH_2$—$CH_2$—, —$CH_2$—O—$CH_2$—, and —O—$CH_2$—$CH_2$—.
In another embodiment, —$X^1$—$X^2$—$X^3$— is —O—$CH_2$—$CH_2$—.
In another embodiment, one of $X^1$ and $X^3$ is $CH_2CHR^4$ and the other one of $X^1$ and $X^3$ is $CHR^4$; and $X^2$ is O, $CHR^4$ or C=O.
In another embodiment, $X^1$ is $CH_2CHR^4$, $X^3$ is $CHR^4$; and $X^2$ is O, $CHR^4$ or C=O.
In another embodiment, $X^3$ is $CH_2CHR^4$, $X^1$ is $CHR^4$; and $X^2$ is O, $CHR^4$ or C=O.
In another embodiment, $R^4$ is H.
In another embodiment —$X^1$—$X^2$—$X^3$— is selected from the group consisting of —$CH_2$—$CH_2$—$CH_2$—$CH_2$, —$CH_2$—O—$CH_2$—$CH_2$—, —$CH(CH_3)$—O—$CH_2$—$CH_2$, —$CH_2$—$CH_2$—O—$CH_2$, and —$CH_2$—C(O)—$CH_2$—$CH_2$.
In another embodiment —$X^1$—$X^2$—$X^3$— is —$CH_2$—O—$CH_2$—$CH_2$—.
In another embodiment, $R^2$ is selected from the group consisting of hydrogen, $C_{1-2}$haloalkyl, methyl and ethyl.
In another embodiment, $R^2$ is selected from the group consisting of hydrogen, methyl and $CHF_2$.
In another embodiment, $R^2$ is hydrogen.
In another embodiment, $R^2$ is $C_{1-3}$haloalkyl.
In another embodiment, $R^2$ is $CHF_2$.
In another embodiment:

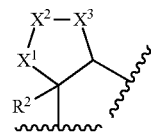

is selected from the group consisting of:

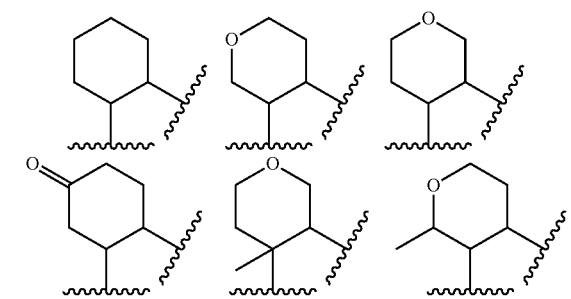

-continued

[chemical structures] and

In another embodiment,

[chemical structures] is

In another embodiment,

[chemical structure]

is selected from the group consisting of:

[chemical structures]

and

In another embodiment,

[chemical structure]

is selected from the group consisting of:

[chemical structures]

and

In another embodiment:

[chemical structure]

is selected from the group consisting of:

[chemical structures]

and .

In another embodiment,

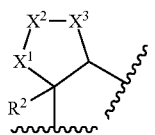

is selected from the group consisting of:

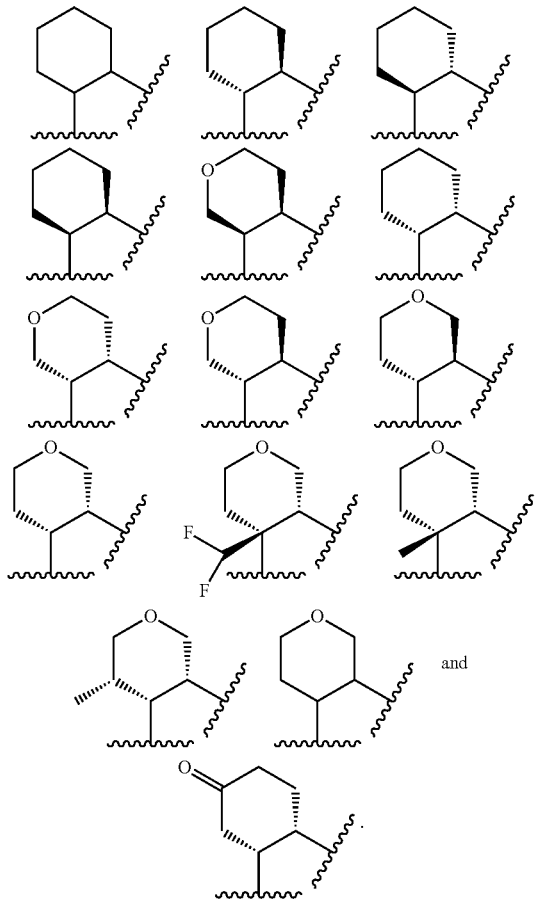

In another embodiment,

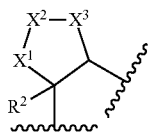

is selected from the group consisting of:

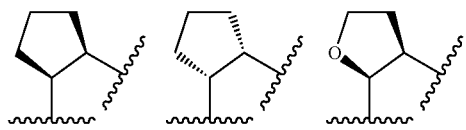

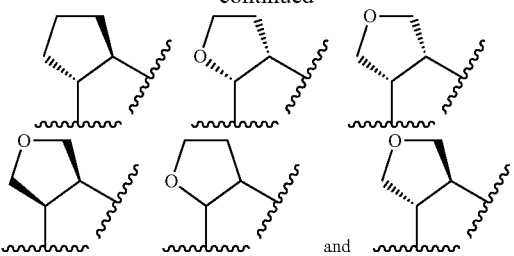

and

In another embodiment,

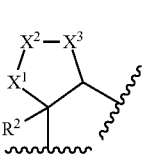 is 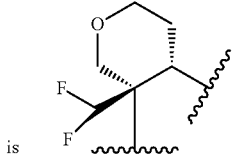.

In another embodiment:

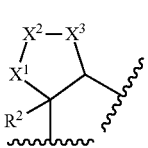 is 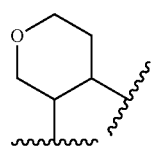 or 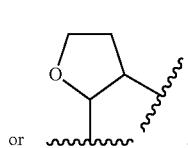.

In another embodiment:

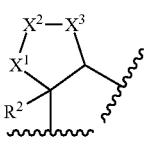 is 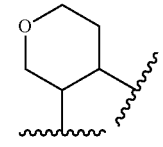.

In another embodiment:

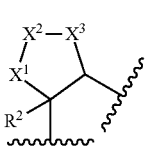 is 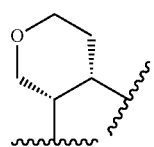 or 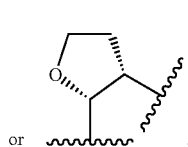.

In another embodiment:

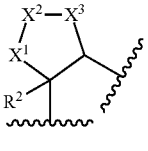 is 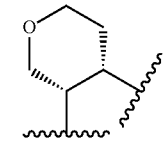.

In another embodiment, $R^1$ is selected from the group consisting of H, $C_{1-3}$alkyl, $C_{1-2}$haloalkyl, and $C_{3-5}$cycloalkyl.

In another embodiment, $R^1$ is selected from the group consisting of hydrogen, methyl, ethyl, propyl, isopropyl, $CH_2CF_3$ and $CH_2CHF_2$ and cyclopropyl.

In another embodiment, R$^1$ is ethyl.

In another embodiment, R$^1$ is selected from the group consisting of C$_{1-4}$haloalkyl and C$_{3-6}$cycloalkyl.

In another embodiment, R$^1$ is selected from the group consisting of CH$_2$CF$_3$, CH$_2$CHF$_2$ and cyclopropyl.

In another embodiment:

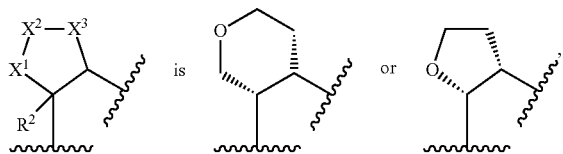

and R$^1$ is ethyl.

In another embodiment, R$^3$ is phenyl substituted with three R$^5$ groups, wherein each R$^5$ is independently selected from the group consisting of methyl, ethyl, and halogen.

In another embodiment, R$^3$ is phenyl substituted with three R$^5$ groups, wherein each R$^5$ is independently selected from the group consisting of methyl, fluoro and chloro.

In another embodiment, R$^3$ is selected from the group consisting of:

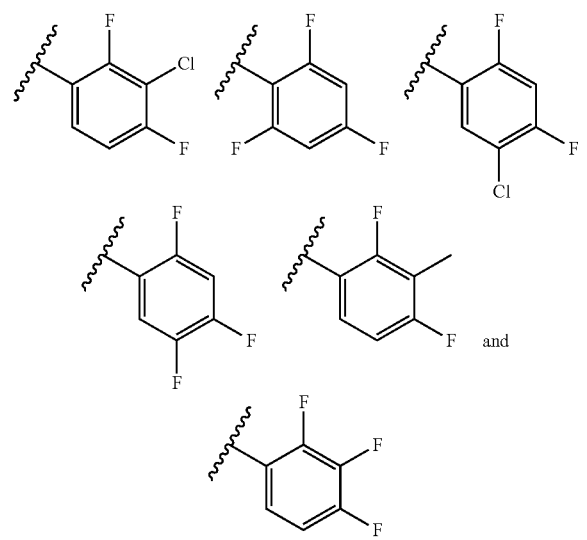

In another embodiment, R$^3$ is selected from the group consisting of:

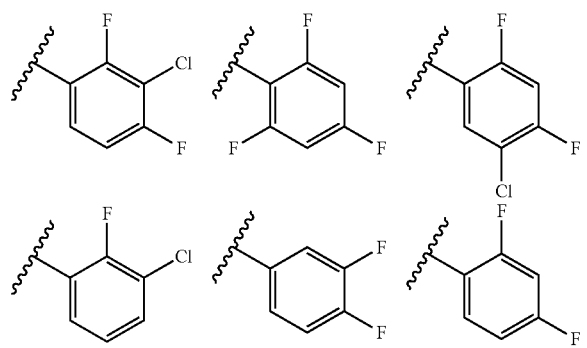

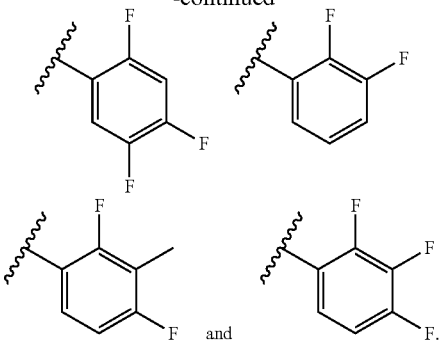

In another embodiment, R$^3$ is phenyl substituted with 3 halogens.

In another embodiment, R$^3$ is phenyl substituted with 2 fluoro groups and one chloro group.

In another embodiment, R$^3$ is

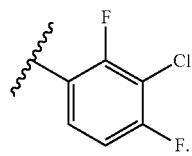 [SMILES: *c1ccc(F)c(Cl)c1F]

In another embodiment:

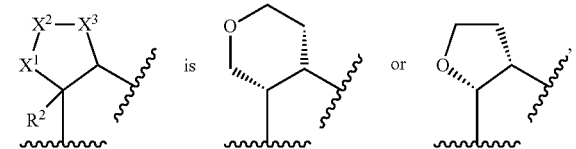

R$^1$ is ethyl, and R$^3$ is

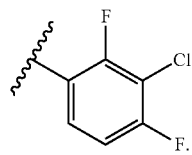 [SMILES: *c1ccc(F)c(Cl)c1F]

In another embodiment, compounds having the following Formula (Ib), or a pharmaceutically acceptable salt thereof, are disclosed wherein:

X$^1$, X$^2$, and X$^3$ are each independently selected from the group consisting of CHR$^4$, O, C=O and CH$_2$CHR$^4$; provided that no more than one of X$^1$, X$^2$, and X$^3$ is O or C=O;

each R$^4$ is independently selected from the group consisting of H and CH$_3$;

R$^1$ is C$_{3-6}$cycloalkyl;

R$^2$ is selected from the group consisting of hydrogen, C$_{1-3}$haloalkyl and C$_{1-3}$alkyl;

R$^3$ is selected from the group consisting of phenyl substituted with 1 to 3 R$^5$ groups;

each R$^5$ is independently selected from the group consisting of C$_{1-3}$alkyl and halogen.

In another embodiment, compounds having the following Formula (Ib), or a pharmaceutically acceptable salt thereof, are disclosed wherein:

$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;

$R^1$ is $C_{1-4}$ haloalkyl;

$R^2$ is selected from the group consisting of hydrogen, $C_{1-3}$haloalkyl and $C_{1-3}$alkyl;

$R^3$ is selected from the group consisting of phenyl substituted with 1 to 3 $R^5$ groups;

each $R^5$ is independently selected from the group consisting of $C_{1-3}$alkyl and halogen.

In another embodiment, compounds having the following Formula (Ib), or a pharmaceutically acceptable salt thereof, are disclosed wherein:

$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;

$R^1$ is selected from the group consisting of H, $C_{1-4}$haloalkyl and $C_{3-6}$cycloalkyl;

$R^2$ is $C_{1-3}$haloalkyl;

$R^3$ is selected from the group consisting of phenyl substituted with 1 to 3 $R^5$ groups;

each $R^5$ is independently selected from the group consisting of $C_{1-3}$alkyl and halogen.

In another embodiment, compounds having the following Formula (Ib), or a pharmaceutically acceptable salt thereof, are disclosed wherein:

$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;

$R^1$ is $C_{3-6}$cycloalkyl;

$R^2$ is selected from the group consisting of hydrogen, $C_{1-3}$haloalkyl and $C_{1-3}$alkyl;

$R^3$ is selected from the group consisting of phenyl substituted with 3 $R^5$ groups;

each $R^5$ is independently selected from the group consisting of $C_{1-3}$alkyl and halogen.

In another embodiment, compounds having the following Formula (Ib), or a pharmaceutically acceptable salt thereof, are disclosed wherein:

$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;

$R^1$ is $C_{1-4}$ haloalkyl;

$R^2$ is selected from the group consisting of hydrogen, $C_{1-3}$haloalkyl and $C_{1-3}$alkyl;

$R^3$ is selected from the group consisting of phenyl substituted with 3 $R^5$ groups;

each $R^5$ is independently selected from the group consisting of $C_{1-3}$alkyl and halogen.

In another embodiment, compounds having the following Formula (Ib), or a pharmaceutically acceptable salt thereof, are disclosed wherein:

$X^1$, $X^2$, and $X^3$ are each independently selected from the group consisting of $CHR^4$, O, C=O and $CH_2CHR^4$; provided that no more than one of $X^1$, $X^2$, and $X^3$ is O or C=O;

each $R^4$ is independently selected from the group consisting of H and $CH_3$;

$R^1$ is selected from the group consisting of H, $C_{1-4}$haloalkyl and $C_{3-6}$cycloalkyl;

$R^2$ is $C_{1-3}$haloalkyl;

$R^3$ is selected from the group consisting of phenyl substituted with 3 $R^5$ groups;

each $R^5$ is independently selected from the group consisting of $C_{1-3}$alkyl and halogen.

In some embodiments, the compounds of Formula (Ib) are not

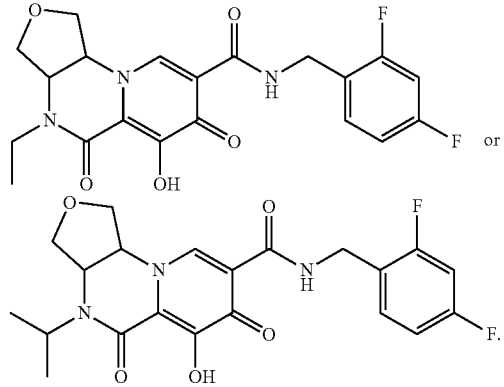

In another embodiment, compounds having the following Formula (Ic) are provided:

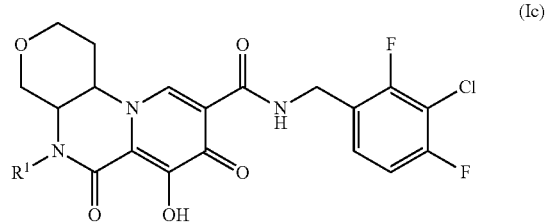

(Ic)

or a pharmaceutically acceptable salt thereof, wherein:

$R^1$ is selected from the group consisting of H, $C_{1-4}$haloalkyl and $C_{3-6}$cycloalkyl.

In another embodiment, compounds having the following Formula (Id) are provided:

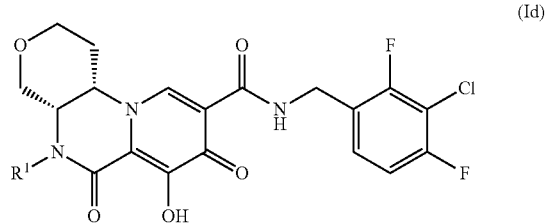

(Id)

or a pharmaceutically acceptable salt thereof, wherein:

$R^1$ is selected from the group consisting of H, $C_{1-4}$haloalkyl and $C_{3-6}$cycloalkyl.

In another embodiment, compounds having the following Formula (Ie) are provided:

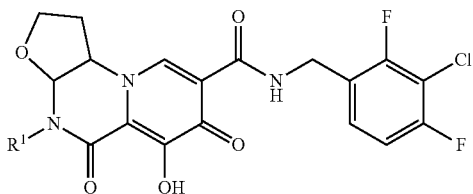

or a pharmaceutically acceptable salt thereof, wherein:
R$^1$ is selected from the group consisting of H, C$_{1-4}$alkyl, C$_{1-4}$haloalkyl and C$_{3-6}$cycloalkyl.

In another embodiment, compounds having the following Formula (If) are provided:

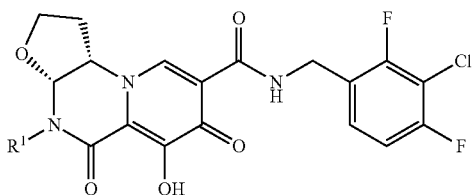

or a pharmaceutically acceptable salt thereof, wherein:
R$^1$ is selected from the group consisting of H, C$_{1-4}$alkyl, C$_{1-4}$haloalkyl and C$_{3-6}$cycloalkyl.

In another embodiment, R$^1$ is selected from the group consisting of H, C$_{1-3}$alkyl, C$_{1-2}$haloalkyl, and C$_{3-5}$cycloalkyl.

In another embodiment, R$^1$ is selected from the group consisting of hydrogen, methyl, ethyl, propyl, isopropyl, CH$_2$CF$_3$, CH$_2$CHF$_2$ and cyclopropyl.

In another embodiment, R$^1$ is ethyl.

In another embodiment, R$^1$ is selected from the group consisting of C$_{1-4}$haloalkyl and C$_{3-6}$cycloalkyl.

In another embodiment, R$^1$ is selected from the group consisting of CH$_2$CF$_3$, CH$_2$CHF$_2$ and cyclopropyl.

In another embodiment, compounds having the following Formula (II) are provided:

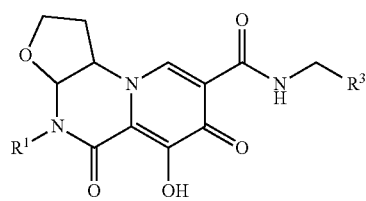

or a pharmaceutically acceptable salt thereof, wherein:
R$^1$ is selected from the group consisting of H, C$_{1-4}$alkyl, C$_{1-4}$haloalkyl and C$_{3-6}$cycloalkyl;
R$^3$ is selected from the group consisting of phenyl substituted with one to three R$^5$ groups; and
each R$^5$ is independently selected from the group consisting of C$_{1-3}$alkyl and halogen.

In another embodiment, compounds of Formula (II), or a pharmaceutically acceptable salt thereof, are disclosed wherein:

R$^1$ is selected from the group consisting of H, C$_{1-4}$alkyl, C$_{1-4}$haloalkyl and C$_{3-6}$cycloalkyl;
R$^3$ is selected from the group consisting of phenyl substituted with three R$^5$ groups; and
each R$^5$ is independently selected from the group consisting of C$_{1-3}$alkyl and halogen.

In another embodiment, the compound of Formula (II) is a compound of the Formula (IIa):

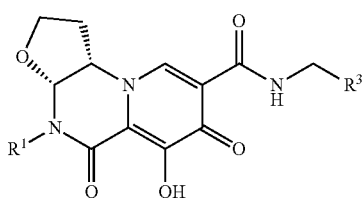

In another embodiment, compounds having the following Formula (III) are provided:

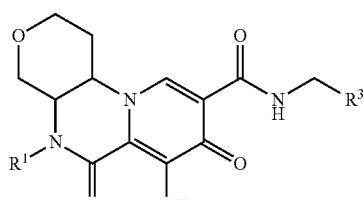

or a pharmaceutically acceptable salt thereof, wherein:
R$^1$ is selected from the group consisting of H, C$_{1-4}$alkyl, C$_{1-4}$haloalkyl and C$_{3-6}$cycloalkyl;
R$^3$ is selected from the group consisting of phenyl substituted with one to three R$^5$ groups; and
each R$^5$ is independently selected from the group consisting of C$_{1-3}$alkyl and halogen.

In another embodiment, compounds having the following Formula (III), or a pharmaceutically acceptable salt thereof, are disclosed wherein:
R$^1$ is selected from the group consisting of H, C$_{1-4}$alkyl, C$_{1-4}$haloalkyl and C$_{3-6}$cycloalkyl;
R$^3$ is selected from the group consisting of phenyl substituted with three R$^5$ groups; and
each R$^5$ is independently selected from the group consisting of C$_{1-3}$alkyl and halogen.

In another embodiment, the compounds of Formula III are compounds of Formula (IIIa):

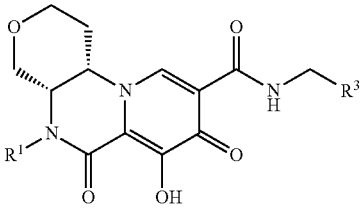

In another embodiment, compounds are provided having the following structures:

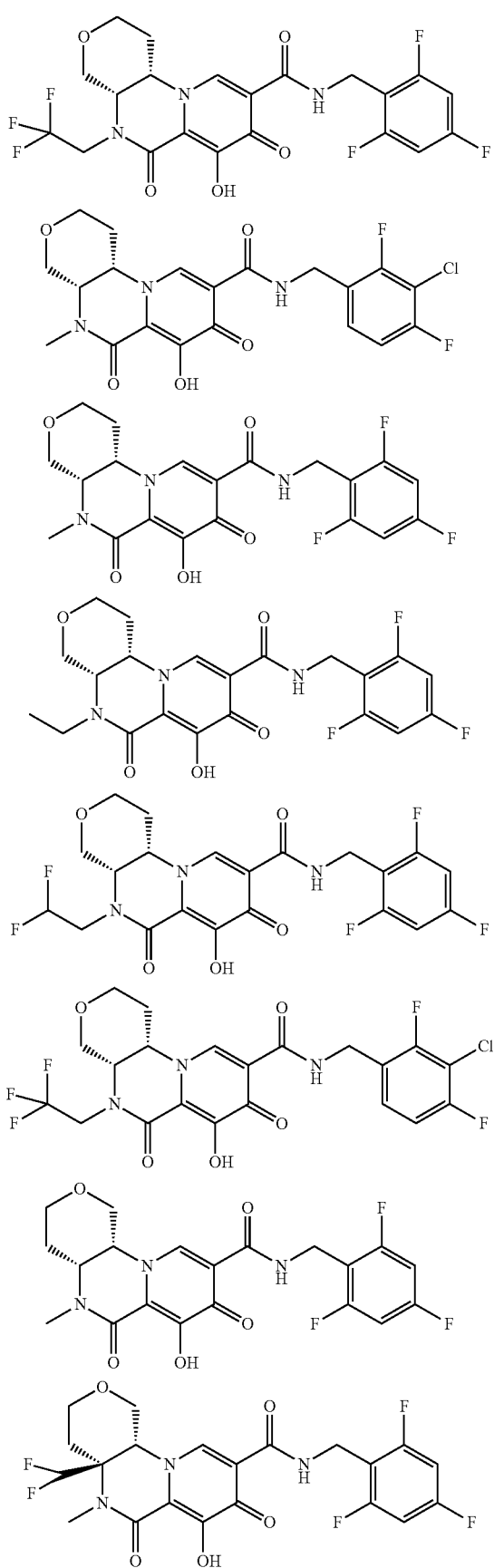
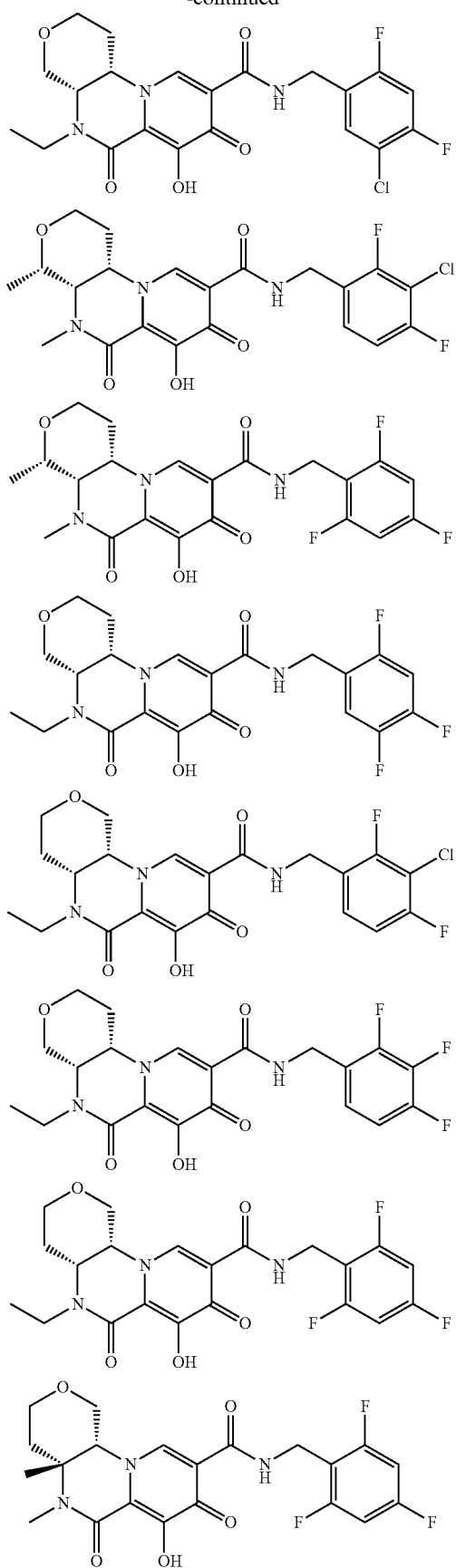
-continued

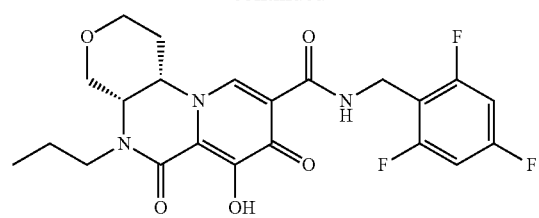
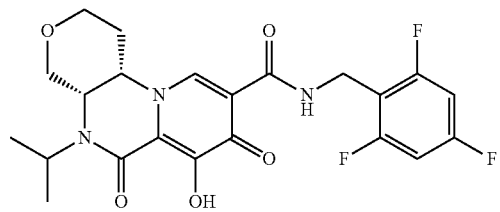
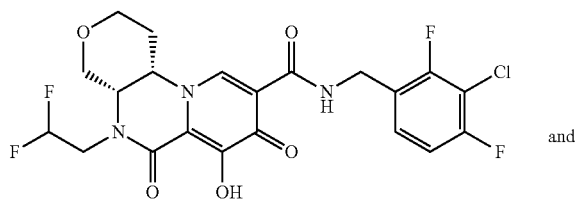
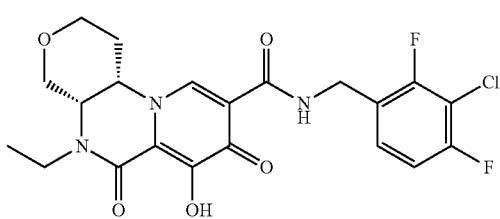
or a pharmaceutically acceptable salt thereof.
In another embodiment, compounds are provided having the following structures:
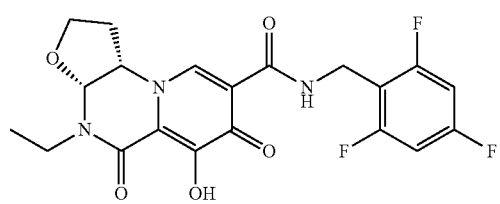
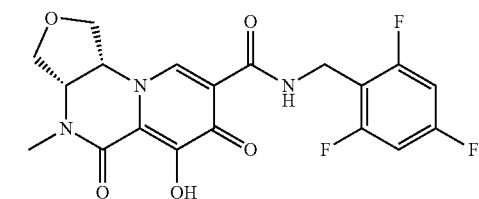
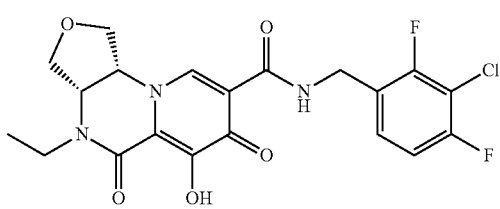
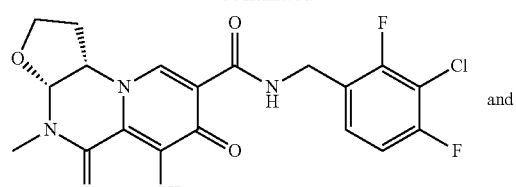
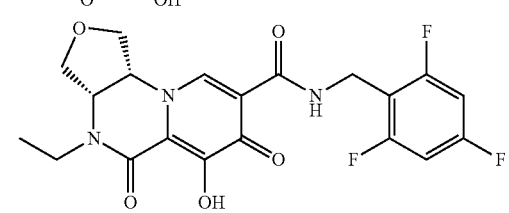
or a pharmaceutically acceptable salt thereof.
In another embodiment, compounds are provided having the following structures:
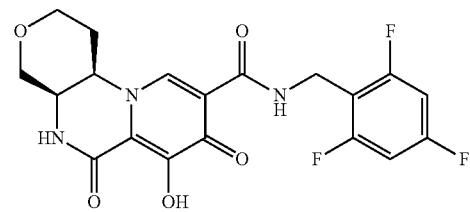
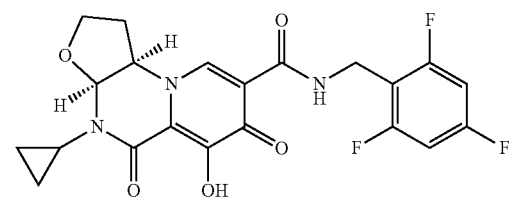
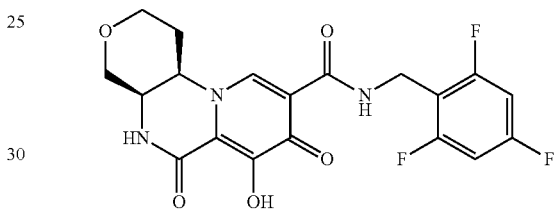
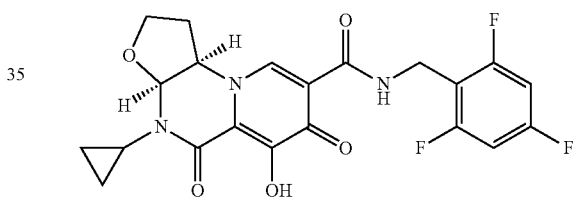
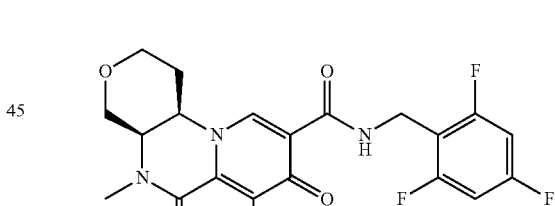
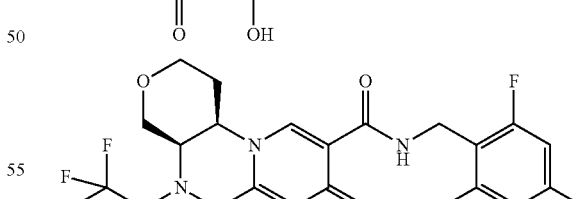
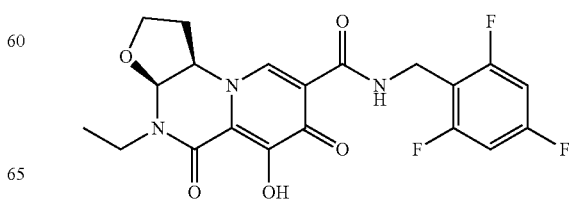

-continued
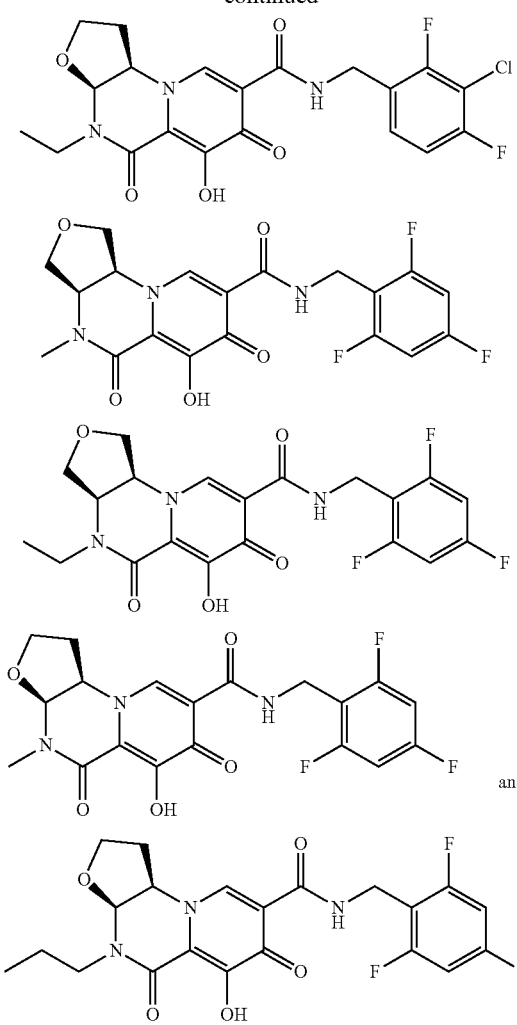
or a pharmaceutically acceptable salt thereof.
In another embodiment, compounds are provided having the following structures:
-continued
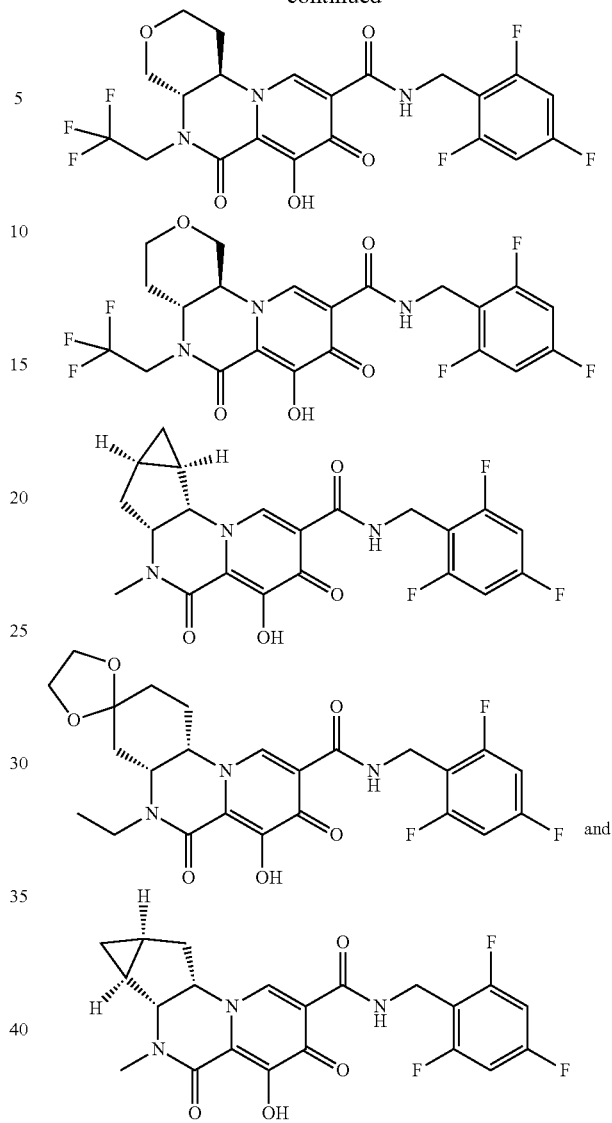
or a pharmaceutically acceptable salt thereof.
In another embodiment, compounds are provided having the following structures:
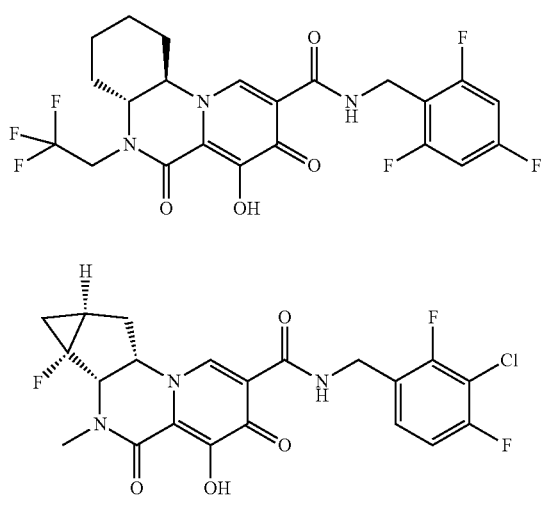

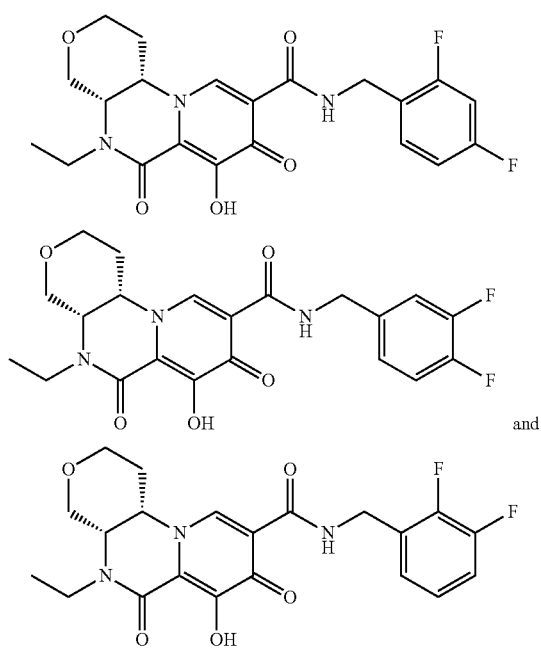
or a pharmaceutically acceptable salt thereof.
In another embodiment, compounds are provided having the following structures:
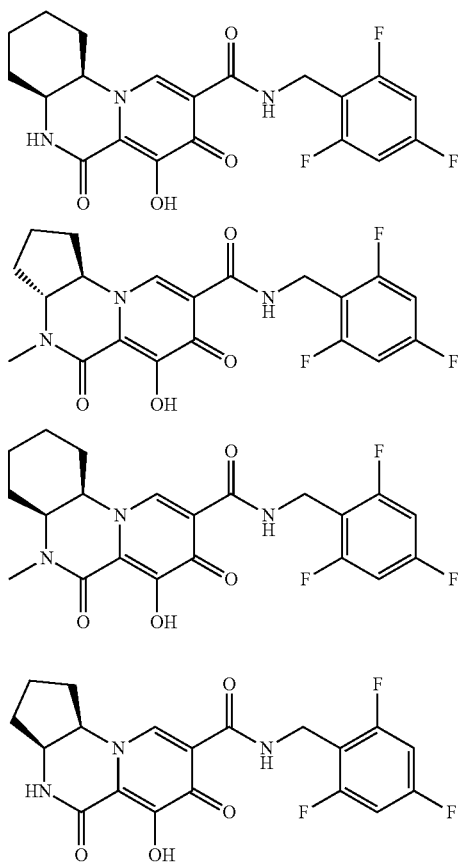
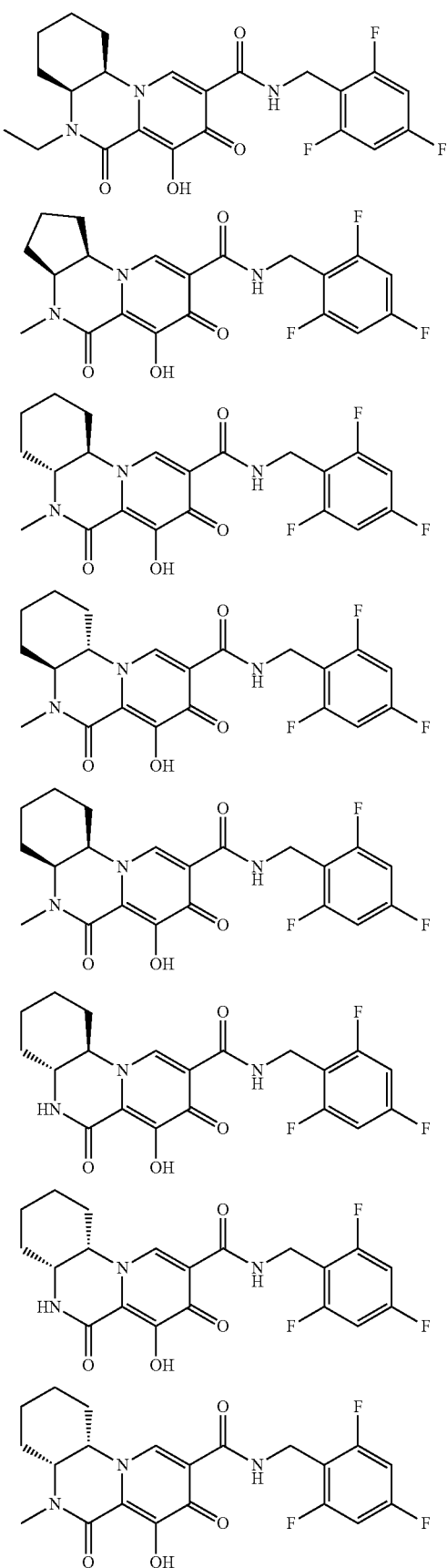

-continued

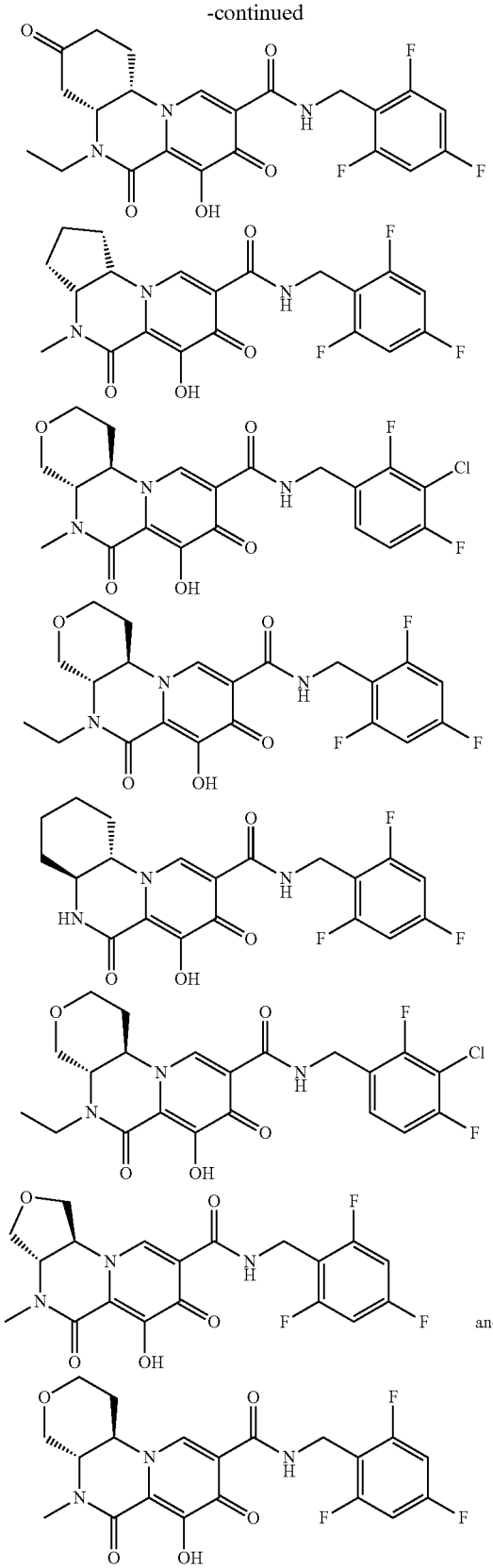

or a pharmaceutically acceptable salt thereof.

In another embodiment, a compound of Formula (25-M) or a pharmaceutically acceptable salt thereof, is provided:

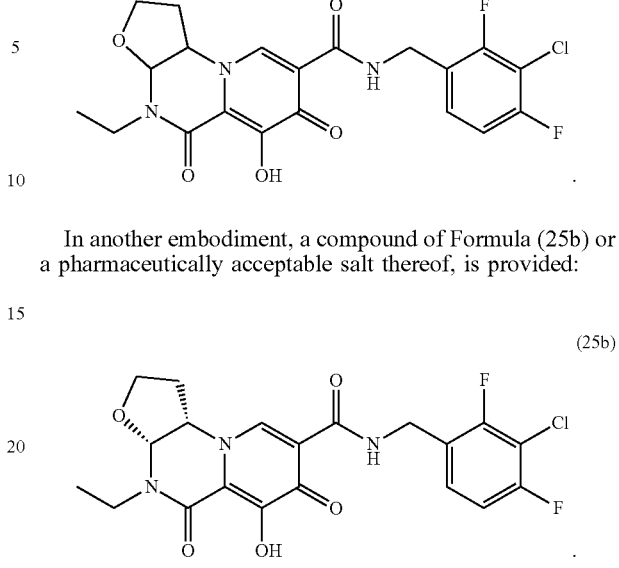

In another embodiment, a compound of Formula (25b) or a pharmaceutically acceptable salt thereof, is provided:

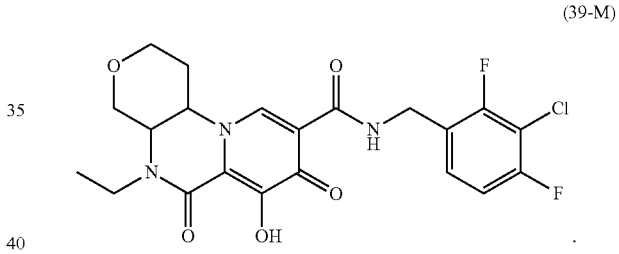

In another embodiment, a compound of the Formula (39-M) or a pharmaceutically acceptable salt thereof, is provided:

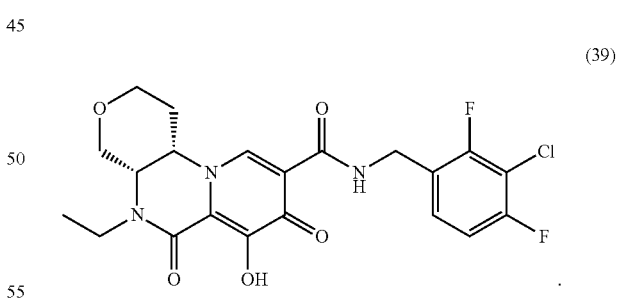

In another embodiment, a compound of Formula (39) or a pharmaceutically acceptable salt thereof, is provided:

(39)

In another embodiment, a pharmaceutical composition is provided comprising a compound having the Formula (Ia), (Ib), (Ic), (Id), (Ie), (If), (II), (IIa), (III), (IIIa), (25-M), (25b), (39-M) or (39) or a pharmaceutically acceptable salt thereof, and a pharmaceutically acceptable excipient.

In another embodiment, the pharmaceutical composition further comprises one or more additional therapeutic agents.

In another embodiment, the pharmaceutical composition further comprises one or more anti-HIV agent.

In another embodiment, the pharmaceutical composition further comprises one or more additional therapeutic agents selected from the group consisting of HIV protease inhibitors, HIV non-nucleoside inhibitors of reverse transcriptase, HIV nucleoside or nucleotide inhibitors of reverse transcriptase, and combinations thereof.

In another embodiment, the pharmaceutical composition further comprises a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the pharmaceutical composition further comprises tenofovir disoproxil fumarate and emtricitabine.

In another embodiment, the pharmaceutical composition further comprises tenofovir alafenamide hemifumarate and emtricitabine.

In another embodiment, a method of treating an HIV infection in a human having or at risk of having the infection by administering to the human a therapeutically effective amount of a compound of Formula (Ia), (Ib), (Ic), (Id), (Ie), (If), (II), (IIa), (III), (IIIa), (25-M), (25b), (39-M) or (39), or a pharmaceutically acceptable salt thereof, or a pharmaceutical composition of a compound of Formula (Ia), (Ib), (Ic), (Id), (Ie), (If), (II), (IIa), (III), (IIIa), (25-M), (25b), (39-M) or (39) or a pharmaceutically acceptable salt thereof, is provided.

In another embodiment, the method of treating an HIV infection in a human having or at risk of having the infection, further comprises administering to the human a therapeutically effective amount of one or more additional therapeutic agents.

In another embodiment, the method of treating an HIV infection in a human having or at risk of having the infection, further comprises administering to the human a therapeutically effective amount of one or more additional anti-HIV agents.

In another embodiment, the method of treating an HIV infection in a human having or at risk of having the infection, further comprises administering to the human a therapeutically effective amount of one or more additional therapeutic agents selected from the group consisting of HIV protease inhibitors, HIV non-nucleoside inhibitors of reverse transcriptase, HIV nucleoside or nucleotide inhibitors of reverse transcriptase, and combinations thereof. In a specific embodiment, the method of treating an HIV infection in a human having or at risk of having the infection, further comprises administering to the human a therapeutically effective amount of HIV non-nucleoside inhibitors of reverse transcriptase.

In another embodiment, the method of treating an HIV infection in a human having or at risk of having the infection, further comprises administering to the human a therapeutically effective amount of a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In another embodiment, the method of treating an HIV infection in a human having or at risk of having the infection, further comprises administering to the human a therapeutically effective amount of tenofovir disoproxil and emtricitabine.

In another embodiment, the method of treating an HIV infection in a human having or at risk of having the infection, further comprises administering to the human a therapeutically effective amount of tenofovir disoproxil fumarate and emtricitabine.

In another embodiment, the method of treating an HIV infection in a human having or at risk of having the infection, further comprises administering to the human a therapeutically effective amount of tenofovir alafenamide and emtricitabine.

In another embodiment, the method of treating an HIV infection in a human having or at risk of having the infection, further comprises administering to the human a therapeutically effective amount of tenofovir alafenamide hemifumarate and emtricitabine.

In another embodiment, a use of a compound of Formula (Ia), (Ib), (Ic), (Id), (Ie), (If), (II), (IIa), (III), (IIIa), (25-M), (25b), (39-M) or (39) or pharmaceutically acceptable salt thereof, or a pharmaceutical composition of a compound of (Ia), (Ib), (Ic), (Id), (Ie), (If), (II), (IIa), (III), (IIIa), (25-M), (25b), (39-M) or (39) or a pharmaceutically acceptable salt thereof, for the treatment of an HIV infection in a human having or at risk of having the infection is provided.

In another embodiment, a compound of Formula (Ia), (Ib), (Ic), (Id), (Ie), (If), (II), (IIa), (III), (IIIa), (25-M), (25b), (39-M) or (39), or a pharmaceutically acceptable salt thereof, or a pharmaceutical composition of a compound of Formula (Ia), (Ib), (Ic), (Id), (Ie), (If), (II), (IIa), (III), (IIIa), (25-M), (25b), (39-M) or (39), or pharmaceutically acceptable salt thereof, for use in medical therapy is provided.

In another embodiment, a compound of Formula (Ia), (Ib), (Ic), (Id), (Ie), (If), (II), (IIa), (III), (IIIa), (25-M), (25b), (39-M) or (39), or a pharmaceutically acceptable salt thereof, or a pharmaceutical composition of a compound of Formula (Ia), (Ib), (Ic), (Id), (Ie), (If), (II), (IIa), (III), (IIIa), (25-M), (25b), (39-M) or (39), or pharmaceutically acceptable salt thereof, for use in the prophylactic or therapeutic treatment of an HIV infection is provided.

In another embodiment, a method of using a compound having the Formula (Ia), (Ib), (Ic), (Id), (Ie), (If), (II), (IIa), (III), (IIIa), (25-M), (25b), (39-M) or (39) in therapy is provided. In particular, a method of treating the proliferation of the HIV virus, treating AIDS, or delaying the onset of AIDS or ARC symptoms in a mammal (e.g., a human) is provided, comprising administering to the mammal a compound having the Formula (Ia), (Ib), (Ic), (Id), (Ie), (If), (II), (IIa), (III), (IIIa), (25-M), (25b), (39-M) or (39), or a stereoisomer or pharmaceutically acceptable salt thereof, and a pharmaceutically acceptable excipient.

In another embodiment, the use of a compound of Formula (Ia), (Ib), (Ic), (Id), (Ie), (If), (II), (IIa), (III), (IIIa), (25-M), (25b), (39-M) or (39) as described herein, or a pharmaceutically acceptable salt thereof, for the manufacture of a medicament for the treatment of an HIV infection in a human being having or at risk of having the infection is disclosed.

In another embodiment, the use of a compound of Formula (Ia), (Ib), (Ic), (Id), (Ie) or (If), (II), (IIa), (III), (IIIa), (25-M), (25b), (39-M) or (39) as described herein or a pharmaceutically acceptable salt thereof, as a research tool, is provided.

In another embodiment, an article of manufacture comprising a composition effective to treat an HIV infection; and packaging material comprising a label which indicates that the composition can be used to treat infection by HIV is disclosed. Exemplary compositions comprise a compound of Formula (Ia), (Ib), (Ic), (Id), (Ie), (If), (II), (IIa), (III), (IIa), (III), (IIIa), (25-M), (25b), (39-M) or (39) according to this embodiments disclosed herein or a pharmaceutically acceptable salt thereof.

In still another embodiment, a method of inhibiting the replication of HIV is disclosed. The method comprises exposing the virus to an effective amount of the compound of Formula (Ia), (Ib), (Ic), (Id), (Ie), (If), (II), (IIa), (III), (IIIa), (25-M), (25b), (39-M) or (39) or a salt thereof, under conditions where replication of HIV is inhibited.

In another embodiment, the use of a compound of Formula (Ia), (Ib), (Ic), (Id), (Ie), (If), (II), (IIa), (III), (IIIa), (25-M), (25b), (39-M) or (39) to inhibit the activity of the HIV integrase enzyme is disclosed.

In another embodiment, the use of a compound of Formula (Ia), (Ib), (Ic), (Id), (Ie), (If), (II), (IIa), (III), (IIIa), (25-M), (25b), (39-M) or (39), or a salt thereof, to inhibit the replication of HIV is disclosed.

The present invention also provides compounds of each of the Formulae herein, as well as each subgroup and embodiment thereof, including a compound selected from the group of Formula (Ia), (Ib), (Ic), (Id), (Ie), (If), (II), (IIa), (III), (IIIa), (25-M), (25b), (39-M) and (39), or a pharmaceutically acceptable salt thereof, or a pharmaceutical composition of a compound of Formula (Ia), (Ib), (Ic), (Id), (Ie), (If), (II), (IIa), (III), (IIIa), (25-M), (25b), (39-M) or (39), or a pharmaceutically acceptable salt thereof, or one of the specific compounds of the examples herein, or a salt thereof for use in any of the methods of the invention as defined herein.

It is understood that any embodiment of the compounds of any one of Formulas (Ia), (Ib), (Ic), (Id), (Ie), (If), (II), (IIa), (III), (IIIa), (25-M), (25b), (39-M) and (39), as set forth above, and any specific substituent set forth herein A', $R^1$, $R^2$, $R^3$, $R^4$, $R^5$ $X^1$, $X^2$ or $X^3$ group in the compounds of Formulas (Ia), (Ib), (Ic), (Id), (Ie), (If), (II), (IIa), (III), (Ma), (25-M), (25b), (39-M) or (39) as set forth above, may be independently combined with other embodiments and/or substituents of compounds of any one of Formulas (Ia), (Ib), (Ic), (Id), (Ie), (If), (II), (IIa), (III), (IIIa), (25-M), (25b), (39-M) and (39) to form embodiments not specifically set forth above. In addition, in the event that a list of substituents is listed for any particular A', $R^1$, $R^2$, $R^3$, $R^4$, $R^5$, $X^1$, $X^2$ or $X^3$ in a particular embodiment and/or claim, it is understood that each individual substituent may be deleted from the particular embodiment and/or claim and that the remaining list of substituents will be considered to be within the scope of the embodiments disclosed herein.

Pharmaceutical Compositions

For the purposes of administration, in certain embodiments, the compounds described herein are administered as a raw chemical or are formulated as pharmaceutical compositions. Pharmaceutical compositions within the scope of the embodiments disclosed herein comprise a compound of Formula (Ia), (Ib), (Ic), (Id), (Ie), (If), (II), (IIa), (III), (IIIa), (25-M), (25b), (39-M) or (39), and a pharmaceutically acceptable excipient. The compound of Formula (Ia), (Ib), (Ic), (Id), (Ie), (If), (II), (IIa), (III), (IIIa), (25-M), (25b), (39-M) or (39), is present in the composition in an amount which is effective to treat a particular disease or condition of interest. The activity of compounds of Formulas (Ia), (Ib), (Ic), (Id), (Ie), (If), (II), (IIa), (III), (IIIa), (25-M), (25b), (39-M) or (39), can be determined by one skilled in the art, for example, as described in the Examples below. Appropriate concentrations and dosages can be readily determined by one skilled in the art.

Administration of the compounds of the embodiments disclosed herein, or their pharmaceutically acceptable salts, in pure form or in an appropriate pharmaceutical composition, can be carried out via any of the accepted modes of administration of agents for serving similar utilities. The pharmaceutical compositions of the embodiments disclosed herein can be prepared by combining a compound of the embodiments disclosed herein with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. Pharmaceutical compositions of the embodiments disclosed herein may be formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the embodiments disclosed herein in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the embodiments disclosed herein, or a pharmaceutically acceptable salt thereof, for treatment of a disease or condition of interest in accordance with the teachings of this disclosure.

The pharmaceutical compositions disclosed herein may be prepared by methodology well known in the pharmaceutical art. For example, a pharmaceutical composition intended to be administered by injection can be prepared by combining a compound of the embodiments disclosed herein with sterile, distilled water so as to form a solution. A surfactant may be added to facilitate the formation of a homogeneous solution or suspension. Surfactants are compounds that non-covalently interact with the compound of the embodiments disclosed herein so as to facilitate dissolution or homogeneous suspension of the compound in the aqueous delivery system.

The compounds of the embodiments disclosed herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

A compound as disclosed herein (e.g., any compound of Formula (Ia), (Ib), (Ic), (Id), (Ie), (If), (II), (IIa), (III), (IIIa), (25-M), (25b), (39-M) or (39)) may be combined with one or more additional therapeutic agents in any dosage amount of the compound of Formula (Ia), (Ib), (Ic), (Id), (Ie), (If), (II), (IIa), (III), (IIIa), (25-M), (25b), (39-M) or (39) (e.g., from 50 mg to 1000 mg of compound).

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable excipient are provided.

In one embodiment, kits comprising a compound disclosed herein, or a pharmaceutically acceptable salt thereof, in combination with one or more (e.g., one, two, three, one or two, or one to three) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formula (Ia), (Ib), (Ic), (Id), (Ie), (If), (II), (IIa), (III), (IIIa), (25-M), (25b), (39-M) or (39) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing. In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® (EVIPLERA®, rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, atazanavir sulfate+cobicistat, darunavir+cobicistat, efavirenz+lamivudine+tenofovir disoproxil fumarate, tenofovir alafenamide hemifumarate+emtricitabine+cobicistat+elvitegravir, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Livexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), TBR-220 (TAK-220), nifeviroc (TD-0232), TD-0680, and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp120 (AIDSVAX), ALVAC HIV (vCP1521)/AIDSVAX B/E (gp120) (RV144), Remune, ITV-1, Contre Vir, Ad5-ENVA-48, DCVax-001 (CDX-2401), PEP-6409, Vacc-4x, Vacc-05, VAC-3S, multiclade DNA recombinant adenovirus-5 (rAdS), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, ThV-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHlVvac, ADVAX, MYM-V201, MVA-CMDR, ETV-01 and DNA-Ad5 gag/pol/nef/nev (HVTN505);

(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8 and VRC07;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCRSRZ, MazF gene therapy, BlockAide, ABX-464, SCY-635, naltrexone and PA-1050040 (PA-040).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein, or a pharmaceutically acceptable salt thereof, is combined with an HIV non-nucleoside inhibitor of reverse transcriptase. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from Triumeq® (dolutegravir+abacavir+lamivudine), dolutegravir+abacavir sulfate+lamivudine, raltegravir, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, tenofovir alafenamide and tenofovir alafenamide hemifumarate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of formula (Ia), (Ib), (Ic), (Id), (Ie), (If), (II), (IIa), (III), (Ma), (25-M), (25b), (39-M) or (39)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of formula (Ia), (Ib), (Ic), (Id), (Ie), (If), (II), (IIa), (III), (IIIa), (25-M), (25b), (39-M) or (39)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents.

For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

General Synthetic Procedures

Some embodiments are also directed to processes and intermediates useful for preparing the subject compounds or pharmaceutically acceptable salts thereof.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Representative syntheses of compounds of the present disclosure are described in schemes below, and the particular examples that follow. Schemes 1 and 2 are provided as further embodiments of the invention and illustrate general methods which were used to prepare compounds having the Formula (Ia), (Ib), (II), (IIa), (III), and (Ma), and which can be used to prepare additional compounds having the Formula (Ia), (Ib), (II), (IIa), (III), and (IIIa). The methodology is compatible with a wide variety of functionalities.

Scheme 1

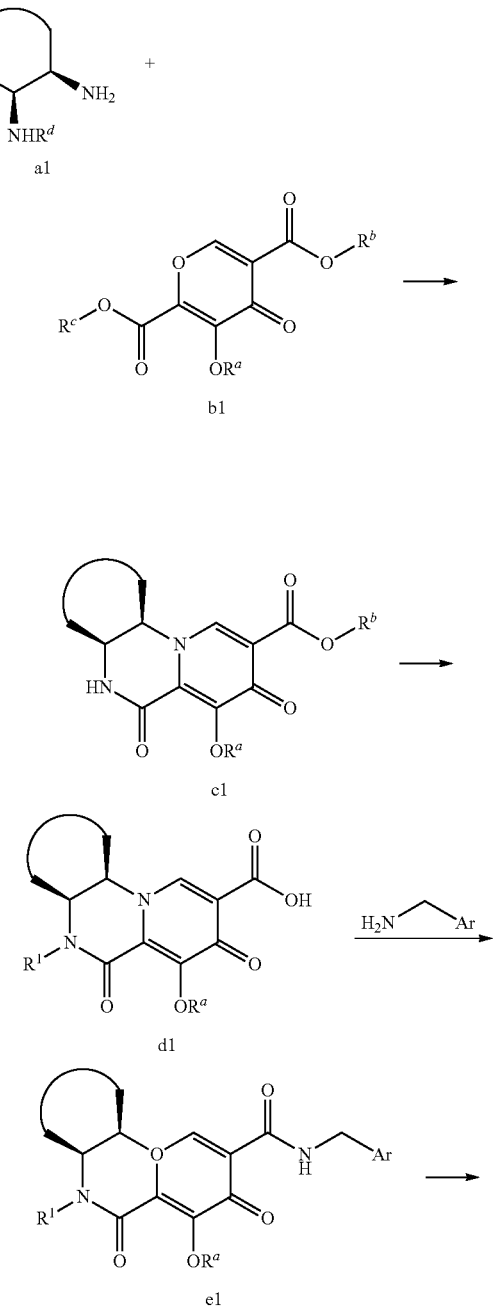

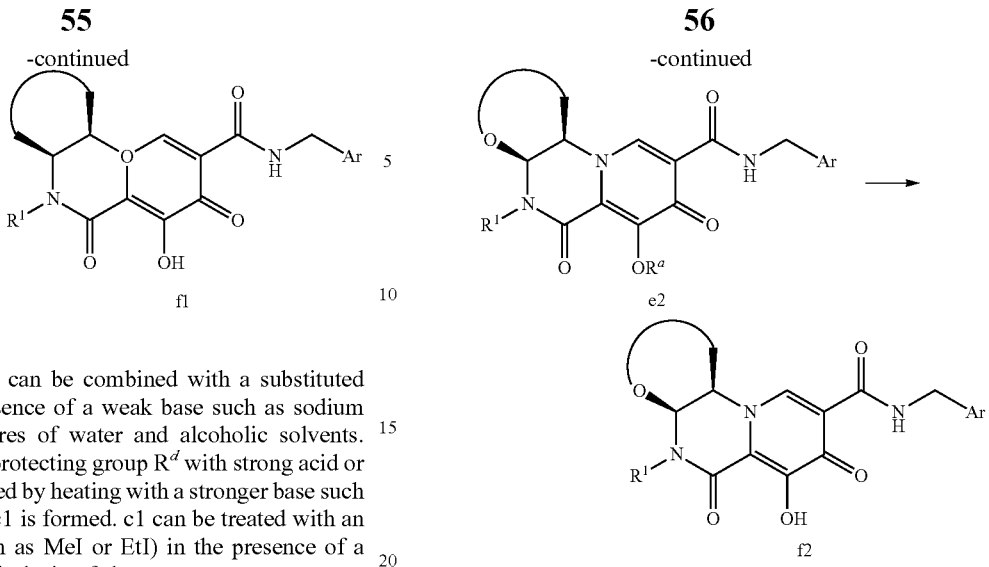

Protected diamine a1 can be combined with a substituted pyrone b1 in the presence of a weak base such as sodium bicarbonate in mixtures of water and alcoholic solvents. After removal of the protecting group $R^d$ with strong acid or hydrogenation followed by heating with a stronger base such as DBU, the tricycle c1 is formed. c1 can be treated with an alkylating agent (such as MeI or EtI) in the presence of a base followed by hydrolysis of the ester to generate compound d1. d1 can be treated with an amine such as a substituted benzyl amine in the presence of a coupling reagent such as HATU or EDCI to generate e1. e1 can be deprotected with an appropriate reagent such as magnesium bromide or lithium bromide or Pd on C in the presence of a hydrogen atmosphere to give f1.

Scheme 2

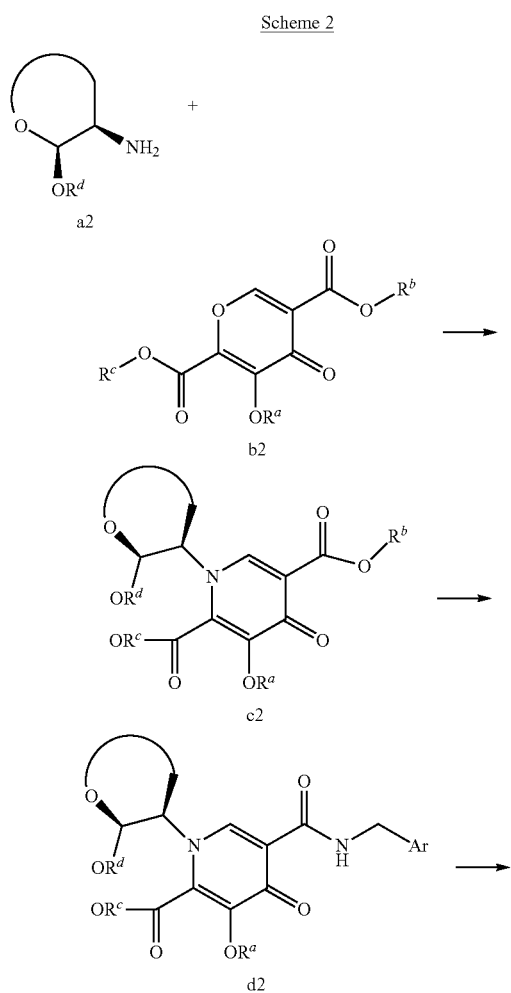

Protected amino-lactol a2 can be combined with a substituted pyrone b2 in the presence of a weak base such as sodium bicarbonate in mixtures of water and alcoholic solvents to give intermediate c2. Hydrolysis of the ester denoted by —O—$R^b$ can be accomplished with 1 equivalent of an appropriate hydroxide reagent such as lithium or sodium hydroxide. At this point, transesterification of ester denoted by —O—$R^c$ may be achieved using an appropriate alkoxide reagent such as lithium isopropoxide, after which an amide coupling with a reagent such as HATU or EDCI and an appropriate benzyl amine generates intermediate d2. Lactol deprotection using a strong acid such as methanesulfonic acid followed by heating with a primary amine ($R^1NH_2$) such as ethylamine or methylamine results in tricycle e2. e2 can be deprotected with an appropriate reagent such as magnesium bromide or lithium bromide or Pd on C in the presence of a hydrogen atmosphere to give f2.

The following Examples illustrate various methods of making compounds of this disclosure, i.e., compound of Formula (Ia):

(Ia)

Wherein A', $R^1$, $R^2$ and $R^3$ are as defined above. It is understood that one skilled in the art may be able to make these compounds by similar methods or by combining other methods known to one skilled in the art. It is also understood that one skilled in the art would be able to make, in a similar manner as described below, other compounds of Formula (Ia), (Ib), (II), (IIa), (III), and (Ma), not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

Example 1

Preparation of Compound 1

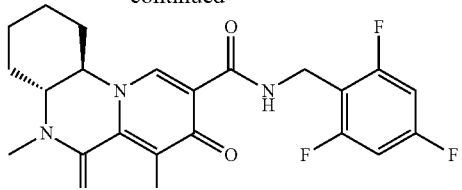

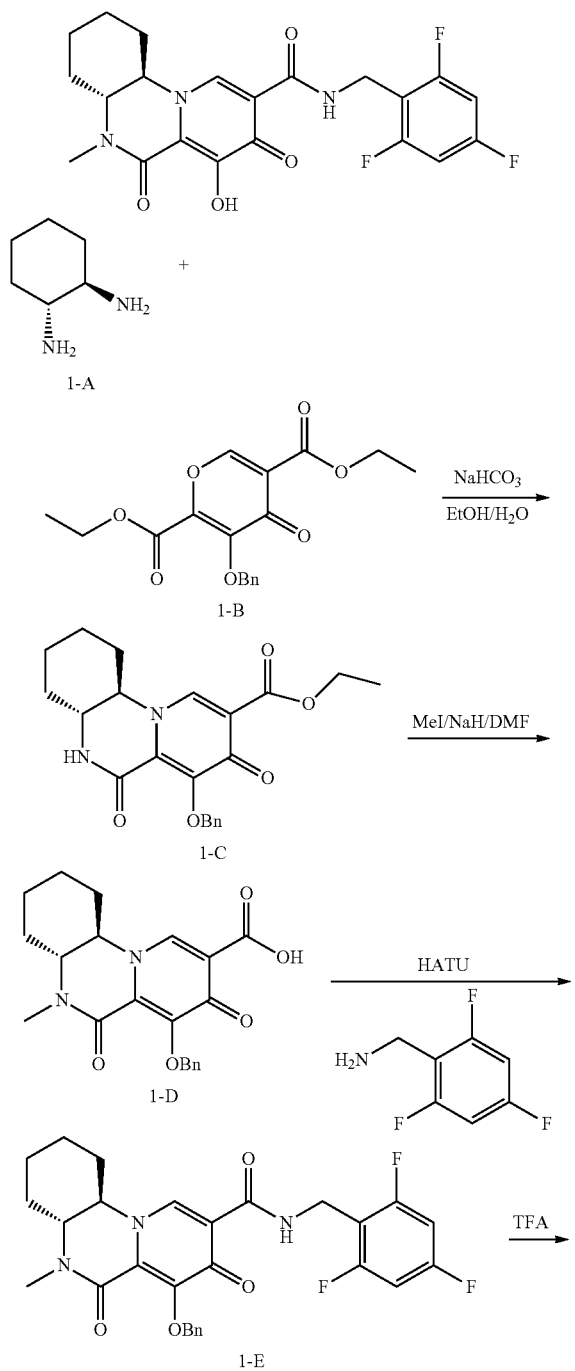

Step 1

A 50-mL 1-neck round bottom flask was charged with reactant 1-A (0.165 g, 1.45 mmol), 1-B (0.50 g, 1.45 mmol) and NaHCO$_3$ (0.25 g, 2.9 mmol) in ethanol (10 ml) and water (10 ml). The reaction mixture was stirred at room temperature overnight. The reaction mixture was concentrated down, re-dissolved in EtOAc (50 mL), washed with water twice and dried over Na$_2$SO$_4$. After concentration, the crude was purified by column chromatography on silica gel with hexane-EtOAc to obtain 1-C. LCMS-ESI$^+$ (m/z): [M+H]$^+$; found: 397.

Step 2

A 50-mL 1-neck round bottom flask was charged with reactant 1-C (0.11 g, 0.27 mmol) in THF (5 mL). NaH (0.033 g, 60% in mineral oil, 0.81 mmol) was added to the reaction mixture. The reaction mixture was stirred at room temperature for 5 minutes. MeI (0.04 g, 0.27 mmol) was added to the reaction mixture. The reaction mixture was stirred at room temperature for 5 minutes. Water (0.5 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 1-D was used for the next step without further purification. LCMS-ESI$^+$ (m/z): [M+H]$^+$ found: 383.

Step 3

A 50-mL 1-neck round bottom flask was charged with reactant 1-D (crude from step 2, 0.27 mmol), 2,4,6-trifluorophenyl methanamine (0.084 g, 0.52 mmol), DIPEA (0.169 g, 1.3 mmol) and HATU (0.20 g, 0.52 mmol) in DCM (10 ml). The reaction mixture was stirred at room temperature for 1 hour. The reaction mixture was concentrated down, re-dissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 1-E. LCMS-ESI$^+$ (m/z): [M+H]$^+$; found: 526.

Steps 4

A 50-mL 1-neck round bottom flask was charged with reactant 1-E (0.03 g, 0.06 mmol) in TFA (2 mL). The reaction mixture was stirred at room temperature for 30 minutes. The solution was concentrated and the residue was purified by CombiFlash (12 g column, used cartridge) using 0 to 20% MeOH in EtOAc as eluents to afford compound 1. $^1$H NMR (400 MHz, Chloroform-d) δ 10.40 (d, J=6.1 Hz, 1H), 8.47 (s, 1H), 6.58 (dd, J=8.7, 7.5 Hz, 2H), 4.58 (d, J=5.7 Hz, 2H), 3.73 (td, J=10.6, 4.0 Hz, 1H), 3.54-3.25 (m, 1H), 3.03 (s, 3H), 2.83-2.56 (m, 1H), 2.56-2.30 (m, 1H), 2.23-1.78 (m, 4H), 1.76-1.21 (m, 3H). $^{19}$F NMR (377 MHz, Chloroform-d) δ −109.17 (t, J=8.3 Hz, 1F), −112.03 (t, J=7.0 Hz, 2F). LCMS-ESI$^+$ (m/z): [M+H]$^+$ found: 436.

Example 2

Preparation of Compound 2

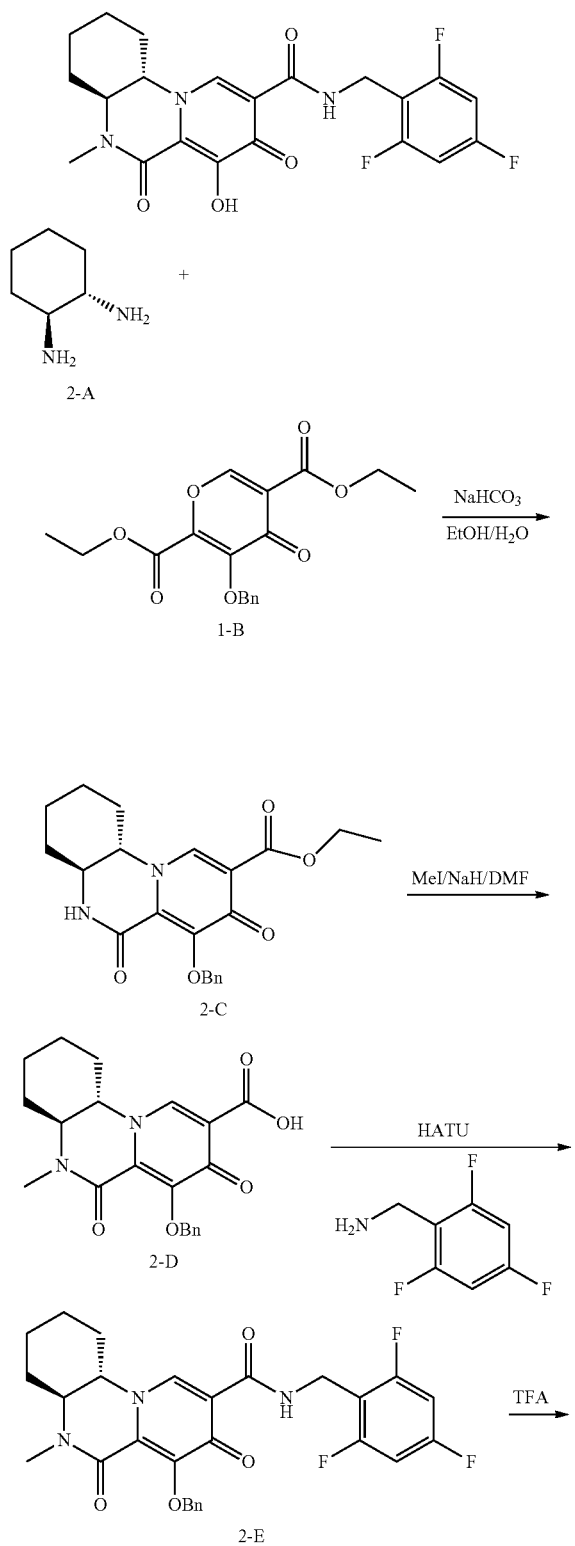
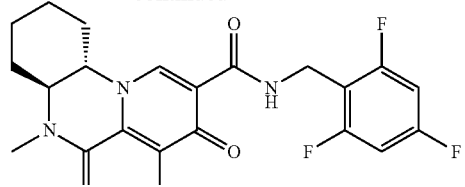

Step 1

A 50-mL 1-neck round bottom flask was charged with reactant 2-A (0.33 g, 2.9 mmol), 1-B (1.0 g, 2.9 mmol) and NaHCO$_3$ (0.5 g, 5.8 mmol) in ethanol (10 ml) and water (10 ml). The reaction mixture was stirred at room temperature overnight. The reaction mixture was concentrated down, re-dissolved in EtOAc (50 mL), washed with water twice and dried over Na$_2$SO$_4$. After concentration, the crude was purified by column chromatography on silica gel with hexane-EtOAc to obtain 2-C. LCMS-ESI$^+$ (m/z): [M+H]$^+$; found: 397.

Step 2

A 50-mL 1-neck round bottom flask was charged with reactant 2-C (0.22 g, 0.54 mmol) in DMF (5 mL). NaH (0.066 g, 60% in mineral oil, 1.62 mmol) was added to the reaction mixture. The reaction mixture was stirred at room temperature for 5 minutes. MeI (0.08 g, 0.54 mmol) was added to the reaction mixture. The reaction mixture was stirred at room temperature for another 5 minutes. Water (0.5 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 2-D was used for next step without further purification. LCMS-ESI$^+$ (m/z): [M+H]$^+$ found: 383.

Step 3

A 50-mL 1-neck round bottom flask was charged with reactant 2-D (crude from step 2, 0.54 mmol), 2,4,6-trifluorophenyl methanamine (0.168 g, 1.04 mmol), DIPEA (0.34 g, 2.6 mmol) and HATU (0.40 g, 1.04 mmol) in DCM (20 ml). The reaction mixture was stirred at room temperature for 1 hour. The reaction mixture was concentrated down, re-dissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 2-E. LCMS-ESI$^+$ (m/z): [M+H]$^+$; found: 526.

Steps 4

A 50-mL 1-neck round bottom flask was charged with reactant 2-E (0.03 g, 0.06 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 2. $^1$H NMR (400 MHz, Chloroform-d) δ 10.48 (t, J=5.1 Hz, 1H), 8.55 (s, 1H), 7.26 (s, 1H), 6.65 (dd, J=8.8, 7.5 Hz, 2H), 4.66 (d, J=5.7 Hz, 2H), 3.83 (td, J=10.9, 4.1 Hz, 1H), 3.65-3.42 (m, 1H), 3.13 (s, 3H), 2.90-2.61 (m, 1H), 2.57-2.40 (m, 1H), 2.07 (dd, J=43.2, 12.6 Hz, 2H), 1.85-1.26 (m, 4H). $^{19}$F NMR (376 MHz, Chloroform-d) δ −109.35 (m, 1F), −112.49 (m, 2F). LCMS-ESI$^+$ (m/z): [M+H]$^+$ found: 436.

Example 3

Preparation of Compound 3

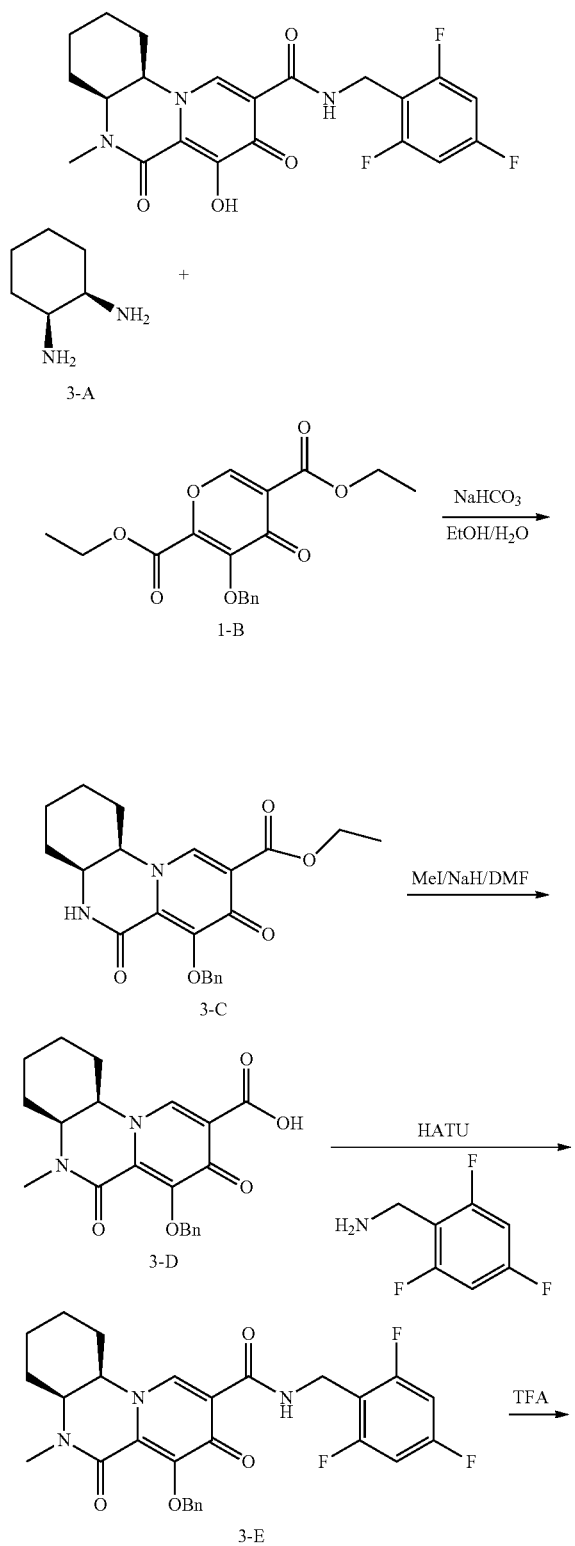

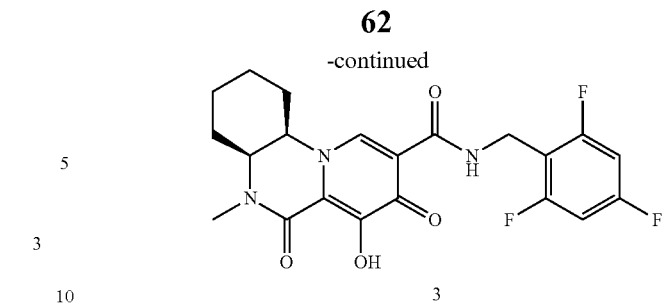

Step 1

A 50-mL 1-neck round bottom flask was charged with reactant 3-A (0.66 g, 5.8 mmol), 1-B (2.0 g, 5.8 mmol) and NaHCO$_3$ (0.97 g, 11.6 mmol) in ethanol (30 ml) and water (30 ml). The reaction mixture was stirred at room temperature overnight. The reaction mixture was concentrated down, re-dissolved in EtOAc (100 mL), washed with water twice and dried over Na$_2$SO$_4$. After concentration, the crude was purified by column chromatography on silica gel with hexane-EtOAc to obtain 3-C. LCMS-ESI$^+$ (m/z): [M+H]$^+$; found: 397.

Step 2

A 50-mL 1-neck round bottom flask was charged with reactant 3-C (0.11 g, 0.27 mmol) in DMF (5 mL). NaH (0.033 g, 60% in mineral oil, 0.81 mmol) was added to the reaction mixture. The reaction mixture was stirred at room temperature for 5 minutes. MeI (0.04 g, 0.27 mmol) was added to the reaction mixture. The reaction mixture was stirred at room temperature for another 5 minutes. Water (0.5 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 3-D was used for the next step without further purification. LCMS-ESI$^+$ (m/z): [M+H]$^+$ found: 383.

Step 3

A 50-mL 1-neck round bottom flask was charged with reactant 3-D (crude from step 2, 0.27 mmol), 2,4,6-trifluorophenyl methanamine (0.084 g, 0.52 mmol), DIPEA (0.169 g, 1.3 mmol) and HATU (0.20 g, 0.52 mmol) in DCM (10 ml). The reaction mixture was stirred at room temperature for 1 hour. The reaction mixture was concentrated down, re-dissolved in EtOAc (50 mL), washed with sat NaHCO$_3$ twice, sat NH$_4$Cl and dried over Na$_2$SO$_4$. After concentration, the crude was purified by column chromatography on silica gel with hexane-EtOAc to obtain 3-E. LCMS-ESI$^+$ (m/z): [M+H]$^+$; found: 526.

Step 4

A 50-mL 1-neck round bottom flask was charged with reactant 3-E (0.10 g, 0.19 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 3 as a mixture of cis enantiomers. $^1$H NMR (400 MHz, DMSO-d6) δ 12.82 (s, 1H), 10.42 (t, J=5.8 Hz, 1H), 8.37 (s, 1H), 7.19 (t, J=8.6 Hz, 2H), 4.80-4.31 (m, 3H), 3.99 (d, J=5.6 Hz, 1H), 3.13 (s, 3H), 1.97 (s, 1H), 1.87-1.62 (m, 3H), 1.43 (d, J=37.9 Hz, 4H). $^{19}$F NMR (376 MHz, DMSO-d6) δ −74.89, −108.61−−110.08 (m, 1F), −112.47 (t, J=7.2 Hz, 2F). LCMS-ESI$^+$ (m/z): [M+H]$^+$ found: 436.

Example 4

Preparation of Compound 4

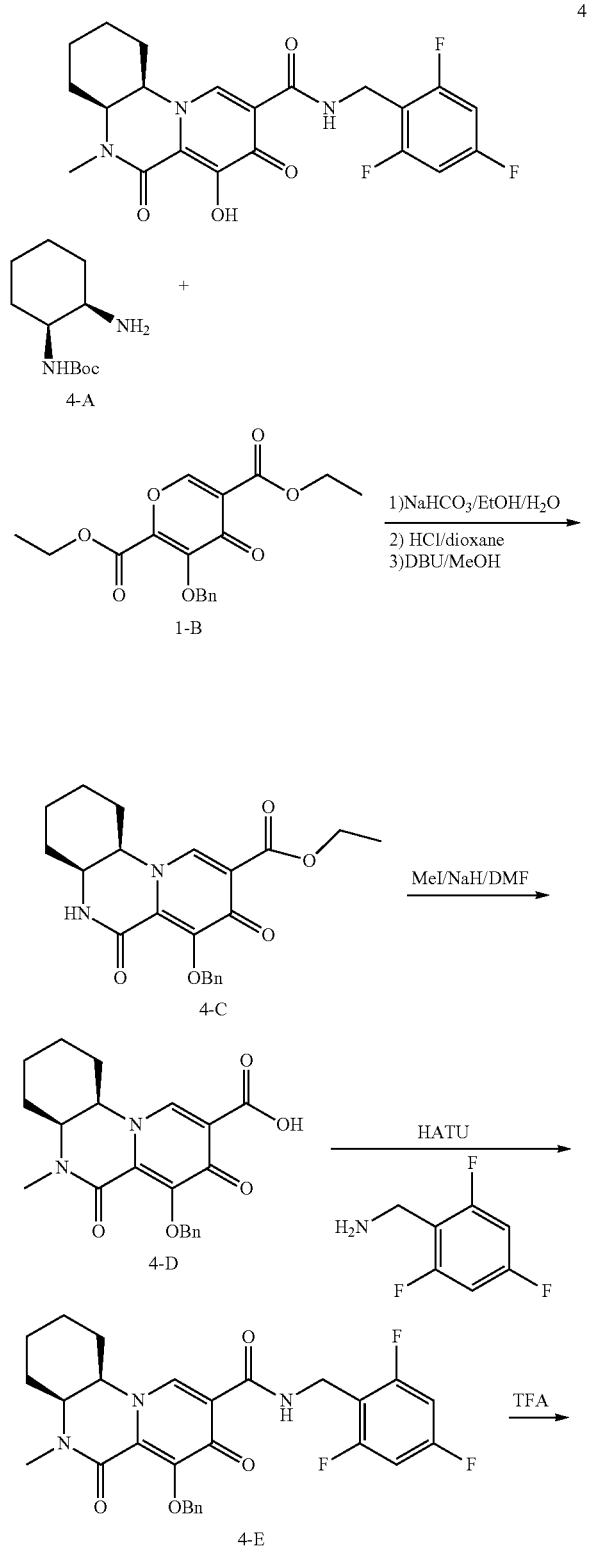

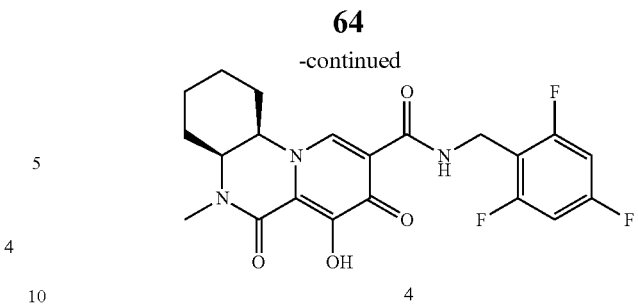

Step 1

A 50-mL 1-neck round bottom flask was charged with reactant 4-A (1.86 g, 8.7 mmol), 1-B (3.0 g, 8.7 mmol) and NaHCO$_3$ (1.45 g, 17.3 mmol) in ethanol (30 ml) and water (30 ml). The reaction mixture was stirred at room temperature overnight. The reaction mixture was concentrated down, re-dissolved in EtOAc (100 mL), washed with water twice and dried over Na$_2$SO$_4$. After concentration, the crude was dissolved in 4N HCl/Dioxane (40 ml) and stirred at room temperature for 3 hours to remove the Boc protecting group. The reaction mixture was concentrated down again. The residue and DBU (6.5 g, 43.5 mmol) were dissolved in EtOH and heated to 50° C. for 20 minutes. After concentration, the crude was purified by column chromatography on silica gel with hexane-EtOAc to obtain 4-C. LCMS-ESI$^+$ (m/z): [M+H]$^+$; found: 397.

Step 2

A 50-mL 1-neck round bottom flask was charged with reactant 4-C (0.4 g, 1.0 mmol) in THF (10 mL). NaH (0.08 g, 60% in mineral oil, 2.0 mmol) was added to the reaction mixture. The reaction mixture was stirred at room temperature for 5 minutes. MeI (0.142 g, 1.0 mmol) was added to the reaction mixture. The reaction mixture was stirred at room temperature for another 5 minutes. Water (1 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 4-D was used for the next step without further purification. LCMS-ESI$^+$ (m/z): [M+H]$^+$ found: 383.

Step 3

A 50-mL 1-neck round bottom flask was charged with reactant 4-D (crude from step 2, 1.0 mmol), 2,4,6-trifluorophenyl methanamine (0.34 g, 2.1 mmol), DIPEA (0.68 g, 5.2 mmol) and HATU (0.80 g, 2.1 mmol) in DCM (10 ml). The reaction mixture was stirred at room temperature for 1 hour. The reaction mixture was concentrated down, re-dissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 4-E. LCMS-ESI$^+$ (m/z): [M+H]$^+$; found: 526.

Step 4

A 50-mL 1-neck round bottom flask was charged with reactant 4-E (0.10 g, 0.19 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 4. $^1$H NMR (400 MHz, DMSO-d6) δ 12.82 (s, 1H), 10.42 (t, J=5.8 Hz, 1H), 8.37 (s, 1H), 7.19 (t, J=8.6 Hz, 2H), 4.80-4.31 (m, 3H), 3.99 (d, J=5.6 Hz, 1H), 3.11 (s, 3H), 1.97 (s, 1H), 1.87-1.62 (m, 3H), 1.43 (d, J=37.9 Hz, 4H). $^{19}$F NMR (376 MHz, DMSO-d6) δ −108.61−−110.08 (m, 1F), −112.47 (t, J=7.2 Hz, 2F). LCMS-ESI⁺ (m/z): [M+H]⁺ found: 436.

Example 5

Preparation of Compound 5

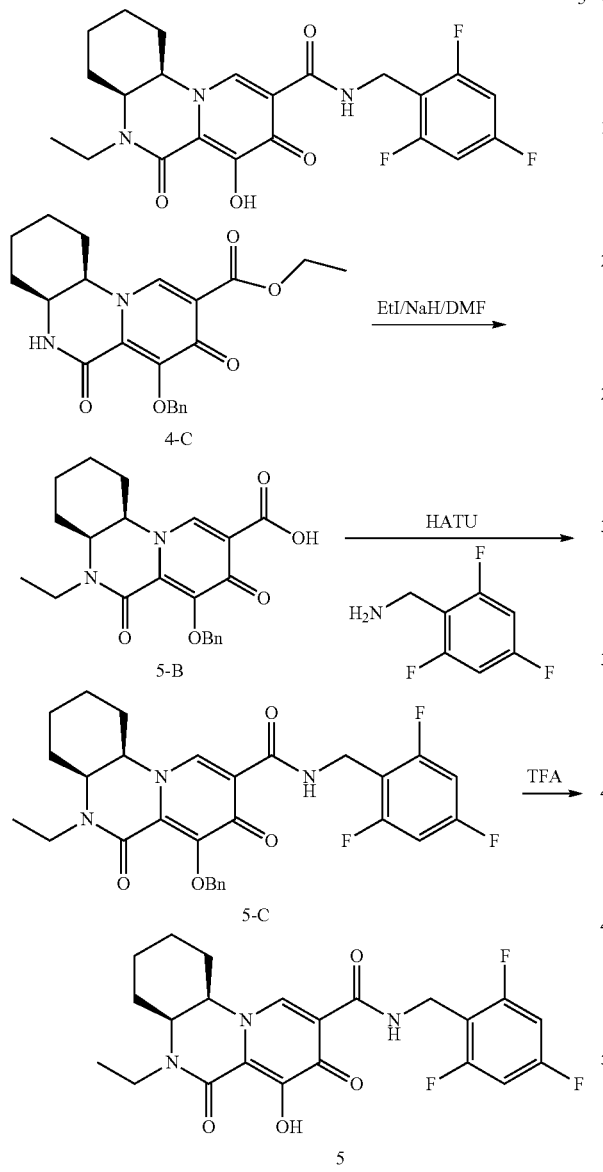

Step 1

A 50-mL 1-neck round bottom flask was charged with reactant 4-C (0.4 g, 1.0 mmol) in THF (10 mL). NaH (0.2 g, 60% in mineral oil, 5.0 mmol) was added to the reaction mixture. The reaction mixture was stirred at room temperature for 5 minutes. Ethyl iodide (0.32 g, 2.0 mmol) was added to the reaction mixture. The reaction mixture was stirred at room temperature for another 5 minutes. Water (1 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 5-B was used for next step without further purification. LCMS-ESI⁺ (m/z): [M+H]⁺ found: 397.

Step 2

A 50-mL 1-neck round bottom flask was charged with reactant 5-B (crude from step 2, 1.0 mmol), 2,4,6-trifluorophenyl methanamine (0.33 g, 2.0 mmol), DIPEA (0.65 g, 5.0 mmol) and HATU (0.77 g, 2.0 mmol) in DCM (10 ml). The reaction mixture was stirred at room temperature for 1 hour. The reaction mixture was concentrated down, re-dissolved in EtOAc (50 mL), washed with saturated NaHCO₃ twice, saturated NH₄Cl and dried over Na₂SO₄. After concentration, the crude was purified by column chromatography on silica gel with hexane-EtOAc to obtain 5-C. LCMS-ESI⁺ (m/z): [M+H]⁺; found: 540.

Step 3

A 50-mL 1-neck round bottom flask was charged with reactant 5-C (0.10 g, 0.19 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 5. ¹H NMR (400 MHz, DMSO-d6) δ 12.88 (s, 1H), 10.42 (t, J=5.8 Hz, 1H), 8.35 (s, 1H), 7.18 (dd, J=9.3, 7.9 Hz, 2H), 4.69-4.43 (m, 2H), 4.29 (m, 1H), 4.06-3.79 (m, 2H), 3.31-3.01 (m, 1H), 2.18 (s, 1H), 1.98-1.58 (m, 3H), 1.61-1.34 (m, 4H), 1.14 (t, J=7.1 Hz, 3H). ¹⁹F NMR (376 MHz, DMSO-d6) δ −109.37 (m, 1F), −111.01−−114.55 (m, 2F). LCMS-ESI⁺ (m/z): [M+H]⁺ found: 450.

Example 6

Preparation of Compound 6

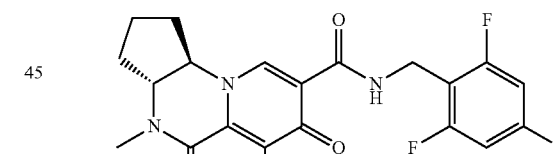

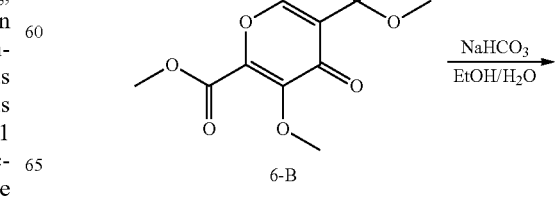

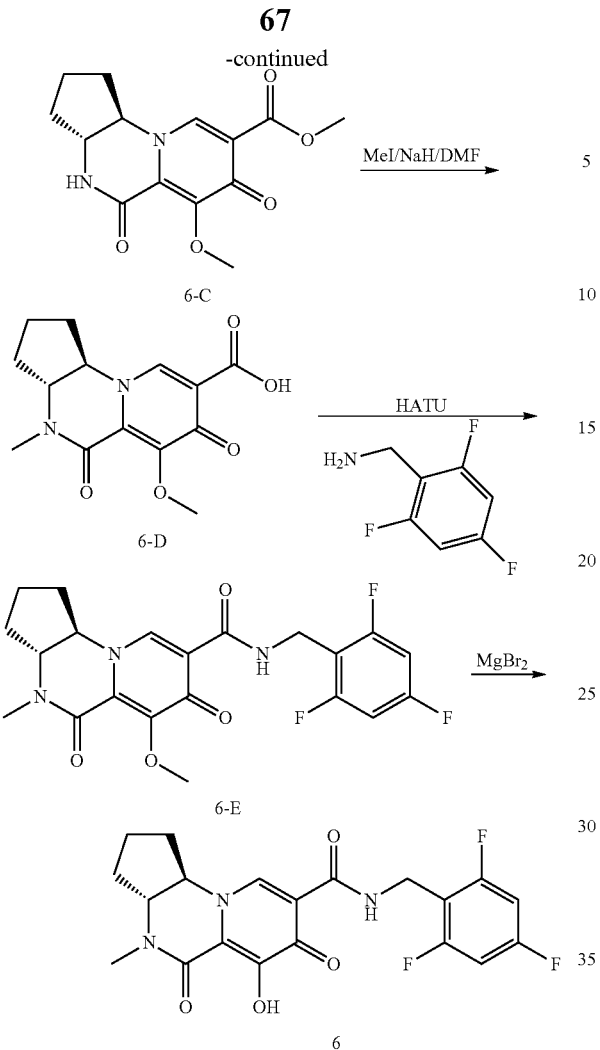

Step 1

A 50-mL 1-neck round bottom flask was charged with reactant 6-A (0.70 g, 4.1 mmol), 6-B (1.0 g, 4.1 mmol) and NaHCO₃ (0.69 g, 8.3 mmol) in methanol (10 ml) and water (10 ml). The reaction mixture was stirred at room temperature overnight. The reaction mixture was concentrated down, re-dissolved in EtOAc (100 mL), washed with water twice and dried over Na₂SO₄. After concentration, the crude was purified by column chromatography on silica gel with hexane-EtOAc to obtain 6-C. LCMS-ESI⁺ (m/z): [M+H]⁺; found: 293.

Step 2

A 50-mL 1-neck round bottom flask was charged with reactant 6-C (0.1 g, 0.34 mmol) in DMF (10 mL). NaH (0.041 g, 60% in mineral oil, 1.0 mmol) was added to the reaction mixture. The reaction mixture was stirred at room temperature for 5 minutes. MeI (0.1 g, 0.68 mmol) was added to the reaction mixture. The reaction mixture was stirred at room temperature for another 5 minutes. Water (0.5 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 6-D was used for next step without further purification. LCMS-ESI⁺ (m/z): [M+H]⁺ found: 293.

Step 3

A 50-mL 1-neck round bottom flask was charged with reactant 6-D (crude from step 2, 0.27 mmol), 2,4,6-trifluorophenyl methanamine (0.088 g, 0.55 mmol), DIPEA (0.177 g, 1.4 mmol) and HATU (0.21 g, 0.55 mmol) in DCM (10 ml). The reaction mixture was stirred at room temperature for 1 hour. The reaction mixture was concentrated down, re-dissolved in EtOAc (50 mL), washed with saturated NaHCO₃ twice, saturated NH₄Cl and dried over Na₂SO₄. After concentration, the crude was purified by column chromatography on silica gel with hexane-EtOAc to obtain 6-E. LCMS-ESI⁺ (m/z): [M+H]⁺; found: 436.

Step 4

A 50-mL 1-neck round bottom flask was charged with reactant 6-E (0.05 g, 0.11 mmol) and magnesium bromide (0.05 g, 0.3 mmol) in acetonitrile (5 mL). The reaction mixture was heated to 50° C. After 10 minutes, the reaction mixture was cooled down to 0° C. and 1 N hydrochloric acid (4 mL) was added. Some water (~5 mL) was added and the solid formed was filtered and washed with water. The solid was transferred to a vial and lyophilized overnight to afford compound 6. ¹H NMR (400 MHz, Chloroform-d) δ 10.47 (s, 1H), 8.26 (s, 1H), 6.79-6.54 (m, 2H), 4.66 (d, J=5.7 Hz, 2H), 4.01 (td, J=10.5, 7.0 Hz, 1H), 3.72 (td, J=11.4, 7.0 Hz, 1H), 3.12 (s, 3H), 2.68-2.41 (m, 1H), 2.31 (d, J=10.3 Hz, 1H), 2.22-1.95 (m, 3H), 2.02-1.73 (m, 1H). ¹⁹F NMR (376 MHz, Chloroform-d) δ −109.17 (m, 1F), −112.02 (t, J=7.0 Hz, 2F). LCMS-ESI⁺ (m/z): [M+H]⁺ found: 422.

Example 7

Preparation of Compound 7

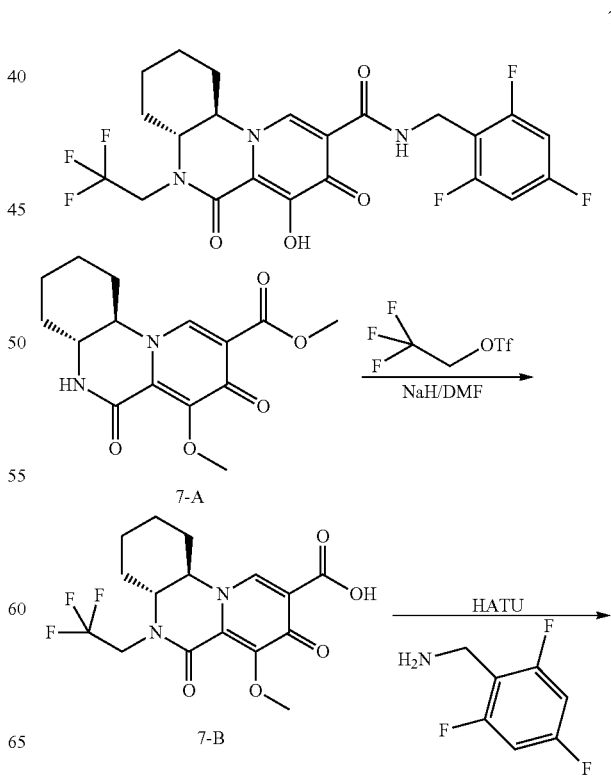

-continued

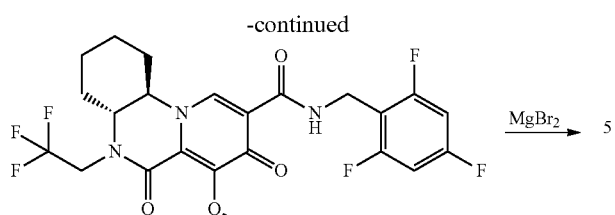

7-C

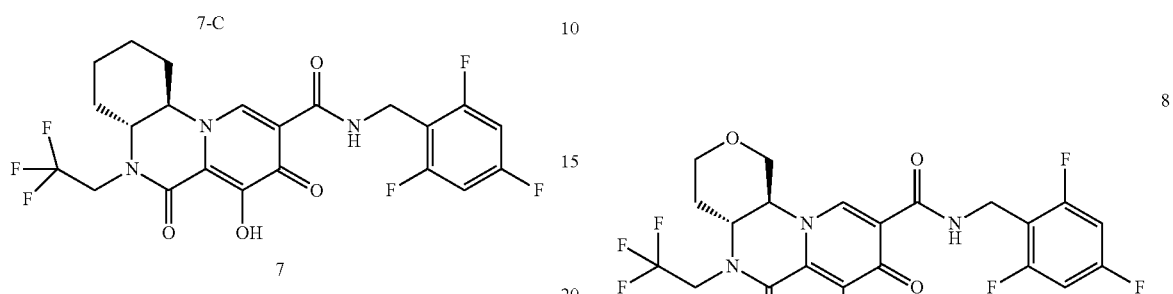

7

Step 1

A 50-mL 1-neck round bottom flask was charged with reactant 7-A (0.1 g, 0.33 mmol; 7-A was prepared in a manner similar to 1-C using 6-B in place of 1-B) in DMF (5 mL). NaH (0.06 g, 60% in mineral oil, 1.5 mmol) was added to the reaction mixture. The reaction mixture was stirred at room temperature for 5 minutes. 2,2,2-trifluoroethyl trifluoromethanesulfonate (0.23 g, 1.0 mmol) was added to the reaction mixture. The reaction mixture was stirred at room temperature for another 5 minutes. Water (1 ml) was added dropwise. The reaction mixture was stirred for 10 minutes at room temperature to hydrolyze the ester and form the acid. After acidification with 1 N HCl, the solution was concentrated to remove the solvent completely and the crude 7-B was used for next step without further purification. LCMS-ESI$^+$ (m/z): [M+H]$^+$ found: 375.

Step 2

A 50-mL 1-neck round bottom flask was charged with reactant 7-B (crude from step 1, 0.33 mmol), 2,4,6-trifluorophenyl methanamine (0.13 g, 0.82 mmol), DIPEA (0.53 g, 4.0 mmol) and HATU (0.37 g, 0.98 mmol) in DCM (5 ml). The reaction mixture was stirred at room temperature for 1 hour. The reaction mixture was concentrated down, redissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 7-C. LCMS-ESI$^+$ (m/z): [M+H]$^+$; found: 518.

Steps 3

A 50-mL 1-neck round bottom flask was charged with reactant 7-C (0.02 g, 0.04 mmol) and magnesium bromide (0.02 g, 0.1 mmol) in acetonitrile (5 mL). The reaction mixture was heated up to 50° C. After 10 minutes, the reaction mixture was cooled down to 0° C. and 1 N hydrochloric acid (4 mL) was added. Additional water was added (~5 mL) and the solid formed was filtered and washed with water. The solid was transferred to a vial and lyophilised overnight to afford compound 7. $^1$H NMR (400 MHz, Chloroform-d) δ 10.32 (s, 1H), 8.52 (s, 1H), 6.58 (dd, J=8.7, 7.5 Hz, 2H), 4.79 (dd, J=15.9, 8.8 Hz, 1H), 4.58 (d, J=5.6 Hz, 2H), 3.78 (ddd, J=15.0, 11.7, 6.1 Hz, 2H), 3.59 (td, J=10.5, 4.4 Hz, 1H), 2.69 (d, J=12.2 Hz, 1H), 2.41 (s, 1H), 2.03 (dd, J=37.1, 9.3 Hz, 2H), 1.64 (q, J=10.4, 8.3 Hz, 1H), 1.39 (q, J=9.9, 7.5 Hz, 3H). $^{19}$F NMR (377 MHz, Chloroform-d) δ −69.01 (t, J=8.5 Hz, 3F), −109.05 (t, J=7.7 Hz, 1F), −112.05 (t, J=7.0 Hz, 2F). LCMS-ESI$^+$ (m/z): [M+H]$^+$ found: 504.

Example 8

Preparation of Compound 8

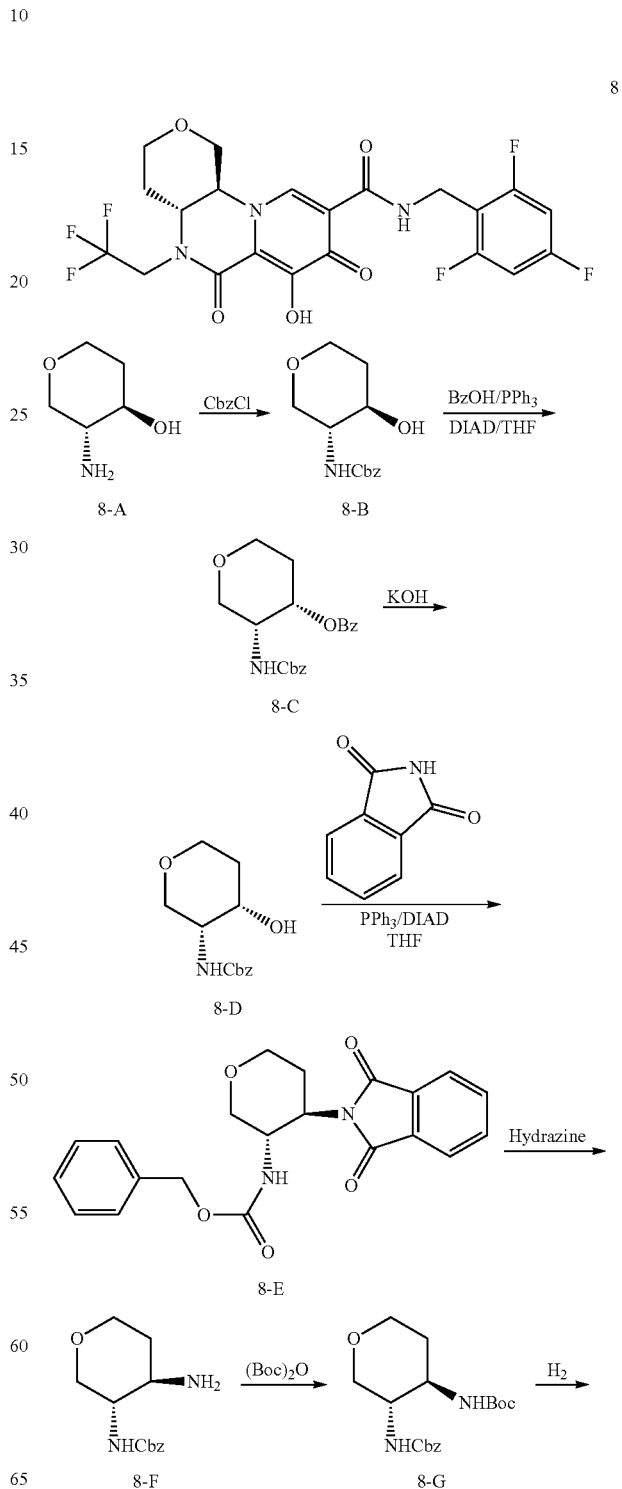

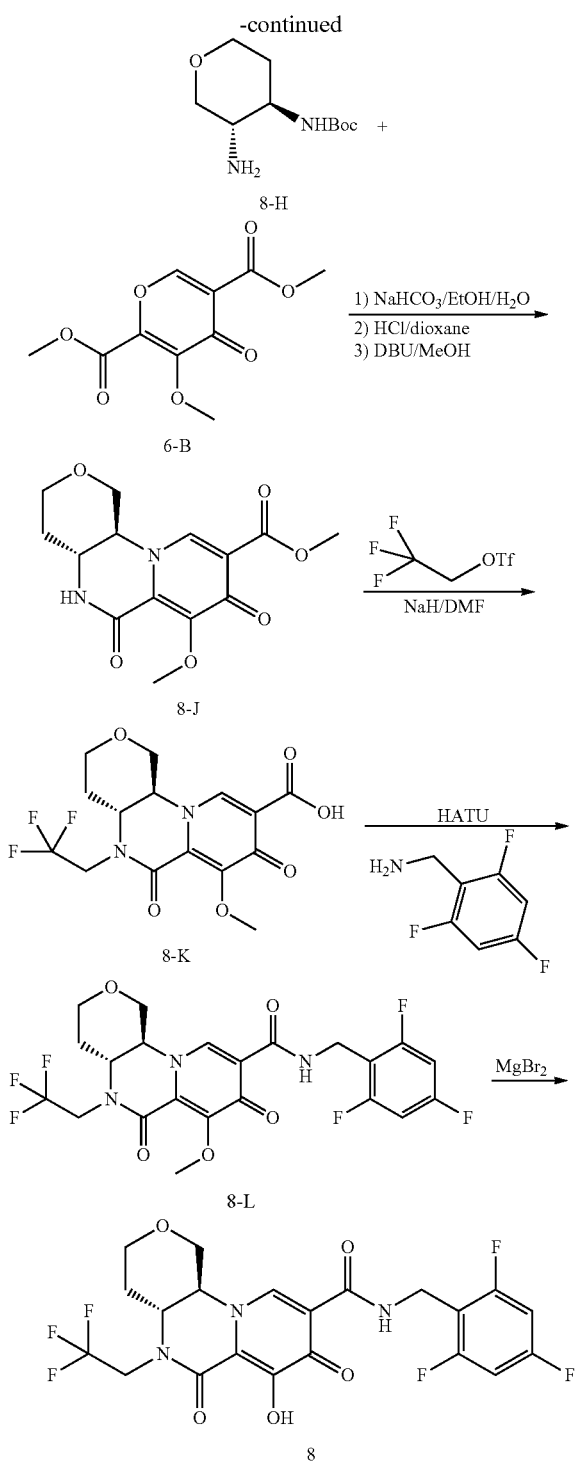

Step 1

A 250-mL 1-neck round bottom flask was charged with reactant 8-A (2.0 g, 17.1 mmol) and triethylamine (2.1 g, 20.7 mmol) in THF (40 ml). The reaction mixture was cooled down to 0° C. Benzyl chloroformate (3.2 g, 19.0 mmol) was added to the reaction mixture dropwise. The reaction mixture was stirred at room temperature for 2 h. The reaction mixture was concentrated down, re-dissolved in EtOAc (100 mL), washed with water twice and dried over $Na_2SO_4$. After concentration, the crude was purified by column chromatography on silica gel with hexane-EtOAc to obtain 8-B. LCMS-ESI$^+$ (m/z): [M+H]$^+$; found: 252.

Step 2

A 250-mL 1-neck round bottom flask was charged with reactant 8-B (1.6 g, 6.4 mmol), benzoic acid (1.24 g, 10.2 mmol) and triphenylphosphine (3.67 g, 14.0 mmol) in THF (40 ml). The reaction mixture was cooled down to 0° C. DIAD (3.0 g, 14.6 mmol) was added to the reaction mixture. The reaction mixture was stirred at room temperature overnight. The reaction mixture was concentrated down; the crude was purified by column chromatography on silica gel with hexane-EtOAc to obtain 8-C. LCMS-ESI$^+$ (m/z): [M+H]$^+$; found: 356.

Steps 3

A 50-mL 1-neck round bottom flask was charged with reactant 8-C (0.36 g, 1.0 mmol) in THF (10 mL) and MeOH (5 mL). 1N KOH (2 mL) was added to the reaction mixture. The reaction mixture was stirred at room temperature for 30 minutes. After acidification with 1 N HCl, the solution was concentrated to remove the solvent completely and the crude was purified by column chromatography on silica gel with hexane-EtOAc to obtain 8-D. LCMS-ESI$^+$ (m/z): [M+H]$^+$ found: 252.

Step 4

A 250-mL 1-neck round bottom flask was charged with reactant 8-D (1.0 g, 4.0 mmol), phthalimide (0.94 g, 6.0 mmol) and triphenylphosphine (2.3 g, 9.0 mmol) in THF (30 ml). The reaction mixture was cooled down to 0° C. DIAD (1.77 g, 9.0 mmol) was added to the reaction mixture. The reaction mixture was stirred at room temperature overnight. The reaction mixture was concentrated down, the crude was purified by column chromatography on silica gel with hexane-EtOAc to obtain 8-E. LCMS-ESI$^+$ (m/z): [M+H]$^+$; found: 381.

Step 5

A 100-mL 1-neck round bottom flask was charged with reactant 8-E (1.2 g, 3.0 mmol) in Ethanol (20 mL). Hydrazine hydrate (0.79 g, 16.0 mmol) was added to the reaction mixture. The reaction mixture was stirred at 70° C. for 3 hours. The reaction mixture was cooled down to room temperature. After filtration to remove the solid, the filtrate was concentrated down and under high vacuum for 1 hour. The crude 8-F was used for the next step without further purification and characterization. LCMS-ESI$^+$ (m/z): [M+H]$^+$ found: 251.

Step 6

A 250-mL 1-neck round bottom flask was charged with reactant 8-F (0.7 g, 2.8 mmol), DIPEA (1.3 g, 10 mmol) and di-tert-butyl dicarbonate (1.2 g, 5.6 mmol) in DCM (20 ml). The reaction mixture was stirred at room temperature for 1 hour. The reaction mixture was concentrated down, re-dissolved in EtOAc (100 mL), washed with water twice and dried over $Na_2SO_4$. After concentration, the crude was purified by column chromatography on silica gel with hexane-EtOAc to obtain 8-G. LCMS-ESI$^+$ (m/z): [M+H]$^+$; found: 351.

Step 7

A 100-mL 1-neck round bottom flask was charged with reactant 8-G (0.23 g, 0.65 mmol) in Ethanol (20 mL) Pd(OH)$_2$/C (0.05 g) was added to the reaction mixture. The reaction mixture was stirred under $H_2$ for 1 hour. After filtration to remove the solid, the filtrate was concentrated down and under high vacuum for 1 hour. The crude 8-H was used for next step without further purification and characterization. LCMS-ESI$^+$ (m/z): [M+H]$^+$ found: 217.

Step 8

A 50-mL 1-neck round bottom flask was charged with reactant 8-H (0.13 g, 0.6 mmol), 6-B (0.14 g, 0.6 mmol) and NaHCO$_3$ (0.11 g, 1.3 mmol) in ethanol (10 ml) and water (10 ml). The reaction mixture was stirred at room temperature overnight. The reaction mixture was concentrated down, re-dissolved in EtOAc (100 mL), washed with water twice and dried over Na$_2$SO$_4$. After concentration, the crude was dissolved in 4N HCl/Dioxane (3.3 ml) and stirred at room temperature for 3 hours to remove the Boc protecting group. The reaction mixture was concentrated down again. The residue and DBU (0.49 g, 3.0 mmol) were dissolved in MeOH (10 mL) and heated up to 50° C. for 20 minutes. After concentration, the crude was purified by column chromatography on silica gel with hexane-EtOAc to obtain 8-J. LCMS-ESI$^+$ (m/z): [M+H]$^+$; found: 309.

Step 9

A 50-mL 1-neck round bottom flask was charged with reactant 8-J (0.01 g, 0.16 mmol) in DMF (5 mL). NaH (0.032 g, 60% in mineral oil, 0.8 mmol) was added to the reaction mixture. The reaction mixture was stirred at room temperature for 5 minutes. 2,2,2-trifluoroethyl trifluoromethanesulfonate (0.075 g, 0.32 mmol) was added. The reaction mixture was stirred at room temperature for another 5 minutes. Water (1 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 8-K was used for next step without further purification. LCMS-ESI$^+$ (m/z): [M+H]$^+$ found: 377.

Step 10

A 50-mL 1-neck round bottom flask was charged with reactant 8-K (crude from step 1, 0.16 mmol), 2,4,6-trifluorophenyl methanamine (0.064 g, 0.4 mmol), DIPEA (0.26 g, 2.0 mmol) and HATU (0.18 g, 0.48 mmol) in DCM (5 ml). The reaction mixture was stirred at room temperature for 1 hour. The reaction mixture was concentrated down, re-dissolved in EtOAc (50 mL), washed with saturated NaHCO$_3$ (twice), washed with saturated NH$_4$Cl and dried over Na$_2$SO$_4$. After concentration, the crude was purified by column chromatography on silica gel with hexane-EtOAc to obtain 8-L. LCMS-ESI$^+$ (m/z): [M+H]$^+$; found: 520.

Step 11

A 50-mL 1-neck round bottom flask was charged with reactant 8-L (0.02 g, 0.04 mmol) and magnesium bromide (0.02 g, 0.1 mmol) in acetonitrile (5 mL). The reaction mixture was heated up to 50° C. After 10 minutes, the reaction mixture was cooled down to 0° C. and 1 N hydrochloric acid (4 mL) was added. Additional water was added (~5 mL) and the solid formed was filtered and washed with water. The solid was transferred to a vial and lyophilized overnight to afford compound 8. $^1$H NMR (400 MHz, Chloroform-d) δ 10.25 (s, 1H), 8.19 (s, 1H), 6.66 (t, J=8.2 Hz, 2H), 4.82 (d, J=10.7 Hz, 2H), 4.65 (d, J=5.6 Hz, 2H), 4.41-4.12 (m, 1H), 3.90 (d, J=63.1 Hz, 1H), 3.77-3.48 (m, 2H), 2.53-2.20 (m, 2H), 1.94 (d, J=52.4 Hz, 1H), 1.63 (s, 1H). $^{19}$F NMR (376 MHz, Chloroform-d) δ −69.01 (t, J=8.3 Hz, 3F), −109.04 (d, J=8.7 Hz, 1F), −112.07 (d, J=7.1 Hz, 2F). LCMS-ESI$^+$ (m/z): [M+H]$^+$ found: 506.

Example 9

Preparation of Compound 9

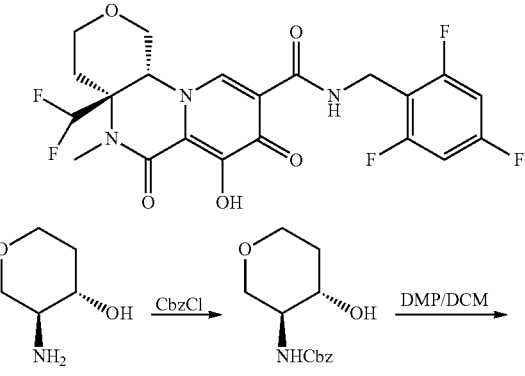

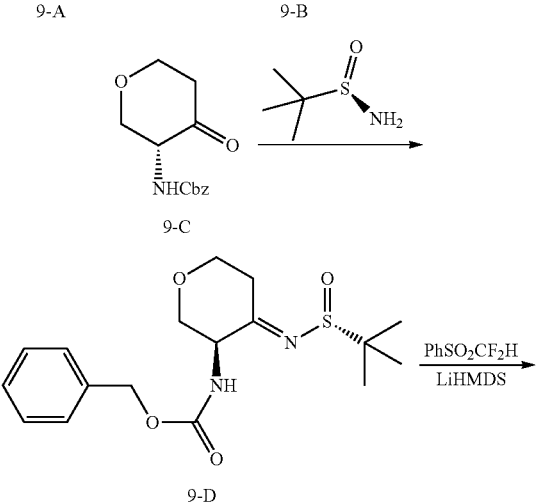

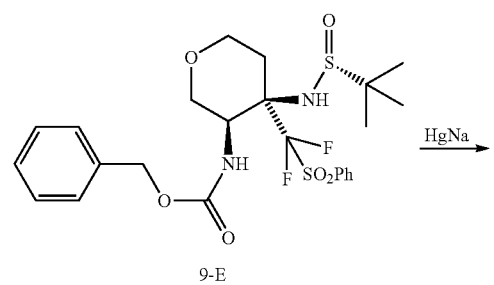

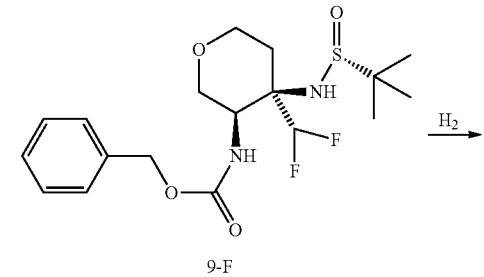

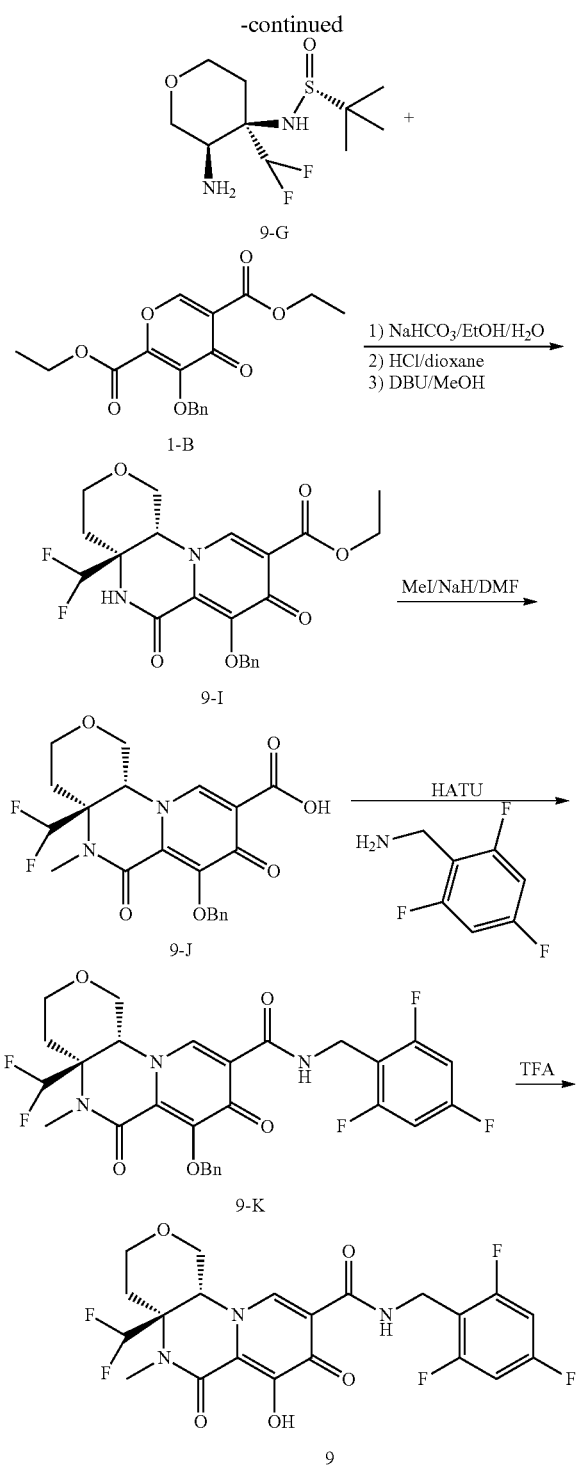

Step 1

A 250-mL 1-neck round bottom flask was charged with reactant 9-A (2.0 g, 17.1 mmol) and triethylamine (2.1 g, 20.7 mmol) in THF (40 ml). The reaction mixture was cooled down to 0° C. Benzyl chloroformate (3.2 g, 19.0 mmol) was added to the reaction mixture dropwise. The reaction mixture was stirred at room temperature for 2 h. The reaction mixture was concentrated down, re-dissolved in EtOAc (100 mL), washed with water twice and dried over $Na_2SO_4$. After concentration, the crude was purified by column chromatography on silica gel with hexane-EtOAc to obtain 9-B. LCMS-ESI$^+$ (m/z): [M+H]$^+$; found: 252.

Step 2

A 250-mL 1-neck round bottom flask was charged with reactant 9-B (2.0 g, 8.0 mmol) in DCM (34 ml). Dess Martin periodinane (4.1 g, 9.6 mmol) was added to the reaction mixture. The reaction mixture was stirred at room temperature for 2 hours. The reaction mixture was concentrated down; the crude was purified by column chromatography on silica gel with hexane-EtOAc to obtain 9-C. LCMS-ESI$^+$ (m/z): [M+H]$^+$; found: 250.

Step 3

A 100-mL 1-neck round bottom flask was charged with reactant 9-C (1.0 g, 4.0 mmol) and t-butyl sulfinimide (0.58 g, 4.8 mmol) in THF (20 mL). Titanium ethoxide (1.8 g, 8.0 mmol) was added to the reaction mixture. The reaction mixture was stirred at room temperature overnight and then diluted with EtOAc (100 mL). A saturated $NaHCO_3$ aqueous solution (2 mL) was added to the reaction mixture. The mixture was filtered through celite pad. The filtrate was concentrated to remove the solvent completely and the crude was purified by column chromatography on silica gel with hexane-EtOAc to obtain 9-D. LCMS-ESI$^+$ (m/z): [M+H]$^+$ found: 353.

Step 4

A 250-mL 1-neck round bottom flask was charged with reactant 9-D (0.5 g, 1.4 mmol) and difluomethyl phenyl sulfonate (0.28 g, 0.14 mmol) in THF (10 ml). The reaction mixture was cooled down to −78° C. LiHMDS (3 mL, 1N in THF, 3 mmol) was added to the reaction mixture. The reaction mixture was stirred at −78° C. for 30 minutes. The reaction mixture was diluted with EtOAc (50 mL) and quenched with water (5 mL). After layers separation, the organic layer was dried over $Na_2SO_4$ and concentrated down, the crude was purified by column chromatography on silica gel with hexane-EtOAc to obtain 9-E. LCMS-ESI$^+$ (m/z): [M+H]$^+$; found: 545.

Step 5

A 100-mL 1-neck round bottom flask was charged with reactant 9-E (1.7 g, 3.1 mmol) and $Na_2HPO_3$ (4.4 g, 31.0 mmol) in methanol (20 mL). The reaction mixture was cooled down to −20° C. Na/Hg (4.2 g, 19.0 mmol) was added to the reaction mixture. The reaction mixture was stirred at −20° C. for 2 hours. The reaction solution was poured to another flask. After concentration, the crude was purified by column chromatography on silica gel with hexane-EtOAc to obtain 9-F. LCMS-ESI$^+$ (m/z): [M+H]$^+$; found: 405.

Step 6

A 100-mL 1-neck round bottom flask was charged with reactant 9-F (0.62 g, 1.5 mmol) in Ethanol (20 mL). Pd(OH)$_2$/C (0.12 g) was added to the reaction mixture. The reaction mixture was stirred under $H_2$ for 1 hour. After filtration to remove the solid, the filtrate was concentrated down and under high vacuum for 1 hour. The crude 9-G was used for next step without further purification and characterization. LCMS-ESI$^+$ (m/z): [M+H]$^+$ found: 271.

Step 7

A 50-mL 1-neck round bottom flask was charged with reactant 9-G (0.39 g, 1.44 mmol), 1-B (0.5 g, 1.44 mmol) and $NaHCO_3$ (0.24 g, 2.8 mmol) in ethanol (10 ml) and water (10 ml). The reaction mixture was stirred at room temperature overnight. The reaction mixture was concentrated down, re-dissolved in EtOAc (100 mL), washed with water twice and dried over $Na_2SO_4$. After concentration, the crude was dissolved in 4N HCl/Dioxane (2 ml) and stirred at room temperature for 3 hours to remove the Boc protecting group. The reaction mixture was concentrated down again. The residue and DBU (1.1 g, 7.0 mmol) were dissolved in MeOH (10 mL) and heated up to 50° C. for 20 minutes. After concentration, the crude was purified by column chromatography on silica gel with hexane-EtOAc to obtain 9-I. LCMS-ESI⁺ (m/z): [M+H]⁺; found: 449.

Step 8

A 50-mL 1-neck round bottom flask was charged with reactant 9-I (0.08 g, 0.18 mmol) in DMF (10 mL). NaH (0.022 g, 60% in mineral oil, 0.54 mmol) was added to the reaction mixture. The reaction mixture was stirred at room temperature for 5 minutes. MeI (0.05 g, 0.36 mmol) was added and the reaction mixture was stirred at room temperature for another 5 minutes. Water (0.5 ml) was added dropwise and the reaction mixture was stirred for 10 minutes at room temperature to hydrolyze the ester and fom the acid. After acidification with 1 N HCl, the solution was concentrated to remove the solvent completely and the crude 9-J was used for next step without further purification. LCMS-ESI⁺ (m/z): [M+H]⁺ found: 435.

Step 9

A 50-mL 1-neck round bottom flask was charged with reactant 9-J (crude from step 1, 0.18 mmol), 2,4,6-trifluorophenyl methanamine (0.033 g, 0.2 mmol), DIPEA (0.25 g, 1.9 mmol) and HATU (0.18 g, 0.48 mmol) in DCM (3 ml). The reaction mixture was stirred at room temperature for 1 hour. The reaction mixture was concentrated down, re-dissolved in EtOAc (50 mL), washed with saturated NaHCO₃ twice, washed with saturated NH₄Cl and dried over Na₂SO₄. After concentration, the crude was purified by column chromatography on silica gel with hexane-EtOAc to obtain 9-K. LCMS-ESI⁺ (m/z): [M+H]⁺; found: 578.

Step 10

A 50-mL 1-neck round bottom flask was charged with reactant 9-K (0.02 g, 0.04 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 9. ¹H NMR (400 MHz, Methanol-d4) δ 8.48 (s, 1H), 6.98-6.82 (m, 2H), 6.13 (t, J=54.3 Hz, 1H), 5.05-4.85 (m, 1H), 4.72-4.55 (m, 2H), 4.15-3.86 (m, 2H), 3.74-3.47 (m, 2H), 3.25 (s, 3H), 2.51 (d, J=15.8 Hz, 1H), 2.19-1.97 (m, 1H). ¹⁹F NMR (376 MHz, Methanol-d4) δ −110.68 (m, 1F), −114.27 (t, J=7.3 Hz, 2F), −128.99 (dd, J=288.0, 54.2 Hz, 1F), −132.26 (dd, J=288.0, 54.5 Hz, 1F). LCMS-ESI⁺ (m/z): [M+H]⁺ found: 488.

Example 10

Preparation of Compound 10

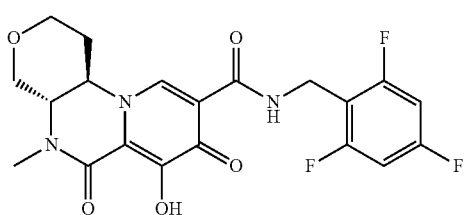

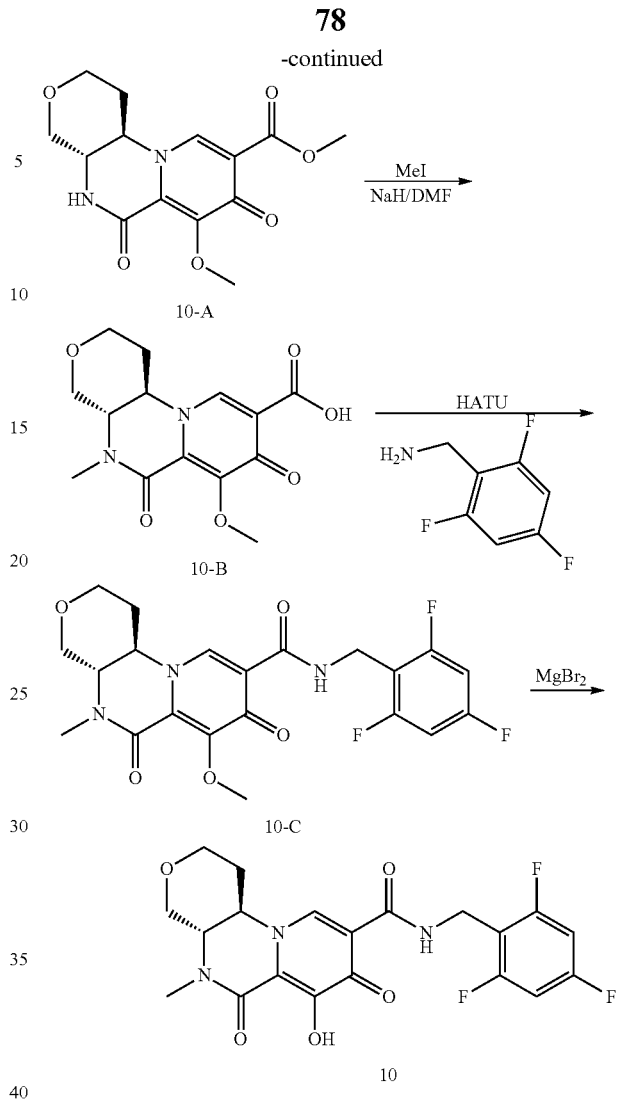

Step 1

A 50-mL 1-neck round bottom flask was charged with reactant 10-A (0.15 g, 0.49 mmol, the synthesis of 10-A is illustrated in example 35) in DMF (3 mL). NaH (0.082 g, 60% in mineral oil, 2.0 mmol) was added to the reaction mixture. The reaction mixture was stirred at room temperature for 5 minutes. MeI (0.1 g, 0.68 mmol) was added and the reaction mixture was stirred at room temperature for another 5 minutes. Water (0.5 ml) was added dropwise and the reaction mixture was stirred for 10 minutes at room temperature to hydrolyze the ester and form the acid. After acidification with 1 N HCl, the solution was concentrated to remove the solvent completely and the crude 10-B was used for next step without further purification. LCMS-ESI⁺ (m/z): [M+H]⁺ found: 309.

Step 2

A 50-mL 1-neck round bottom flask was charged with reactant 10-B (crude from step 1, 0.27 mmol), 2,4,6-trifluorophenyl methanamine (0.043 g, 0.27 mmol), DIPEA (0.33 g, 2.5 mmol) and HATU (0.18 g, 0.49 mmol) in DCM (3 ml). The reaction mixture was stirred at room temperature for 1 hour. The reaction mixture was concentrated down, re-dissolved in EtOAc (50 mL), washed with saturated NaHCO₃ twice, washed with saturated NH₄Cl and dried over Na₂SO₄. After concentration, the crude was purified by column chromatography on silica gel with hexane-EtOAc to obtain 10-C. LCMS-ESI+ (m/z): [M+H]+; found: 452.

Step 3

A 50-mL 1-neck round bottom flask was charged with reactant 10-C (0.01 g, 0.022 mmol) and magnesium bromide (0.01 g, 0.058 mmol) in acetonitrile (5 mL). The reaction mixture was heated to 50° C. After 10 minutes, the reaction mixture was cooled down to 0° C. and 1 N hydrochloric acid (4 mL) was added. Additional water (~5 mL) was added and the solid formed was filtered and washed with water. The solid was transferred to a vial and lyophilized overnight to afford compound 10. $^1$H NMR (400 MHz, Methanol-d4) δ 8.43 (s, 1H), 7.05-6.79 (m, 2H), 4.66 (s, 2H), 4.63-4.42 (m, 1H), 4.25 (td, J=12.1, 5.8 Hz, 2H), 4.10 (q, J=7.1 Hz, 1H), 3.76 (td, J=10.6, 4.6 Hz, 1H), 3.67-3.53 (m, 1H), 3.51 (t, J=10.8 Hz, 1H), 3.07 (s, 3H), 2.59 (d, J=12.4 Hz, 1H). $^{19}$F NMR (376 MHz, Methanol-d4) δ −110.71 (ddd, J=8.9, 6.2, 2.7 Hz, 1F), −114.26 (t, J=7.1 Hz, 2F). LCMS-ESI+ (m/z): [M+H]+ found: 438.

Example 11

Preparation of Compound 11

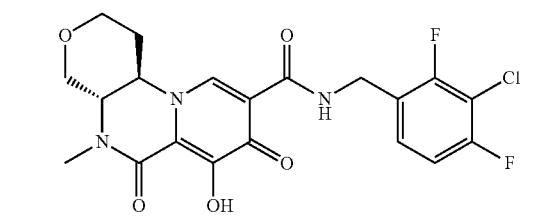

11

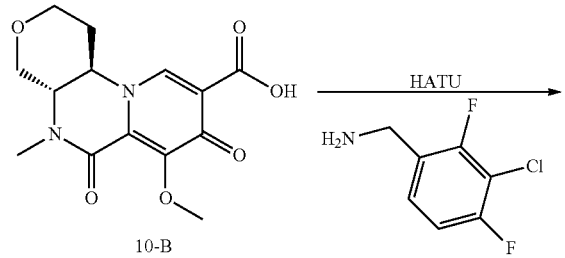

10-B

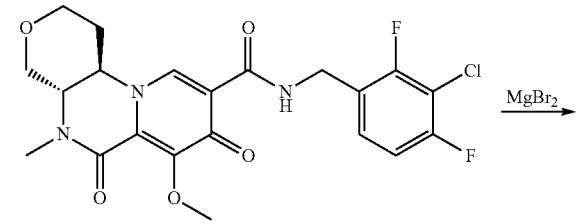

11-B

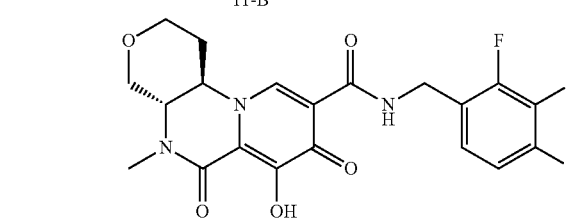

11

Step 1

A 50-mL 1-neck round bottom flask was charged with reactant 10-B (0.075 g, 0.24 mmol), (3-chloro-2,4-difluorophenyl)methanamine (0.047 g, 0.27 mmol), DIPEA (0.33 g, 2.5 mmol) and HATU (0.18 g, 0.49 mmol) in DCM (3 ml). The reaction mixture was stirred at room temperature for 1 hour. The reaction mixture was concentrated down, re-dissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 11-B. LCMS-ESI+ (m/z): [M+H]+; found: 468.

Step 2

A 50-mL 1-neck round bottom flask was charged with 11-B (0.03 g, 0.064 mmol) and magnesium bromide (0.03 g, 0.167 mmol) in acetonitrile (5 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. The solid was transferred to a vial and lyophilised overnight to afford compound 11. $^1$H NMR (400 MHz, Methanol-d4) δ 8.43 (s, 1H), 7.38 (td, J=8.4, 6.0 Hz, 1H), 7.09 (td, J=8.7, 1.8 Hz, 1H), 4.65 (s, 2H), 4.51 (dd, J=10.9, 4.6 Hz, 1H), 4.35-4.07 (m, 2H), 3.78 (td, J=10.7, 4.6 Hz, 1H), 3.60 (td, J=12.1, 2.2 Hz, 1H), 3.50 (d, J=10.8 Hz, 1H), 3.08 (s, 3H), 2.58 (ddt, J=14.4, 4.2, 2.0 Hz, 1H), 2.03 (qd, J=12.0, 5.0 Hz, 1H). $^{19}$F NMR (376 MHz, Methanol-d4) δ −117.31 (s, 1F), −119.84 (d, J=7.8 Hz, 1F). LCMS-ESI+ (m/z): [M+H]+ found: 454.

Example 12

Preparation of Compound 12

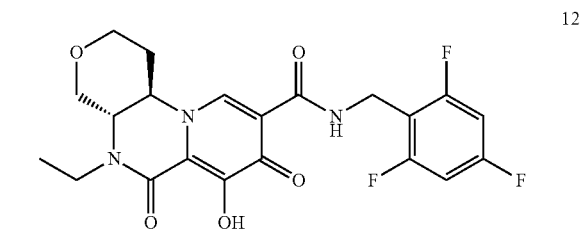

12

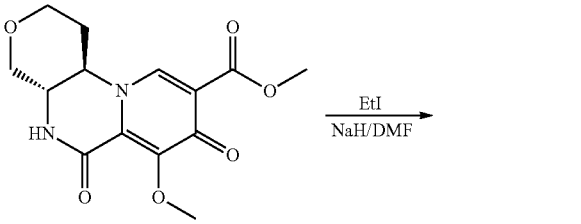

10-A

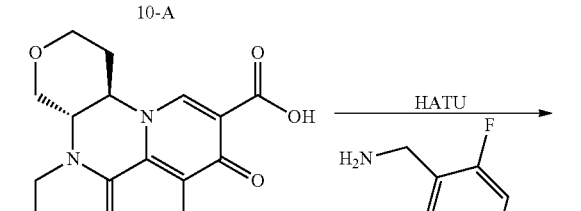

12-B

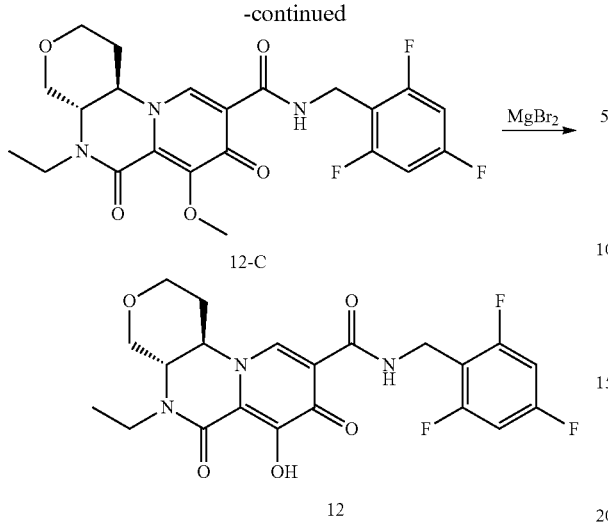

12-C

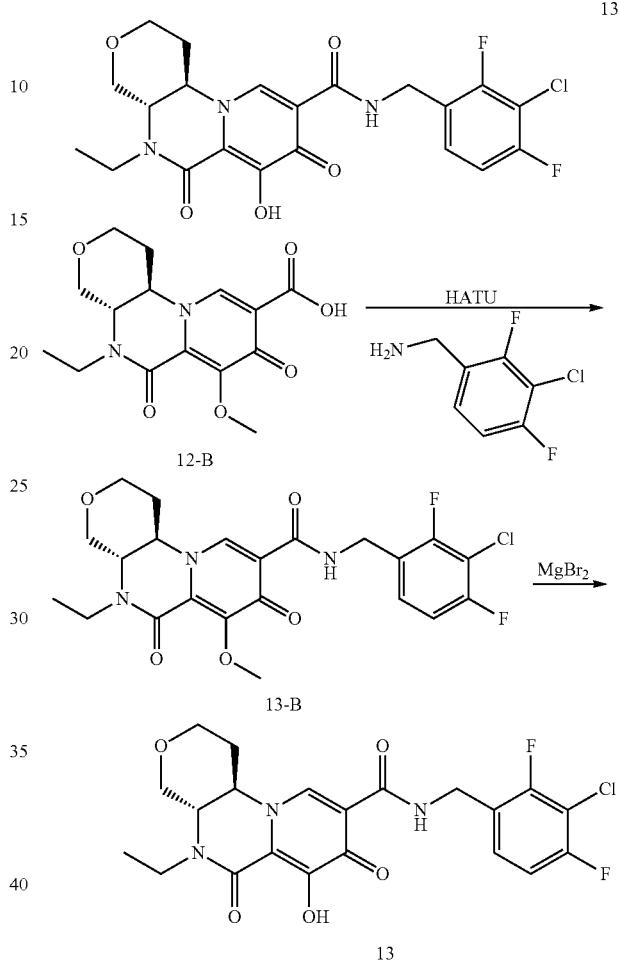

Example 13

Preparation of Compound 13

Step 1

A 50-mL 1-neck round bottom flask was charged with reactant 10-A (0.1 g, 0.32 mmol) in DMF (3 mL). NaH (0.064 g, 60% in mineral oil, 1.6 mmol) was added to the reaction mixture. The reaction mixture was stirred at room temperature for 5 minutes. EtI (0.1 g, 0.64 mmol) was added to the reaction mixture. The reaction mixture was stirred at room temperature for another 5 minutes. Water (0.5 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 12-B was used for next step without further purification. LCMS-ESI+ (m/z): [M+H]+ found: 323.

Step 2

A 50-mL 1-neck round bottom flask was charged with reactant 12-B (0.075 g, 0.23 mmol), 2,4,6-trifluorophenyl methanamine (0.041 g, 0.26 mmol), DIPEA (0.33 g, 2.5 mmol) and HATU (0.18 g, 0.49 mmol) in DCM (3 ml). The reaction mixture was stirred at room temperature for 1 hour. The reaction mixture was concentrated down, re-dissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 12-C. LCMS-ESI+ (m/z): [M+H]+; found: 466.

Step 3

A 50-mL 1-neck round bottom flask was charged with reactant 12-C (0.03 g, 0.066 mmol) and magnesium bromide (0.03 g, 0.174 mmol) in acetonitrile (5 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 12. $^1$H NMR (400 MHz, Methanol-d4) δ 8.42 (s, 1H), 6.89 (dd, J=9.0, 7.9 Hz, 2H), 4.66 (s, 2H), 4.49 (dd, J=11.1, 4.5 Hz, 1H), 4.29-4.17 (m, 2H), 4.09 (q, J=7.1 Hz, 1H), 3.97-3.80 (m, 2H), 3.67-3.43 (m, 2H), 2.69-2.53 (m, 1H), 2.18-1.99 (m, 2H), 1.21 (dt, J=17.1, 7.2 Hz, 3H). $^{19}$F NMR (377 MHz, Methanol-d4) δ −109.27−−111.99 (m, 1F), −114.23 (t, J=7.1 Hz, 2F). LCMS-ESI+ (m/z): [M+H]+ found: 452.

Step 1

A 50-mL 1-neck round bottom flask was charged with reactant 12-B (0.04 g, 0.12 mmol), (3-chloro-2,4-difluorophenyl)methanamine (0.024 g, 0.14 mmol), DIPEA (0.17 g, 1.28 mmol) and HATU (0.094 g, 0.25 mmol) in DCM (3 ml). The reaction mixture was stirred at room temperature for 1 hour. The reaction mixture was concentrated down, re-dissolved in EtOAc (50 mL), washed with saturated NaHCO$_3$ twice, saturated NH$_4$Cl and dried over Na$_2$SO$_4$. After concentration, the crude was purified by column chromatography on silica gel with hexane-EtOAc to obtain 13-B. LCMS-ESI+ (m/z): [M+H]+; found: 483.

Step 2

A 50-mL 1-neck round bottom flask was charged with reactant 13-B (0.015 g, 0.031 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 13. $^1$H NMR (400

MHz, Methanol-d4) δ 8.44 (s, 1H), 7.38 (td, J=8.4, 6.1 Hz, 1H), 7.08 (td, J=8.7, 1.8 Hz, 1H), 4.66 (s, 2H), 4.50 (dd, J=11.0, 4.8 Hz, 1H), 4.27 (qd, J=11.5, 4.6 Hz, 2H), 4.08 (d, J=7.1 Hz, 1H), 4.02-3.79 (m, 3H), 3.65-3.48 (m, 2H), 2.60 (d, J=14.0 Hz, 1H), 1.21 (q, J=7.0 Hz, 3H). $^{19}$F NMR (376 MHz, Methanol-d4) δ −117.31 (s, 1F), −119.84 (d, J=7.8 Hz, 1F). LCMS-ESI$^+$ (m/z): [M+H]$^+$ found: 469.

Example 14

Preparation of Compound 14

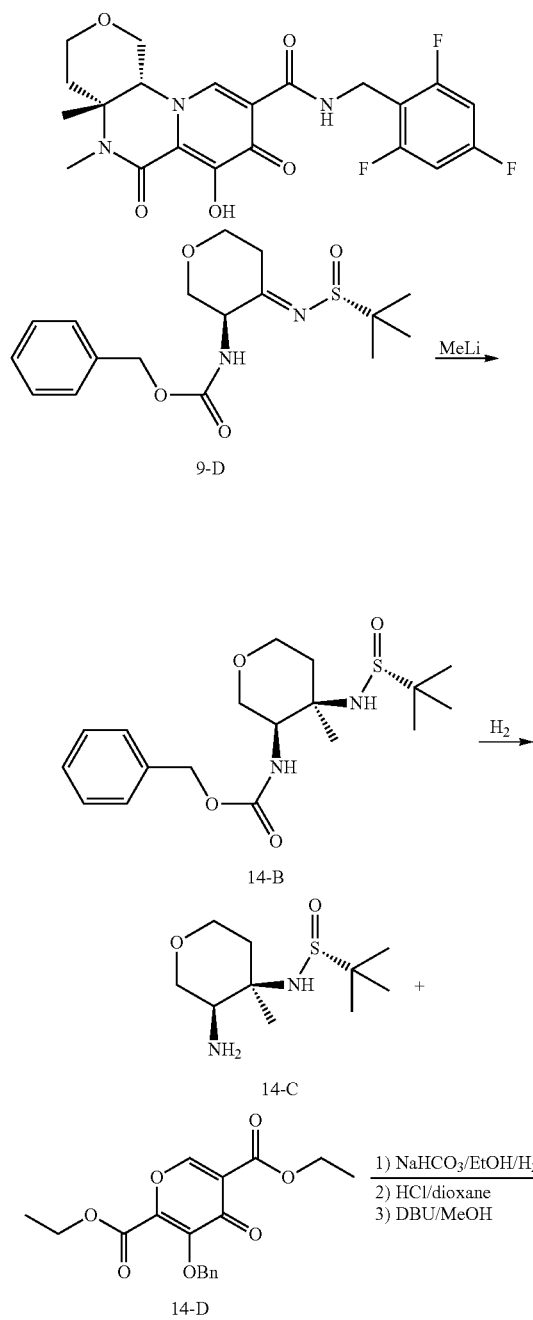

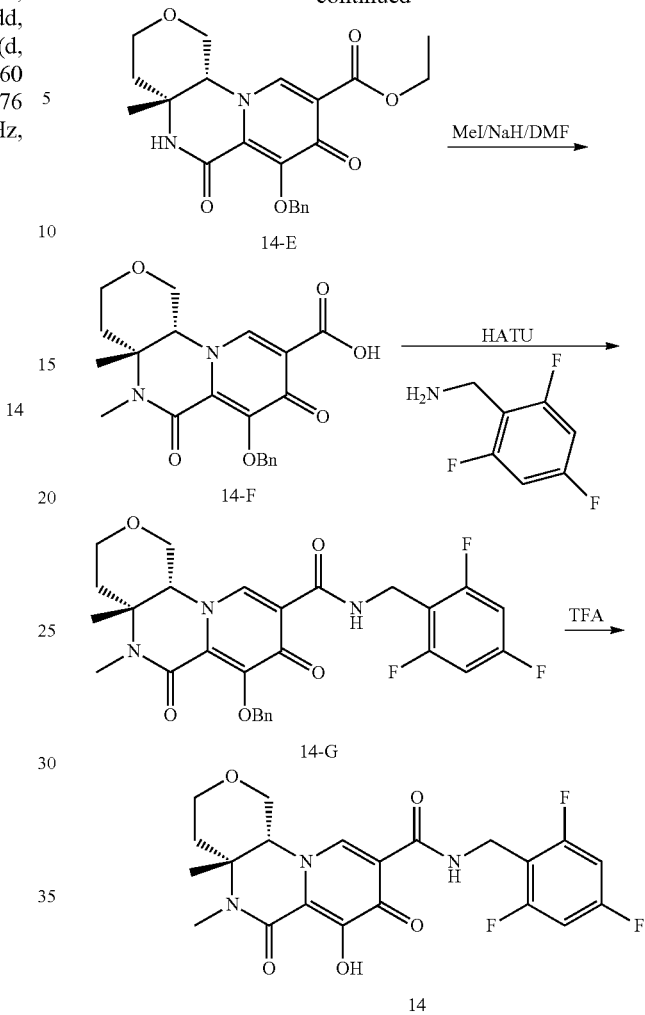

Step 1

A 250-mL 1-neck round bottom flask was charged with reactant 9-D (0.6 g, 1.7 mmol) in THF (10 ml). The reaction mixture was cooled down to −78° C. Methyl lithium (3.86 mL, 1.14 M in diethyl ether, 4.4 mmol) was added to the reaction mixture. The reaction mixture was stirred at −78° C. for 2 hours. The reaction mixture was diluted with EtOAc (50 mL) and quenched with water (5 mL). After layers separation, the organic layer was dried over Na$_2$SO$_4$ and concentrated down, the crude was purified by column chromatography on silica gel with hexane-EtOAc to obtain 14-B. LCMS-ESI$^+$ (m/z): [M+H]$^+$; found: 369.

Step 2

A 100-mL 1-neck round bottom flask was charged with reactant 14-B (0.13 g, 0.35 mmol) in Ethanol (10 mL). Pd(OH)$_2$/C (0.03 g) was added to the reaction mixture. The reaction mixture was stirred under H$_2$ for 1 hour. After filtration to remove the solid, the filtrate was concentrated down and under high vacuum for 1 hour. The crude 14-C was used for next step without further purification and characterization. LCMS-ESI$^+$ (m/z): [M+H]$^+$ found: 235.

Step 3

A 50-mL 1-neck round bottom flask was charged with reactant 14-C (0.08 g, 0.38 mmol), 14-D (0.13 g, 0.38 mmol) and NaHCO$_3$ (0.064 g, 0.75 mmol) in ethanol (5 ml) and water (5 ml). The reaction mixture was stirred at room temperature overnight. The reaction mixture was concentrated down, re-dissolved in EtOAc (50 mL), washed with water twice and dried over Na₂SO₄. After concentration, the crude was dissolved in 4N HCl/Dioxane and stirred for 2 hours. The reaction mixture was concentrated down again. The residue and DBU (0.15 g, 1.0 mmol) were dissolved in EtOH (5 mL) and heated up to 50° C. for 20 minutes. After concentration, the crude was purified by column chromatography on silica gel with hexane-EtOAc to obtain 14-E. LCMS-ESI⁺ (m/z): [M+H]⁺; found: 413.

Step 4

A 50-mL 1-neck round bottom flask was charged with reactant 14-E (0.05 g, 0.12 mmol) in DMF (5 mL). NaH (0.014 g, 60% in mineral oil, 0.36 mmol) was added to the reaction mixture. The reaction mixture was stirred at room temperature for 5 minutes. MeI (0.034 g, 0.24 mmol) was added to the reaction mixture. The reaction mixture was stirred at room temperature for another 5 minutes. Water (0.5 ml) was added dropwise to the reaction mixture. The reaction mixture was stirred for 10 minutes at room temperature to hydrolyze the ester and form the acid. After acidification with 1 N HCl, the solution was concentrated to remove the solvent completely and the crude 14-F was used for next step without further purification. LCMS-ESI⁺ (m/z): [M+H]⁺ found: 399.

Step 5

A 50-mL 1-neck round bottom flask was charged with reactant 14-F (0.048, 0.12 mmol), 2,4,6-trifluorophenyl methanamine (0.033 g, 0.2 mmol), DIPEA (0.25 g, 1.9 mmol) and HATU (0.18 g, 0.48 mmol) in DCM (3 ml). The reaction mixture was stirred at room temperature for 1 hour. The reaction mixture was concentrated down, re-dissolved in EtOAc (50 mL), washed with saturated NaHCO₃ twice, washed with saturated NH₄Cl and dried over Na₂SO₄. After concentration, the crude was purified by column chromatography on silica gel with hexane-EtOAc to obtain 14-G. LCMS-ESI⁺ (m/z): [M+H]⁺; found: 542.

Step 6

A 50-mL 1-neck round bottom flask was charged with reactant 14-G (0.07 g, 0.13 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 14. ¹H NMR (400 MHz, Methanol-d4) δ 8.47 (s, 1H), 6.89 (dd, J=9.0, 7.9 Hz, 2H), 4.66 (s, 2H), 4.55 (dd, J=11.1, 5.1 Hz, 1H), 3.86 (dd, J=11.4, 5.4 Hz, 2H), 3.51 (dt, J=29.8, 11.8 Hz, 2H), 3.11 (s, 3H), 2.40 (d, J=15.7 Hz, 1H), 2.05-1.79 (m, 1H), 1.33 (s, 3H). ¹⁹F NMR (376 MHz, Methanol-d4) δ −109.24−−112.06 (m, 1F), −114.26 (t, J=7.2 Hz, 2F). LCMS-ESI⁺ (m/z): [M+H]⁺ found: 452.

Example 15

Preparation of Compound 15

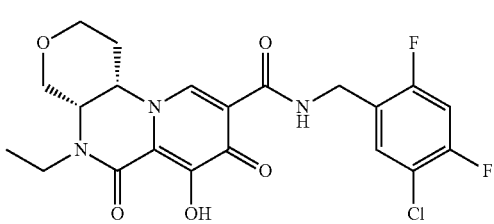

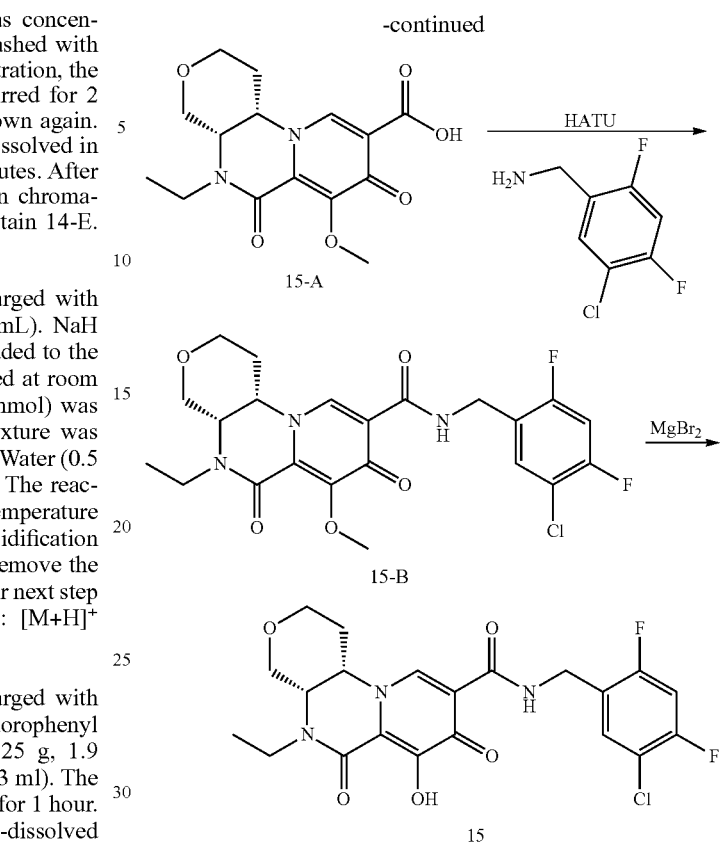

Step 1

A 50-mL 1-neck round bottom flask was charged with reactant 15-A (0.015 g, 0.047 mmol, the synthesis of 15-A is described in example 41), (5-chloro-2,4-difluorophenyl) methanamine (0.009 g, 0.05 mmol), DIPEA (0.06 g, 0.47 mmol) and HATU (0.035 g, 0.09 mmol) in DCM (3 ml). The reaction mixture was stirred at room temperature for 1 hour. The reaction mixture was concentrated down, re-dissolved in EtOAc (50 mL), washed with saturated NaHCO₃ twice, washed with saturated NH₄Cl and dried over Na₂SO₄. After concentration, the crude was purified by column chromatography on silica gel with hexane-EtOAc to obtain 15-B. LCMS-ESI⁺ (m/z): [M+H]⁺; found: 483.

Step 2

A 50-mL 1-neck round bottom flask was charged with reactant 15-B (0.015 g, 0.031 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 15. ¹H NMR (400 MHz, Methanol-d4) δ 8.48 (s, 1H), 7.50 (t, J=7.9 Hz, 1H), 7.15 (t, J=9.4 Hz, 1H), 4.61 (s, 2H), 4.34 (d, J=13.6 Hz, 1H), 4.07 (dd, J=14.4, 7.4 Hz, 2H), 3.94 (d, J=4.0 Hz, 1H), 3.83-3.63 (m, 2H), 3.50 (dt, J=14.2, 7.0 Hz, 1H), 2.35-2.04 (m, 1H), 2.00-1.84 (m, 1H), 1.25 (t, J=7.2 Hz, 3H). ¹⁹F NMR (376 MHz, Methanol-d4) δ −115.23 (q, J=8.2 Hz, 1F), −117.95 (d, J=8.6 Hz, 1F). LCMS-ESI⁺ (m/z): [M+H]⁺ found: 469.

Example 16

Preparation of Compound 16

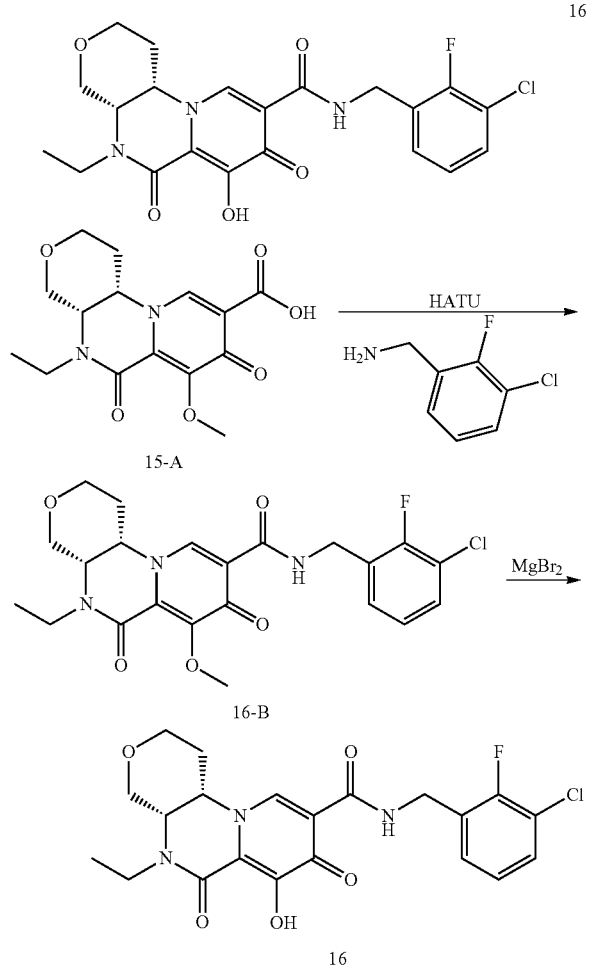

Step 1

A 50-mL 1-neck round bottom flask was charged with reactant 15-A (0.015 g, 0.047 mmol), (3-chloro-2-fluorophenyl) methanamine (0.008 g, 0.05 mmol), DIPEA (0.06 g, 0.47 mmol) and HATU (0.035 g, 0.09 mmol) in DCM (3 ml). The reaction mixture was stirred at room temperature for 1 hour. The reaction mixture was concentrated down, re-dissolved in EtOAc (50 mL), washed with saturated NaHCO$_3$ twice, washed with saturated NH$_4$Cl and dried over Na$_2$SO$_4$. After concentration, the crude was purified by column chromatography on silica gel with hexane-EtOAc to obtain 16-B. LCMS-ESI$^+$ (m/z): [M+H]$^+$; found: 465.

Step 2

A 50-mL 1-neck round bottom flask was charged with reactant 16-B (0.015 g, 0.032 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 16. $^1$H NMR (400 MHz, Methanol-d4) δ 8.49 (s, 1H), 7.46-7.27 (m, 2H), 7.19-7.05 (m, 1H), 4.78 (dt, J=11.1, 4.2 Hz, 1H), 4.68 (s, 2H), 4.34 (d, J=13.7 Hz, 1H), 4.15-3.98 (m, 2H), 4.00-3.86 (m, 1H), 3.78-3.59 (m, 2H), 3.58-3.41 (m, 1H), 2.31-2.05 (m, 1H), 2.00-1.80 (m, 1H), 1.25 (t, J=7.2 Hz, 3H). $^{19}$F NMR (376 MHz, Methanol-d4) δ -123.45 (s, 1F). LCMS-ESI$^+$ (m/z): [M+H]$^+$ found: 451.

Example 17

Preparation of Compound 17

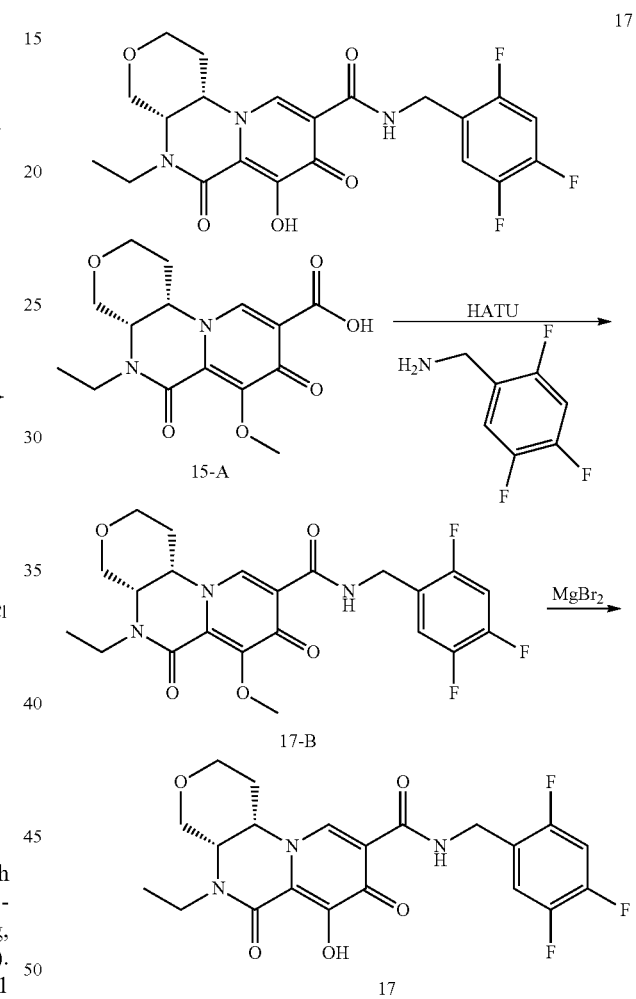

Step 1

A 50-mL 1-neck round bottom flask was charged with reactant 15-A (0.015 g, 0.047 mmol), (2,4,5-trifluorophenyl) methanamine (0.008 g, 0.05 mmol), DIPEA (0.06 g, 0.47 mmol) and HATU (0.035 g, 0.09 mmol) in DCM (3 ml). The reaction mixture was stirred at room temperature for 1 hour. The reaction mixture was concentrated down, re-dissolved in EtOAc (50 mL), washed with saturated NaHCO$_3$ twice, washed with saturated NH$_4$Cl and dried over Na$_2$SO$_4$. After concentration, the crude was purified by column chromatography on silica gel with hexane-EtOAc to obtain 17-B. LCMS-ESI$^+$ (m/z): [M+H]$^+$; found: 466.

Step 2

A 50-mL 1-neck round bottom flask was charged with reactant 17-B (0.015 g, 0.032 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 17. $^1$H NMR (400 MHz, Chloroform-d) δ 10.58 (s, 1H), 8.47 (s, 1H), 7.25-7.09 (m, 1H), 6.92 (td, J=9.6, 6.4 Hz, 1H), 4.68-4.52 (m, 2H), 4.49-4.33 (m, 1H), 4.24 (t, J=14.9 Hz, 1H), 4.15 (dt, J=14.6, 7.3 Hz, 1H), 4.11-3.89 (m, 2H), 3.77-3.58 (m, 2H), 3.42 (dq, J=14.2, 6.9 Hz, 1H), 2.29 (d, J=10.7 Hz, 1H), 2.11-1.85 (m, 1H), 1.27 (t, J=7.2 Hz, 3H). $^{19}$F NMR (376 MHz, Chloroform-d) δ -120.46 (dd, J=10.1, 6.3 Hz, 1F), -134.38--136.34 (m, 1F), -140.61--145.04 (m, 1F). LCMS-ESI$^+$ (m/z): [M+H]$^+$ found: 452.

Example 18

Preparation of Compound 18

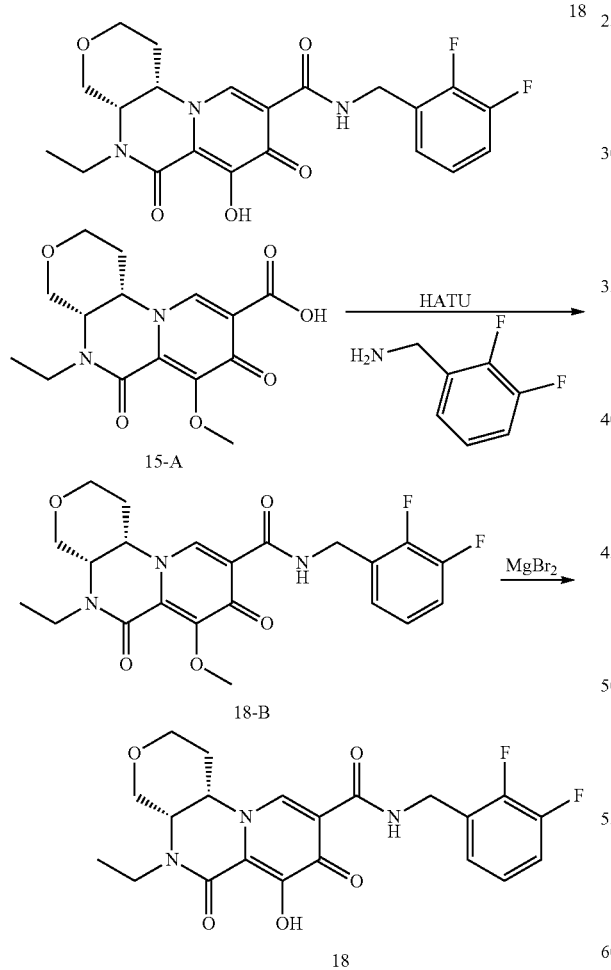

Step 1

A 50-mL 1-neck round bottom flask was charged with reactant 15-A (0.015 g, 0.047 mmol), (2,3-difluorophenyl)methanamine (0.007 g, 0.05 mmol), DIPEA (0.06 g, 0.47 mmol) and HATU (0.035 g, 0.09 mmol) in DCM (3 ml). The reaction mixture was stirred at room temperature for 1 hour. The reaction mixture was concentrated down, re-dissolved in EtOAc (50 mL), washed with saturated NaHCO$_3$ twice, washed with saturated NH$_4$Cl and dried over Na$_2$SO$_4$. After concentration, the crude was purified by column chromatography on silica gel with hexane-EtOAc to obtain 18-B. LCMS-ESI$^+$ (m/z): [M+H]$^+$; found: 448.

Step 2

A 50-mL 1-neck round bottom flask was charged with reactant 18-B (0.02 g, 0.045 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 18. $^1$H NMR (400 MHz, Chloroform-d) δ 10.62 (d, J=6.5 Hz, 1H), 8.52 (s, 1H), 7.20-6.97 (m, 3H), 4.86-4.59 (m, 2H), 4.43 (dt, J=10.8, 4.0 Hz, 1H), 4.34-4.06 (m, 2H), 4.00 (d, J=17.8 Hz, 2H), 3.78-3.53 (m, 2H), 3.43 (dq, J=14.2, 6.8 Hz, 1H), 2.39-2.16 (m, 1H), 1.95 (d, J=13.8 Hz, 1H), 1.26 (t, J=7.2 Hz, 3H). $^{19}$F NMR (377 MHz, Chloroform-d) δ -138.97 (ddd, J=20.8, 9.7, 5.1 Hz, 1F), -143.93 (dt, J=20.7, 6.5 Hz, 1F). LCMS-ESI$^+$ (m/z): [M+H]$^+$ found: 434.

Example 19

Preparation of Compound 19

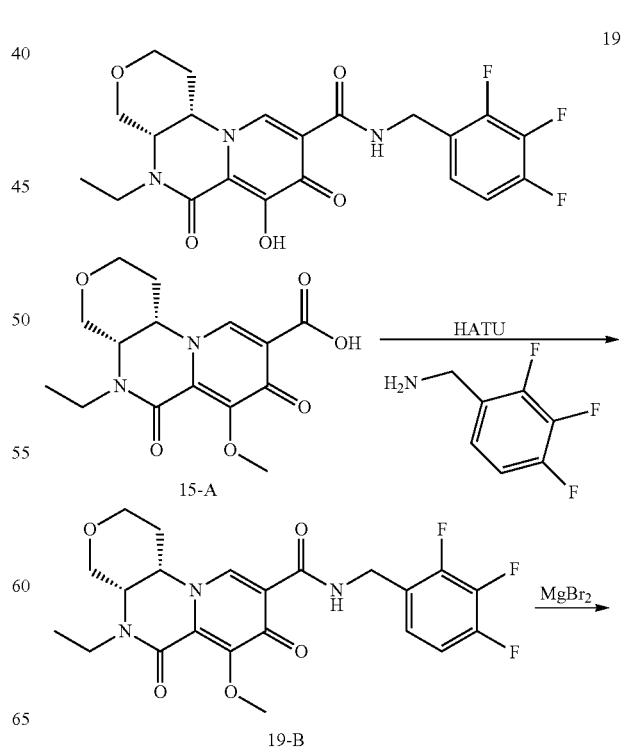

-continued

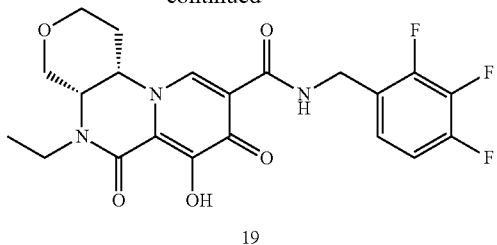

19

Step 1

A 50-mL 1-neck round bottom flask was charged with reactant 15-A (0.015 g, 0.047 mmol), (2,3,4-trifluorophenyl)methanamine (0.008 g, 0.05 mmol), DIPEA (0.06 g, 0.47 mmol) and HATU (0.035 g, 0.09 mmol) in DCM (3 ml). The reaction mixture was stirred at room temperature for 1 hour. The reaction mixture was concentrated down, re-dissolved in EtOAc (50 mL), washed with saturated NaHCO$_3$ twice, washed with saturated NH$_4$Cl and dried over Na$_2$SO$_4$. After concentration, the crude was purified by column chromatography on silica gel with hexane-EtOAc to obtain 19-B. LCMS-ESI$^+$ (m/z): [M+H]$^+$; found: 466.

Step 2

A 50-mL 1-neck round bottom flask was charged with reactant 19-B (0.015 g, 0.032 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 19. $^1$H NMR (400 MHz, Chloroform-d) δ 10.59 (t, J=5.9 Hz, 1H), 8.48 (s, 1H), 7.08 (t, J=6.8 Hz, 1H), 6.91 (tdd, J=9.1, 6.9, 2.1 Hz, 1H), 4.81-4.53 (m, 2H), 4.43 (dt, J=10.7, 4.1 Hz, 1H), 4.36-4.22 (m, 1H), 4.15 (dq, J=14.6, 7.3 Hz, 1H), 4.00 (d, J=12.3 Hz, 2H), 3.77-3.59 (m, 2H), 3.43 (dq, J=14.1, 6.8 Hz, 1H), 2.40-2.13 (m, 1H), 1.95 (d, J=13.9 Hz, 1H), 1.27 (t, J=7.1 Hz, 3H). $^{19}$F NMR (376 MHz, Chloroform-d) δ −134.81−−137.16 (m, 1F), −139.27 (dt, J=20.1, 7.0 Hz, 1F), −158.56−−162.98 (m, 1F). LCMS-ESI$^+$ (m/z): [M+H]$^+$ found: 452.

Example 20

Preparation of Compound 20

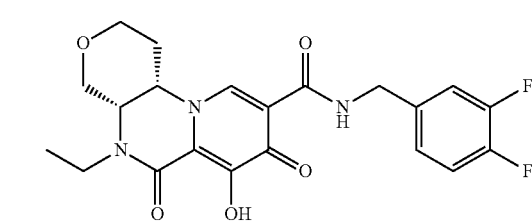

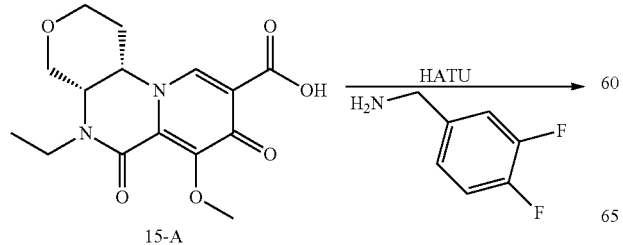

-continued

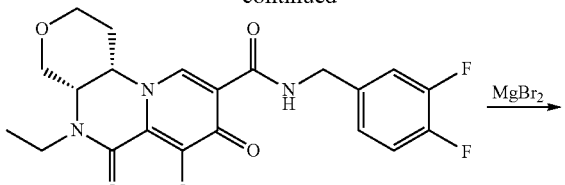

20-B

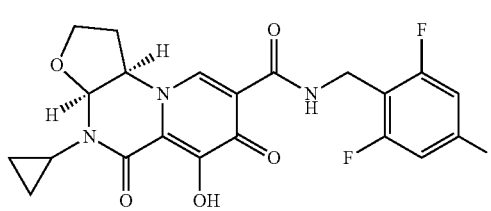

20

Step 1

A 50-mL 1-neck round bottom flask was charged with reactant 15-A (0.015 g, 0.047 mmol), (3,4-difluorophenyl)methanamine (0.007 g, 0.05 mmol), DIPEA (0.06 g, 0.47 mmol) and HATU (0.035 g, 0.09 mmol) in DCM (3 ml). The reaction mixture was stirred at room temperature for 1 hour. The reaction mixture was concentrated down, re-dissolved in EtOAc (50 mL), washed with saturated NaHCO$_3$ twice, washed with saturated NH$_4$Cl and dried over Na$_2$SO$_4$. After concentration, the crude was purified by column chromatography on silica gel with hexane-EtOAc to obtain 20-B. LCMS-ESI$^+$ (m/z): [M+H]$^+$; found: 448.

Step 2

A 50-mL 1-neck round bottom flask was charged with reactant 20-B (0.02 g, 0.045 mmol) and magnesium bromide (0.015 g, 0.081 mmol) in acetonitrile (3 mL). The reaction mixture was heated up to 50° C. After 10 minutes, the reaction mixture was cooled down to 0° C. and 1 N hydrochloric acid (4 mL) was added. Additional water (~5 mL) was added and the solid formed was filtered and washed with water. Then the solid was transferred to a vial and lyophilized overnight to afford compound 20. $^1$H NMR (400 MHz, Chloroform-d) δ 10.79-10.57 (m, 1H), 8.57 (s, 1H), 7.22-6.96 (m, 3H), 4.58 (qd, J=15.2, 5.9 Hz, 2H), 4.46 (dt, J=10.8, 4.1 Hz, 1H), 4.28 (d, J=13.8 Hz, 1H), 4.15 (dt, J=14.6, 7.3 Hz, 1H), 4.07-3.91 (m, 2H), 3.80-3.58 (m, 2H), 3.43 (dq, J=14.1, 7.0 Hz, 1H), 2.26 (dd, J=12.6, 8.4 Hz, 1H), 1.97 (t, J=13.6 Hz, 1H), 1.27 (t, J=7.2 Hz, 3H). $^{19}$F NMR (376 MHz, Chloroform-d) δ −137.90 (ddd, J=21.2, 11.0, 7.5 Hz, 1F), −139.18−−141.35 (m, 1F). LCMS-ESI$^+$ (m/z): [M+H]$^+$ found: 434.

Example 21

Preparation of Compound 21

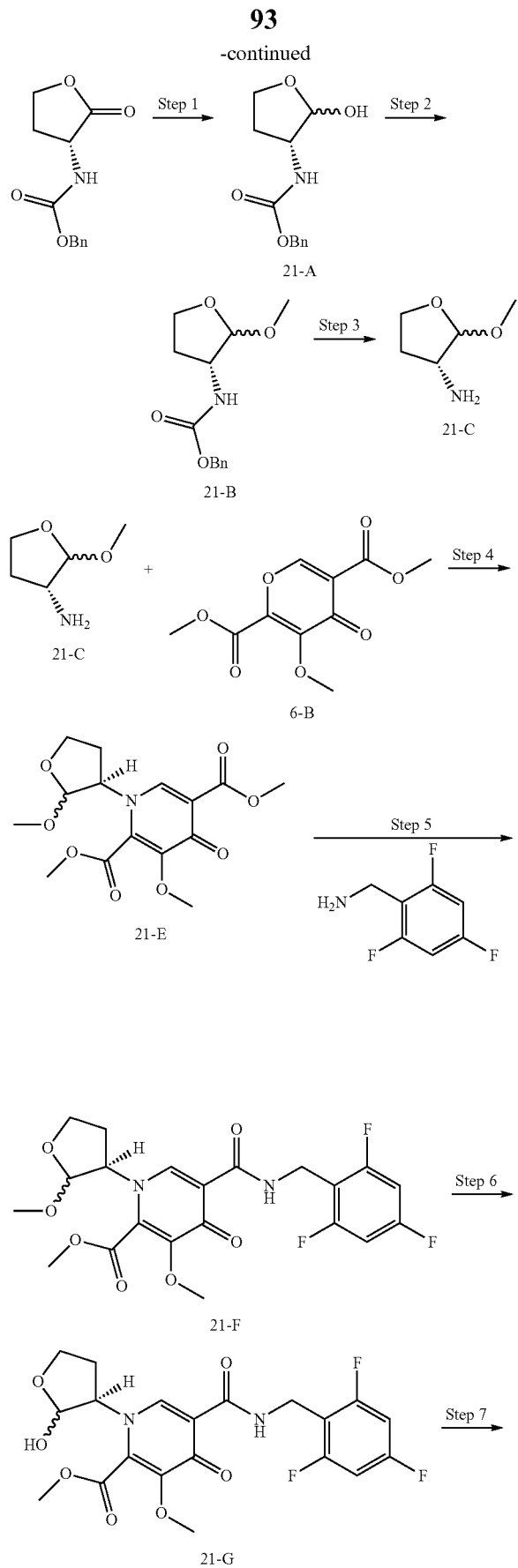

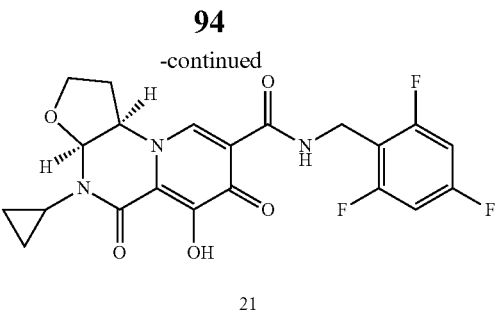

Step 1

(R)-benzyl (2-oxotetrahydrofuran-3-yl)carbamate (3.29 g, 14.0 mmol) was azeotropically dried by evaporation from toluene and dissolved in dichloromethane (25 mL). The solution was cooled down in a −78° C. bath resulting in precipitation. The mixture was allowed to warm until mostly homogenous and DIBAL-H (29.4 mL, 1.0 M in toluene, 29.4 mmol) was added while the reaction mixture was re-cooled down to −78° C. Additional dichloromethane (10 mL) was added to maintain homogeneity. The reaction mixture was stirred at −78° C. for 2 h and then quenched by addition of ethyl acetate (2-3 mL's). Subsequently, Rochelle's Salt (20 mL, saturated aq solution) was added and the mixture was allowed to warm to room temperature. After partitioning between ethyl acetate and water, additional Rochelle's salt solution was added to afford homogenous biphasic layers. The layers were separated and the aqueous was extracted again with ethyl acetate. The combined organic layers were dried over sodium sulfate (anhyd), filtered and concentrated to afford crude lactol 21-A as a mixture of diastereomers.

Step 2

Lactol 21-A (3.18 g, 13.4 mmol) was dissolved in methanol (65 mL) and treated with methanesulfonic acid (0.044 mL, 0.67 mmol). The reaction mixture was capped and stirred at room temperature. After 16 h, approximately half the solvent was removed in vacuo and the remaining solution was partitioned between ethyl acetate and sodium bicarbonate (saturated aq). The layers were separated and the organic layer was washed with water and brine and dried over sodium sulfate. After filtration, the solvent was removed in vacuo and the residue was purified by flash chromatography on silica gel (20-60% ethyl acetate: hexanes) to afford desired ketal 21-B.

Step 3

Ketal 21-B (2.14 g, 8.52 mmol) and 10% palladium on carbon were combined in a round bottom flask, purged with nitrogen and suspended in ethanol (35 mL). The reaction mixture was vacuum purged with hydrogen gas (via balloon) three times and stirred at room temperature for 1¾ h. After vacuum purging with nitrogen several times, the mixture was filtered through celite. The filter cake was washed several times with methanol and the resulting solution was carefully concentrated to a volume of approximately 20 mL. This solution of crude amino-ketal 21-C was carried on crude to the next step.

Step 4

Amino-ketal 21-C (8.5 mmol) in ethanol (~20 mL) was diluted with water (20 mL) and treated with dimethyl 3-methoxy-4-oxo-4H-pyran-2,5-dicarboxylate 6-B (2.06 g, 8.5 mmol) and sodium bicarbonate (1.43 g, 17.0 mmol). The mixture was stirred at room temperature for 2 h and concentrated to an orange solid. The residue was resuspended in methanol and stirred 16 h at 50° C. After cooling, most of the solvent was removed in vacuo and the remainder was partitioned between ethyl acetate and water. The organic was separated and the aqueous was extract again with ethyl acetate. The aqueous was treated with sodium chloride (solid) and extract again with ethyl acetate and 2-butanol. The combined organic layers were dried over sodium sulfate, filtered and concentrated to afford crude diester 21-E.

Step 5

Crude diester 21-E (2.15 g, 6.30 mmol) was dissolved in THF (8 mL) and methanol (4 mL) and treated with lithium hydroxide (2.36 mL, 2 M aq solution, 4.72 mmol) over about 2 min. After stirring for 20 min, the reaction mixture was diluted with ethyl acetate (40 mL) and carefully quenched with HCl (12.6 mL, 0.5 M aqueous solution). After separating the layers, the aqueous layer was treated with brine and extracted again with ethyl acetate. The combined organic layers were dried over sodium sulfate, filtered and concentrated to afford crude carboxylic acid: LCMS-ESI$^+$ (m/z): [M+H]$^+$ calculated for $C_{19}H_{18}F_3N_3O_5$: 328.10; found: 328.0.

The crude carboxylic acid intermediate (2.1 g, 6.41 mmol) and 2,4,6-trifluorobenzylamine (1.14 g, 7.06 mmol) were dissolved in acetonitrile (15 mL) and treated with N-ethyl-N-isopropylpropan-2-amine (1.24 g, 9.6 mmol) and HATU (2.68 g, 7.05 mmol). After stirring for 1 h at room temperature, the reaction mixture was diluted with ethyl acetate (100 mL) and washed with 0.5 M HCl and water. After drying over sodium sulfate, the solution was filtered and concentrated. Flash chromatography (0-40% ethyl acetate:dichloromethane) afforded the desired amide 21-F: LCMS-ESI$^+$ (m/z): [M+H]$^+$ calculated for $C_{21}H_{22}F_3N_2O_7$: 471.14; found: 471.1.

Step 6

Amide 21-F (0.476 g, 1.01 mmol) in a mixture of acetonitrile (3.6 mL) and acetic acid (0.4 mL) was treated with methanesulfonic acid (0.020 mL, 0.30 mmol). The reaction mixture was capped, and stirred in a 75° C. bath. After 18 h, water (0.040 mL) was added and the mixture was stirred at 75° C. for an additional 16 h to afford crude lactol 21-G: LCMS-ESI$^+$ (m/z): [M+H]$^+$ calculated for $C_{20}H_{20}F_3N_2O_7$: 457.12; found: 457.1.

Step 7

A portion of the crude lactol solution from Step 6 (1 mL solution, 0.25 mmol) was diluted with acetonitrile (1 mL), treated with cyclopropylamine (0.069 mL, 1.00 mmol), capped and stirred at 75° C. After 30 min, the reaction mixture was cooled down, diluted with acetonitrile (1 mL) and treated with magnesium bromide (0.129 g, 0.7 mmol). The mixture was capped and stirred at 50° C. for 15 min, cooled down and partitioned between dichloromethane and 0.5 M HCl. The organic layer was separated and dried over sodium sulfate. After filtering and concentrating under vacuum, the residue was purified by prep HPLC (acetonitrile/water gradient containing 0.1% TFA) to afford the desired compound 21 as a mixture of enantiomers. $^1$H NMR (400 MHz, DMSO-d$_6$) δ 12.59 (s, 1H), 10.34 (t, J=5.9 Hz, 1H), 8.50 (s, 1H), 7.35-7.04 (m, 2H), 5.45 (d, J=5.2 Hz, 1H), 5.09 (dt, J=7.6, 5.6 Hz, 1H), 4.64-4.54 (m, 1H), 4.49 (dd, J=14.6, 5.7 Hz, 1H), 3.95-3.83 (m, 2H), 2.78-2.70 (m, 1H), 2.64-2.55 (m, 1H), 2.28-2.16 (m, 1H), 1.01-0.88 (m, 1H), 0.87-0.73 (m, 3H). LCMS-ESI$^+$ (m/z): [M+H]$^+$ calculated for $C_{21}H_{19}F_3N_3O_5$: 450.13; found: 450.2.

Example 22

Preparation of Compound 22

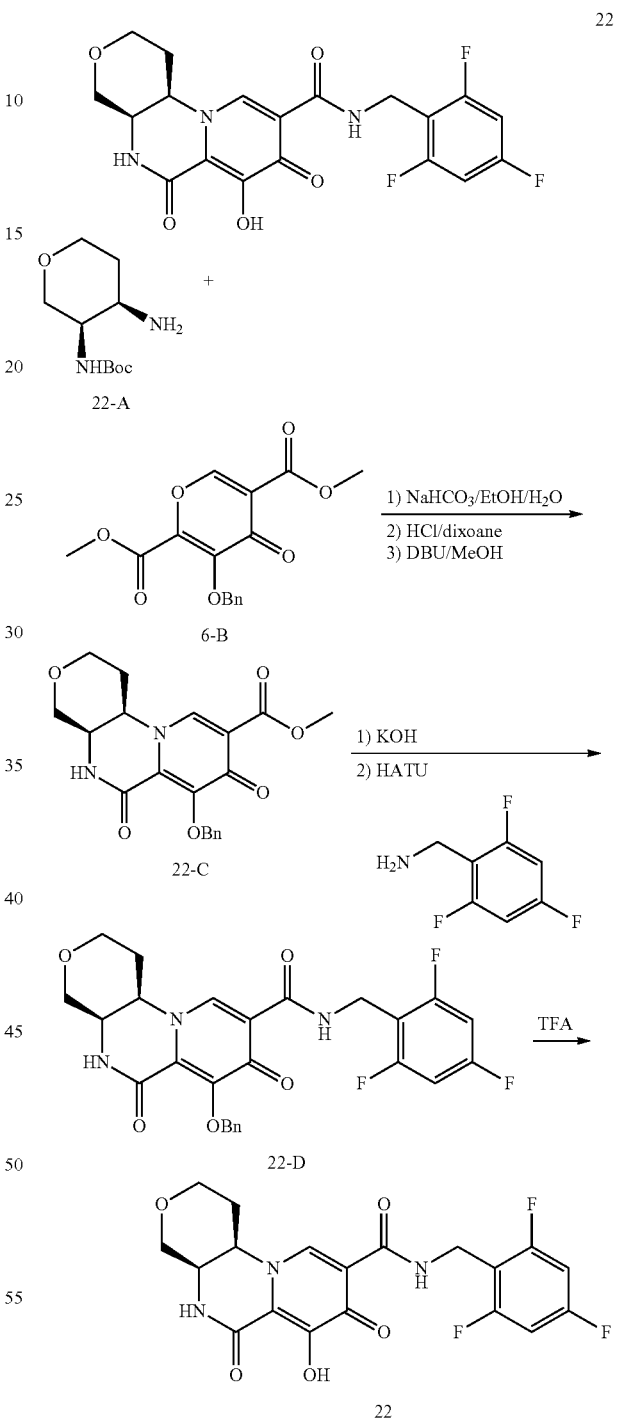

Step 1

A 50-mL 1-neck round bottom flask was charged with reactant 22-A (0.50 g, 2.31 mmol), 6-B (0.80 g, 2.31 mmol) and NaHCO$_3$ (0.39 g, 4.6 mmol) in ethanol (10 ml) and water (10 ml). The reaction mixture was stirred at room temperature overnight. The reaction mixture was concentrated down, re-dissolved in EtOAc (100 mL), washed with water (2×) and dried over Na$_2$SO$_4$. After concentration, the crude was dissolved in 4N HCl/Dioxane (11 ml) and stirred at room temperature for 3 hours to de-Boc. The reaction mixture was concentrated down again. The residue and DBU (1.58 g, 10.4 mmol) were dissolved in EtOH (10 mL). Heated to 50° C. for 20 minutes. After concentration, the crude was purified by column chromatography on silica gel with hexane-EtOAc to obtain 22-C. LCMS-ESI$^+$ (m/z): [M+H]$^+$; found: 399.

Step 2

A 50-mL 1-neck round bottom flask was charged with reactant 22-C (0.10 g, 0.25 mmol) in THF (5 mL) and MeOH (5 mL). 1 N KOH in water (1.0 mL) was added to the reaction solution. The reaction mixture was stirred at room temperature for 1 hour. After acidification with 1 N HCl, the solution was concentrated to remove the solvent completely and the crude acid was used for next step without further purification. The crude acid (0.25 mmol), 2,4,6-trifluorophenyl methanamine (0.08 g, 0.5 mmol), DIPEA (0.169 g, 1.3 mmol) and HATU (0.20 g, 0.52 mmol) in DCM (10 ml) were stirred at room temperature for 1 hour. The reaction mixture was concentrated down, re-dissolved in EtOAc (50 mL), washed with saturated NaHCO$_3$ (2×), saturated NH$_4$Cl and dried over Na$_2$SO$_4$. After concentration, the crude was purified by column chromatography on silica gel with hexane-EtOAc to obtain 22-D. LCMS-ESI$^+$ (m/z): [M+H]$^+$; found: 514.

Step 3

A 50-mL 1-neck round bottom flask was charged with reactant 22-D (0.10 g, 0.19 mmol) in TFA (2 mL). The reaction mixture was stirred at room temperature for 30 minutes. The solution was concentrated and the residue was purified by CombiFlash (12 g column, used cartridge) using EtOAc-20% MeOH in EtOAc as eluents to afford compound 22. $^1$H NMR (400 MHz, Chloroform-d) δ 11.70 (s, 1H), 10.65-10.18 (m, 1H), 8.27 (s, 1H), 7.26 (m, 1H), 6.90 (td, J=9.7, 6.4 Hz, 1H), 4.89 (s, 1H), 4.60 (d, J=6.0 Hz, 2H), 4.09 (dd, J=11.4, 2.6 Hz, 1H), 3.96-3.66 (m, 2H), 2.68 (s, 1H), 2.15-1.43 (m, 6H). $^{19}$F NMR (376 MHz, Chloroform-d) δ 120.53--120.85 (m, 1F), -134.68--136.79 (m, 1F), -142.26--144.11 (m, 1F). LCMS-ESI$^+$ (m/z): [M+H]$^+$ found: 424.

Example 23

Preparation of Compound 23

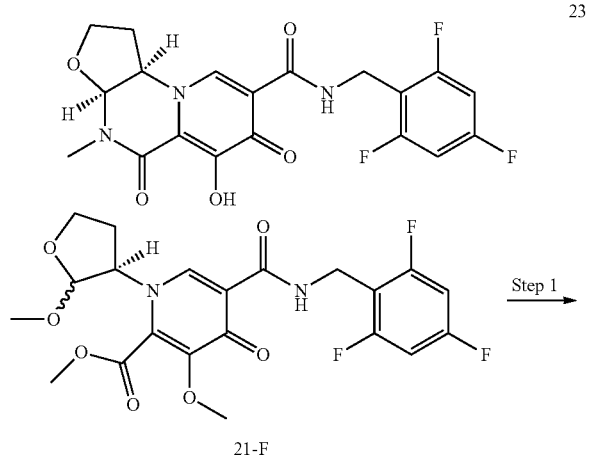

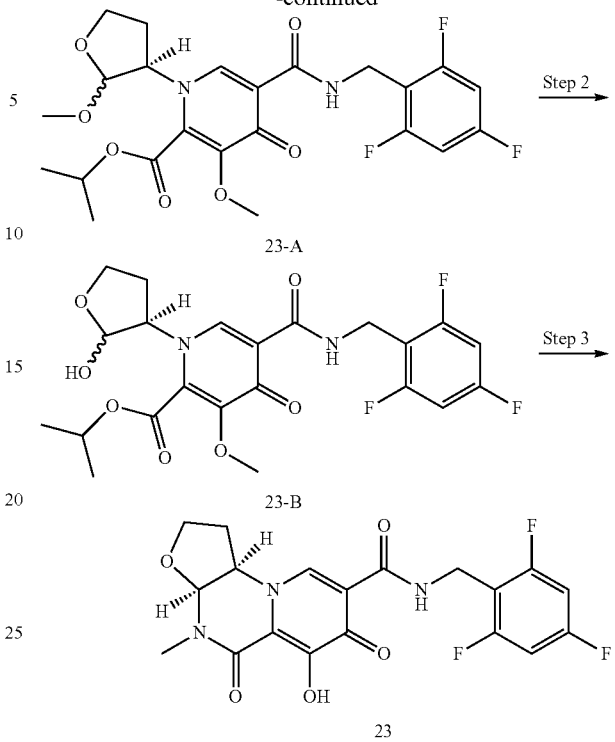

Step 1

Amide 21-F (0.102 g, 0.217 mmol) in 2-methyl-THF (1 mL) was treated with a solution of lithium isopropoxide in THF (0.119 mL, 2 M solution, 0.239 mmol), capped and stirred at room temperature. After a few minutes, additional lithium isopropoxide in THF (0.109 mL, 2 M solution, 0.217 mmol) was added. After 3 h the reaction mixture was partitioned between dichloromethane and 0.5 M HCl. The layers were separated and the aqueous layer was extracted again with dichloromethane. The combined organic layers were dried over sodium sulfate, filtered and concentrated to afford isopropyl ester 23-A which was taken on crude to the next step: LCMS-ESI$^+$ (m/z): [M+H]$^+$ calculated for C$_{23}$H$_{26}$F$_3$N$_2$O$_7$: 499.17; found: 499.1.

Step 2

Isopropyl ester 23-A (0.102 g, 0.205 mmol) was dissolved in acetonitrile (1 mL), treated with methanesulfonic acid (0.004 mL, 0.06 mmol), acetic acid (0.1 mL) and water (0.009 mL, 0.51 mmol). The reaction mixture was capped and stirred at 75° C. for 16 h to afford a crude solution of lactol 23-B: LCMS-ESI$^+$ (m/z): [M+H]$^+$ calculated for C$_{22}$H$_{24}$F$_3$N$_2$O$_7$: 485.15; found: 485.1.

Step 3

A portion of the crude lactol solution from Step 2 (0.5 mL solution, 0.1 mmol) was diluted with acetonitrile (0.3 mL), treated with methylamine (0.200 mL, 2M in THF, 0.40 mmol), capped and stirred at 50° C. After 2 h, the reaction mixture was cooled down, and treated with magnesium bromide (0.074 g, 0.4 mmol). The mixture was capped and stirred at 50° C. for 15 min, cooled down and partitioned between dichloromethane and 0.5 M HCl. The organic layer was separated and dried over sodium sulfate. After filtering and concentrating in vacuo, the residue was purified by prep HPLC (acetonitrile/water gradient containing 0.1% TFA) to afford the desired compound 23 as a mixture of enantiomers: $^1$H NMR (400 MHz, Chloroform-d) δ 10.34 (s, 1H), 8.40 (s, 1H), 6.66 (t, J=8.3 Hz, 2H), 5.39 (d, J=5.4 Hz, 1H), 4.80-4.58 (m, 3H), 4.22-3.97 (m, 2H), 3.13 (s, 3H), 2.74-2.57 (m, 1H), 2.22-2.04 (m, 1H). LCMS-ESI$^+$ (m/z): [M+H]$^+$ calculated for $C_{19}H_{17}F_3N_3O_5$: 424.11; found: 424.1.

Example 24

Preparation of Compound 24

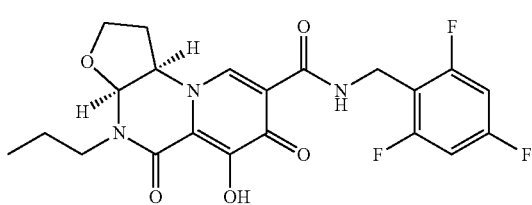

Compound 24 was prepared in a manner similar to Compound 23 using propyl amine at 75° C. in place of methylamine in the final step, affording 24 as a mixture of enantiomers: $^1$H NMR (400 MHz, Chloroform-d) δ 10.41 (s, 1H), 8.44 (s, 1H), 6.66 (t, J=8.2 hz, 2H), 5.44 (d, J=5.2 Hz, 1H), 4.82-4.52 (m, 3H), 4.23-3.99 (m, 2H), 3.76-3.58 (m, 1H), 3.58-3.40 (m, 1H), 2.77-2.57 (m, 1H), 2.31-2.12 (m, 1H), 1.87-1.56 (m, 2H), 1.49-1.35 (m, 1H), 0.98 (t, J=7.4 Hz, 3H). LCMS-ESI$^+$ (m/z): [M+H]$^+$ calculated for $C_{20}H_{19}F_3N_3O_5$: 452.14; found: 452.1.

Example 25

Preparation of Compounds 25a and 25b

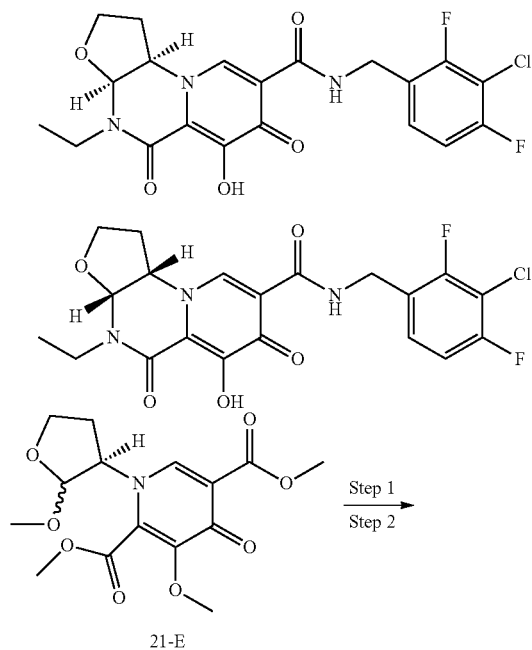

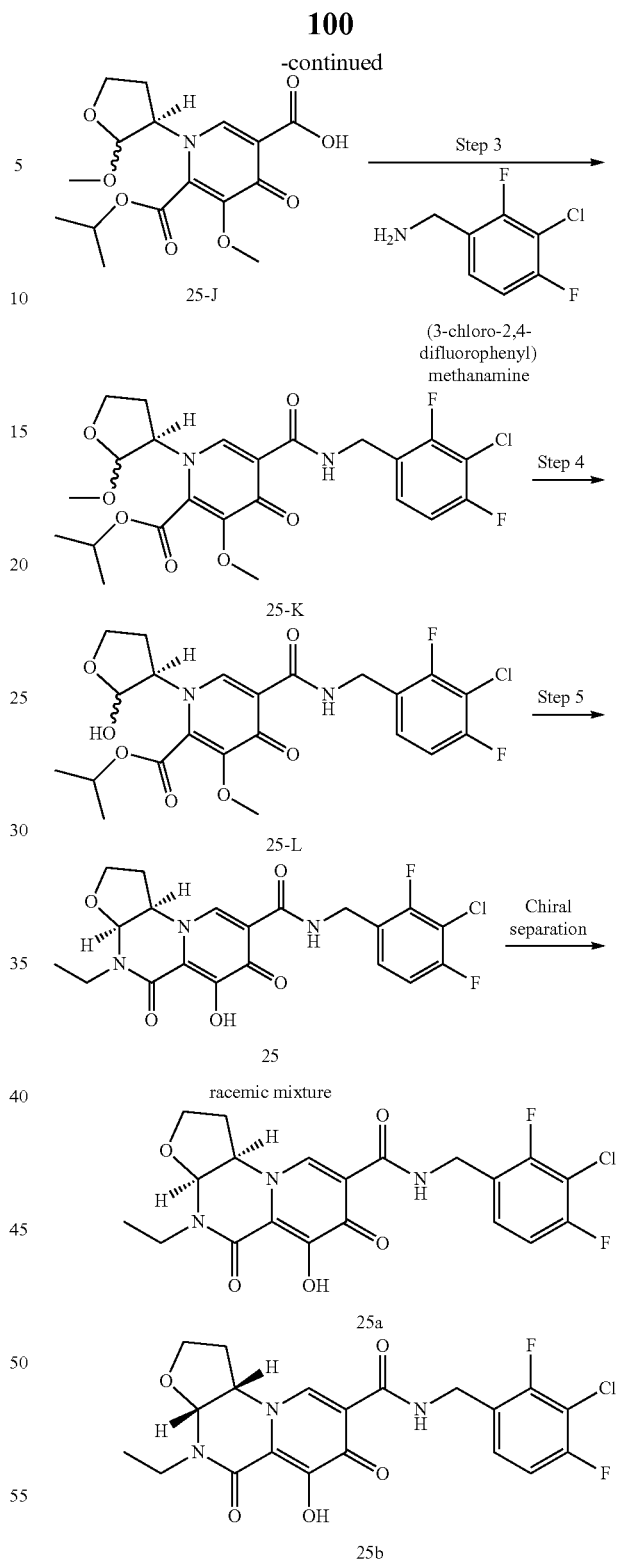

Steps 1 and 2

Diester 21-E (3.80 g, 11.1 mmol) was stirred in THF (14 mL) and methanol (11 mL) until nearly dissolved. Lithium hydroxide (6.97 mL, 2 M aqueous solution, 13.9 mmol) was added in portions over approximately 2 h. After stirring an additional 1 h, the reaction mixture was treated with 0.5 M HCl (35 mL) and ethyl acetate (200 mL). The organic layer was separated. The aqueous was treated with brine and extracted again with ethyl acetate. The combined organic layers were dried over sodium sulfate, filtered and concentrated to afford crude acid which was carried on:

LCMS-ESI⁺ (m/z): [M+H]⁺ calculated for $C_{14}H_{18}NO_8$: 328.10; found: 328.1.

Crude acid (0.500 g, 1.53 mmol) in methyl-THF (6 mL) was added to a solution of lithium isopropoxide (prepared by treating isopropanol (0.351 mL) in methyl-THF with n-BuLi (1.528 mL, 2.5M in hexanes) at 0° C. The reaction mixture was allowed to warm to room temperature. After 16 h the mixture was partitioned between 0.5 M HCl and ethyl acetate. The layers were separated and the aqueous layer was extracted again with ethyl acetate. The combined organics were dried over sodium sulfate, filtered and concentrated to desired isopropyl ester 25-J:

LCMS-ESI⁺ (m/z): [M+H]⁺ calculated for $C_{16}H_{22}NO_8$: 356.13; found: 356.1.

Step 3

Isopropyl ester 25-J (0.543 g, 1.53 mmol) and (3-chloro-2,4-difluorophenyl)methanamine (0.326 g, 1.83 mmol) were suspended in acetonitrile and treated with DIEA (0.546 mL, 3.06 mmol) and HATU (0.697 g, 1.834 mmol). The reaction mixture was capped and stirred at room temperature. After 16 h, the mixture was concentrated and partitioned between ethyl acetate and 0.5 M HCl. The layers were separated and the aqueous layer was extracted again with ethyl acetate. The combined organics were dried over sodium sulfate, filtered and concentrated. The residue was purified by flash chromatography on silica gel (10-60% ethyl acetate: hexanes) to afford desired amide 25-K: LCMS-ESI⁺ (m/z): [M+H]⁺ calculated for $C_{23}H_{26}ClF_2N_2O_7$: 515.14; found: 515.2.

Steps 4 and 5

Steps 4 and 5 were done in a similar manner to Steps 2 and 3 for Compound 23 using ethyl amine in place of methylamine in the final step, affording a mixture of enantiomers which was separated by chiral HPLC on a ChiralPak AD-H column (EtOH) to afford single enantiomers 25a and 25b.

For 25a: ¹H NMR (400 MHz, DMSO-d6) δ 12.81 (s, 1H), 10.40 (t, J=6.2 Hz, 1H), 8.54 (s, 1H), 7.38 (td, J=8.3, 6.2 Hz, 1H), 7.29 (td, J=8.7, 1.3 Hz, 1H), 5.57 (d, J=5.5 Hz, 1H), 5.26-5.14 (m, 1H), 4.68-4.48 (m, 2H), 4.01-3.90 (m, 2H), 3.64-3.42 (m, 2H), 2.65-2.53 (m, 1H), 2.21-2.05 (m, 1H), 1.16 (t, J=7.1 Hz, 3H).

LCMS-ESI⁺ (m/z): [M+H]⁺ calculated for $C_{20}H_{19}ClF_2N_3O_5$: 454.2; found: 454.1.

For 25b: ¹H NMR (400 MHz, DMSO-d6) δ 12.81 (s, 1H), 10.40 (t, J=6.4 Hz, 1H), 8.54 (s, 1H), 7.44-7.33 (m, 1H), 7.29 (td, J=8.7, 1.3 Hz, 1H), 5.57 (d, J=5.6 Hz, 1H), 5.20 (td, J=9.8, 9.3, 5.7 Hz, 1H), 4.68-4.49 (m, 2H), 3.95 (m, 2H), 3.63-3.44 (m, 2H), 2.65-2.53 (m, 1H), 2.20-2.07 (m, 1H), 1.17 (t, J=7.1 Hz, 4H).

LCMS-ESI⁺ (m/z): [M+H]⁺ calculated for $C_{20}H_{19}ClF_2N_3O_5$: 454.2; found: 454.1.

Example 26

Preparation of Compounds 26a and 26b

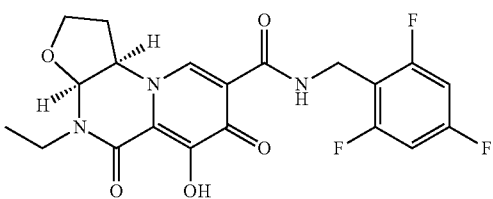

26a

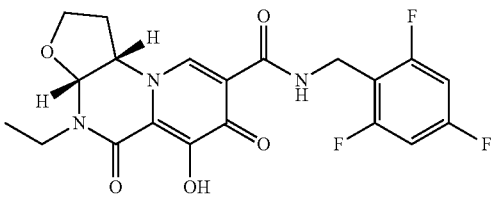

26b

Compounds 26a and 26b were prepared in a manner similar to Compound 23 using ethyl amine in place of methylamine in the final step, affording a mixture of enantiomers which was separated by chiral HPLC on a ChiralPak AD-H column (EtOH) to afford single enantiomers 26a and 26b.

For 26a: ¹H NMR (400 MHz, DMSO-d6) δ 12.79 (s, 1H), 10.44-10.25 (m, 1H), 8.52 (s, 1H), 7.33-7.07 (m, 2H), 5.56 (d, J=5.4 Hz, 1H), 5.29-5.09 (m, 1H), 4.59 (dd, J=14.6, 5.2 Hz, 1H), 4.50 (dd, J=14.2, 5.7 Hz, 1H), 4.01-3.89 (m, 2H), 3.61-3.42 (m, 2H), 2.56 (s, 1H), 2.09 (s, 1H), 1.16 (t, J=7.1 Hz, 3H).

LCMS-ESI⁺ (m/z): [M+H]⁺ calculated for $C_{20}H_{18}F_3N_3O_5$: 438.13; found: 438.2.

For 26b: ¹H NMR (400 MHz, DMSO-d6) δ 12.79 (s, 1H), 10.35 (t, J=6.0 Hz, 1H), 8.52 (s, 1H), 7.20 (t, J=8.7 Hz, 2H), 5.56 (d, J=5.4 Hz, 1H), 5.19 (td, J=8.5, 5.5 Hz, 1H), 4.59 (dd, J=14.8, 6.0 Hz, 1H), 4.50 (dd, J=14.6, 5.7 Hz, 1H), 4.01-3.87 (m, 2H), 3.63-3.42 (m, 2H), 2.64-2.52 (m, 1H), 2.20-2.04 (m, 1H), 1.16 (t, J=7.1 Hz, 3H).

LCMS-ESI⁺ (m/z): [M+H]⁺ calculated for $C_{20}H_{18}F_3N_3O_5$: 438.13; found: 438.2.

Example 27

Preparation of Compound 27

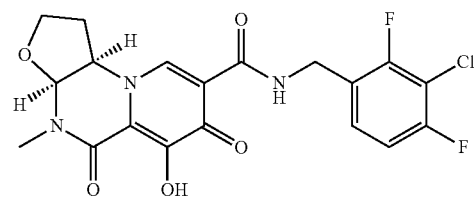

27

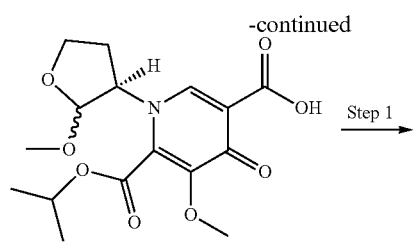

25-J

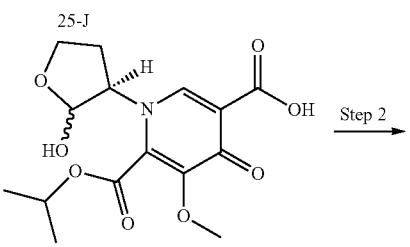

27-N

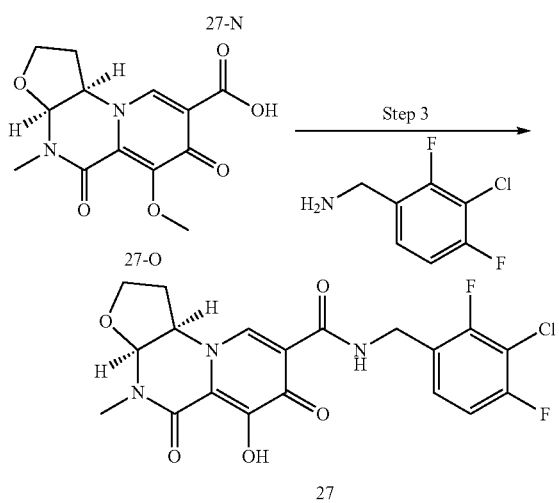

27-O

27

Step 1

Isopropyl ester 25-J (0.232 g, 0.65 mmol) was dissolved in acetonitrile (1.8 mL) and acetic acid (0.2 mL) containing methane sulfonic acid (0.013 mL) and water (0.002 mL). The mixture was capped and stirred at 75° C. After 16 h, the reaction mixture was cooled down to afford the desired lactol 27-N and carried on crude to the next step: LCMS-ESI$^+$ (m/z): [M+H]$^+$ calculated for $C_{15}H_{20}NO_8$: 342.12; found: 342.1.

Step 2

Crude lactol 27-N (0.119 g, 0.35 mmol) solution from the previous step (~1 mL) was treated with potassium carbonate (0.097 g, 0.70 mmol) and methylamine (0.467 mL, 2 M solution in THF, 0.70 mmol), capped and stirred at 50° C. After 50 min, the reaction mixture was cooled down and treated with TFA (0.134 mL, 1.7 mmol). The mixture was concentrated onto silica gel and purified by flash chromatography (5% EtOH:dichloromethane) to afford acid 27-0: LCMS-ESI$^+$ (m/z): [M+H]$^+$ calculated for $C_{13}H_{15}N_2O_6$: 295.09; found: 295.1.

Step 3

Acid 27-0 (0.044 g, 0.150 mmol) and (3-chloro-2,4-difluorophenyl)methanamine (0.053 g, 0.30 mmol) were suspended in acetonitrile and treated with DIEA (0.053 mL, 0.30 mmol) and HATU (0.068 g, 0.179 mmol). The reaction mixture was stirred for a few minutes at room temperature and stored at 10° C. After 3 days, the crude amide was treated with magnesium bromide (0.083 g, 0.45 mmol) and stirred at 50° C. for 10 min. An additional portion of acetonitrile (1 mL) and magnesium bromide (0.041 mg) were added and the mixture was stirred at 50° C. for a few minutes. After cooling, the reaction mixture was partitioned between dichloromethane and 0.5 M HCl. The layers were separated and the organic layer was dried over sodium sulfate, filtered and concentrated. Flash chromatography on silica gel (0-10% ethanol:dichloromethane) afforded the desired product 27 as a mixture of enantiomers: LCMS-ESI$^+$ (m/z): [M+H]$^+$ calculated for $C_{13}H_{15}N_2O_6$: 440.08; found: 440.2.

Example 28

Preparation of Compound 28

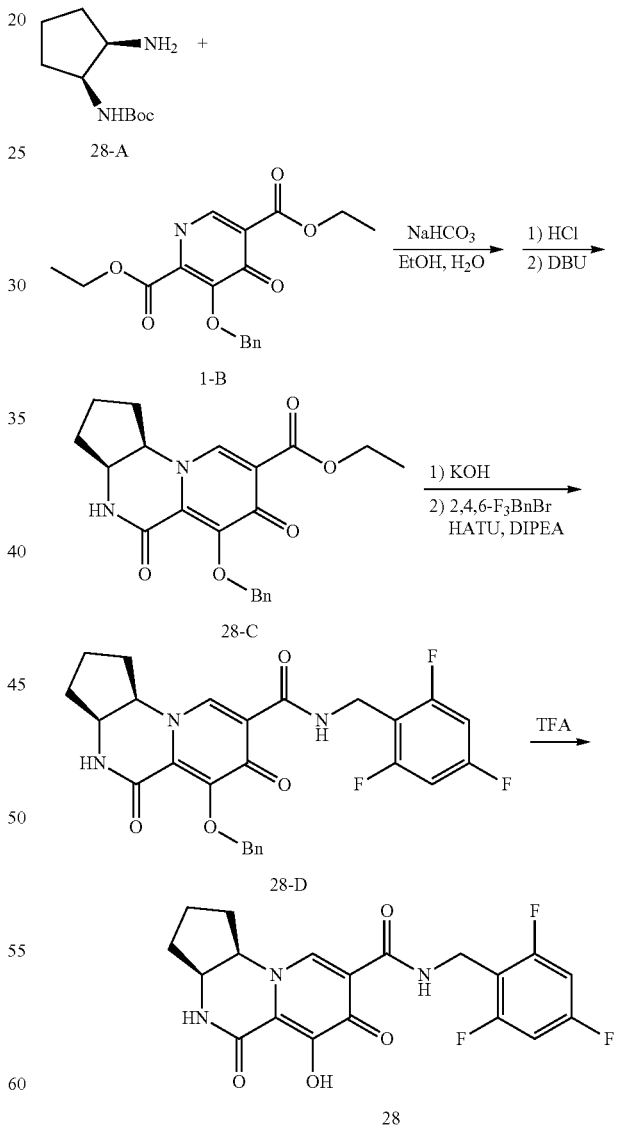

Step 1

A mixture of compound 28-A (501 mg, 2.502 mmol), the pyrone 1-B (865 mg, 2.498 mmol), and NaHCO$_3$ (424 mg, 5.047 mmol) in water (5 mL) and ethanol (5 mL) was stirred at room temperature. After 1.25 h, the reaction mixture was diluted with water and extracted with ethyl acetate (×2). After the extracts were washed with water, the organic fractions were combined, dried (Na$_2$SO$_4$), and concentrated. The residue was dried in vacuo for 30 min, dissolved in dichloromethane (2 mL), and treated with 4 N HCl in dioxane (6 mL) for 1 h. The solution was concentrated, coevaporated with toluene (×1), and dried in vacuum for 30 min A mixture of the residue and DBU (1.5 mL, 10.03 mmol) in toluene (15 mL) was stirred at 100° C. bath. After the mixture was cooled down to room temperature and dissolved with dichloromethane, the solution was concentrated. The residue was purified by column chromatograpy on silica gel (80 g column) using ethyl acetate-20% methanol in ethyl acetate as eluents to obtain compound 28-C. $^1$H NMR (400 MHz, Chloroform-d) δ 8.41 (s, 1H), 7.66-7.53 (m, 2H), 7.37-7.27 (m, 3H), 6.69 (s, 1H), 5.41 (d, J=10.0 Hz, 1H), 5.20 (d, J=10.0 Hz, 1H), 4.43 (q, J=7.2 Hz, 3H), 4.14 (m, 1H), 2.45-2.20 (m, 2H), 2.11-1.80 (m, 4H), 1.42 (t, J=7.1 Hz, 3H). LCMS-ESI$^+$ (m/z): [M+H]$^+$ calculated for C$_{21}$H$_{23}$N$_2$O$_5$: 383.16; found: 383.24.

Step 2

A mixture of the reactant 28-C (50 mg, 0.131 mmol) in THF (1 mL) and ethanol (1 mL) was stirred at room temperature and 1 N KOH (0.26 mL) was added. After 30 min, the reaction mixture was diluted with water and washed with ether (×1). After the aqueous fraction was acidified with 1 N HCl (0.3-0.4 mL), the product was extracted with dichloromethane (×3). The combined extracts were dried (Na$_2$SO$_4$), and concentrated and dried in vacuum to get the crude acid. A mixture of the crude acid, 2,4,6-trifluorobenzylamine (28 mg, 0.174 mmol), and HATU (76 mg, 0.200 mmol) in dichloromethane (5 mL) was stirred at room temperature as DIPEA (0.2 mL, 1.148 mmol) was added. After 30 min, the reaction mixture was diluted with ethyl acetate, washed with saturated NH$_4$Cl (×2), water (×1), saturated NaHCO$_3$ (×2), and brine (×1). After the aqueous fractions were extracted with ethyl acetate (×1), two organic fractions were combined, dried (Na$_2$SO$_4$) and concentrated. The residue was purified by column chromatograpy on silica gel (12 g column) using ethyl acetate as eluent to get compound 28-D. $^1$H NMR (400 MHz, Chloroform-d) δ 10.40 (s, 1H), 8.48 (s, 1H), 7.59-7.53 (m, 2H), 7.32 (dddd, J=12.2, 7.0, 4.5, 2.3 Hz, 3H), 6.74-6.60 (m, 2H), 6.43 (s, 1H), 5.37 (d, J=10.2 Hz, 1H), 5.20 (d, J=10.1 Hz, 1H), 4.75-4.58 (m, 2H), 4.35 (s, 1H), 4.07 (t, J=4.1 Hz, 1H), 2.31 (s, 1H), 2.11-1.77 (m, 5H). $^{19}$F NMR (376 MHz, Chloroform-d) δ −109.05 (s, 1F), −111.85 (s, 2F). LCMS-ESI$^+$ (m/z): [M+H]$^+$ calculated for C$_{26}$H$_{23}$F$_3$N$_3$O$_4$: 498.16; found: 498.10.

Step 3

Compound 28-D (35 mg, 0.070 mmol) was dissolved in trifluoroacetic acid (1 mL) at room temperature and stirred at room temperature. After 30 min, the solution was concentrated and the residue was dissolved in dichloromethane. After the solution was washed with 0.1 N HCl (×1), the aqueous fraction was extracted with dichloromethane (×2). The organic fractions were combined, dried (Na$_2$SO$_4$), and concentrated.

The residue was purified by column chromatography on silica gel (12 g column) using dichloromethane-20% methanol in dichloromethane as eluents to give compound 28. $^1$H NMR (400 MHz, Chloroform-d) δ 12.35 (s, 1H), 10.47 (t, J=5.7 Hz, 1H), 8.55 (s, 1H), 7.40 (s, 1H), 6.74-6.52 (m, 2H), 4.70 (dd, J=14.5, 5.8 Hz, 1H), 4.61 (dd, J=14.5, 5.6 Hz, 1H), 4.52 (td, J=8.7, 4.5 Hz, 1H), 4.35-4.18 (m, 1H), 2.32 (dq, J=11.8, 7.6, 6.3 Hz, 1H), 2.22-1.97 (m, 3H), 1.90 (dq, J=17.2, 10.0, 8.1 Hz, 2H). $^{19}$F NMR (376 MHz, Chloroform-d) 6-108.93 (ddd, J=15.1, 8.6, 6.0 Hz, 1F), −112.07 (t, J=6.9 Hz, 2F). LCMS-ESI$^+$ (m/z): [M+H]$^+$ calculated for C$_{19}$H$_{17}$F$_3$N$_3$O$_4$: 408.12; found: 408.12.

Example 29

Preparation of Compound 29

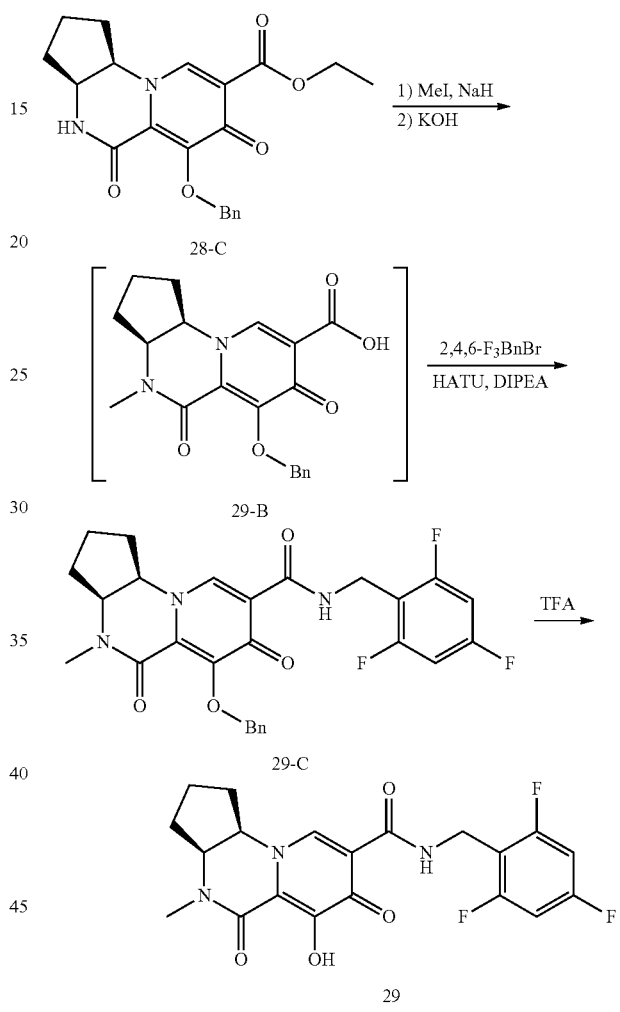

Step 1

To a mixture of compound 28-C (129 mg, 0.337 mmol) in THF (3 mL) was added 60% NaH (30 mg, 0.75 mmol) at room temperature. After 5 min, MeI (0.03 mL, 0.482 mmol) was added. After stirring at room temperature for 1 h, water was added (~3 mL) to the mixture. After ~15 min, 1 N KOH (0.5 mL) was added to complete the hydrolysis. After 10 min, the reaction mixture was diluted with water, and washed with ether (×1). The aqueous fraction was acidified with 1 N HCl (~1 mL), and the product was extracted with dichloromethane (×3). After the extracts were washed with water (×1), the extracts were combined, dried (Na$_2$SO$_4$), and concentrated to get the crude acids 29-B. A mixture of the crude acid 29-B, the 2,4,6-trifluorobenzylamine (75 mg, 0.465 mmol), and HATU (195 mg, 0.513 mmol) in dichloromethane (5 mL) was stirred at room temperature as DIPEA (0.55 mL, 3.158 mmol) was added. After 30 min, the reaction mixture was diluted with ethyl acetate, washed with saturated NH₄Cl (×2), water (×1), saturated NaHCO₃ (×2), and brine (×1). After the aqueous fractions were extracted with ethyl acetate (×1), two organic fractions were combined, dried (Na₂SO₄), and concentrated. The residue was purified by column chromatography on silica gel (12 g column) using ethyl acetate as eluent to get 126 mg of the partially purified compound 29-C. LCMS-ESI⁺ (m/z): [M+H]+ calculated for $C_{27}H_{25}F_3N_3O_4$: 512.18; found: 512.16.

Step 2

The partially purified compound 29-C (126 mg) was dissolved in TFA (1.5 mL) at room temperature and stirred at room temperature. After 30 min, the solution was concentrated and the residue was dissolved in DMF before filtered (~2.8 mL). The solution was injected on preparative HPLC. The combined fraction of the desired product was concentrated to remove most of acetonitrile, and the product was extracted with dichloromethane (×2), the extracts were washed with water (×1), dried (Na₂SO₄), and concentrated to give compound 29. ¹H NMR (400 MHz, Chloroform-d) δ 12.79 (s, 1H), 10.42 (t, J=5.7 Hz, 1H), 8.38 (s, 1H), 6.78-6.45 (m, 2H), 4.69 (dd, J=14.5, 5.8 Hz, 1H), 4.64-4.55 (m, 1H), 4.50 (q, J=6.9 Hz, 1H), 4.10 (q, J=4.6 Hz, 1H), 3.11 (s, 3H), 2.31 (dq, J=14.0, 7.3 Hz, 1H), 2.10 (dt, J=7.3, 4.4 Hz, 2H), 1.99 (m, 1H), 1.91-1.76 (m, 2H). ¹⁹F NMR (376 MHz, Chloroform-d) δ -109.22 (p, J=7.7 Hz, 1F), -111.83--112.22 (m, 2F). LCMS-ESI⁺ (m/z): [M+H]⁺ calculated for $C_{20}H_{19}F_3N_3O_4$: 422.13; found: 422.19.

Example 30

Preparation of Compound 30

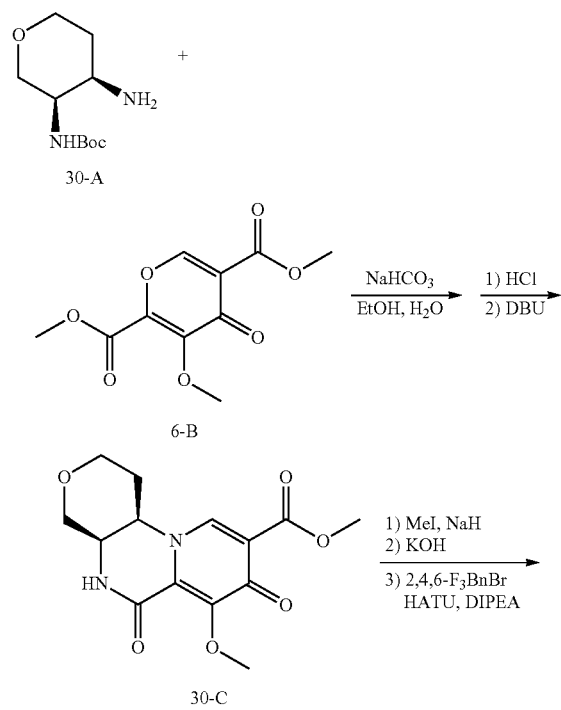

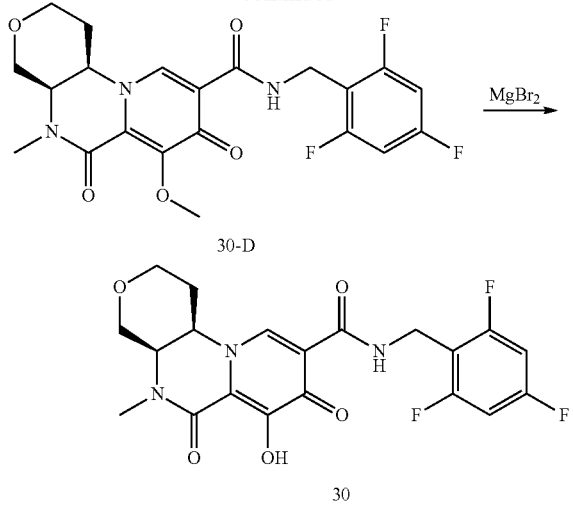

Step 1

A mixture of compound 30-A (553 mg, 2.556 mmol), the pyrone 6-B (619 mg, 2.556 mmol), and NaHCO₃ (435 mg, 5.178 mmol) in water (5 mL) and ethanol (5 mL) was stirred at room temperature. After 30 min, the reaction mixture was concentrated to remove most of the solvent and the residue was mixed with dichloromethane (about 40 mL) and stirred vigorously before drying (MgSO₄). The dried solution was concentrated. The residue was dissolved in Dichloromethane (2 mL) and treated with 4 N HCl in dioxane (6 mL). After 40 min, the mixture was concentrated and dried in vacuum overnight. A mixture of the residue and DBU (1.9 mL, 12.71 mmol) in toluene (19 mL) was stirred at 100° C. After 30 min, the reaction mixture was cooled down to room temperature, dissolved in dichloromethane, and concentrated. The residue was purified by column chromatograpy on silica gel (40 g column) using ethyl acetate-20% methanol in ethyl acetate as eluents to obtain impure compound 30-C. The impure compound 30-C was dissolved in DMF and purified by preparative HPLC to get compound 30-C as 1:1 mixture with trifluoroacetic acid. ¹H NMR (400 MHz, Chloroform-d) δ 9.92 (s, 1H), 8.33 (s, 1H), 7.67 (s, 1H), 4.51 (dt, J=12.2, 4.1 Hz, 1H), 4.21-4.04 (m, 3H), 3.95 (s, 3H), 3.84 (s, 3H), 3.73 (d, J=12.8 Hz, 1H), 3.54 (td, J=12.3, 2.2 Hz, 1H), 2.24 (qd, J=12.6, 4.8 Hz, 1H), 1.94 (dd, J=13.1, 4.9 Hz, 1H). LCMS-ESI⁺ (m/z): [M+H]⁺ calculated for $C_{14}H_{17}N_2O_6$: 309.11; found: 309.17.

Step 2

To a mixture of compound 30-C, TFA (85 mg, 0.201 mmol) and 60% NaH (40 mg, 1 mmol) was added THF (3 mL) at room temperature. After 5 min, MeI (0.04 mL, 0.643 mmol) was added. After stirring at room temperature for about 40 min, DMF (1 mL) was added. After the mixture was stirred at room temperature overnight, 1 N HCl (~1.5 mL) was added to the reaction mixture and the resulting mixture was concentrated to almost dryness to get the crude acid.

A mixture of the crude acid, 2,4,6-trifluorobenzylamine (96 mg, 0.596 mmol), and HATU (204 mg, 0.537 mmol) in dichloromethane (3 mL) was stirred at room temperature as DIPEA (0.5 mL, 2.871 mmol) was added. After 30 min, the reaction mixture was diluted with ethyl acetate, washed with saturated NH₄Cl (×2), water (×1), saturated NaHCO₃ (×2), and brine (×1). After the aqueous fractions were extracted with ethyl acetate (×1), two organic fractions were combined, dried (Na$_2$SO$_4$) and concentrated. The residue was purified by column chromatograpy on silica gel (12 g column) using ethyl acetate-20% methanol in ethyl acetate as eluent to get compound 30-D $^1$H NMR (400 MHz, Chloroform-d) δ 10.37 (d, J=7.3 Hz, 1H), 8.46 (s, 1H), 6.81-6.54 (m, 2H), 4.63 (d, J=5.6 Hz, 2H), 4.34 (d, J=11.1 Hz, 1H), 4.31-4.22 (m, 1H), 4.02 (s, 3H), 4.01-3.92 (m, 1H), 3.86 (d, J=3.2 Hz, 1H), 3.65 (dd, J=13.4, 1.9 Hz, 1H), 3.62-3.55 (m, 1H), 3.22 (s, 3H), 2.23 (qd, J=10.8, 4.5 Hz, 1H), 2.01-1.90 (m, 1H). $^{19}$F NMR (377 MHz, Chloroform-d) δ −108.92 (s, 1F), −112.01 (s, 2F). LCMS-ESI$^+$ (m/z): [M+H]$^+$ calculated for C$_{21}$H$_{21}$F$_3$N$_3$O$_5$: 452.14; found: 452.11.

Step 3

To a solution of compound 30-D (48 mg, 0.106 mmol) in MeCN (3 mL) was added MgBr$_2$ (60 mg, 0.326 mmol) at room temperature and the resulting mixture was stirred at 50° C. After 30 min, the reaction mixture was stirred at 0° C. and 1 N HCl (~1 mL) was added to make the mixture a solution and diluted with water before the product was extracted with dichloromethane (×3). The combined extracts were dried (Na$_2$SO$_4$) and concentrated. The residue was purified by column chromatograpy on silica gel (12 g column) using dichloromethane and 20% methanol in dichloromethane as eluents to obtain compound 30.

$^1$H NMR (400 MHz, Chloroform-d) δ 10.37 (d, J=7.3 Hz, 1H), 8.46 (s, 1H), 6.81-6.54 (m, 2H), 4.63 (d, J=5.6 Hz, 2H), 4.34 (d, J=11.1 Hz, 1H), 4.31-4.22 (m, 1H), 4.02 (s, 3H), 4.01-3.92 (m, 1H), 3.86 (d, J=3.2 Hz, 1H), 3.65 (dd, J=13.4, 1.9 Hz, 1H), 3.62-3.55 (m, 1H), 3.22 (s, 3H), 2.23 (qd, J=10.8, 4.5 Hz, 1H), 2.01-1.90 (m, 1H). $^{19}$F NMR (377 MHz, Chloroform-d) δ −108.92 (s, 1F), −112.01 (s, 2F). LCMS-ESt (m/z): [M+H]$^+$ calculated for C$_{20}$H$_{19}$F$_3$N$_3$O$_5$: 438.13; found: 438.29.

Example 31

Preparation of Compound 31

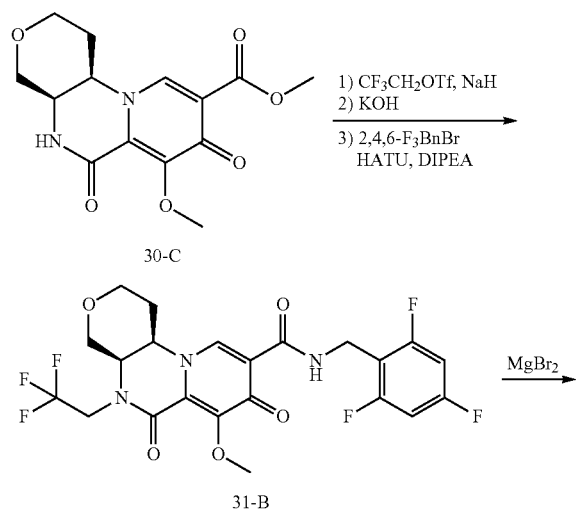

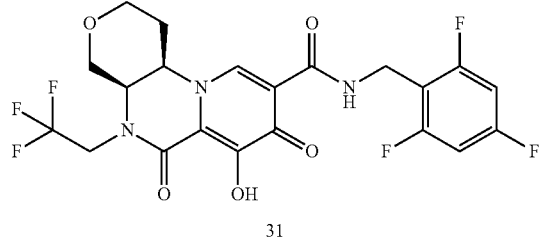

Step 1

To a mixture of compound 30-C (97 mg, 0.230 mmol) and 60% NaH (46 mg, 1.15 mmol) was added THF (2 mL) and DMF (0.5 mL) at room temperature. After 5 min, CF$_3$CH$_2$OTf (0.1 mL, 0.694 mmol) was added. After stirring at room temperature for ~40 min, additional DMF (1 mL) was added. After 2 h, water (~2 mL) was added to the reaction mixture and after about 15 min at room temperature, the mixture was stirred in an ice bath while 1 N KOH (0.5 mL) was added. After about 30 min, the resulting mixture was acidified with 1 N HCl (2 mL) and concentrated to almost dryness to get the crude acid.

A mixture of the crude acid, 2,4,6-trifluorobenzylamine (96 mg, 0.596 mmol), and HATU (272 mg, 0.715 mmol) in dichloromethane (3 mL) was stirred at room temperature as DIPEA (0.5 mL, 2.871 mmol) was added. After 30 min, the reaction mixture was diluted with ethyl acetate, washed with saturated NH$_4$Cl (×2), water (×1), saturated NaHCO$_3$ (×2), and brine (×1). After the aqueous fractions were extracted with ethyl acetate (×1), two organic fractions were combined, dried (Na$_2$SO$_4$) and concentrated. The residue was purified by column chromatography on silica gel (12 g column) using ethyl acetate-20% methanol in ethyl acetate as eluent to get compound 31-B, which contained 10-15% of impurities. $^1$H NMR (400 MHz, Chloroform-d) δ 10.30 (s, 1H), 8.49 (s, 1H), 6.64 (t, J=8.1 Hz, 2H), 5.16 (dq, J=18.5, 9.5 Hz, 1H), 4.71-4.50 (m, 2H), 4.43 (dt, J=11.8, 3.6 Hz, 1H), 4.34 (d, J=14.7 Hz, 1H), 4.06 (s, 1H), 4.02 (s, 4H), 3.79 (dq, J=16.3, 8.2 Hz, 1H), 3.69 (d, J=14.3 Hz, 1H), 3.62 (dd, J=11.9, 2.6 Hz, 1H), 2.23-2.07 (m, 1H), 1.97 (dd, J=12.4, 4.0 Hz, 1H). $^{19}$F NMR (377 MHz, Chloroform-d) δ −69.91 (t, J=8.8 Hz, 3F), −71.39, −73.29, −108.51 (s, 1F), −112.21 (t, J=7.0 Hz, 2F). LCMS-ESI$^+$ (m/z): [M+H]$^+$ calculated for C$_{22}$H$_{20}$F$_6$N$_3$O$_5$: 520.13; found: 520.22.

Step 2

To a solution of the reactant 31-B (32 mg, 0.062 mmol) in MeCN (3 mL) was added MgBr$_2$ (34 mg, 0.185 mmol) at room temperature and the resulting mixture was stirred at 50° C. After 30 min, the reaction mixture was stirred at 0° C. and 1 N HCl was added to make the mixture a solution (~1 mL). The resulting solution was further diluted with water before the product was extracted with dichloromethane (×3). The combined extracts were dried (Na$_2$SO$_4$) and concentrated. The residue was purified by preparative HPLC and freeze-dried to get compound 31 as 1:1 mixture with CF$_3$COOH. $^1$H NMR (400 MHz, Chloroform-d) δ 10.50 (t, J=5.8 Hz, 1H), 8.59 (s, 1H), 6.67 (t, J=8.1 Hz, 2H), 5.09 (dq, J=18.3, 9.2 Hz, 1H), 4.72 (dd, J=14.5, 5.4 Hz, 1H), 4.63 (dd, J=14.5, 5.2 Hz, 1H), 4.43 (t, J=13.0 Hz, 2H), 4.13 (s, 1H), 4.06 (d, J=11.8 Hz, 1H), 3.80 (dq, J=17.1, 9.1, 8.6 Hz, 1H), 3.75-3.58 (m, 2H), 2.16 (s, 1H), 1.94 (d, J=13.9 Hz, 1H). $^{19}$F NMR (377 MHz, Chloroform-d) δ −69.07 (t, J=8.6 Hz, 3F), −76.38 (s, 3F), −108.45 (m, 1F), −112.06 (m, 2F). LCMS-ESI$^+$ (m/z): [M+H]$^+$ calculated for C$_{21}$H$_{18}$F$_6$N$_3$O$_5$: 506.12; found: 506.33.

Example 32

Preparation of Compound 32

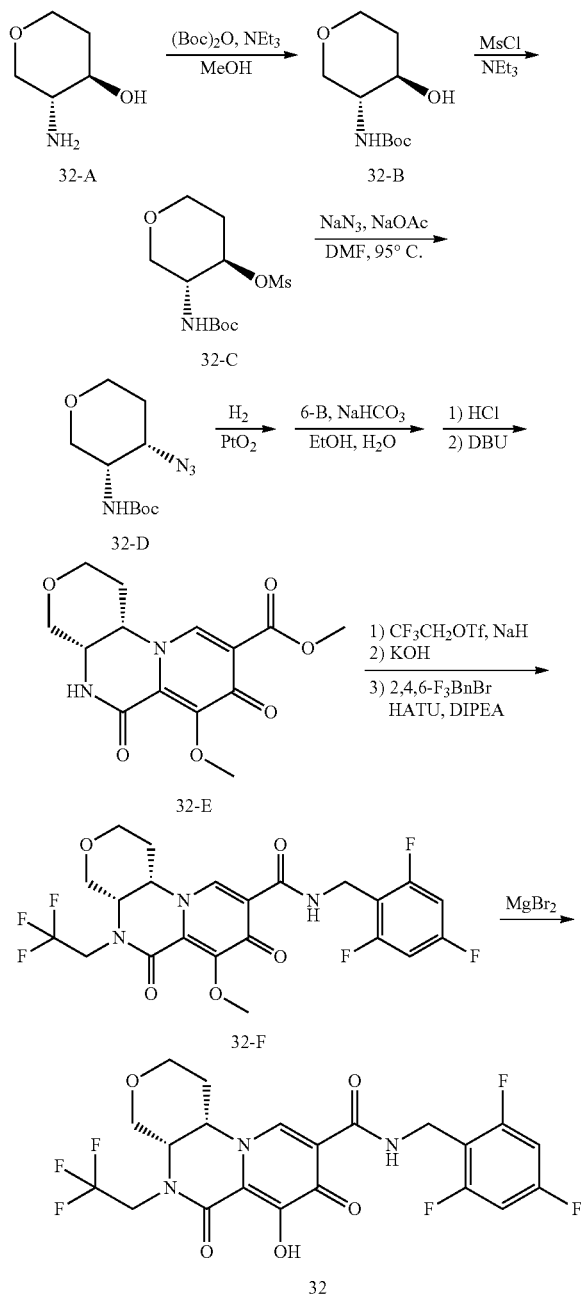

Step 1

A solution of compound 32-A (2010 mg, 17.160 mmol) and Boc$_2$O (4128 mg, 18.910 mmol) in methanol (40 mL) was stirred at 0° C. as NEt$_3$ (2.9 mL, 20.81 mmol) was added. The resulting mixture was stirred at 0° C. for 2 h and then stirred at room temperature for 17 h. The solution was concentrated and the residue was dissolved in ethyl acetate before washing with water (×2). After the aqueous fractions were extracted with ethyl acetate (×1), the organic fractions were combined, dried (Na$_2$SO$_4$), and concentrated. The residue was purified by column chromatography on silica gel (120 g column) using hexanes-ethyl acetate as eluents to get compound 32-B. $^1$H NMR (400 MHz, Chloroform-d) δ 4.67 (s, 1H), 4.01 (dd, J=11.3, 4.2 Hz, 1H), 3.91 (dt, J=11.7, 4.5 Hz, 1H), 3.65 (q, J=7.1, 6.6 Hz, 1H), 3.47 (br, 1H), 3.44 (ddd, J=12.0, 9.4, 3.1 Hz, 1H), 3.24-3.08 (m, 1H), 2.01 (dtd, J=13.7, 4.7, 3.1 Hz, 1H), 1.64 (dtd, J=13.4, 9.1, 4.3 Hz, 1H), 1.45 (s, 9H). LCMS-ESI$^+$ (m/z): [M+H–C$_4$H$_8$]$^+$ calculated for C$_6$H$_{12}$NO$_4$: 162.08; found: 161.93.

Step 2

A solution of compound 32-B (2493 mg, 11.47 mmol) and triethylamine (1.95 mL, 13.99 mmol) in dichloromethane (40 mL) was stirred at 0° C. as Mesyl chloride (1 mL, 12.92 mmol) was added dropwise. After 20 min at 0° C., the mixture was stirred at room temperature for 30 min. The reaction mixture was diluted with ethyl acetate and washed with water. After the aqueous fractions were extracted with ethyl acetate (×1), the organic fractions were combined, dried (Na$_2$SO$_4$), and concentrated to obtain compound 32-C after drying in vacuum. $^1$H NMR (400 MHz, Chloroform-d) δ 4.96 (s, 1H), 4.74 (td, J=6.7, 4.0 Hz, 1H), 4.00 (dd, J=11.9, 3.6 Hz, 1H), 3.86 (ddd, J=11.5, 7.7, 3.5 Hz, 1H), 3.66 (s, 1H), 3.60 (ddd, J=11.4, 6.6, 3.9 Hz, 1H), 3.45 (dd, J=11.9, 5.9 Hz, 1H), 3.09 (s, 3H), 2.19 (ddd, J=12.2, 8.0, 4.0 Hz, 1H), 1.93 (d, J=13.3 Hz, 1H), 1.45 (s, 9H). LCMS-ESI$^+$ (m/z): [M+H–C$_4$H$_8$]$^+$ calculated for C$_7$H$_{14}$NO$_6$S: 240.05; found: 239.73.

Step 3

A mixture of compound 32-C (3389 mg, 11.47 mmol), sodium acetate (1890 mg, 23.04 mmol), and sodium azide (1496 mg, 23.01 mmol) in DMF (20 mL) was stirred at 95° C. bath for 6.5 h. The mixture was diluted with water and the product was extracted with ethyl acetate (×2). After the extracts were washed with water (×1), they were combined, dried (Na$_2$SO$_4$), and concentrated. The residue was purified by column chromatograpy on silica gel (120 g column) using hexanes-ethyl acetate as eluents to get compound 32-D. $^1$H NMR (400 MHz, Chloroform-d) δ 4.82 (s, 1H), 3.89 (m, 2H), 3.74 m, 1H), 3.62 (dt, J=9.6, 4.9 Hz, 2H), 3.51 (dd, J=11.4, 7.5 Hz, 1H), 2.01-1.82 (m, 2H), 1.46 (s, 9H).

Step 4

A mixture of compound 32-D (2.066 g, 8.528 mmol) and PtO$_2$ (201 mg, 0.885 mmol) in ethanol (30 mL) was stirred under H$_2$ atmosphere. After 2.5 h, the mixture was filtered through celite. After the celite pad was washed with ethanol (~10 mL), the filtrate and washing were concentrated to obtain the crude amine.

The mixture of the crude amine, compound 6-B (2070 mg, 8.547 mmol), and sodium bicarbonate (1432 mg, 17.05 mmol) in water (~15 mL) and ethanol (~20 mL) was stirred at room temperature. After 30 min, the reaction mixture was concentrated to remove most of the solvent and the residue was dissolved in dichloromethane (~100 mL). After the resulting mixture was dried (MgSO$_4$), and concentrated, the residue was dissolved in dichloromethane (8 mL) and treated with 4 N HCl in dioxane (24 mL). After stirring at room temperature for 2.5 h, the mixture was concentrated and dried in vacuum.

The residue and DBU (6.4 mL, 42.64 mmol) were dissolved in MeOH (50 mL) and stirred at room temperature for 20 min After dilution with toluene (~20 mL), the solution was concentrated and purified by column chromatography on silica gel (120 g column) using ethyl acetate-20% MeOH in ethyl acetate as eluents to get compound 32-E. $^1$H NMR (400 MHz, Chloroform-d) δ 8.27 (d, J=1.3 Hz, 1H), 6.98 (s, 1H), 4.43-4.29 (m, 1H), 4.17-4.08 (m, 2H), 4.08-4.05 (m, 2H), 4.03 (s, 3H), 3.90 (s, 3H), 3.72 (dd, J=13.1, 1.6 Hz, 1H), 3.53 (td, J=12.4, 2.2 Hz, 1H), 2.26 (qd, J=12.7, 4.9 Hz, 1H), 1.93 (dd, J=13.3, 4.8 Hz, 1H). LCMS-ESI+ (m/z): [M+H]+ calculated for $C_{14}H_{17}N_2O_6$: 309.11; found: 309.06.

Step 5

To a mixture of compound 32-E (251 mg, 814 mmol) and 60% NaH (132 mg, 3.300 mmol) was added THF (4 mL) and DMF (2 mL) at room temperature. After 5 min, CF$_3$CH$_2$OTf (0.35 mL, 2.429 mmol) was added. After stirring at room temperature for ~30 min, the reaction mixture was stirred at 0° C. while 1 N KOH (2 mL) was added. After 10 min, the resulting mixture was acidified with concentrated HCl (~0.45 mL) and concentrated to almost dryness to get the crude acid.

A mixture of the crude acid, 2,4,6-trifluorobenzylamine (153 mg, 0.950 mmol), and HATU (626 mg, 1.647 mmol) in dichloromethane (7 mL) was stirred at room temperature as DIPEA (1 mL, 5.741 mmol) was added. After 30 min, the reaction mixture was diluted with ethyl acetate, washed with saturated NH$_4$Cl (×2), water (×1), saturated NaHCO$_3$ (×2), water (×1), and brine (×1). After the aqueous fractions were extracted with ethyl acetate (×1), two organic fractions were combined, dried (Na$_2$SO$_4$), and concentrated. The residue was purified by column chromatograpy on silica gel (40 g column) using Hexane-ethyl acetate-20% MeOH in ethyl acetate as eluents to get compound 32-F. $^1$H NMR (400 MHz, Chloroform-d) δ 10.29 (t, J=5.3 Hz, 1H), 8.44 (s, 1H), 6.77-6.50 (m, 2H), 5.15 (dq, J=18.4, 9.5 Hz, 1H), 4.72-4.56 (m, 2H), 4.33 (d, J=14.4 Hz, 2H), 4.09-3.98 (m, 2H), 4.02 (s, 3H), 3.79 (dq, J=16.3, 8.3 Hz, 1H), 3.72-3.65 (m, 1H), 3.65-3.59 (m, 1H), 2.28-2.09 (m, 1H), 2.02-1.92 (m, 1H). $^{19}$F NMR (376 MHz, Chloroform-d) δ −69.87 (t, J=8.8 Hz, 3F), −108.85 (p, J=7.5 Hz, 1F), −112.05 (t, J=6.9 Hz, 2F). LCMS-ESI+ (m/z): [M+H]+ calculated for $C_{22}H_{20}F_6N_3O_5$: 520.13; found: 520.34.

Step 6

To a solution of compound 32-F (139 mg, 0.268 mmol) in MeCN (3 mL) was added MgBr$_2$ (129 mg, 0.701 mmol) at room temperature and the resulting mixture was stirred at 50° C. bath for 30 min. The reaction mixture was stirred at 0° C. and as 1 N HCl (~1 mL) was added to make the mixture a solution. The resulting solution was further diluted with water before the product was extracted with dichloromethane (×3). The combined extracts were dried (Na$_2$SO$_4$) and concentrated. The residue was purified by column chromatography on silica gel (24 g column) using dichloromethane-20% MeOH in dichloromethane as eluents to get compound 32. $^1$H NMR (400 MHz, Chloroform-d) δ 11.84 (s, 1H), 10.27 (t, J=5.9 Hz, 1H), 8.41 (s, 1H), 6.83-6.49 (m, 2H), 5.08 (dq, J=15.6, 9.2 Hz, 1H), 4.76-4.54 (m, 2H), 4.45 (s, 1H), 4.39 (d, J=14.0 Hz, 1H), 4.21-4.12 (m, 1H), 4.08-4.00 (m, 1H), 3.80 (dt, J=15.9, 8.0 Hz, 1H), 3.75-3.60 (m, 2H), 2.17 (d, J=12.8 Hz, 1H), 1.93 (d, J=13.0 Hz, 1H). $^{19}$F NMR (376 MHz, Chloroform-d) δ −69.10 (t, J=8.5 Hz, 3F), −108.95 (s, 1F), −111.36--112.46 (m, 2F). LCMS-ESI+ (m/z): [M+H]+ calculated for $C_{21}H_{18}F_6N_3O_5$: 506.12; found: 506.31.

Example 33

Preparation of Compound 33

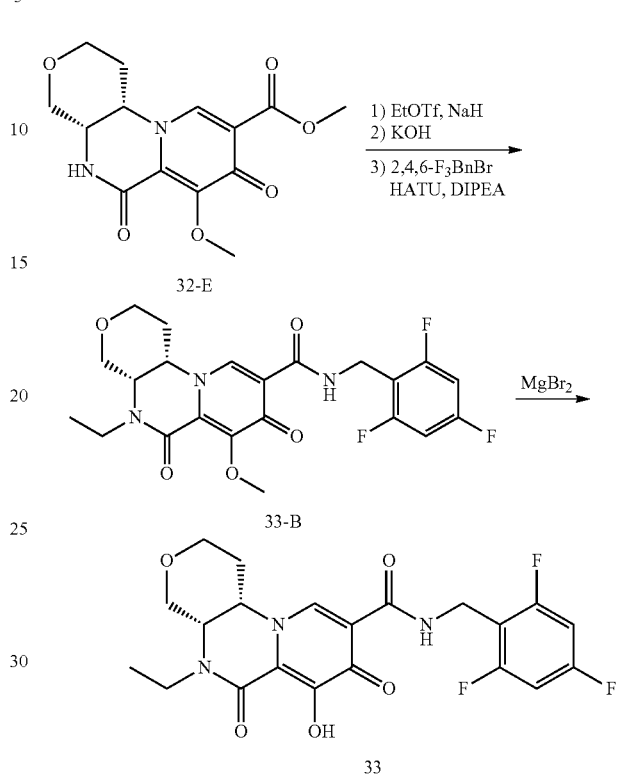

Step 1

To a mixture of compound 32-E (132 mg, 428 mmol) and 60% NaH (75 mg, 1.875 mmol) was added THF (2 mL) and DMF (1 mL) at room temperature. After 5 min, EtOTf (0.17 mL, 1.311 mmol) was added. After 1 h, additional 60% NaH (35 mg, 0.875 mmol) and EtOTf (0.08 mL, 0.617 mmol) were added. After 30 min, water (0.5 mL) was added to the reaction mixture. After 30 min, the reaction mixture was concentrated and the residual residue was coevaporated with toluene (×1) to get the crude acid.

A mixture of the crude acid, 2,4,6-trifluorobenzylamine (833 mg, 0.515 mmol), and HATU (327 mg, 0.860 mmol) in dichloromethane (4 mL) was stirred at room temperature as DIPEA (0.55 mL, 3.158 mmol) was added. After 30 min, the reaction mixture was diluted with ethyl acetate, washed with saturated NH$_4$Cl (×2), water (×1), saturated NaHCO$_3$ (×2), and brine (×1). After the aqueous fractions were extracted with ethyl acetate (×1), two organic fractions were combined, dried (Na$_2$SO$_4$) and concentrated. The residue was purified by preparative HPLC and the product containing fractions were pooled and concentrated to remove MeCN. The remained aqueous mixture was neutralized with sodium bicarbonate, diluted with brine, and the product was extracted with dichloromethane (×3). After the extracts were washed with water (×1), the organic fractions were combined, dried (Na$_2$SO$_4$), and concentrated to get compound 33-B.

$^1$H NMR (400 MHz, Chloroform-d) δ 10.51-10.17 (m, 1H), 8.44 (s, 1H), 6.66 (t, J=8.1 Hz, 2H), 4.74-4.54 (m, 2H), 4.33 (dt, J=8.2, 3.6 Hz, 1H), 4.11 (dt, J=15.3, 7.6 Hz, 1H), 4.03 (s, 3H), 4.01 (m, 1H), 3.84 (dq, J=8.2, 5.0, 3.8 Hz, 2H), 3.67 (dtd, J=11.9, 8.9, 7.7, 4.1 Hz, 2H), 3.37 (dq, J=14.2, 7.1 Hz, 1H), 2.37 (dtd, J=13.3, 9.0, 4.0 Hz, 1H), 2.05 (dd, J=8.0, 3.9 Hz, 1H), 1.23 (t, J=7.1 Hz, 3H). $^{19}$F 19F NMR (376 MHz, Chloroform-d) δ −108.99 (p, J=7.5 Hz, 1F), −111.82−−112.20 (m, 2F). LCMS-ESI$^+$ (m/z): [M+H]$^+$ calculated for $C_{22}H_{23}F_3N_3O_5$: 466.16; found: 466.24.

Step 2

To a solution of compound 33-B (32 mg, 0.062 mmol) in MeCN (3 mL) was added MgBr$_2$ (34 mg, 0.185 mmol) at room temperature and the resulting mixture was stirred at 50° C. bath. After 30 min, the reaction mixture was stirred at 0° C. and added 1 N HCl (~1 mL) to make the mixture a solution. The resulting solution was further diluted with water before the product was extracted with dichloromethane (×3). The combined extracts were dried (Na$_2$SO$_4$) and concentrated. The residue was purified by preparative HPLC and freeze-dried to get compound 33 as 1:1 mixture with CF$_3$COOH. $^1$H NMR (400 MHz, Chloroform-d) δ 10.57 (d, J=6.5 Hz, 1H), 8.56 (s, 1H), 6.67 (dd, J=8.8, 7.5 Hz, 2H), 4.76-4.57 (m, 2H), 4.43 (dt, J=10.7, 4.0 Hz, 1H), 4.26 (d, J=13.6 Hz, 1H), 4.15 (dq, J=14.6, 7.3 Hz, 1H), 4.05-3.92 (m, 2H), 3.76-3.61 (m, 2H), 3.42 (dq, J=14.2, 7.0 Hz, 1H), 2.40-2.16 (m, 1H), 1.99-1.88 (m, 1H), 1.26 (t, J=7.2 Hz, 3H). $^{19}$F NMR (376 MHz, Chloroform-d) δ −76.38 (s, 3F), −108.50 (ddd, J=15.2, 8.8, 6.5 Hz, 1F), −112.04 (t, J=7.1 Hz, 2F). LCMS-ER$^+$ (m/z): [M+H]$^+$ calculated for $C_{21}H_{21}F_3N_3O_5$: 452.14; found: 452.43.

Example 34

Preparation of Compound 34

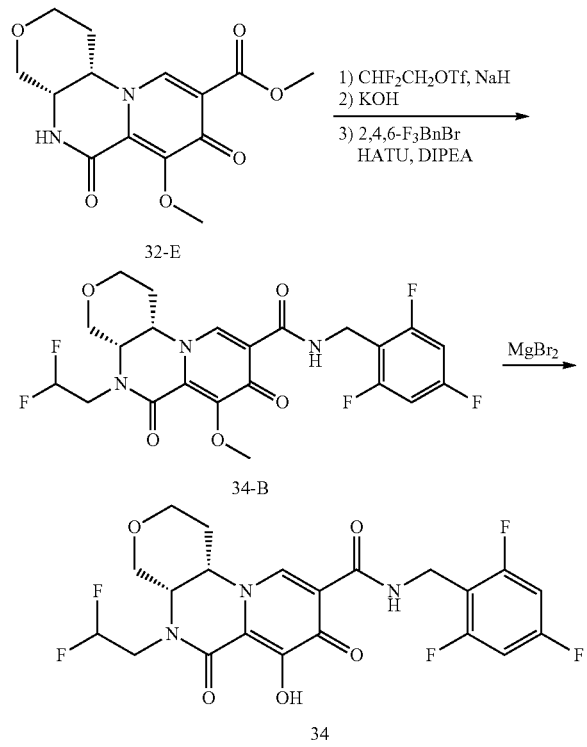

Step 1

To a mixture of compound 32-E (162 mg, 0.525 mmol) and 60% NaH (90 mg, 2.25 mmol) was added DMF (4 mL) at 0° C. After 20 min, CHF$_2$CH$_2$OTf (~0.22 mL, 360 mg, 1.681 mmol) was added. After stirring at room temperature for ~15 min, the reaction mixture was stirred at 0° C. and added 1 N KOH (1 mL). After 10 min, the mixture was acidified with concentrated HCl (0.35 mL), and concentrated to almost dryness to get the crude acid.

A mixture of the crude acid, 2,4,6-trifluorobenzylamine (95 mg, 0.590 mmol), and HATU (400 mg, 1.052 mmol) in dichloromethane (5 mL) was stirred at room temperature as DIPEA (0.65 mL, 3.732 mmol) was added. After 20 min, the reaction mixture was diluted with ethyl acetate, washed with saturated NH$_4$Cl (×2), water (×1, +some brine), saturated NaHCO$_3$ (×2), and brine (×1). After the aqueous fractions were extracted with ethyl acetate (×1), two organic fractions were combined, dried (Na$_2$SO$_4$), and concentrated. The residue was purified by column chromatography on silica gel (40 g column) using hexane-ethyl acetate-20% MeOH in ethyl acetate as eluents to get compound 34-B. $^1$H NMR (400 MHz, Chloroform-d) δ 10.30 (t, J=5.9 Hz, 1H), 8.44 (s, 1H), 6.73-6.56 (m, 2H), 6.03 (dddd, J=57.1, 54.5, 6.4, 2.2 Hz, 1H), 4.73-4.50 (m, 3H), 4.42-4.23 (m, 2H), 4.03 (s, 3H), 3.98 (m, 2H), 3.65 (ddt, J=21.7, 14.4, 4.9 Hz, 3H), 2.31-2.15 (m, 1H), 1.99 (dd, J=14.0, 3.8 Hz, 1H). $^{19}$F NMR (376 MHz, Chloroform-d) δ −108.79 (dq, J=14.7, 7.2, 6.5 Hz, 1F), −112.08 (t, J=7.0 Hz, 2F), −120.33 (ddt, J=291.1, 54.4, 8.1 Hz, 1F), −123.23 (dddd, J=290.8, 57.2, 26.6, 13.6 Hz, 1F). LCMS-ESI$^+$ (m/z): [M+H]$^+$ calculated for $C_{22}H_{21}F_5N_3O_5$: 502.14; found: 502.19.

Step 2

To a solution of compound 34-B (86 mg, 0.172 mmol) in MeCN (3 mL) was added MgBr$_2$ (84 mg, 0.456 mmol) at room temperature and the resulting mixture was stirred at 50° C. bath. After 30 min, the reaction mixture was stirred at 0° C. and 1 N HCl was added to make the mixture a solution. The resulting solution was further diluted with water before the product was extracted with dichloromethane (×3). The combined extracts were dried (Na$_2$SO$_4$) and concentrated. The residue was purified by column chromatograpy on silica gel (12 g column) using dichloromethane-20% MeOH in dichloromethane and the product containing fractions were pooled and freeze-dried to get compound 34. $^1$H NMR (400 MHz, Chloroform-d) δ 12.02 (s, 1H), 10.27 (t, J=5.8 Hz, 1H), 8.39 (s, 1H), 6.78-6.49 (m, 2H), 6.07 (dddd, J=56.8, 54.3, 6.3, 2.2 Hz, 1H), 4.69 (dd, J=14.5, 5.9 Hz, 1H), 4.59 (dd, J=14.5, 5.6 Hz, 1H), 4.52 (ddd, J=15.3, 9.9, 2.3 Hz, 1H), 4.47-4.34 (m, 2H), 4.02 (dt, J=12.0, 3.7 Hz, 1H), 3.75-3.59 (m, 3H), 2.21 (tq, J=11.0, 4.7 Hz, 1H), 1.97-1.86 (m, 1H). $^{19}$F NMR (376 MHz, Chloroform-d) δ −108.99 (ddd, J=15.0, 8.9, 6.4 Hz, 1F), −112.11 (t, J=7.0 Hz, 2F), −119.30−−120.56 (ddt, J=293.0, 52.7, 9.4 Hz, 1F), −122.96 (dddd, J=293.0, 57.3, 25.9, 13.9 Hz, 1F). LCMS-ESI$^+$ (m/z): [M+H]$^+$ calculated for $C_{21}H_{19}F_5N_3O_5$: 488.12; found: 488.34.

Example 35

Preparation of Compound 35

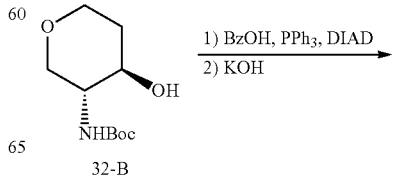

32-B

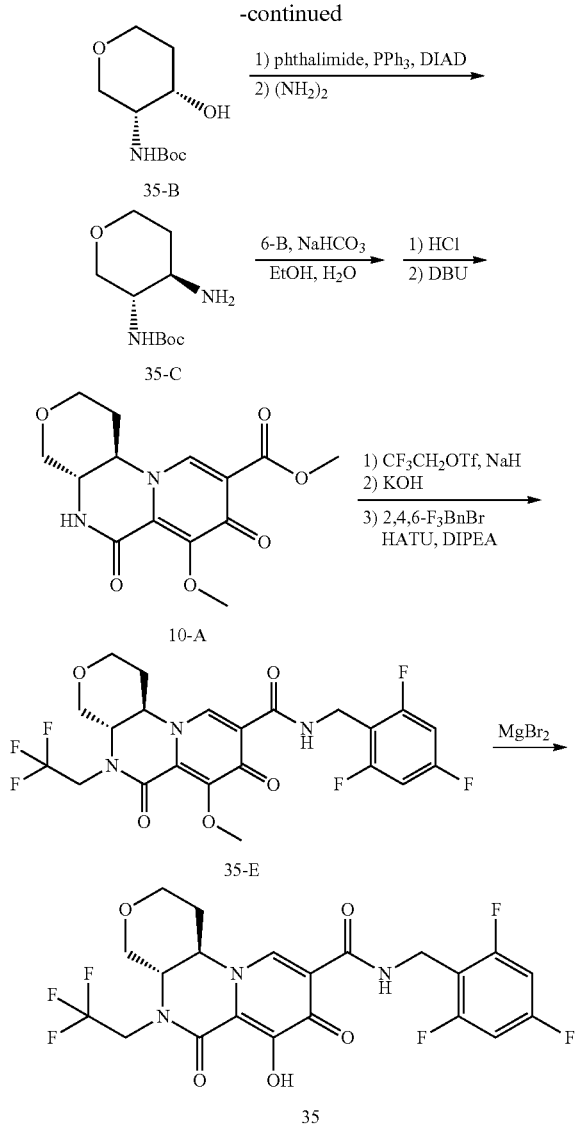

Step 1

A mixture of compound 32-B (2086 mg, 9.601 mmol), benzoic acid (2006 mg, 16.43 mmol), and triphenylphosphine (5560 mg, 21.2 mmol) in THF (40 mL) was stirred at 0° C. bath as DIAD (4.35 mL, 22.09 mmol) was added After 5 min at 0° C., the mixture was stirred at room temperature for 22 h. The solution was concentrated and the residual syrup was partially purified by Column chromatograpy on silica gel (120 g column) using ethyl acetate-hexanes as eluents to get a major fraction (5.324 g).

The major fraction was dissolved in THF (20 mL) and MeOH (20 mL) and stirred at 0° C. as 1 N KOH (10 mL) was added. After 1.25 h stirring at 0° C., the solution was stirred at room temperature for 1 h. The solution was concentrated to ~½ volume and diluted with water (to ~100 mL) before extraction with dichloromethane (2×~100 mL). After the extracts were washed with water (×1), the combined organic fractions were dried ($Na_2SO_4$) and concentrated. The residue was purified by column chromatography on silica gel (120 g column) using hexanes-ethyl acetate as eluents to get compound 35-B. $^1$H NMR (400 MHz, Chloroform-d) δ 5.12 (s, 1H), 3.96 (dt, J=8.1, 3.8 Hz, 1H), 3.84 (dt, J=10.6, 5.0 Hz, 2H), 3.70 (dd, J=11.9, 5.2 Hz, 1H), 3.57 (dd, J=11.5, 3.1 Hz, 1H), 3.47 (ddd, J=11.8, 8.3, 3.6 Hz, 1H), 2.71 (s, 1H), 1.94-1.78 (m, 1H), 1.72 (dtd, J=13.7, 8.4, 4.1 Hz, 1H), 1.44 (s, 9H). LCMS-ESI$^+$ (m/z): [M+H-$C_4H_8$]$^+$ calculated for $C_6H_{12}NO_4$: 162.08; found: 161.90.

Step 2

A mixture of compound 35-B (1824 mg, 8.395 mmol), phthalimide (2017 mg, 13.71 mmol), and $PPh_3$ (4872 mg, 18.58 mmol) in THF (50 mL) was stirred at 0° C. bath as DIAD (3.75 mL, 19.05 mmol) was added dropwise. After addition, the mixture was stirred at 0° C. for 30 min and then at room temperature overnight. The mixture was concentrated to syrup, dissolved in ether (~200 mL) and the insoluble material was filtered. The filtrate was concentrated and the filtrate was concentrated. The residue was purified by column chromatograpy on silica gel (120 g column) using hexanes-ethyl acetate as eluents to get impure phthalimide product. LCMS-ESI$^+$ (m/z): [M+H-$C_4H_8$]$^+$ calculated for $C_{14}H_{15}N_2O_5$: 291.10; found: 291.08 To a solution of impure phthalimide product (3.309 g) in ethanol (50 mL) was added hydrazine hydrate (1.65 mL, 33.92 mmol) at room temperature and the resulting solution was stirred at 70° C. bath for 3 h. The mixture was diluted with ether, stirred at room temperature, and filtered off the insoluble material. The filtrate was concentrated. The residue was dissolved in water with some 1 N HCl and washed with ethyl acetate (×1). The aqueous fraction was neutralized with aqueous $NaHCO_3$ solution, and then extracted with dichloromethane (×3) and discarded. The aqueous fraction was saturated with NaCl and extracted again with dichloromethane (×6), combined, dried ($Na_2SO_4$), and concentrated to get compound 35-C. LCMS-ESI$^+$ (m/z): [M+H-$C_4H_8$]$^+$ calculated for $C_6H_{13}N_2O_3$: 161.09; found: 161.00.

Step 3

The mixture of compound 6-B (810 mg, 3.345 mmol), compound 35-C (724 mg, 3.348 mmol), and $NaHCO_3$ (566 mg, 6.738 mmol) in water (6 mL) and EtOH (8 mL) was stirred at room temperature. After 30 min, the reaction mixture was concentrated to remove most of solvent and the residue was dissolved in dichloromethane (100 mL). The resulting mixture was dried ($MgSO_4$), and concentrated.

The concentrated residue was dissolved in dichloromethane (3 mL) and treated with 4 N HCl in dioxane (10 mL). After 2 h, the mixture was concentrated and dried in vacuum.

The concentrated residue and DBU (2.5 mL, 42.64 mmol) were dissolved in MeOH (20 mL) and stirred at 50° C. bath. After 15 min, the solution was concentrated and the residue was triturated with dichloromethane (20 mL) with heating. The mixture was filtered and the insoluble compound 10-A was collected. The filtrate was purified by column chromatograpy on silica gel (80 g column) using ethyl acetate-20% MeOH in ethyl acetate as eluents to get compound 10-A. Two crops of compound 10-A were combined and triturated with methanol (25 mL) at room temperature for 1.5 h and then at 0° C. for 30 min before filtration. The solids were washed with methanol and dried in vacuum overnight to get compound 10-A. $^1$H NMR (400 MHz, Chloroform-d) δ 8.23 (s, 1H), 6.01 (d, J=4.5 Hz, 1H), 4.38-4.27 (m, 1H), 4.21-4.13 (m, 1H), 4.10 (d, J=1.2 Hz, 3H), 3.97-3.90 (m, 1H), 3.92 (s, 3H), 3.69-3.57 (m, 2H), 3.36 (t, J=10.7 Hz, 1H), 2.48 (d, J=12.7 Hz, 1H), 2.04 (dd, J=11.5, 5.2 Hz, 1H). LCMS-ESI$^+$ (m/z): [M+H]$^+$ calculated for $C_{14}H_{17}N_2O_6$: 309.11; found: 309.06.

Step 4

To a mixture of compound 10-A (133 mg, 0.431 mmol) and 60% NaH (92 mg, 2.300 mmol) was added DMF (3 mL)

at 0° C. After 15 min, CF₃CH₂OTf (0.25 mL, 1.735 mmol) was added. After stirring 2 h at room temperature, the reaction mixture was stirred at 0° C. and 1 N KOH (0.9 mL) was added. After 30 min, the resulting mixture was acidified with concentrated HCl (0.35 mL) and the mixture was concentrated to almost dryness.

A mixture of the above residue, 2,4,6-trifluorobenzylamine (182 mg, 0.509 mmol), and HATU (343 mg, 0.902 mmol) in dichloromethane (4 mL) was stirred at room temperature as DIPEA (0.55 mL, 3.158 mmol) was added. After 20 min, the reaction mixture was diluted with ethyl acetate, washed with saturated NH₄Cl (×2), water (×1), saturated NaHCO₃ (×2), and brine (×1). After the aqueous fractions were extracted with ethyl acetate (×1), two organic fractions were combined, dried (Na₂SO₄), and concentrated. The residue was purified by preparative HPLC. The product containing fractions were pooled and concentrated to remove acetonitrile, neutralized with saturated NaHCO₃, and the organic product was extracted with dichloromethane (×3), combined, dried (Na₂SO₄) and concentrated to get compound 35-E. ¹H NMR (400 MHz, Chloroform-d) δ 10.29 (d, J=6.8 Hz, 1H), 8.66-8.42 (m, 1H), 6.78-6.53 (m, 2H), 4.85 (dq, J=17.8, 9.1 Hz, 1H), 4.64 (qd, J=14.5, 5.4 Hz, 2H), 4.51-4.41 (m, 1H), 4.35-4.24 (m, 1H), 4.06 (td, J=11.0, 4.7 Hz, 1H), 4.01 (s, 3H), 3.77 (td, J=10.3, 4.6 Hz, 1H), 3.63-3.45 (m, 2H), 3.38 (t, J=10.7 Hz, 1H), 2.57 (d, J=12.2 Hz, 1H), 2.06 (qd, J=12.3, 5.3 Hz, 1H). ¹⁹F NMR (376 MHz, Chloroform-d) δ −69.94 (t, J=8.6 Hz, 3F), −109.00 (t, J=8.2 Hz, 1F), −111.70--112.47 (m, 2F). LCMS-ESI⁺ (m/z): [M+H]⁺ calculated for C₂₂H₂₀F₆N₃O₅: 520.13; found: 520.18.

Step 5

To a solution of compound 35-E (42 mg, 0.081 mmol) in MeCN (3 mL) was added MgBr₂ (42 mg, 0.228 mmol) at room temperature and the resulting mixture was stirred at 50° C. bath. After 15 min, the reaction mixture was stirred at 0° C. and 1 N HCl (~0.6 mL) was added to make the mixture a solution. The resulting solution was further diluted with water before the product was extracted with dichloromethane (×3). The combined extracts were dried (Na₂SO₄) and concentrated. The residue was purified by column chromatograpy on silica gel (12 g column) using dichloromethane-20% MeOH in dichloromethane to obtain compound 35. ¹H NMR (400 MHz, Chloroform-d) δ 10.32 (s, 1H), 8.54 (s, 1H), 6.77-6.49 (m, 2H), 4.72-4.55 (m, 3H), 4.48 (dd, J=10.9, 4.3 Hz, 1H), 4.32 (dt, J=12.1, 3.0 Hz, 1H), 4.14 (td, J=11.5, 11.0, 4.1 Hz, 1H), 3.83 (td, J=10.3, 4.3 Hz, 1H), 3.72 (dq, J=16.8, 8.9, 8.5 Hz, 1H), 3.66-3.54 (m, 1H), 3.43 (t, J=10.7 Hz, 1H), 2.65 (d, J=12.5 Hz, 1H), 2.09 (qd, J=12.8, 12.4, 5.5 Hz, 1H). ¹⁹F NMR (376 MHz, Chloroform-d) δ −69.17 (t, J=8.4 Hz, 3F), −108.90 (h, J=7.9, 6.9 Hz, 1F), −111.77--112.55 (m, 2F). LCMS-ESI⁺ (m/z): [M+H]⁺ calculated for C₂₁H₁₈F₆N₃O₅: 506.12; found: 506.25.

Example 36

Preparation of Compound 36

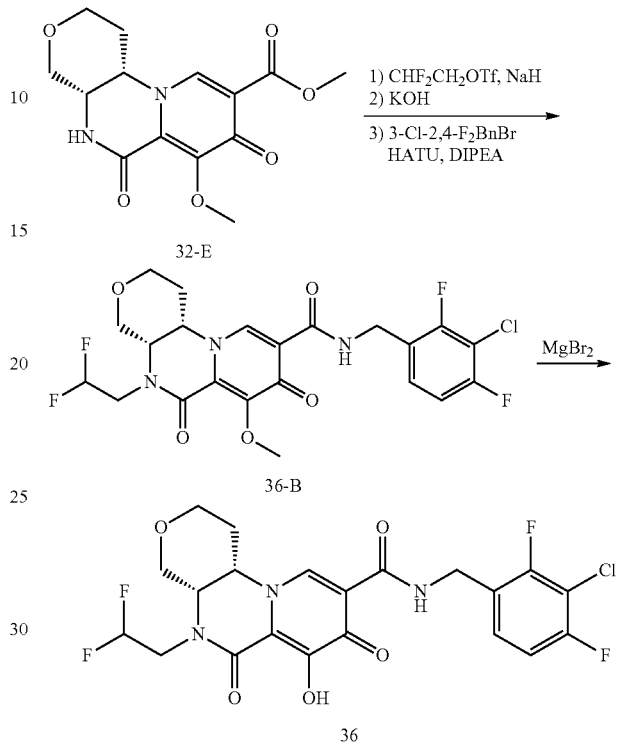

Step 1

To a mixture of compound 32-E (148 mg, 0.480 mmol) and 60% NaH (77 mg, 1.92 mmol) was added DMF (3 mL) at 0° C. After 20 min, CHF₂CH₂OTf (360 mg, 1.681 mmol) was added. After stirring at room temperature for ~30 min, the reaction mixture was stirred at 0° C. and 1 N KOH (0.5 mL) was added to the mixture. After 10 min, the reaction mixture was acidified with of concentrated HCl (0.35 mL) and concentrated to almost dryness.

A mixture of the above residue, 3-chloro-2,4-difluorobenzylamine (103 mg, 0.580 mmol), and HATU (385 mg, 1.013 mmol) in dichloromethane (5 mL) was stirred at room temperature as DIPEA (0.7 mL, 4.019 mmol) was added. After 30 min, the reaction mixture was diluted with ethyl acetate, washed with saturated NH₄Cl (×2), water (×1, +some brine), saturated NaHCO₃ (×2), and brine (×1). After the aqueous fractions were extracted with ethyl acetate (×1), two organic fractions were combined, dried (Na₂SO₄), and concentrated. The residue was purified by column chromatography on silica gel (40 g column) using Hexane-ethyl acetate-20% MeOH in ethyl acetate as eluents to obtain compound 36-B. ¹H NMR (400 MHz, Chloroform-d) δ 10.42 (t, J=6.1 Hz, 1H), 8.49 (s, 1H), 7.36-7.18 (m, 1H), 6.92 (td, J=8.5, 1.9 Hz, 1H), 6.04 (dddd, J=57.1, 54.4, 6.4, 2.2 Hz, 1H), 4.78-4.50 (m, 3H), 4.43-4.20 (m, 2H), 4.05 (s, 3H), 4.04-3.91 (m, 2H), 3.65 (dddd, J=15.1, 13.8, 7.3, 4.4 Hz, 3H), 2.35-2.13 (m, 1H), 2.13-1.93 (m, 1H). ¹⁹F NMR (377 MHz, Chloroform-d) δ −114.75 (q, J=5.3, 3.8 Hz, 1F), −117.28 (d, J=7.7 Hz, 1F), −120.31 (ddt, J=291.4, 54.6, 8.1 Hz, 1F), −123.21 (dddd, J=290.8, 57.4, 26.5, 13.9 Hz, 1F).

LCMS-ESI⁺ (m/z): [M+H]⁺ calculated for $C_{22}H_{21}ClF_4N_3O_5$: 518.11; found: 518.30.

Step 2

To a solution of compound 36-B (85 mg, 0.164 mmol) in MeCN (3 mL) was added MgBr₂ (83 mg, 0.451 mmol) at room temperature and the resulting mixture was stirred at 50° C. bath. After 30 min, the reaction mixture was stirred at 0° C. and 1 N HCl (~1 mL) was added to make the mixture a solution. The resulting solution was further diluted with water before the product was extracted with dichloromethane (×3). The combined extracts were dried (Na₂SO₄) and concentrated. The residue was purified by preparative HPLC and the product containing fractions were pooled and freeze-dried to get compound 36. ¹H NMR (400 MHz, Chloroform-d) δ 10.59 (t, J=6.1 Hz, 1H), 11-9 (br, 1H), 8.70 (s, 1H), 7.42-7.15 (m, 1H), 6.94 (td, J=8.5, 1.8 Hz, 1H), 6.30-5.82 (m, 1H), 4.77-4.41 (m, 6H), 4.15 (d, J=3.5 Hz, 1H), 4.06 (dd, J=11.3, 4.3 Hz, 1H), 3.70 (td, J=12.5, 6.0 Hz, 3H), 2.31-2.08 (m, 1H), 1.96 (dd, J=13.3, 3.8 Hz, 1H). ¹⁹F NMR (376 MHz, Chloroform-d) δ -76.41 (s, 3F), -114.13 (d, J=7.7 Hz, 1F), -117.04 (s, 1F), -119.86 (ddt, J=293.4, 54.4, 8.6 Hz, 1F), -122.96 (dddd, J=293.0, 56.7, 24.7, 14.3 Hz, 1F). LCMS-ESI⁺ (m/z): [M+H]⁺ calculated for $C_{21}H_{19}ClF_4N_3O_5$: 504.09; found: 504.30.

Example 37

Preparation of Compound 37

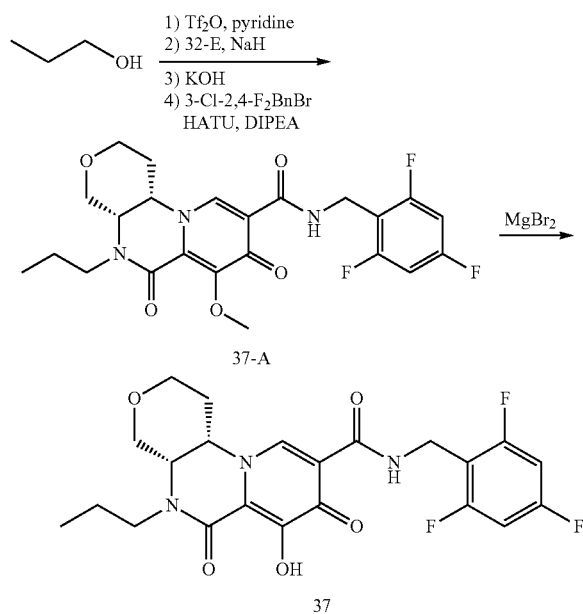

Step 1

A solution of n-PrOH (0.667 mL, 8.964 mmol) and pyridine (0.72 mL, 8.918 mmol) in dichloromethane (12 mL) was stirred at -40° C. bath as triflic anhydride (1.5 mL, 8.918 mmol) was added dropwise. The bath temperature was warmed to 0° C. over 30 min After then, the resulting mixture was stirred at room temperature for 30 min. The mixture was cooled down to 0° C. and the mixture was diluted with anhydrous pentane (12 mL). After 20 min, the mixture was filtered through celite pad. The filtrate was stored in freezer until used. (Assuming 100% yield, concentration of the solution was 0.3716 mM.)

To a mixture of compound 32-E (103 mg, 0.334 mmol) and 60% NaH (58 mg, 1.45 mmol) was added DMF (2 mL) at 0° C. After 15 min, the above solution of n-PrOTf (2.7 mL, ~1.003 mmol) was added. After stirring at 0° C. for 30 min, 1 N KOH (0.5 mL) was added to the mixture. After 1 h, the reaction mixture was acidified with of concentrated HCl (0.35 mL) and concentrated to almost dryness.

A mixture of the above residue, 2,4,6-trifluorobenzylamine (64 mg, 0.397 mmol), and HATU (280 mg, 0.736 mmol) in dichloromethane (3 mL) was stirred at room temperature as DIPEA (0.6 mL, 3.445 mmol) was added. After 20 min, the reaction mixture was diluted with ethyl acetate, washed with saturated NH₄Cl (×2), saturated NaHCO₃ (×2), and brine (×1). After the aqueous fractions were extracted with ethyl acetate (×1), two organic fractions were combined, dried (Na₂SO₄), and concentrated. The residue was purified by preparative HPLC.

The product containing fractions were pooled and concentrated to remove acetonitrile, neutralized with saturated NaHCO₃ (~2 mL), diluted with brine (20 mL), and the organic product was extracted with dichloromethane (×3), combined, dried (Na₂SO₄) and concentrated to get compound 37-A. ¹H NMR (400 MHz, Chloroform-d) δ 10.39 (s, 1H), 8.48 (s, 1H), 6.78-6.54 (m, 2H), 4.77-4.51 (m, 2H), 4.37 (d, J=8.8 Hz, 1H), 4.02 (s, 5H), 3.84 (s, 2H), 3.75-3.60 (m, 2H), 3.22 (ddd, J=14.5, 9.5, 5.5 Hz, 1H), 2.36 (d, J=12.0 Hz, 1H), 2.03 (dd, J=11.6, 7.6 Hz, 1H), 1.75-1.51 (m, 2H), 0.95 (t, J=7.4 Hz, 3H). ¹⁹F NMR (376 MHz, Chloroform-d) δ -108.95 (s, 1F), -111.96 (d, J=10.7 Hz, 2F). LCMS-ESI⁺ (m/z): [M+H]⁺ calculated for $C_{23}H_{25}F_3N_3O_5$: 480.17; found: 480.45.

Step 2

To a solution of compound 37-A (26 mg, 0.054 mmol) in MeCN (2 mL) was added MgBr₂ (28 mg, 0.152 mmol) at room temperature and the resulting mixture was stirred at 50° C. bath. After 30 min, the reaction mixture was stirred at 0° C. and 1 N HCl (~1 mL) was added to make the mixture a solution. The resulting solution was further diluted with water before the product was extracted with dichloromethane (×3). The combined extracts were dried (Na₂SO₄) and concentrated. The residue was purified by preparative HPLC and the product containing fractions were pooled and freeze-dried to get compound 37. ¹H NMR (400 MHz, Chloroform-d) δ 10.52 (t, J=5.5 Hz, 1H), 8.55 (s, 1H), 6.66 (t, J=8.2 Hz, 2H), 4.79-4.65 (m, 1H), 4.65-4.55 (m, 1H), 4.48 (s, 1H), 4.20 (d, J=12.0 Hz, 1H), 4.05 (dt, J=15.5, 8.2 Hz, 1H), 3.97 (d, J=11.1 Hz, 2H), 3.80-3.55 (m, 2H), 3.36-3.19 (m, 1H), 2.27 (s, 1H), 1.94 (d, J=13.0 Hz, 1H), 1.66 (q, J=7.7 Hz, 2H), 0.98 (t, J=7.2 Hz, 3H). ¹⁹F NMR (376 MHz, Chloroform-d) δ -76.43 (s, 3F), -108.54 (p, J=7.2 Hz, 1F), -111.64--112.56 (m, 2F). LCMS-ESI⁺ (m/z): [M+H]⁺ calculated for $C_{22}H_{23}F_3N_3O_5$: 466.16; found: 466.19.

Example 38

Preparation of Compound 38

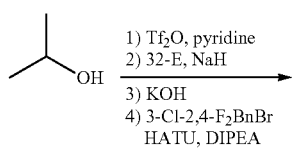

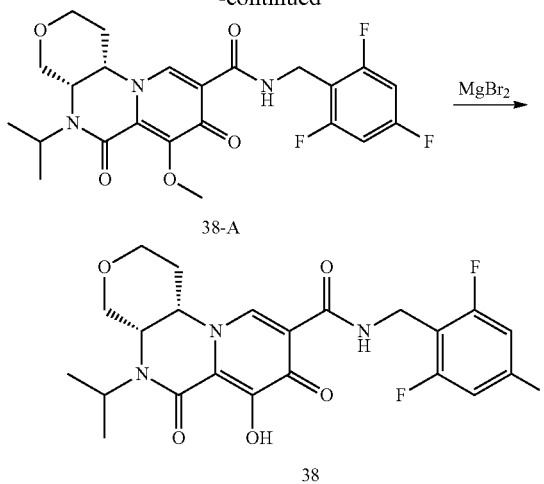

38-A

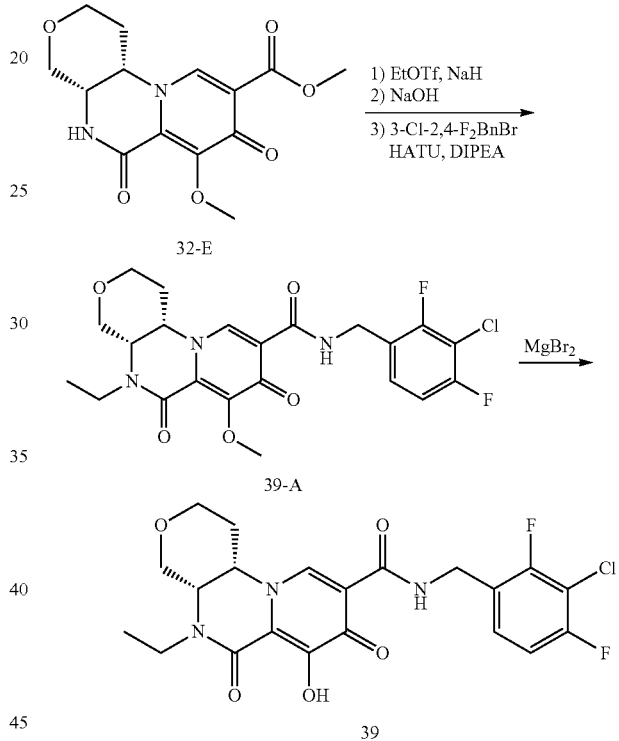

38

Step 1

A solution of i-PrOH (0.685 mL, 8.948 mmol) and pyridine (0.72 mL, 8.929 mmol) in dichloromethane (12 mL) was stirred at −40° C. as triflic anhydride (1.5 mL, 8.918 mmol) was added dropwise. The bath temp was warmed to 0° C. over 30 min After then the resulting mixture was stirred at room temperature for 30 min. The mixture was cooled down to 0° C. and the mixture was diluted with anhydrous pentane (12 mL). After 20 min, the mixture was filtered through celite pad. The filtrate was stored in freezer until used. (Assuming 100% yield, concentration of the solution was 0.3716 mM.)

To a mixture of compound 32-E (101 mg, 0.328 mmol) and 60% NaH (58 mg, 1.45 mmol) was added DMF (2 mL) at 0° C. After 10 min, the above solution of i-PrOTf (2.7 mL, ~1.003 mmol) was added. After stirring at 0° C. for 1.75 h, 1 N KOH (0.5 mL) was added to the mixture. After 1.25 h, the reaction mixture was acidified with of concentrated HCl (0.35 mL) and concentrated to almost dryness.

A mixture of the above residue, 2,4,6-trifluorobenzylamine (64 mg, 0.397 mmol), and HATU (280 mg, 0.736 mmol) in dichloromethane (3 mL) was stirred at room temperature as DIPEA (0.6 mL, 3.445 mmol) was added. After 30 min, the reaction mixture was diluted with ethyl acetate, washed with saturated NH$_4$Cl (×2), saturated NaHCO$_3$ (×2), and brine (×1). After the aqueous fractions were extracted with ethyl acetate (×1), two organic fractions were combined, dried (Na$_2$SO$_4$), and concentrated. The residue was purified by preparative HPLC to get compound 38-A. $^1$H NMR (400 MHz, Chloroform-d) δ 10.67 (s, 1H), 8.65 (s, 1H), 6.80-6.56 (m, 2H), 4.94-4.80 (m, 1H), 4.79-4.69 (m, 1H), 4.62 (dd, J=15.0, 4.6 Hz, 1H), 4.47 (d, J=3.6 Hz, 1H), 4.04 (s, 3H), 3.92-3.65 (m, 3H), 3.26 (td, J=11.5, 10.9, 6.0 Hz, 2H), 2.77 (d, J=15.6 Hz, 1H), 2.37 (t, J=14.1 Hz, 1H), 1.27 (d, J=6.7 Hz, 6H). $^{19}$F NMR (376 MHz, Chloroform-d) δ −76.30 (s, 3F), −108.39 (ddd, J=15.1, 8.6, 6.1 Hz, 1F), −112.00 (t, J=6.9 Hz, 2F). LCMS-ESI$^+$ (m/z): [M+H]$^+$ calculated for C$_{23}$H$_{25}$F$_3$N$_3$O$_5$: 480.17; found: 480.23.

Step 2

To a solution of compound 38-A (3 mg-0.006 mmol) in MeCN (1 mL) was added MgBr$_2$ (5 mg, 0.027 mmol) at room temperature and the resulting mixture was stirred at 50° C. bath. After 30 min, the reaction mixture was stirred at 0° C. and 1 N HCl (~0.1 mL) was added to make the mixture a solution. The resulting solution was further diluted with water (0.3 mL) and DMF (1 mL), filtered, and purified by preparative HPLC and the product containing fraction was freeze-dried to get compound 38. $^1$H NMR (400 MHz, Chloroform-d) δ 10.57 (d, J=6.1 Hz, 1H), 8.58 (s, 1H), 6.80-6.54 (m, 2H), 4.79-4.56 (m, 3H), 4.48 (s, 1H), 3.87 (q, J=8.6, 7.0 Hz, 3H), 3.49 (t, J=11.9 Hz, 1H), 3.44-3.31 (m, 1H), 2.79 (d, J=15.9 Hz, 1H), 2.34 (t, J=14.0 Hz, 1H), 1.35 (d, J=6.8 Hz, 3H), 1.34 (d, J=6.8 Hz, 3H). $^{19}$F NMR (376 MHz, Chloroform-d) δ −76.38 (s, 3F), −108.68 (d, J=10.1 Hz, 1F), −112.01 (s, 2F). LCMS-ESI$^+$ (m/z): [M+H]$^+$ calculated for C$_{22}$H$_{23}$F$_3$N$_3$O$_5$: 466.16; found: 466.21.

Example 39

Preparation of Compound 39

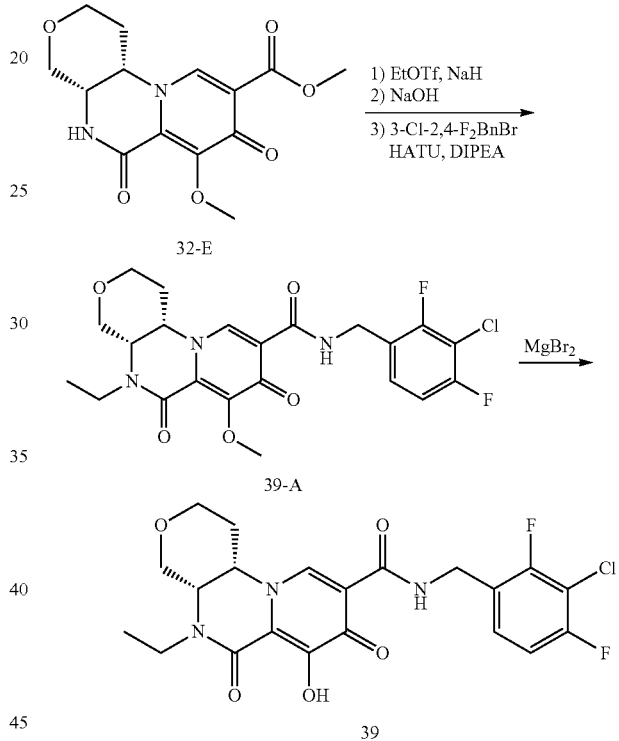

Step 1

To a mixture of compound 32-E (120 mg, 0.389 mmol) and 60% NaH (69 mg, 1.725 mmol) was added DMF (2 mL) at 0° C. After 5 min, EtOTf (0.17 mL, 1.311 mmol) was added. After 20 min, 2 N NaOH (0.8 mL) was added to the mixture. After 20 min, the reaction mixture was acidified with 2 N HCl (~2 mL) and the acidified reaction mixture was concentrated to almost dryness.

A mixture of the above residue, 3-chloro-2,4-difluorobenzylamine (79 mg, 0.445 mmol), and HATU (315 mg, 0.829 mmol) in dichloromethane (4 mL) was stirred at room temperature as DIPEA (0.7 mL, 4.019 mmol) was added. After 1 h, the reaction mixture was diluted with ethyl acetate, washed with saturated NH$_4$Cl (×2), saturated NaHCO$_3$ (×2), and brine (×1). After the aqueous fractions were extracted with ethyl acetate (×1), two organic fractions were combined, dried (Na$_2$SO$_4$), and concentrated. The residue was purified by column chromatograpy on silica gel (12 g column) using hexane-ethyl acetate-20% MeOH in ethyl acetate as eluents to get impure compound 39-A.

LCMS-ESI+ (m/z): [M+H]+ calculated for C$_{22}$H$_{23}$ClF$_2$N$_3$O$_5$: 482.13; found: 482.41.

Step 2

To a solution of compound 39-A (43 mg-0.089 mmol) in MeCN (3 mL) was added MgBr$_2$ (44 mg, 0.239 mmol) at room temperature and the resulting mixture was stirred at 50° C. bath. After 30 min, the reaction mixture was stirred at 0° C. and 1 N HCl (~0.2 mL) was added to make the mixture a solution. The resulting solution was further diluted with water before the product was extracted with dichloromethane (×3). The combined extracts were dried (Na$_2$SO$_4$) and concentrated. The residue was purified by preparative HPLC and the product containing fractions were pooled and freeze-dried to get compound 39. $^1$H NMR (400 MHz, Chloroform-d) δ 10.68-10.40 (m, 1H), 8.52 (s, 1H), 7.36-7.20 (m, 1H), 6.93 (td, J=8.6, 1.9 Hz, 1H), 4.65 (qd, J=15.2, 5.4 Hz, 2H), 4.48 (s, 1H), 4.36-4.21 (m, 1H), 4.13 (dq, J=14.5, 7.3 Hz, 1H), 4.05 (s, 1H), 4.00 (d, J=12.2 Hz, 1H), 3.86-3.55 (m, 2H), 3.43 (dq, J=14.0, 6.9 Hz, 1H), 2.38-2.14 (m, 1H), 2.03-1.82 (m, 1H), 1.27 (t, J=7.1 Hz, 3H). $^{19}$F NMR (376 MHz, Chloroform-d) δ −76.43 (s, 3F), −114.60 (s, 1F), −117.24 (d, J=7.7 Hz, 1F). LCMS-ESI+ (m/z): [M+H]+ calculated for C$_{21}$H$_{21}$ClF$_2$N$_3$O$_5$: 468.11; found: 468.20.

Example 40

Preparation of Compound 40a and 40b

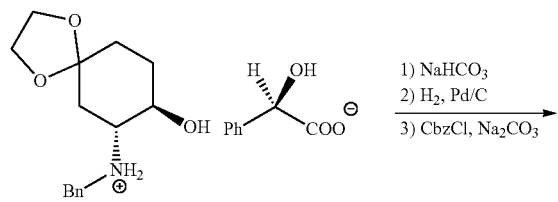

40-A

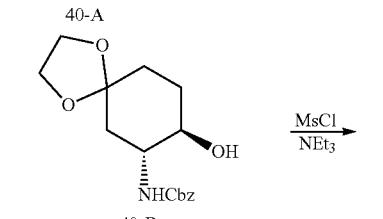

40-B

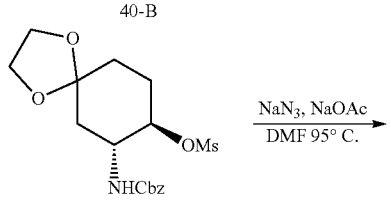

40-C

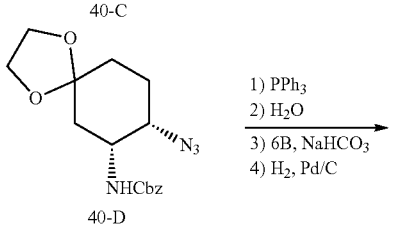

40-D

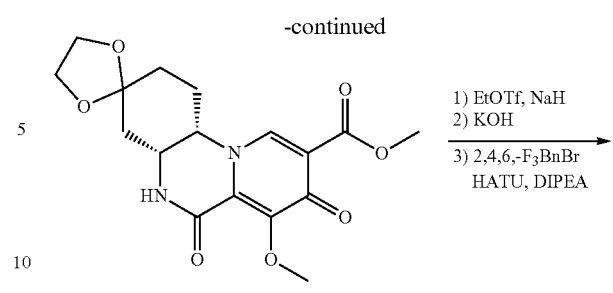

40-E

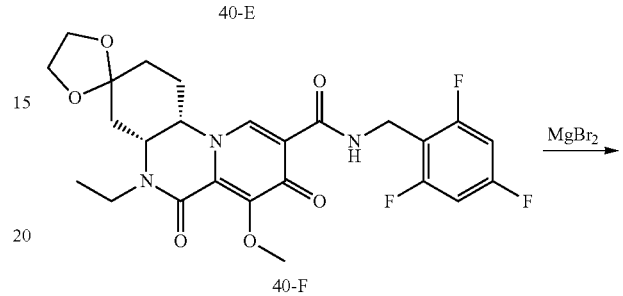

40-F

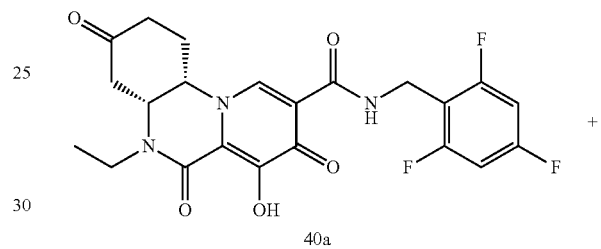

40a

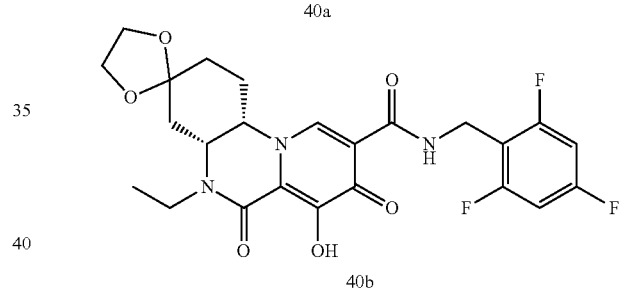

40b

Step 1

Compound 40-A (9.999 g, 24.07 mmol) was dissolved in dichloromethane (100 mL) and saturated NaHCO$_3$ solution (200 mL). After two layers were separated, the aqueous fraction was extracted with dichloromethane (100 mL). Two organic fractions were washed with water (×1), combined, dried (MgSO$_4$), concentrated, and dried in vacuum.

The dried residue was dissolved in ethanol with 10% Pd/C (2.11 g) and the resulting mixture was shaken for 20 h under 40-50 psi H$_2$ atmosphere. The mixture was filtered through celite pad, and the filtrate was concentrated to almost dryness.

The residue and Na$_2$CO$_3$ (3830 mg, 36.14 mmol) in water (200 mL) was stirred at 0° C. as benzyl chloroformate (4.35 mL, 95% purity, 28.95 mmol) was added. The resulting mixture was stirred at room temperature for 67 h and the product was extracted with dichloromethane (100 mL×3). The extracts were washed with water (×1) before combining, drying (Na$_2$SO$_4$) and concentration.

The residue was purified by column chromatography on silica gel (120 g column) using hexanes-ethyl acetate as eluents to get compound 40-B. $^1$H NMR (400 MHz, Chloroform-d) δ 7.44-7.28 (m, 5H), 5.45 (d, J=8.2 Hz, 1H), 5.10 (d, J=4.3 Hz, 2H), 3.94 (m, 4H), 3.87-3.74 (m, 1H), 3.65 (m, 1H), 2.14 (ddd, J=13.2, 4.6, 1.8 Hz, 1H), 1.93 (dq, J=12.5, 4.0 Hz, 1H), 1.87-1.75 (m, 1H), 1.68 (ddd, J=12.4, 10.1, 5.7 Hz, 1H), 1.62-1.47 (m, 2H). LCMS-ESI$^+$ (m/z): [M+H]$^+$ calculated for $C_{16}H_{22}NO_5$: 308.15; found: 307.89.

Step 2

A solution of compound 40-B (1066 mg, 3.468 mmol) and triethylamine (0.59 mL, 4.233 mmol) in dichloromethane (12 mL) was stirred at 0° C. as methanesulfonyl chloride (0.3 mL, 3.876 mmol) was added dropwise. After 20 min at 0° C., the mixture was stirred at room temperature for 30 min and the reaction mixture was diluted with ethyl acetate and washed with water (×2). After the aqueous fractions were extracted with ethyl acetate (×1), the organic fractions were combined, dried ($Na_2SO_4$), and concentrated. The residue was purified by column chromatograpy on silica gel (40 g column) using hexanes-ethyl acetate as eluents to get compound 40-C. $^1$H NMR (400 MHz, Chloroform-d) δ 7.46-7.29 (m, 5H), 5.86 (s, 1H), 5.10 (q, J=12.2 Hz, 2H), 4.68 (s, 1H), 4.06 (s, 1H), 4.00-3.85 (m, 4H), 3.07 (s, 3H), 2.24-2.10 (m, 1H), 2.06 (q, J=6.5, 4.3 Hz, 2H), 1.86 (d, J=11.9 Hz, 1H), 1.75-1.57 (m, 2H). LCMS-ESI$^+$ (m/z): [M+H]$^+$ calculated for $C_{17}H_{24}NO_7S$: 386.13; found: 386.04.

Step 3

A mixture of compound 40-C (1282 mg, 3.326 mmol), NaOAc (547 mg, 6.668 mmol), and sodium azide (441 mg, 6.784 mmol) in DMF (6 mL) was stirred at 95° C. bath for 9 h. The mixture was diluted with water and the product was extracted with ethyl acetate (×2). After the extracts were washed with water (×1), combined, dried ($Na_2SO_4$), and concentrated, the residue was purified by column chromatography on silica gel (80 g column) using hexanes-ethyl acetate as eluents to get 40-D. $^1$H NMR (400 MHz, Chloroform-d) δ 7.43-7.28 (m, 5H), 5.22 (d, J=9.2 Hz, 1H), 5.11 (s, 2H), 4.08 (t, J=7.0 Hz, 1H), 3.93 (dd, J=4.6, 2.7 Hz, 4H), 3.83 (s, 1H), 2.01-1.83 (m, 2H), 1.83-1.67 (m, 3H), 1.64-1.56 (m, 1H). LCMS-ESI$^+$ (m/z): [M+H]$^+$ calculated for $C_{16}H_{21}N_4O_4$: 333.16; found: 332.83.

Step 4

A solution of compound 40-D (680 mg, 2.046 mmol) and triphenylphosphine (600 mg, 2.288 mmol) in THF (10 mL) was stirred at room temperature for 18 h and water (2 mL) was added. The mixture was refluxed at 70° C. bath for 4 h and concentrated and dried in vacuum for 30 min After the residue was dissolved in dichloromethane (~50 mL) and dried ($MgSO_4$), insoluble material was filtered off and the filtrate was concentrated.

The mixture of the concentrated residue, compound 6-B (496 mg, 2.048 mmol), and $NaHCO_3$ (345 mg, 4.107 mmol) in water (3 mL) and MeOH (6 mL) was stirred at room temperature for 5 h. The mixture was concentrated and dried in vacuum for 30 min. The residue was triturated with methanol (~20 mL) and stirred in 50° C. bath for 5.5 h. The resulting mixture was concentrated and the residue was dissolved in dichloromethane and dried ($MgSO_4$). After the insoluble material was filtered off, the filtrate was concentrated.

The concentrated residue and 10% Pd/C (140 mg) in ethanol (30 mL) was stirred under $H_2$ atmosphere. After 2 h, more Pd/C (400 mg) was added. After another hour, more Pd/C (700 mg) was added. After additional 1.25 h, more Pd/C (580 mg) was added. The mixture was stirred overnight under $H_2$ atmosphere. The mixture was filtered and concentrated. The residue was purified by column chromatography on silica gel (40 g column) using ethyl acetate-20% MeOH in ethyl acetate as eluents to get compound 40-E. $^1$H NMR (400 MHz, Methanol-d4) δ 8.56 (s, 1H), 4.54-4.42 (m, 1H), 4.22 (m, 1H), 4.12-4.02 (m, 1H), 4.00-3.88 (m, 3H), 3.92 (s, 3H), 3.86 (s, 3H), 2.15 (td, J=12.7, 4.1 Hz, 1H), 2.05 (m, 2H), 2.03-1.94 (m, 1H), 1.86 (d, J=13.9 Hz, 1H), 1.78 (td, J=13.4, 4.0 Hz, 1H). LCMS-ESI$^+$ (m/z): [M+H]$^+$ calculated for $C_{17}H_{21}N_2O_7$: 365.13; found: 365.17.

Step 5

To a mixture of compound 40-E (49 mg, 0.134 mmol) and 60% NaH (25 mg, 0.625 mmol) was added DMF (2 mL) at 0° C. After 15 min, EtOTf (0.06 mL, 0.463 mmol) was added. After 20 min, 1 N KOH (0.2 mL) was added to the reaction mixture. After 20 min, the reaction mixture was acidified with 2 N HCl (~2 mL) and the acidified reaction mixture was concentrated to remove all the solvents. The residue was purified by preparative HPLC to get 28 mg (55%) of the acid.

A mixture of the acid, 2,4,6-trifluorobenzylamine (25 mg, 0.155 mmol), and HATU (90 mg, 0.237 mmol) in dichloromethane (3 mL) was stirred at room temperature as DIPEA (0.3 mL, 1.722 mmol) was added. After 30 min, the reaction mixture was diluted with ethyl acetate, washed with saturated $NH_4Cl$ (×2), saturated $NaHCO_3$ (×2), and brine (×1). After the aqueous fractions were extracted with ethyl acetate (×1), two organic fractions were combined, dried ($Na_2SO_4$) and concentrated.

The residue was purified by prep HPLC to get compound 40-F. $^1$H NMR (400 MHz, Chloroform-d) δ 10.75-10.48 (m, 1H), 8.58 (s, 1H), 6.80-6.45 (m, 2H), 5.25 (s, 1H), 4.73 (dd, J=14.5, 5.7 Hz, 1H), 4.60 (dd, J=14.7, 5.3 Hz, 1H), 4.36 (d, J=3.3 Hz, 1H), 4.02 (s, 3H), 3.95 (ddd, J=7.0, 5.4, 3.9 Hz, 3H), 3.86 (dq, J=14.2, 7.2 Hz, 1H), 3.75 (dt, J=12.5, 3.8 Hz, 1H), 3.29 (dq, J=14.2, 7.1 Hz, 1H), 2.72 (dd, J=16.2, 3.5 Hz, 1H), 2.30-2.14 (m, 1H), 1.92 (dt, J=13.4, 3.1 Hz, 1H), 1.76-1.64 (m, 1H), 1.55 (t, J=12.9 Hz, 1H), 1.45 (td, J=14.3, 3.5 Hz, 1H), 1.27 (t, J=7.1 Hz, 3H). $^{19}$F NMR (376 MHz, Chloroform-d) δ −76.37 (s, 3F), −108.71 (ddd, J=15.0, 8.8, 6.3 Hz, 1F), −111.97 (t, J=6.9 Hz, 2F). LCMS-ESI$^+$ (m/z): [M+H]$^+$ calculated for $C_{25}H_{27}F_3N_3O_6$: 522.19; found: 522.25.

Step 6

To a solution of compound 40-F (10 mg, 0.01574 mmol) in MeCN (1 mL) was added $MgBr_2$ (10 mg, 0.054 mmol) at room temperature and the resulting mixture was stirred at 50° C. After ~25 min, the reaction mixture was stirred at 0° C. and 0.1 N HCl (~3-4 drops) was added to the mixture to make the mixture a solution. The resulting solution was diluted with DMF, filtered, and the filtrate was purified by preparative HPLC and two fractions containing product, respectively, were freeze-dried to get compound 40a and compound 40b, respectively.

Compound 40a: $^1$H NMR (400 MHz, Chloroform-d) δ 10.50 (s, 1H), 8.68 (s, 1H), 6.67 (t, J=8.1 Hz, 2H), 4.67 (q, J=15.6, 15.1 Hz, 3H), 4.32 (s, 2H), 4.11 (s, 1H), 3.39-3.07 (m, 1H), 2.97-2.40 (m, 4H), 2.30 (s, 1H), 1.25 (dd, J=8.7, 6.8 Hz, 3H). $^{19}$F NMR (376 MHz, Chloroform-d) δ −76.36 (s, 3F), −108.47 (s, 1F), −112.01 (s, 2F). LCMS-ESI$^+$ (m/z): [M+H]$^+$ calculated for $C_{22}H_{23}F_3N_3O_5$: 464.14; found: 464.17.

Compound 40b: $^1$H NMR (400 MHz, Chloroform-d) δ 10.56 (s, 1H), 8.57 (s, 1H), 6.66 (dd, J=8.7, 7.5 Hz, 2H), 4.67 (d, J=5.2 Hz, 2H), 4.37 (s, 1H), 4.07-3.90 (m, 5H), 3.86 (d, J=11.7 Hz, 1H), 3.21 (dd, J=13.9, 7.0 Hz, 1H), 2.76 (d, J=15.7 Hz, 1H), 2.20 (t, J=14.4 Hz, 1H), 1.98 (d, J=13.1 Hz, 1H), 1.75 (d, J=14.3 Hz, 1H), 1.64 (q, J=12.2 Hz, 2H), 1.29 (t, J=7.2 Hz, 3H). $^{19}$F NMR (376 MHz, Chloroform-d) δ −76.36 (s, 3F), −108.92 (s, 1F), −111.96 (s, 2F). LCMS-ESI$^+$ (m/z): [M+H]$^+$ calculated for $C_{24}H_{25}F_3N_3O_6$: 508.17; found: 508.19.

Example 41

Preparation of Compound 41

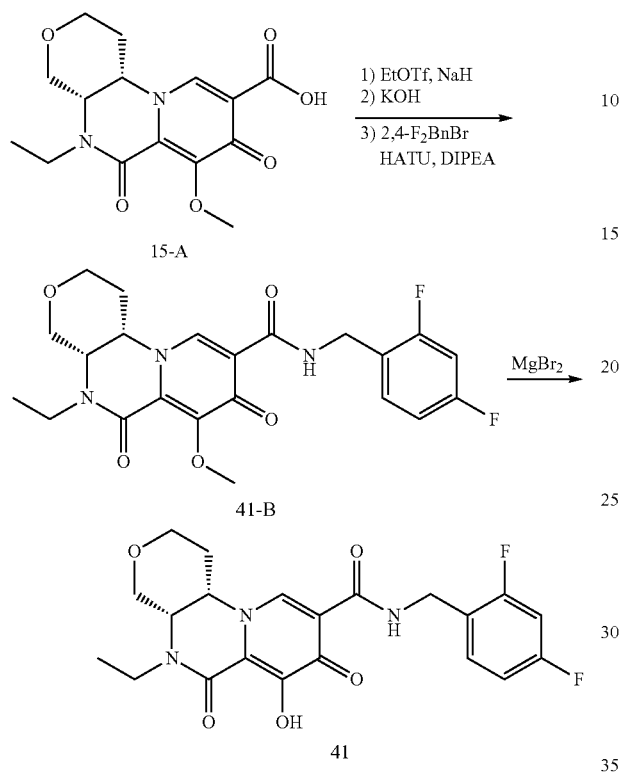

Step 1

Intermediate 41-B was prepared in a manner similar to 39-A substituting 2,4-difluorobenzylamine for 3-chloro-2,4-difluorobenzylamine: $^1$H NMR (400 MHz, Chloroform-d) δ 10.46 (s, 1H), 8.48 (s, 1H), 7.44-7.29 (m, 1H), 6.90-6.68 (m, 2H), 4.62 (dt, J=4.9, 1.9 Hz, 2H), 4.36 (s, 1H), 4.28 (q, J=7.1 Hz, 1H), 4.13 (dq, J=9.9, 7.1 Hz, 1H), 4.05 (s, 3H), 3.85 (t, J=6.4 Hz, 2H), 3.76-3.59 (m, 2H), 3.38 (dqd, J=14.1, 7.0, 2.7 Hz, 1H), 2.39 (dd, J=14.6, 7.9 Hz, 1H), 2.04 (s, 1H), 1.25 (td, J=7.3, 3.2 Hz, 3H). $^{19}$F NMR (376 MHz, Chloroform-d) δ -112.03 (s, 1F), -114.69 (s, 1F). LCMS-ESI$^+$ (m/z): [M+H]$^+$ calculated for $C_{22}H_{24}F_2N_3O_5$: 448.17; found: 448.18.

Step 2

To a solution of compound 41-B (16 mg, 0.036 mmol) in MeCN (1 mL) was added MgBr$_2$ (17 mg, 0.093 mmol) at room temperature and the resulting mixture was stirred at 50° C. bath. After 30 min, the reaction mixture was stirred at 0° C. and 1 N HCl (~0.1 mL) was added to make the mixture a solution. The resulting solution was further diluted with water (~0.3 mL) and DMF (1 mL), filtered, and purified by preparative HPLC. The product containing fraction was freeze-dried to get compound 41. $^1$H NMR (400 MHz, Chloroform-d) δ 10.60 (s, 1H), 8.64 (s, 1H), 7.35 (q, J=7.9 Hz, 1H), 6.83 (q, J=9.2, 8.7 Hz, 2H), 4.65 (qd, J=15.3, 5.3 Hz, 2H), 4.50 (s, 1H), 4.29 (d, J=13.5 Hz, 1H), 4.16 (dq, J=14.6, 7.3 Hz, 1H), 4.02 (d, J=10.0 Hz, 2H), 3.79-3.61 (m, 2H), 3.44 (dq, J=14.1, 7.0 Hz, 1H), 2.26 (q, J=11.8, 10.7 Hz, 1H), 1.95 (d, J=13.8 Hz, 1H), 1.27 (t, J=7.1 Hz, 3H). $^{19}$F NMR (376 MHz, Chloroform-d) δ -76.40 (s, 3F), -111.08--111.68 (m, 1F)), -114.43 (q, J=8.6, 8.0 Hz, 1F). LCMS-ESI$^+$ (m/z): [M+H]$^+$ calculated for $C_{21}H_{21}ClF_2N_3O_5$: 434.15; found: 434.19.

Example 42

Preparation of Compound 42

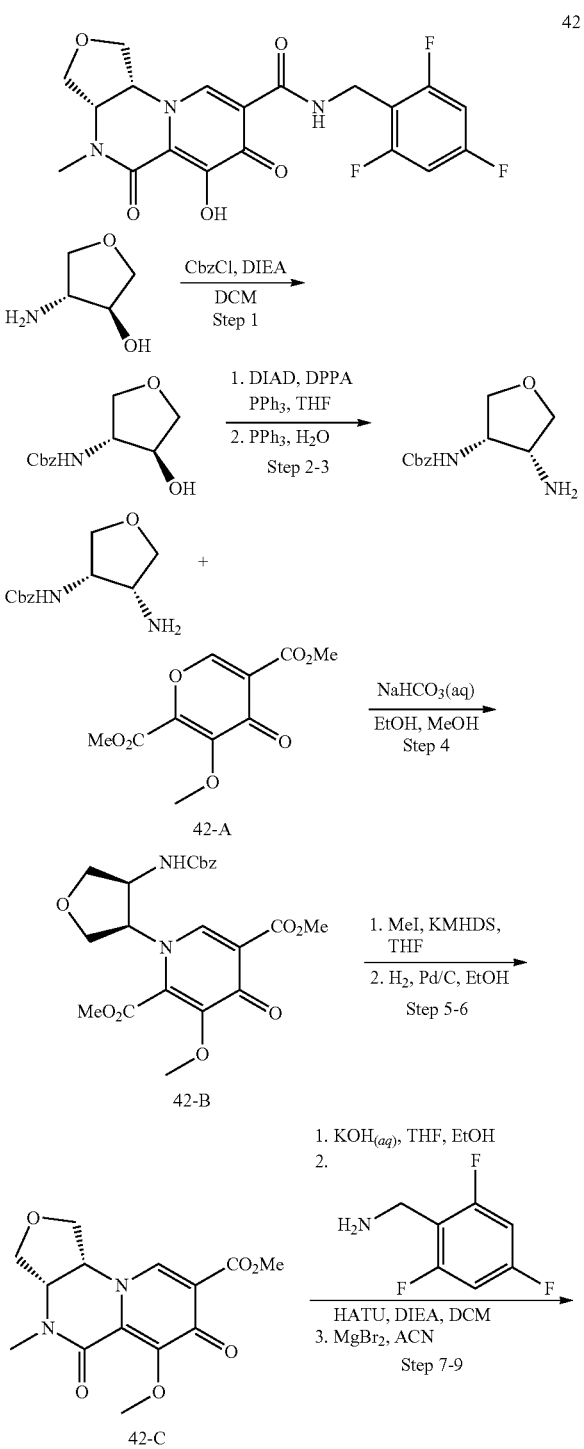

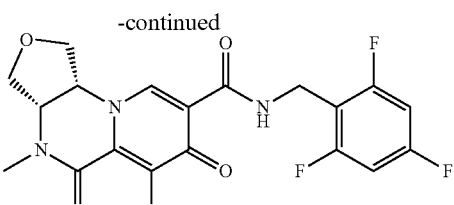

42

Step 1

A solution of (3S,4R)-4-aminotetrahydrofuran-3-ol (1.99 g, 19.3 mmol) in dichloromethane (100 mL) under nitrogen was cooled down to 0° C. and treated with N,N-Diisopropylethylamine (5 ml, 29 mmol) followed by benzyl chloroformate (3 ml, 21 mmol). The reaction mixture was allowed to gradually warm to room temperature and stirred for 18 hours. The reaction mixture was then washed sequentially with water, saturated NaHCO$_{3(aq)}$, and brine, dried over Na$_2$SO$_4$, filtered, and concentrated to afford benzyl ((3R,4S)-4-hydroxytetrahydrofuran-3-yl)carbamate which was carried forward without further purification.

Steps 2-3

To a solution of benzyl ((3R,4S)-4-hydroxytetrahydrofuran-3-yl)carbamate (1.00 g, 4.2 mmol) and triphenylphosphine (1.32 g, 5.2 mmol) in tetrahydrofuran (20 ml) was added N,N-diisopropylethylamine (0.75 ml, 4.3 mmol). The mixture was then cooled down to 0° C. and diisopropyl azodicarboxylate (1 ml, 5.1 mmol) was added dropwise. The reaction mixture was allowed to stir for 10 minutes, at which point diphenyl phosphoryl azide (1.1 ml, 5.1 mmol) was added dropwise and the reaction mixture was allowed to gradually warm to and stirred for 3 hours.

The reaction mixture was then recooled down to 0° C. and a solution of triphenylphosphine (1.44 g, 5.5 mmol) in tetrahydrofuran (2 mL) was added dropwise. The reaction solution was warmed to room temperature and stirred for 2 hours, at which point water (1 mL) was added and the reaction stirred at 50° C. for 18 hours. An additional 1 mL water was added, reaction temperature raised to 70° C., and stirring continued for 6 hours to drive the reaction to completion, at which point the reaction solution was cooled down, washed with basified brine, dried over Na$_2$SO$_4$, filtered, and concentrated. Purification by silica gel chromatography (0-10% MeOH/DCM) afforded benzyl ((3S,4R)-4-aminotetrahydrofuran-3-yl)carbamate.

Step 4

A solution of intermediate 42-A (356 mg, 1.47 mmol), benzyl ((3S,4R)-4-aminotetrahydrofuran-3-yl)carbamate (346 mg, 1.46 mmol), and sodium bicarbonate (260 mg, 3.09 mmol) in 1:1 water:ethanol (10 mL) was stirred at room temperature for 18 hours. The reaction mixture was concentrated, taken up in methanol (10 mL) and stirred at 50° C. for 3 hours to afford complete conversion. The reaction mixture was concentrated, partitioned between brine and ethyl acetate, and the aqueous phase was extracted three times with ethyl acetate. The combined organic phases were dried over Na$_2$SO$_4$, filtered, and concentrated to afford intermediate 42-B which was carried forward without further purification.

Steps 5-6

A solution of intermediate 42-B (151 mg, 0.33 mmol) in N,N-diemethylformamide (1 mL) was cooled down to 0° C. and treated dropwise with a 1M solution of KHMDS in tetrahydrofuran (0.5 mL, 0.5 mmol). The reaction solution was then warmed to room temperature, stirred for 15 minutes, treated dropwise with a solution of iodomethane (60 µL, 0.96 mmol) in N,N-dimethylformamide (1 mL), and stirred for an additional 18 hours. The reaction solution was then partitioned between saturated NH$_4$Cl$_{(aq)}$ and ethyl acetate. The aqueous phase was extracted three times with ethyl acetate, the combined organic phases washed with brine, dried over Na$_2$SO$_4$, filtered, and concentrated.

To this crude residue was added 10 wt % palladium on carbon (84 mg, 0.08 mmol) and ethanol (5 mL). The reaction was stirred under 1 atmosphere hydrogen for 18 hours, at which point LCMS showed complete conversion to intermediate 42-C. The reaction solution was filtered thru celite and concentrated to afford crude intermediate 42-C which was carried forward without further purification.

Steps 7-9

To a solution of intermediate 42-C (0.33 mmol maximum) in 1:1 tetrahydrofuran:ethanol (6 mL) was added a 1M solution of KOH$_{(aq)}$ (0.65 mL). The reaction solution was stirred for 2 hours, diluted with ethyl acetate, acidified with 10% HCl$_{(aq)}$ and partitioned between ethyl acetate and brine. The aqueous phase was extracted three times with ethyl acetate and further extracted to 2-butanol. The combined organic phases were dried over Na$_2$SO$_4$, filtered, concentrated, and carried to the next step as crude.

The residue from the previous step was taken up in dichloromethane (5 mL) and treated sequentially with (dimethylamino)-N,N-dimethyl(3H-[1,2,3]triazolo[4,5-b]pyridin-3-yloxy)methaniminium hexafluorophosphate (HATU, 0.16 g, 0.41 mmol), (2,4,6-trifluorophenyl)methanamine (50 µL, 0.41 mmol), and N,N-diisopropylethylamine (240 µL, 1.34 mmol). The reaction mixture was stirred for 30 minutes and then partitioned between NH$_4$Cl$_{(aq)}$ and ethyl acetate. The aqueous phase was extracted three times with ethyl acetate and the combined organics dried over Na$_2$SO$_4$, concentrated and carried to the next step as crude.

The residue from the previous step was taken up in acetonitrile (2 mL), treated with magnesium bromide (133 mg, 0.72 mmol), and heated up at 50° C. for 1 hour. The reaction was quenched by addition of 0.5M HCl$_{(aq)}$, was extracted three times with dichloromethane, dried over Na$_2$SO$_4$, filtered, concentrated, and purified by silica gel chromatography (0-10% MeOH/DCM) to afford compound 42. $^1$H NMR (400 MHz, CDCl$_3$) δ 12.78 (br s, 1H), 10.28 (t, J=5.6 Hz, 1H), 8.34 (s, 1H), 6.64 (t, J=8.1 Hz, 2H), 4.96 (q, J=7.1 Hz, 1H), 4.67 (dd, J=14.4, 5.9 Hz, 1H), 4.56 (dd, J=14.4, 5.5 Hz, 1H), 4.42-4.36 (m, 1H), 4.32 (dd, J=9.3, 7.8 Hz, 1H), 4.20 (dd, J=10.4, 2.7 Hz, 1), 4.13 (dd, J=10.4, 4.3 Hz, 1H), 3.84 (dd, J=9.4, 7.2 Hz, 1H), 3.16 (s, 3H). LCMS-ESI$^+$ (m/z): [M+H]$^+$ calculated for C$_{19}$H$_{17}$F$_3$N$_3$O$_5$: 424.11; found: 424.2.

Example 43

Preparation of Compound 43

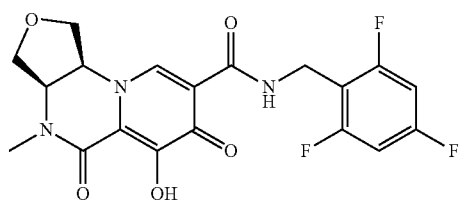

43

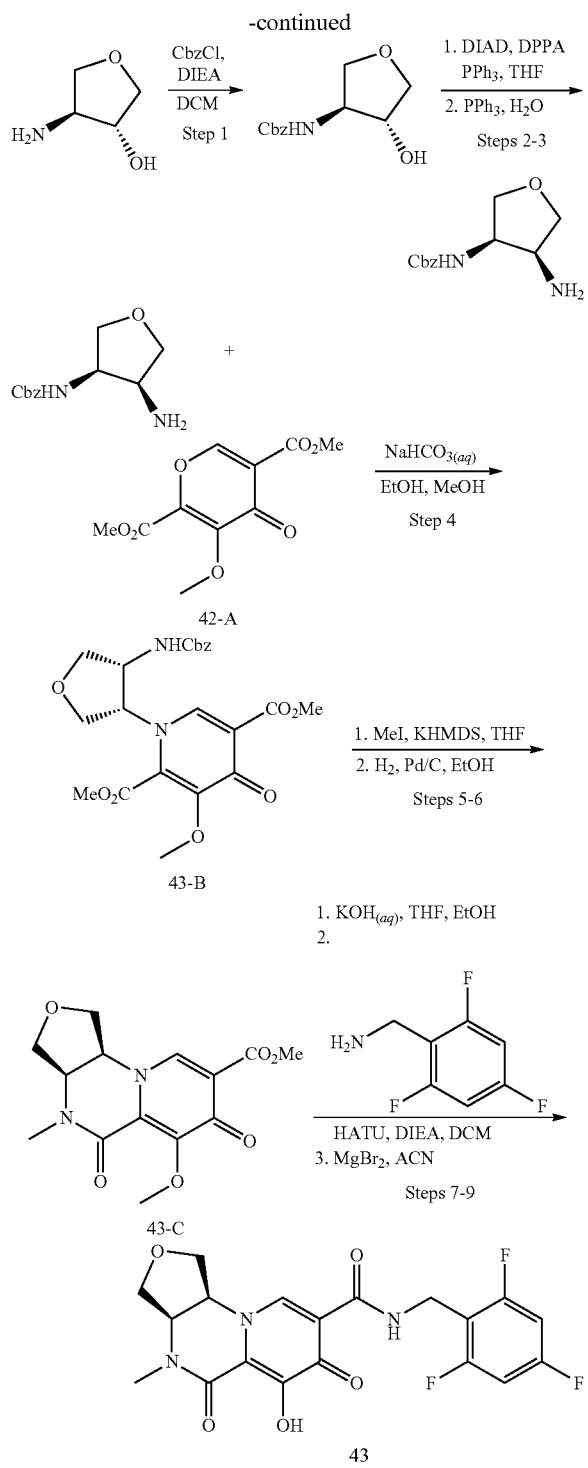

4R)-4-hydroxytetrahydrofuran-3-yl)carbamate which was carried forward without further purification.

Steps 2-3

To a solution of benzyl ((3S,4R)-4-hydroxytetrahydrofuran-3-yl)carbamate (1.0 g, 4.2 mmol) and triphenylphosphine (1.31 g, 5.0 mmol) in tetrahydrofuran (20 ml) was added N,N-diisopropylethylamine (0.75 ml, 4.3 mmol). The mixture was then cooled down to 0° C. and diisopropyl azodicarboxylate (1 ml, 5.1 mmol) was added dropwise. The reaction mixture was allowed to stir for 10 minutes, at which point diphenyl phosphoryl azide (1.1 ml, 5.1 mmol) was added dropwise and the reaction mixture was allowed to gradually warm to and stirred for 3 hours.

The reaction mixture was then recooled down to 0° C. and a solution of triphenylphosphine (1.43 g, 5.4 mmol) in tetrahydrofuran (2 mL) was added dropwise. The reaction solution was warmed to room temperature and stirred for 2 hours, at which point water (1 mL) was added and the reaction stirred at 50° C. for 18 hours. An additional 1 mL water was added, reaction temperature raised to 70° C., and stirring continued for 6 hours to drive the reaction to completion, at which point the reaction solution was cooled down, washed with basified brine, dried over $Na_2SO_4$, filtered, and concentrated. Purification by silica gel chromatography (0-10% MeOH/DCM) afforded benzyl ((3R,4S)-4-aminotetrahydrofuran-3-yl)carbamate.

Step 4

A solution of intermediate 42-A (325 mg, 1.34 mmol), benzyl ((3R,4S)-4-aminotetrahydrofuran-3-yl)carbamate (316 mg, 1.34 mmol), and sodium bicarbonate (226 mg, 2.69 mmol) in 1:1 water:ethanol (10 mL) was stirred at room temperature for 18 hours. The reaction mixture was concentrated, taken up in methanol (10 mL) and stirred at 50° C. for 3 hours to afford complete conversion. The reaction mixture was concentrated, partitioned between brine and ethyl acetate, and the aqueous phase was extracted three times with ethyl acetate. The combined organic phases were dried over $Na_2SO_4$, filtered, and concentrated to afford intermediate 43-B which was carried forward without further purification.

Steps 5-6

A solution of intermediate 43-B (149 mg, 0.32 mmol) in N,N-diemethylformamide (1 mL) was cooled down to 0° C. and treated dropwise with a 1M solution of KHMDS in tetrahydrofuran (0.5 mL, 0.5 mmol). The reaction solution was then warmed to room temperature, stirred for 15 minutes, treated dropwise with a solution of iodomethane (60 µL, 0.96 mmol) in N,N-dimethylformamide (1 mL), and stirred for an additional 18 hours. The reaction solution was then partitioned between saturated $NH_4Cl_{(aq)}$ and ethyl acetate. The aqueous phase was extracted three times with ethyl acetate, the combined organic phases washed with brine, dried over $Na_2SO_4$, filtered, and concentrated.

To this crude residue was added 10 wt % palladium on carbon (72 mg, 0.07 mmol) and ethanol (5 mL). The reaction was stirred under 1 atmosphere hydrogen for 18 hours, at which point LCMS showed complete conversion to intermediate 43-C. The reaction solution was filtered thru celite and concentrated to afford the intermediate 43-C which was carried forward without further purification.

Steps 7-9

To a solution of intermediate 43-C (0.32 mmol maximum) in 1:1 tetrahydrofuran:ethanol (6 mL) was added a 1M solution of $KOH_{(aq)}$ (0.65 mL). The reaction solution was stirred for 2 hours, neutralized with $HCl_{(aq)}$ and concentrated to near dryness under vacuum. The resultant residue was carried on to the next step as crude.

Step 1

A solution of (3R,4S)-4-aminotetrahydrofuran-3-ol (2.02 g, 19.5 mmol) in dichloromethane (100 mL) under nitrogen was cooled down to 0° C. and treated with N,N-Diisopropylethylamine (5 ml, 29 mmol) followed by benzyl chloroformate (3 ml, 21 mmol). The reaction mixture was allowed to gradually warm to room temperature and stirred for 18 hours. The reaction mixture was then washed sequentially with water, saturated $NaHCO_{3(aq)}$, and brine, dried over $Na_2SO_4$, filtered, and concentrated to afford benzyl ((3S, The residue from the previous step was taken up in dichloromethane (5 mL) and treated sequentially with (dimethylamino)-N,N-dimethyl(3H-[1,2,3]triazolo[4,5-b]pyridin-3-yloxy)methaniminium hexafluorophosphate (HATU, 0.16 g, 0.42 mmol), (2,4,6-trifluorophenyl)methanamine (50 µL, 0.41 mmol), and N,N-diisopropylethylamine (240 µL, 1.34 mmol). The reaction mixture was stirred for 45 minutes and then partitioned between NH$_4$Cl$_{(aq)}$ and ethyl acetate. The aqueous phase was extracted three times with ethyl acetate and the combined organics dried over Na$_2$SO$_4$, concentrated, and carried to the next step as crude.

The residue from the previous step was taken up in acetonitrile (2 mL), treated with magnesium bromide (119 mg, 0.65 mmol), and heated up at 50° C. for 1 hour. The reaction was quenched by addition of 0.5M HCl$_{(aq)}$, was extracted three times with dichloromethane, dried over Na$_2$SO$_4$, filtered, concentrated, and purified by silica gel chromatography (0-10% MeOH/DCM) to afford compound 43: $^1$H NMR (400 MHz, CDCl$_3$) δ 12.73 (br s, 1H), 10.28 (t, J=5.6 Hz, 1H), 8.34 (s, 1H), 6.64 (t, J=8.1 Hz, 2H), 4.99 (q, J=7.1 Hz, 1H), 4.67 (dd, J=14.5, 5.9 Hz, 1H), 4.55 (dd, J=14.5, 5.4 Hz, 1H), 4.43-4.37 (m, 1H), 4.32 (dd, J=9.4, 7.8 Hz, 1H), 4.20 (dd, J=10.4, 2.7 Hz, 1H), 4.13 (dd, J=10.4, 4.3 Hz, 1H), 3.83 (dd, J=9.4, 7.1 Hz, 1H), 3.16 (s, 3H). LCMS-ESI$^+$ (m/z): [M+H]$^+$ calculated for C$_{19}$H$_{17}$F$_3$N$_3$O$_5$: 424.11; found: 424.2.

Example 44

Preparation of Compound 44

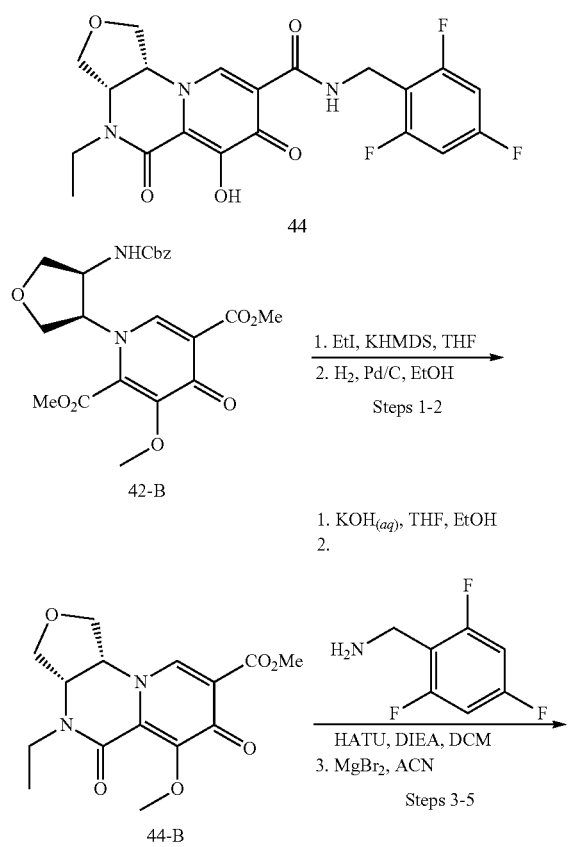

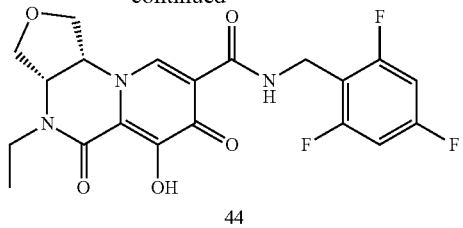

Steps 1-2

A solution of intermediate 42-B (236 mg, 0.51 mmol) in N,N-diemethylformamide (2 mL) was cooled down to 0° C. and treated dropwise with a 1M solution of KHMDS in tetrahydrofuran (0.8 mL, 0.8 mmol). The reaction solution was then warmed to room temperature, stirred for 15 minutes, treated dropwise with a solution of iodoethane (130 µL, 1.62 mmol) in N,N-dimethylformamide (1 mL), and stirred for an additional 18 hours. The reaction solution was then partitioned between saturated NH$_4$Cl$_{(aq)}$ and ethyl acetate. The aqueous phase was extracted three times with ethyl acetate, the combined organic phases washed with brine, dried over Na$_2$SO$_4$, filtered, and concentrated.

To this crude residue was added 10 wt % palladium on carbon (160 mg, 0.15 mmol) and ethanol (4 mL). The reaction was stirred under 1 atmosphere hydrogen for 18 hours, at which point LCMS showed complete conversion. The reaction solution was filtered thru celite and concentrated to afford the crude intermediate 44-B which was carried forward without further purification.

Steps 3-5

To a solution of intermediate 44-B (0.64 mmol maximum) in 1:1 tetrahydrofuran:ethanol (6 mL) was added a 1M solution of KOH$_{(aq)}$ (1.3 mL). The reaction solution was stirred for 1 hour, neutralized with HCl$_{(aq)}$ and concentrated to near dryness under vacuum. The resultant residue was carried on to the next step as crude.

The residue from the previous step was taken up in dichloromethane (10 mL) and treated sequentially with (dimethylamino)-N,N-dimethyl(3H-[1,2,3]triazolo[4,5-b]pyridin-3-yloxy)methaniminium hexafluorophosphate (HATU, 300 mg, 0.79 mmol), (2,4,6-trifluorophenyl)methanamine (100 µL, 0.82 mmol), and N,N-diisopropylethylamine (470 µL, 2.63 mmol). The reaction mixture was stirred for 30 minutes and then partitioned between NH$_4$Cl$_{(aq)}$ and ethyl acetate. The aqueous phase was extracted three times with ethyl acetate and the combined organics dried over Na$_2$SO$_4$, concentrated, and carried to the next step as crude.

The residue from the previous step was taken up in acetonitrile (3 mL), treated with magnesium bromide (225 mg, 1.2 mmol), and heated up at 50° C. for 3 hours. The reaction was quenched by addition of 0.5M HCl$_{(aq)}$, extracted three times with dichloromethane, dried over Na$_2$SO$_4$, filtered, concentrated, and purified by silica gel chromatography (0-10% MeOH/DCM) to afford compound 44: $^1$H NMR (400 MHz, CDCl$_3$) δ 12.99 (br s, 1H), 10.28 (t, J=5.6 Hz, 1H), 8.34 (s, 1H), 6.65 (t, J=8.4 Hz, 2H), 4.94 (q, J=6.4 Hz, 1H), 4.67 (dd, J=14.3, 6.0 Hz, 1H), 4.57 (dd, J=14.5, 5.5 Hz, 1H), 4.48-4.40 (m, 1H), 4.33 (dd, J=9.8, 7.0 Hz, 1H), 4.19 (dd, J=10.1, 4.9 Hz, 1H), 4.07 (dd, J=10.1, 3.9 Hz, 1H), 3.99 (dd, J=9.8, 6.1 Hz, 1H), 3.78-3.66 (m, 3H), 1.29 (t, J=7.2 Hz, 3H). LCMS-ESI$^+$ (m/z): [M+H]$^+$ calculated for C$_{20}$H$_{19}$F$_3$N$_3$O$_5$: 438.13; found: 438.1.

Example 45

Preparation of Compound 45

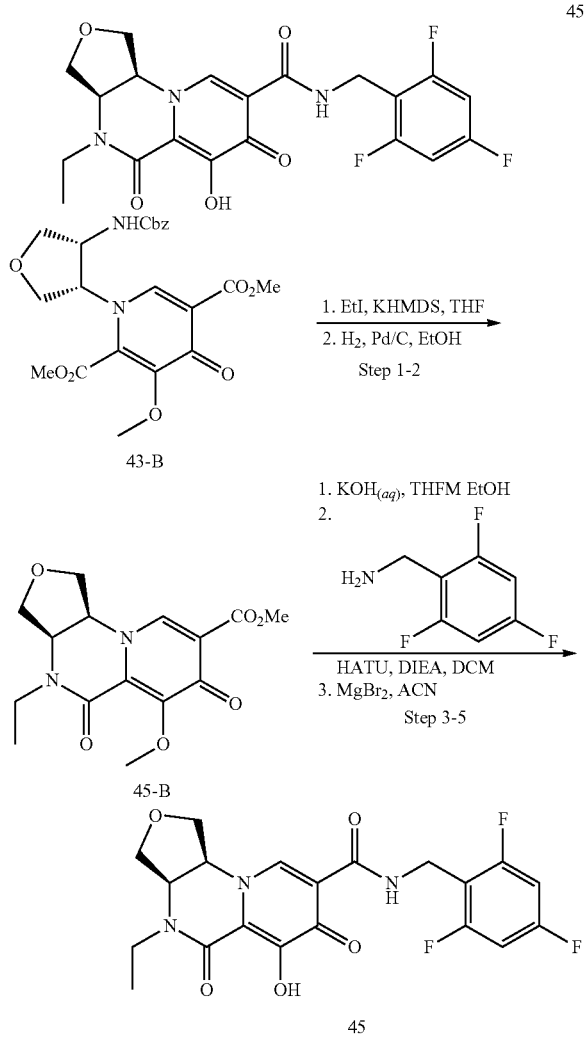

Steps 1-2

A solution of intermediate 43-B (240 mg, 0.52 mmol) in N,N-diemethylformamide (2 mL) was cooled down to 0° C. and treated dropwise with a 1M solution of KHMDS in tetrahydrofuran (0.8 mL, 0.8 mmol). The reaction solution was then warmed to room temperature, stirred for 15 minutes, treated dropwise with a solution of iodoethane (130 µL, 1.62 mmol) in N,N-dimethylformamide (1 mL), and stirred for an additional 18 hours. The reaction solution was then partitioned between saturated $NH_4Cl_{(aq)}$ and ethyl acetate. The aqueous phase was extracted three times with ethyl acetate, the combined organic phases washed with brine, dried over $Na_2SO_4$, filtered, and concentrated.

To this crude residue was added 10 wt % palladium on carbon (145 mg, 0.13 mmol) and ethanol (4 mL). The reaction was stirred under 1 atmosphere hydrogen for 18 hours, at which point LCMS showed complete conversion. The reaction solution was filtered thru celite and concentrated to afford the crude intermediate 45-B which was carried forward without further purification.

Steps 3-5

To a solution of intermediate 45-B (0.52 mmol maximum) in 1:1 tetrahydrofuran:ethanol (6 mL) was added a 1M solution of $KOH_{(aq)}$ (0.75 mL). The reaction solution was stirred for 1 hour, neutralized with $HCl_{(aq)}$ and concentrated to near dryness under vacuum. The resultant residue was carried on to the next step as crude.

The residue from the previous step was taken up in dichloromethane (5 mL) and treated sequentially with (dimethylamino)-N,N-dimethyl(3H-[1,2,3]triazolo[4,5-b]pyridin-3-yloxy)methaniminium hexafluorophosphate (HATU, 160 mg, 0.42 mmol), (2,4,6-trifluorophenyl)methanamine (100 µL, 0.45 mmol), and N,N-diisopropylethylamine (260 µL, 1.46 mmol). The reaction mixture was stirred for 45 minutes and then partitioned between $NH_4Cl_{(aq)}$ and ethyl acetate. The aqueous phase was extracted 3 times with ethyl acetate and the combined organics dried over $Na_2SO_4$, concentrated, and carried to the next step as crude.

The residue from the previous step was taken up in acetonitrile (2 mL), treated with magnesium bromide (145 mg, 0.8 mmol), and heated up at 50° C. for 2 hours. The reaction was quenched by addition of 0.5M $HCl_{(aq)}$, was extracted three times with dichloromethane, dried over $Na_2SO_4$, filtered, concentrated, and purified by silica gel chromatography (0-10% MeOH/DCM) to afford compound 45: $^1H$ NMR (400 MHz, $CDCl_3$) δ 13.04 (br s, 1H), 10.28 (t, J=5.5 Hz, 1H), 8.34 (s, 1H), 6.65 (t, J=7.2 Hz, 2H), 4.95 (q, J=6.4 Hz, 1H), 4.67 (dd, J=14.4, 5.9 Hz, 1H), 4.61-4.53 (m, 1H), 4.45 (ddd, J=6.2, 4.8, 3.7 Hz, 1H), 4.33 (dd, J=9.8, 7.0 Hz, 1H), 4.18 (dd, J=10.2, 4.9 Hz, 1H), 4.07 (dd, J=10.2, 3.9 Hz, 1H), 3.99 (dd, J=9.8, 6.0 Hz, 1H), 3.77-3.66 (m, 2H), 1.29 (t, J=7.2 Hz, 3H). LCMS-ESI$^+$ (m/z): [M+H]$^+$ calculated for $C_{20}H_{19}F_3N_3O_5$: 438.13; found: 438.2.

Example 46

Preparation of Compound 46

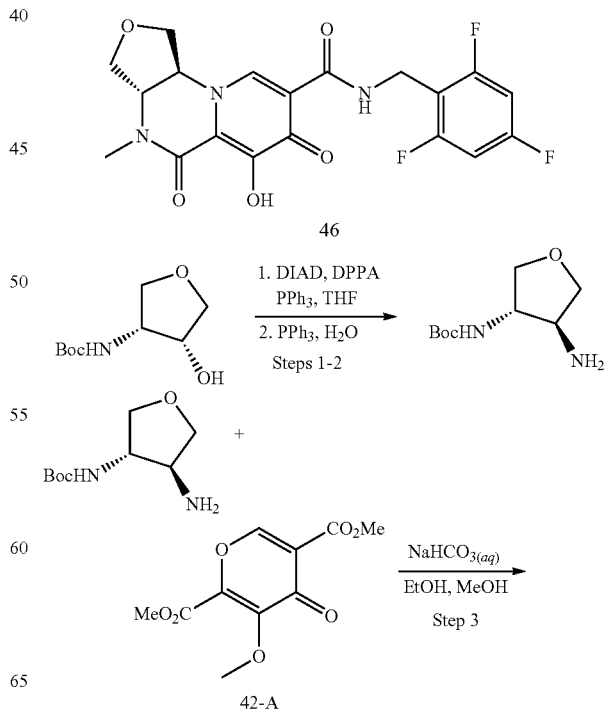

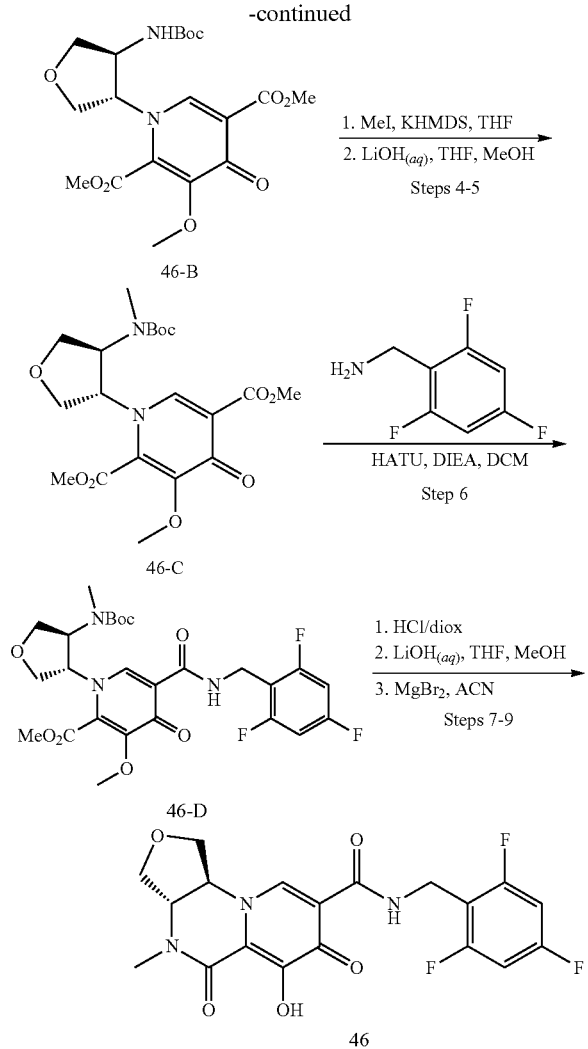

Steps 1-2

To a solution of tert-butyl ((3R,4R)-4-hydroxytetrahydrofuran-3-yl)carbamate (0.52 g, 2.55 mmol) and triphenylphosphine (0.8 g, 3.1 mmol) in tetrahydrofuran (12 ml) was added N,N-diisopropylethylamine (0.45 ml, 2.6 mmol). The mixture was then cooled down to 0° C. and diisopropyl azodicarboxylate (0.6 ml, 3.1 mmol) was added dropwise. The reaction mixture was allowed to stir for 10 minutes, at which point diphenyl phosphoryl azide (0.65 ml, 3.0 mmol) was added dropwise and the reaction mixture was allowed to gradually warm to and stirred for 2 hours.

The reaction mixture was then recooled down to 0° C. and a solution of triphenylphosphine (0.88 g, 3.35 mmol) in tetrahydrofuran (3 mL) was added dropwise. The reaction solution was warmed to room temperature and stirred for 2 hours, at which point water (2 mL) was added and the reaction stirred at 60° C. for 18 hours. The reaction solution was then cooled down, washed with basified brine, dried over Na$_2$SO$_4$, filtered, and concentrated. Purification by silica gel chromatography (0-10% MeOH/DCM) afforded tert-butyl ((3S,4S)-4-aminotetrahydrofuran-3-yl)carbamate.

Step 3

A solution of intermediate 42-A (537 mg, 2.22 mmol), tert-butyl ((3S,4S)-4-aminotetrahydrofuran-3-yl)carbamate (444 mg, 2.2 mmol), and sodium bicarbonate (386 mg, 4.59 mmol) in 1:1 water:methanol (15 mL) was stirred at room temperature for 2 hours. The reaction mixture was concentrated, taken up in methanol (10 mL) and stirred at 50° C. for 1.5 hours to afford complete conversion. The reaction mixture was concentrated, partitioned between brine and ethyl acetate, and the aqueous phase was extracted three times with ethyl acetate. The combined organic phases were dried over Na$_2$SO$_4$, filtered, and concentrated to afford 577 mg (62% yield) intermediate 46-B which was carried forward without further purification.

Steps 4-5

A solution of intermediate 46-B (95 mg, 0.22 mmol) in N,N-diemethylformamide (1 mL) was cooled down to 0° C. and treated dropwise with a 1M solution of KHMDS in tetrahydrofuran (0.4 mL, 0.4 mmol). The reaction solution was then warmed to room temperature, stirred for 15 minutes, treated dropwise with a solution of iodomethane (45 μL, 0.72 mmol) in N,N-dimethylformamide (0.5 mL), and stirred for an additional 18 hours. The reaction solution was then partitioned between saturated NH$_4$Cl$_{(aq)}$ and ethyl acetate. The aqueous phase was extracted 3 times with ethyl acetate, the combined organic phases washed with brine, dried over Na$_2$SO$_4$, filtered, concentrated, and purified by silica gel chromatography (0-10% MeOH/DCM) to afford the methylated product.

This material (38.2 mg, 0.09 mmol) was dissolved in 2:1 THF:MeOH (1.5 mL) and 0.5M LiOH$_{(aq)}$ (162 μL) was carefully titrated in to afford mono ester hydrolysis product 46-C. After completion of reaction the solution was quenched by addition of 0.5M HCl$_{(aq)}$ (180 μL). The aqueous phase was extracted 3 times with ethyl acetate, the combined organic phases dried over Na$_2$SO$_4$, filtered, concentrated, and carried on to the next step as crude.

Step 6

To a solution of crude intermediate 46-C (0.09 mmol) in dichloromethane (2 mL) was added sequentially (dimethylamino)-N,N-dimethyl (3H-[1,2,3]triazolo[4,5-b]pyridin-3-yloxy)methaniminium hexafluorophosphate (HATU, 0.40 g, 0.11 mmol), (2,4,6-trifluorophenyl)methanamine (40 μL, 0.32 mmol), and N,N-diisopropylethylamine (60 μL, 0.34 mmol). The reaction mixture was stirred for 45 minutes, concentrated onto silica gel, and purified by silica gel chromatorgraphy (0-100% EtOAc/hexanes) to afford intermediate 46-D.

Steps 7-9

A solution of intermediate 46-D (36.4 mg, 0.06 mmol) in 4M HCl/dioxane (0.8 mL) was stirred at room temperature for one hour. After complete Boc deprotection the reaction mixture was concentrated, azeotroped three times from toluene, and carried on as crude.

The residue from the previous step was dissolved in 2:1 THF:MeOH (1.5 mL), treated with 0.5M LiOH$_{(aq)}$ (0.5 mL) and stirred for 2 hours until completion. The reaction was neutralized with 0.5M HCl$_{(aq)}$, extracted to dichloromethane, dried over Na$_2$SO$_4$, filtered, concentrated, and carried on as crude.

The residue from the previous step was taken up in acetonitrile (1 mL), treated with magnesium bromide (29 mg, 0.16 mmol), and heated up at 50° C. for 30 minutes. The reaction was quenched by addition of 0.5M HCl$_{(aq)}$, was extracted 3 times with dichloromethane, dried over Na$_2$SO$_4$, filtered, concentrated, and purified by silica gel chromatography (0-10% MeOH/DCM) to afford compound 46: $^1$H NMR (400 MHz, CDCl$_3$) δ 12.22 (s, 1H), 10.33-10.18 (m, 1H), 7.95 (s, 1H), 6.65 (t, J=8 Hz, 2H), 4.64 (d, J=5.7 Hz, 2H), 4.59 (t, J=7.4 Hz, 1H), 4.49-4.35 (m, 2H), 4.24-4.13

(m, 2H), 4.00 (dd, J=10.5, 7.6 Hz, 1H), 3.08 (s, 3H). LCMS-ESI+ (m/z): [M+H]+ calculated for C19H17F3N3O5: 424.11; found: 424.2.

Example 47

Preparation of Compound 47

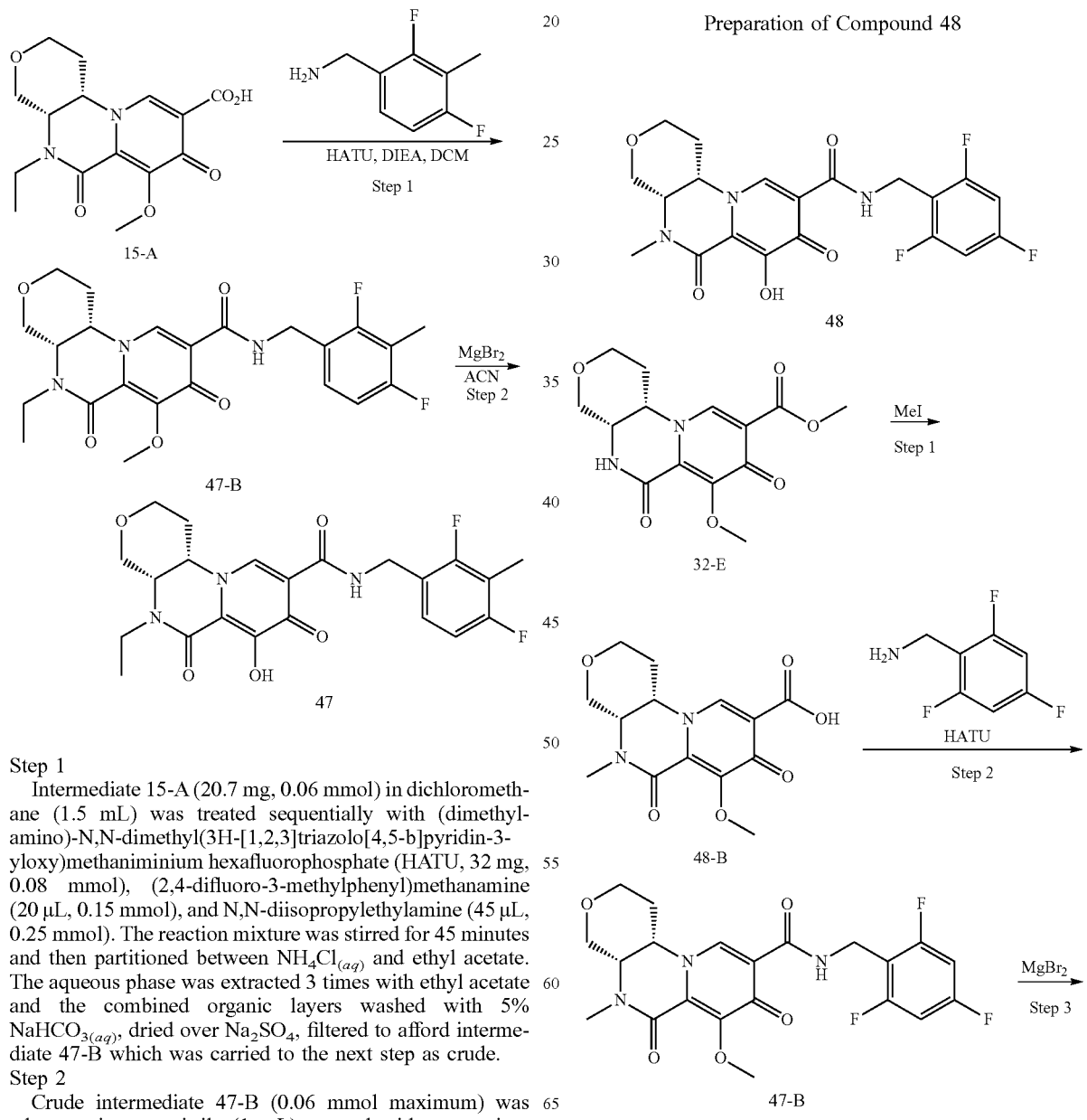

Step 1

Intermediate 15-A (20.7 mg, 0.06 mmol) in dichloromethane (1.5 mL) was treated sequentially with (dimethylamino)-N,N-dimethyl(3H-[1,2,3]triazolo[4,5-b]pyridin-3-yloxy)methaniminium hexafluorophosphate (HATU, 32 mg, 0.08 mmol), (2,4-difluoro-3-methylphenyl)methanamine (20 µL, 0.15 mmol), and N,N-diisopropylethylamine (45 µL, 0.25 mmol). The reaction mixture was stirred for 45 minutes and then partitioned between NH4Cl(aq) and ethyl acetate. The aqueous phase was extracted 3 times with ethyl acetate and the combined organic layers washed with 5% NaHCO3(aq), dried over Na2SO4, filtered to afford intermediate 47-B which was carried to the next step as crude.

Step 2

Crude intermediate 47-B (0.06 mmol maximum) was taken up in acetonitrile (1 mL), treated with magnesium bromide (26 mg, 0.14 mmol), and heated up at 50° C. for 1 hour. The reaction was quenched by addition of 0.5M HCl(aq), was extracted 3 times with dichloromethane, dried over Na2SO4, filtered, concentrated, and purified by silica gel chromatography (0-10% MeOH/DCM) to afford compound 47: 1H NMR (400 MHz, CDCl3) δ 12.71 (s, 1H), 10.40 (t, J=5.4 Hz, 1H), 8.36 (s, 1H), 7.15 (q, J=8.2 Hz, 1H), 6.76 (t, J=8.8 Hz, 1H), 4.58 (qd, J=15.3, 5.8 Hz, 2H), 4.46-4.38 (m, 1H), 4.23 (d, J=15.5 Hz, 1H), 4.12 (dt, J=14.4, 7.2 Hz, 1H), 4.01-3.92 (m, 2H), 3.73-3.62 (m, 2H), 3.41 (dd, J=14.2, 7.1 Hz, 1H), 2.31-2.19 (m, 1H), 2.17 (s, 3H), 1.96-1.87 (m, 1H), 1.26 (t, J=7.2 Hz, 3H). LCMS-ESI+ (m/z): [M+H]+ calculated for C22H24F2N3: 448.17; found: 448.2.

Example 48

Preparation of Compound 48

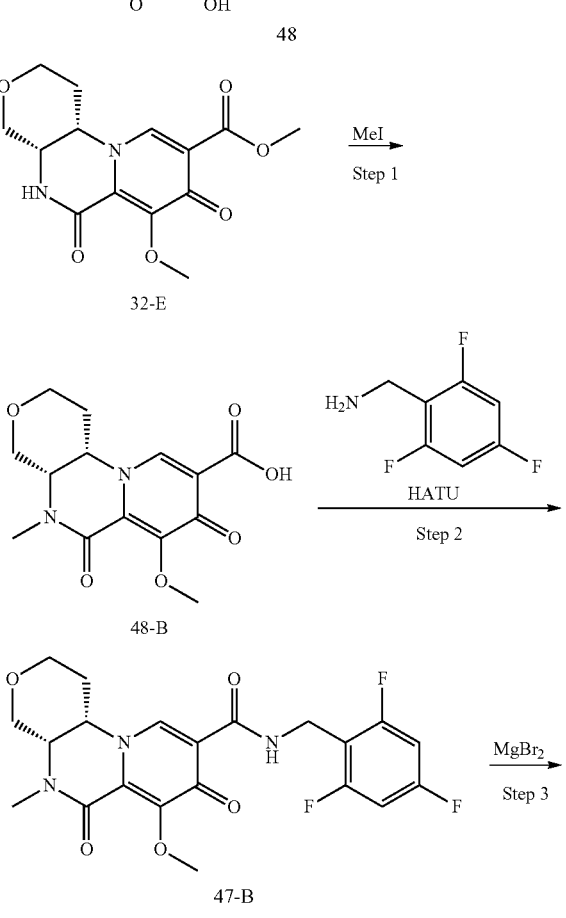

143

-continued

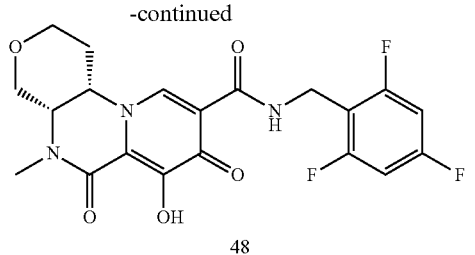

48

Step 1

Intermediate 32-E (0.10 g, 0.32 mmol) was dissolved in a 1:1 mixture of DMF:THF (2 mL) and sodium hydride (60%, 0.026 g, 0.65 mmol) was added. The solution was stirred at room temperature for 5 min and then iodomethane (0.05 mL, 0.8 mmol) was added. After stirring for 1.5 hours, aqueous potassium hydroxide (1M, 0.5 mL, 0.5 mmol) was added. The solution was stirred for an additional 45 min before aqueous hydrochloric acid (6M, 0.22 mL 1.3 mmol) was added and the solution was concentrated to dryness. The resulting crude material was used in the subsequent step.

LCMS-ESI$^+$ (m/z): [M+H]$^+$ calculated for $C_{14}H_{16}N_2O_6$: 309.11; found: 309.09.

Step 2

To a slurry of Intermediate 48-B (0.1 g, 0.32 mmol) on $CH_2Cl_2$ (4 mL) was added (2,4,6-trifluorophenyl)methanamine (0.078 g, 0.48 mmol), HATU (0.15 g, 0.41 mmol), and N,N-diisopropylethylamine (0.2 mL, 1.15 mmol). The resulting solution was stirred at room temperature for 1 h and then diluted with $CH_2Cl_2$. The solution was then washed with HCl (aqueous, 1M). The aqueous layer was back-extracted with $CH_2Cl_2$ (2 times) and the combined organic layers were dried over magnesium sulfate and concentrated to dryness. The crude material was then purified by column chromatography (SiO$_2$, 2→10% MeOH in $CH_2Cl_2$) to provide Intermediate 48-C.

LCMS-ESI$^+$ (m/z): [M+H]$^+$ calculated for $C_{21}H_{20}F_3N_3O_5$: 452.14; found: 452.23.

Step 3

To a solution of Intermediate 48-C (0.15 g, 0.34 mmol) in acetonitrile (5 mL) was added MgBr$_2$ (0.12 g, 0.68 mmol). The reaction mixture was stirred at 45° C. for 1.5 hours and diluted with $CH_2Cl_2$. The solution was washed with aqueous hydrochloric acid (1N) and aqueous NaCl (saturated). The combined aqueous layers were back-extracted with $CH_2Cl_2$ (2 times). The combined organic layers were concentrated and the resulting crude material was purified by preparative HPLC (10→60% ACN/H$_2$O with 0.1% TFA modifier) to afford compound 48:

$^1$H NMR (400 MHz, DMSO-d6) δ 12.67 (s, 1H), 10.39 (t, 1H), 8.44 (s, 1H), 7.19 (t, 2H), 4.85 (dt, 1H), 4.53 (qd 2H), 4.38-4.26 (m, 1H), 4.08-4.00 (m, 1H), 3.90-3.82 (m, 1H), 3.50 (ddd, 2H), 3.09 (s, 3H), 1.98-1.76 (m, 2H). LCMS-ESI$^+$ (m/z): [M+H]$^+$ calculated for $C_{20}H_{18}F_3N_3O_5$: 438.13; found: 438.74.

144

Example 49

Preparation of Compound 49

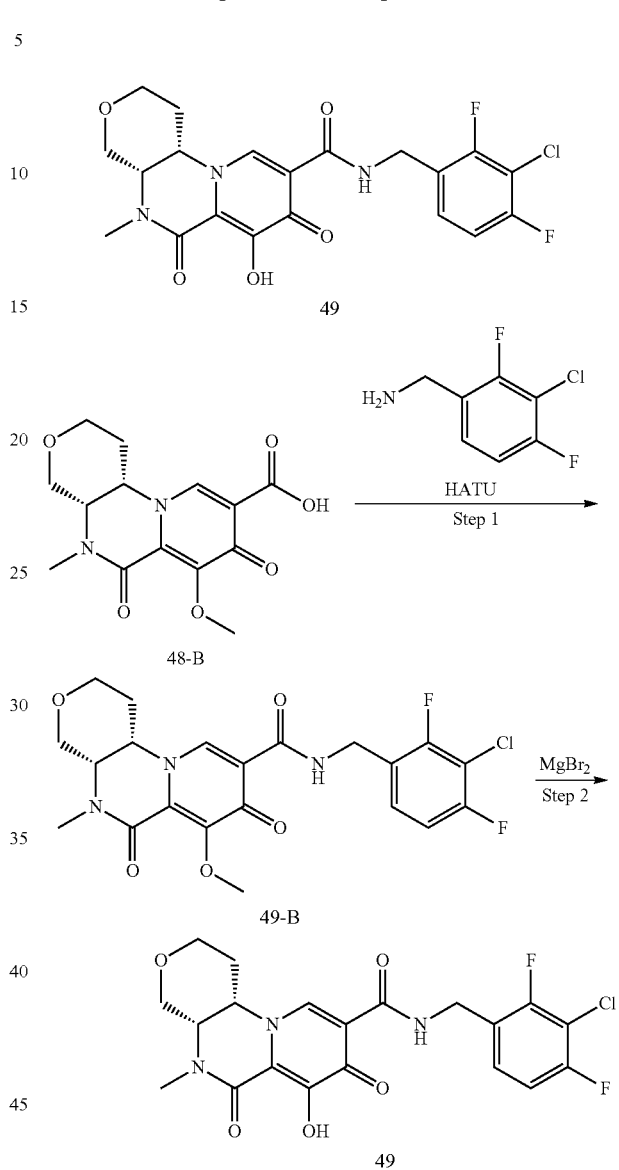

Step 1

To a slurry of Intermediate 48-B (0.1 g, 0.32 mmol) on $CH_2Cl_2$ (4 mL) was added (3-chloro-2,4-difluorophenyl)methanamine (0.075 g, 0.42 mmol), HATU (0.15 g, 0.41 mmol), and N,N-diisopropylethylamine (0.2 mL, 1.15 mmol). The resulting solution was stirred at room temperature for 1 h and then diluted with $CH_2Cl_2$. The solution was then washed with HCl (aqueous, 1M). The aqueous layer was back-extracted with $CH_2Cl_2$ (2 times) and the combined organic layers were dried over magnesium sulfate and concentrated to dryness. The crude material was then purified by column chromatography (SiO$_2$, 2→10% MeOH in $CH_2Cl_2$) to provide Intermediate 49-B.

LCMS-ESI$^+$ (m/z): [M+H]$^+$ calculated for $C_{21}H_{20}ClF_2N_3O_5$: 468.11; found: 468.44.

Step 3

To a solution of Intermediate 49-B (0.11 g, 0.23 mmol) in acetonitrile (4 mL) was added MgBr$_2$ (0.1 g, 0.54 mmol).

The reaction mixture was stirred at 45° C. for 45 min and diluted with CH₂Cl₂. The solution was washed with aqueous hydrochloric acid (1N) and aqueous NaCl (saturated). The combined aqueous layers were back-extracted with CH₂Cl₂ (2 times). The combined organic layers were concentrated and the resulting crude material was purified by preparative HPLC (10→65% ACN/H₂O with 0.1% TFA modifier) to afford compound 49:

¹H NMR (400 MHz, DMSO-d6) δ 12.70 (s, 1H), 10.44 (t, 1H), 8.46 (s, 1H), 7.37 (td, 1H), 7.28 (td, 1H), 4.87 (dt, 1H), 4.62-4.52 (m, 2H), 4.34 (dd, 1H), 4.04 (d, 1H), 3.94-3.79 (m, 1H), 3.50 (ddd, 2H), 3.10 (s, 3H), 1.99-1.73 (m, 2H). LCMS-ESI⁺ (m/z): [M+H]⁺ calculated for C₂₀H₁₈ClF₂N₃O₅: 454.10; found: 455.17.

Example 50

Preparation of Compound 50

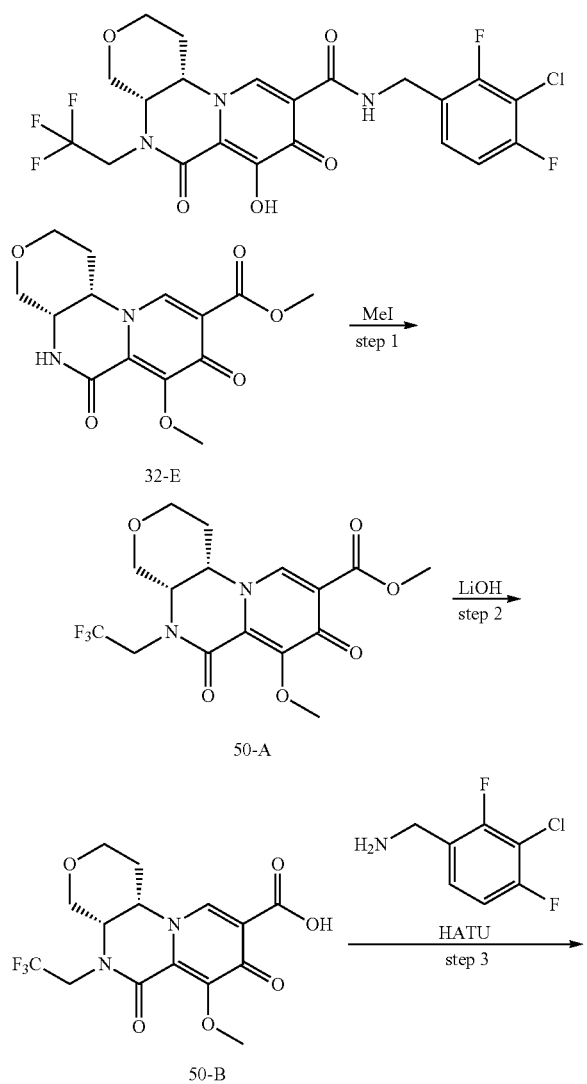

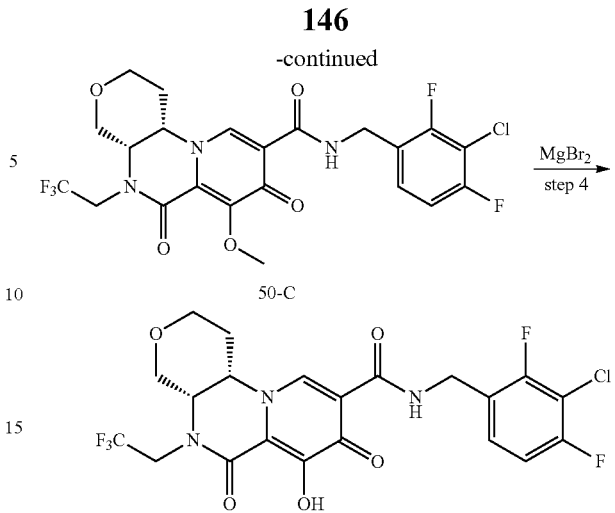

Step 1

Intermediate 32-E (0.25 g, 0.81 mmol) was dissolved in a 1:1 mixture of DMF:THF (2 mL) and sodium hydride (60%, 0.065 g, 1.63 mmol) was added. The solution was stirred at room temperature for 5 min and then 2,2,2-trifluoroethyl trifluoromethanesulfonate (0.25 ml, 1.74 mmol) was added. After stirring for 1.5 hours, and quenched with the addition of MeOH. The solution was diluted with EtOAc and washed with aqueous NH₄Cl (50%) The aqueous layer was back-extracted with EtOAc (2 times) and the combined organic layers were dried over sodium sulfate and concentrated to dryness. The crude material was purified by column chromatography (SiO₂, 2→10% MeOH in CH₂Cl₂) to provide Intermediate 50-A.

Step 2

To a solution of Intermediate 50-A (0.22 g, 0.56 mmol) in a 3:1:1 mixture of THF:MeOH:H₂O (5 mL) was added lithium hydroxide (0.05 g, 1.19 mmol). The solution was stirred for an additional 2 h before aqueous hydrochloric acid (6M, 0.25 mL 2 mmol) was added and the solution was concentrated to dryness. The resulting crude material 50-B was used in the subsequent step.

Step 3

To a slurry of Intermediate 50-B (0.21 g, 0.56 mmol) on CH₂Cl₂ (4 mL) was added (3-chloro-2,4-difluorophenyl)methanamine (0.12 g, 0.69 mmol), HATU (0.25 g, 0.67 mmol), and N,N-diisopropylethylamine (0.3 mL, 1.67 mmol). The resulting solution was stirred at room temperature for 1 h and additional HATU (0.25 g, 0.67 mmol) and N,N-diisopropylethylamine (0.3 mL, 1.67 mmol) were added. After stirring at room temperature for 18 hours, then solution was diluted with CH₂Cl₂. The solution was then washed with HCl (aqueous, 1M). The aqueous layer was back-extracted with CH₂Cl₂ (2 times) and the combined organic layers were dried over magnesium sulfate and concentrated to dryness. The crude material was then purified by column chromatography (SiO₂, 2→10% MeOH in CH₂Cl₂) to provide Intermediate 50-C.

Step 4

To a solution of Intermediate 50-C (0.06 g, 0.12 mmol) in acetonitrile (5 mL) was added MgBr₂ (0.05 g, 0.26 mmol). The reaction mixture was stirred at 45° C. for 1.5 hours and diluted with CH₂Cl₂. The solution was washed with aqueous hydrochloric acid (1N) and aqueous NaCl (saturated). The combined aqueous layers were back-extracted with CH₂Cl₂

(2 times). The combined organic layers were concentrated and the resulting crude material was purified by preparative HPLC (10→75% ACN/H$_2$O with 0.1% TFA modifier) to afford compound 50: $^1$H NMR (400 MHz, DMSO-d6) δ 11.80 (s, 1H), 10.35 (t, 1H), 8.50 (s, 1H), 7.32 (dt, 2H), 4.89 (dt, 2H), 4.67-4.51 (m, 2H), 4.32-4.02 (m, 3H), 3.84 (d, 1H), 3.64 (d, 1H), 2.09-1.81 (m, 2H). LCMS-ESI$^+$ (m/z): [M+H]$^+$ calculated for C$_{21}$H$_{17}$ClF$_5$N$_3$O$_5$: 522.09; found: 522.64.

Example 51

Preparation of Compound 51

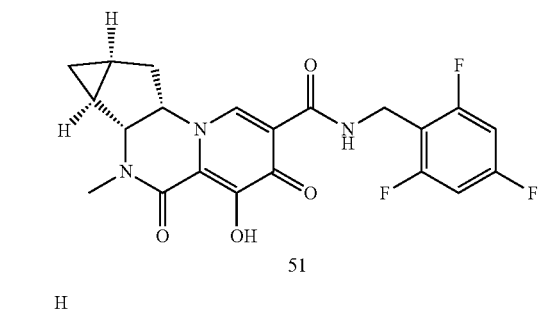
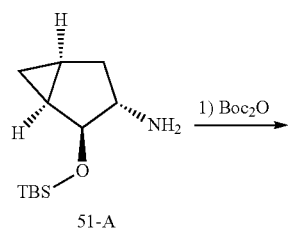
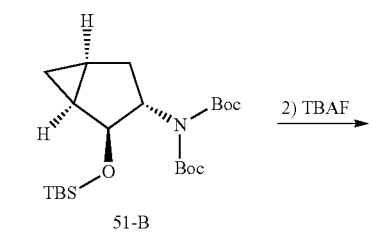
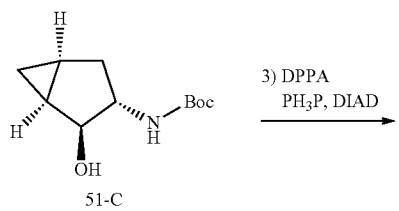
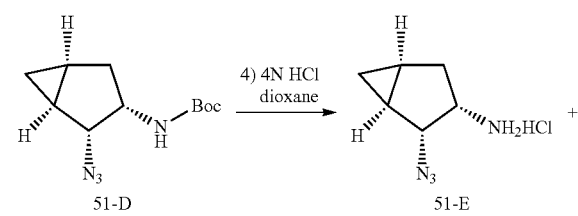
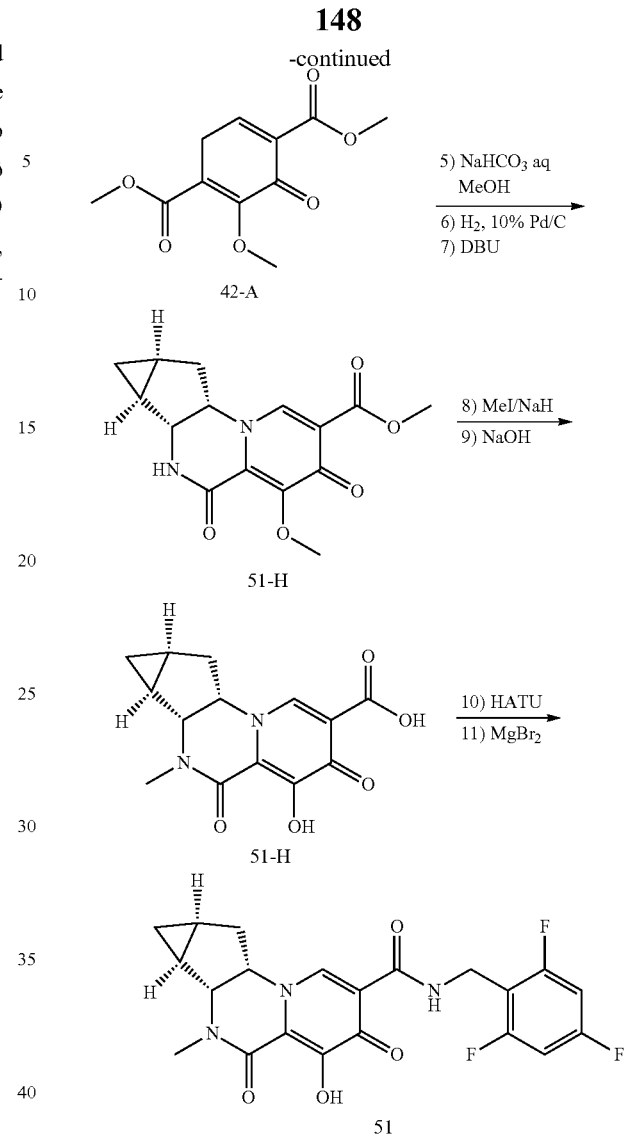

Step 1

Reactant 51-A (1S,2S,3S,5S)-2-((tert-butyldimethylsilyl)oxy)bicyclo[3.1.0]hexan-3-amine (2.06 g, 9.06 mmol) in dichloromethane (100 ml) was stirred at room temperature as N,N-Diisopropylethylamine (6.31 ml, 36.23 mmol) and Di-tert-butyl dicarbonate 97% (3.95 g, 18.12 mmol) were added. After 16 h, the reaction mixture was concentrated. The residue was purified by flash chromatography using 0-50% of ethyl acetate/Hexane as eluent to give (1S,2S,3 S,5S)-2-((tert-butyldimethylsilyl)oxy)bicyclo[3.1.0] hexan-3-amine 51-B: $^1$H NMR (400 MHz, Chloroform-d) δ 4.23 (s, 1H), 4.11 (dd, J=7.7, 4.8 Hz, 1H), 3.32 (s, 1H), 2.05 (dd, J=12.6, 7.6 Hz, 1H), 1.68-1.47 (m, 1H), 1.46 (s, 9H), 1.35 (s, 9H), 1.31-1.20 (m, 1H), 1.20-1.10 (m, 1H), 0.83 (s, 9H), 0.56 (q, J=4.3 Hz, 1H), 0.30 (td, J=8.0, 5.5 Hz, 1H), 0.01 (d, J=7.0 Hz, 6H). LCMS-ESI$^+$ (m/z): [M+H]$^+$ calculated for Chemical Formula: C$_{22}$H$_{41}$NO$_5$Si, Molecular Weight: 427.65; found: 327.73 (M+1-100).

Step 2

To a cold (0° C.) solution of the silyl ether 51-B (6.93 mmol) in dry tetrahydrofuran (70 mL), was added tetra-n-butylammonium fluoride (TBAF) (13.9 mL of a 1 M solution in tetrahydrofuran, 13.9 mmol) and the resulting solution was stirred and warmed to 60° C. for 3 h. The reaction mixture was cooled down down to room temperature, diluted with EtOAc (100 mL) and washed with saturated NaHCO$_3$ and brine (50 mL) then dried over magnesium sulfate, followed by solvent reduction in vacuo. The crude product was purified by flash chromatography (0-100% ethyl acetate/Hexane) to give tert-butyl ((1S,2S,3S,5S)-2-hydroxybicyclo[3.1.0]hexan-3-yl)carbamate 51-C. $^1$H NMR (400 MHz, Chloroform-d) δ 4.54 (s, 1H), 4.28-4.20 (m, 1H), 3.35 (q, J=7.9 Hz, 1H), 2.55 (br, 1H), 2.19 (dd, J=12.4, 7.7 Hz, 1H), 1.71-1.51 (m, 2H), 1.43 (s, 9H), 1.37-1.23 (m, 1H), 0.65 (q, J=4.0 Hz, 1H), 0.47 (td, J=7.8, 5.5 Hz, 1H).

Step 3

To tert-butyl ((1S,2S,3S,5S)-2-hydroxybicyclo[3.1.0]hexan-3-yl) carbamate 51-C (1.63 g, 7.64 mmol) and triphenylphosphine (2.6 g, 9.9 mmol) in 76 ml THF was added N,N-diisopropylethylamine (1.5 ml, 8.6 mmol) then cooled down in an ice bath. Diisopropyl azodicarboxylate, 95% (1.8 ml, 9.17 mmol) was slowly added and the mixture stirred for 10 minutes. Diphenyl phosphoryl azide (2.0 ml, 9.28 mmol) was added dropwise and the reaction gradually warmed to room temperature over 2 h and held at room temperature for another 3 h. It was diluted with ether and a white solid was filtered off. The organic was washed with saturated NH$_4$Cl, saturated NaHCO$_3$ and brine. After drying over sodium sulfate and concentrating, the residue was purified by flash chromatography (0-50% ethyl acetate/Hexane) to give of tert-butyl ((1S,2R,3S,5S)-2-azidobicyclo[3.1.0]hexan-3-yl)carbamate 51-D: 1H NMR (400 MHz, Chloroform-d) δ 4.30 (s, 1H), 3.56 (d, J=5.3 Hz, 1H), 3.40 (t, J=8.4 Hz, 1H), 1.68 (dd, J=12.4, 7.3 Hz, 1H), 1.28-1.07 (m, 3H), 1.06 (s, 9H), 0.19 (td, J=8.2, 6.0 Hz, 1H), 0.02 (q, J=4.1 Hz, 1H).

Step 4

1 g of tert-butyl ((1S,2R,3S,5S)-2-azidobicyclo[3.1.0]hexan-3-yl)carbamate 51-D was dissolved in dichloromethane (10 mL) at room temperature. 4 N HCl in dioxane (4 mL) was added. The mixture was stirred at room temperature for 60 min, concentrated and azeotropically dried twice by evaporation from toluene to give (1S,2R,3S,5S)-2-azidobicyclo[3.1.0]hexan-3-amine hydrochloride 51-E: LCMS-ESI$^+$ (m/z): [M+H]$^+$ calculated for Chemical Formula: C$_6$H$_{10}$N$_4$, Molecular Weight: 138.17; found: 138.98.

Step 5, 6, 7

A mixture of the pyrone 42-A (1017 mg, 4.2 mmol), (1S,2R,3S,5S)-2-azidobicyclo[3.1.0]hexan-3-amine hydrochloride 51-E (733 mg, 4.2 mmol) with sodium bicarbonate (2.12 g, 25.19 mmol) in water (50 mL) and methanol (20 mL) was stirred at ambient temperature for 4 h. The mixture was concentrated, co-evaporated with acetonitrile to remove water. Ethanol (150 mL) was added and the insoluble was filtered off through Celite. The filtrate was treated with 4 mL of 4N HCl/Dioxane, stirred for 1 h, and used for the next reaction as is.

To the crude mixture was added 0.5 g of 10% Pd/C catalyst. It was purged with hydrogen three times and stirred under hydrogen atmosphere for 18 h. After filtering off the catalyst, the mixture was concentrated to dryness. After purification, it gave (6aR,6bS,7aS,8aS)-methyl 4-methoxy-3,5-dioxo-5,6,6a,6b,7,7a,8,8a-octahydro-3H-cyclopropa[4,5]cyclopenta[1,2-e]pyrido[1,2-a]pyrazine-2-carboxylate 51-G: LCMS-ESI$^+$ (m/z): [M+H]$^+$ calculated for Chemical Formula: C$_{15}$H$_{16}$N$_2$O$_5$, Molecular Weight: 304.30; found: LCMS[m+1]=305.16.

Step 8, 9

To (6aR,6bS,7aS,8aS)-methyl 4-methoxy-3,5-dioxo-5,6,6a,6b,7,7a,8,8a-octahydro-3H-cyclopropa[4,5]cyclopenta[1,2-e]pyrido[1,2-a]pyrazine-2-carboxylate 51-G (422 mg, 1.387 mmol) in THF (20 mL) and DMF (8 mL) was added sodium hydride (60%, 222 mg, 5.55 mmol) at room temperature. After 5 min, iodomethane (345 μl, 5.55 mmol) was added. After stirring at room temperature for 120 min, 1N NaOH (5 mL) was added. It was stirred at room temperature for ~5 min. The resulting mixture was acidified with 3 N HCl and concentrated to afford (6aR,6bS,7aS,8aS)-4-methoxy-6-methyl-3,5-dioxo-5,6,6a,6b,7,7a,8,8a-octahydro-3H-cyclopropa[4,5]cyclopenta[1,2-e]pyrido[1,2-a]pyrazine-2-carboxylic acid 51-H which was used for the next step: LCMS-ESI$^+$ (m/z): [M+H]$^+$ Chemical Formula: C15H16N2O5, Molecular Weight: 304.30; found: 305.18.

Step 10, 11

Steps 10 and 11 were performed in a manner similar to Steps 2 and 3 for Compound 48 to give 51 (6aR,6bS,7aS,8aS)-4-hydroxy-6-methyl-3,5-dioxo-N-(2,4,6-trifluorobenzyl)-5,6,6a,6b,7,7a,8,8a-octahydro-3H-cyclopropa[4,5]cyclopenta[1,2-e]pyrido[1,2-a]pyrazine-2-carboxamide: $^1$H NMR (400 MHz, Chloroform-d) δ 12.75 (s, 1H), 10.36 (t, J=5.6 Hz, 1H), 8.23 (s, 1H), 6.82-6.51 (m, 2H), 5.29 (s, 1H), 4.76-4.47 (m, 2H), 4.31-4.00 (m, 2H), 3.23 (s, 3H), 2.32 (dd, J=12.7, 7.4 Hz, 1H), 2.14-1.95 (m, 1H), 1.90 (ddd, J=9.1, 6.0, 3.6 Hz, 1H), 1.59 (ddd, J=10.2, 8.2, 4.2 Hz, 1H), 1.34-1.19 (m, 1H), 0.78 (q, J=7.7 Hz, 1H), 0.56 (dt, J=7.0, 3.8 Hz, 1H). $^{19}$F NMR (377 MHz, Chloroform-d) δ −109.19 (p, J=7.4 Hz), −111.98 (t, J=6.9 Hz). LCMS-ESt (m/z): [M+H]$^+$ Chemical Formula: C$_{21}$H$_{18}$F$_3$N$_3$O$_4$, Molecular Weight: 433.38; found: 434.61.

Example 52

Preparation of Compound 52

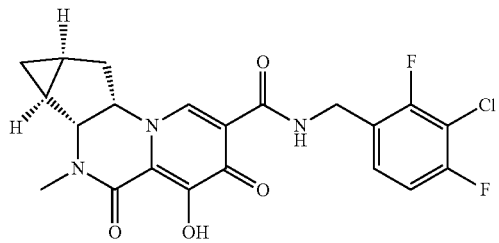

Compound 52 was prepared in a manner similar to compound 51 using (3-chloro-2,4-difluorophenyl)methanamine in place of 2,4,6-trifluorobenzylamine to give 52 (6aR,6bS,7aS,8aS)-N-(3-chloro-2,4-difluorobenzyl)-4-hydroxy-6-methyl-3,5-dioxo-5,6,6a,6b,7,7a,8,8a-octahydro-3H-cyclopropa[4,5]cyclopenta[1,2-e]pyrido[1,2-a]pyrazine-2-carboxamide: $^1$H NMR (400 MHz, Chloroform-d) δ 12.82 (s, 1H), 10.49 (t, J=5.9 Hz, 1H), 8.24 (s, 1H), 7.41-7.11 (m, 1H), 6.90 (td, J=8.5, 1.8 Hz, 1H), 4.74-4.46 (m, 2H), 4.25-4.15 (m, 2H), 3.23 (s, 3H), 2.44-2.27 (m, 1H), 2.10-2.04 (m, 1H), 1.91 (ddd, J=8.6, 6.0, 3.6 Hz, 1H), 1.60 (ddd, J=8.0, 4.3, 1.3 Hz, 1H), 0.77 (q, J=7.9 Hz, 1H), 0.57 (dt, J=6.4, 3.8 Hz, 1H). $^{19}$F NMR (376 MHz, Chloroform-d) δ −72.01, −73.90, −113.53--116.27 (m), −117.43 (dd, J=8.6, 3.0 Hz). LCMS-ESI$^+$ (m/z): [M+H]$^+$ Chemical Formula: C$_{21}$H$_{18}$ClF$_2$N$_3$O$_4$, Molecular Weight: 449.84; found: 450.47.

Example 53

Preparation of Compound 53

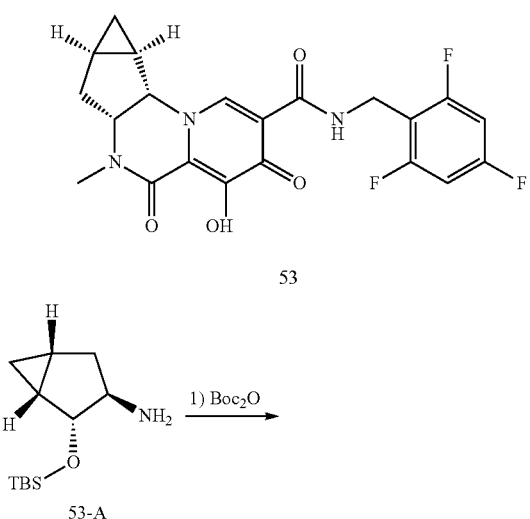

53

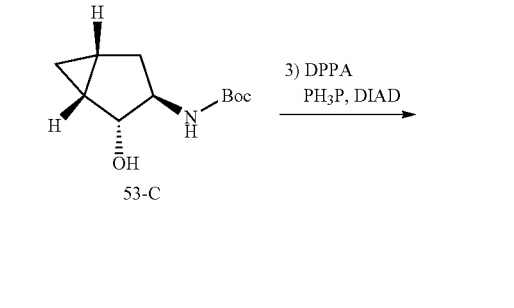

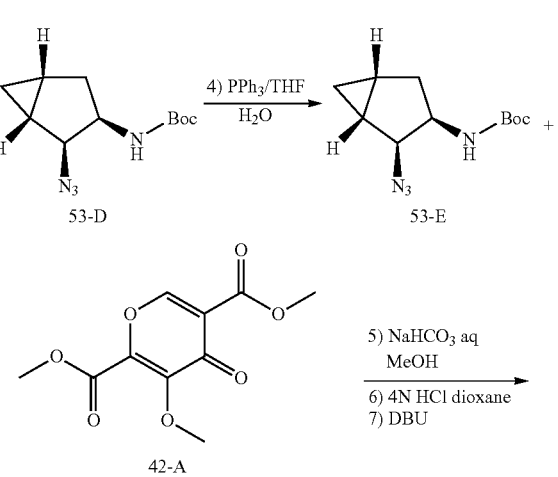

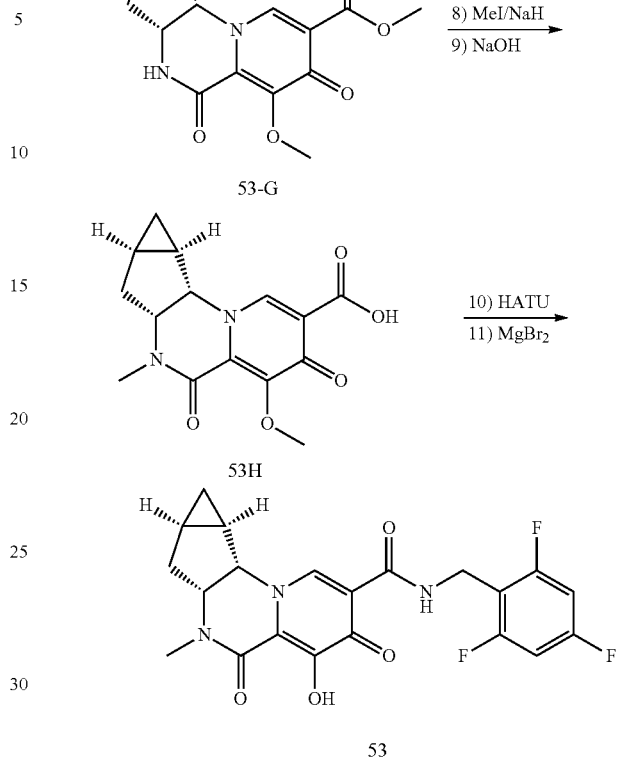

Step 1

53-A (1R,2R,3R,5R)-2-((tert-butyldimethylsilyl)oxy)bicycle[3.1.0]hexan-3-amine (2.3 g, 10.11 mmol) in dichloromethane (100 ml) was stirred at room temperature as N,N-Diisopropylethylamine (3.5 ml, 20.22 mmol) and Di-tert-butyl dicarbonate 97% (2.65 g, 12.14 mmol) were added. After 16 h, the reaction mixture was concentrated. The residue was purified by flash using 0-50% of ethyl acetate/Hexane as eluent to give (1R,2R,3R,5R)-2-((tert-butyldimethylsilyl)oxy)bicycle[3.1.0]hexan-3-amine 53-B: $^1$H (400 MHz, Chloroform-d) δ 4.34-4.01 (m, 2H), 3.33 (d, J=11.0 Hz, 1H), 2.05 (dd, J=12.6, 7.6 Hz, 1H), 1.53 (d, J=11.9 Hz, 1H), 1.46 (s, 2H), 1.35 (s, 9H), 1.31-1.22 (m, 1H), 1.21-1.09 (m, 1H), 0.83 (s, 9H), 0.61-0.52 (m, 1H), 0.30 (td, J=7.7, 5.3 Hz, 1H), 0.01 (d, J=7.1 Hz, 6H). LCMS-ESI$^+$ (m/z): [M+H]$^+$ calculated for Chemical Formula: $C_{17}H_{33}NO_3Si$, Molecular Weight: 327.53; found: 227.73 (M+1-100).

Step 2

To a cold (0° C.) solution of the silyl ether 53-B (3.23 g, 9.86 mmol) in dry tetrahydrofuran (70 mL), was added tetra-n-butylammonium fluoride (TBAF) (23 mL of a 1 M solution in tetrahydrofuran, 23 mmol) and the resulting solution was stirred warmed to 60° C. for 2 h. The reaction mixture was cooled down to room temperature, diluted with EtOAc (100 mL) and washed with saturated NaHCO$_3$ and brine (50 mL) then dried over magnesium sulfate, followed by solvent reduction in vacuo. The crude product was purified by flash column chromatography (0-100% ethyl acetate/Hexane) to give tert-butyl ((1R,2R,3R,5R)-2-hydroxybicyclo[3.1.0]hexan-3-yl)carbamate 53-C: $^1$H NMR (400 MHz, Chloroform-d) δ 4.53 (s, 1H), 4.24 (dd, J=6.7, 5.0 Hz, 1H), 3.35 (dt, J=11.4, 5.9 Hz, 1H), 2.19 (dd, J=12.4, 7.6 Hz, 1H), 1.73-1.51 (m, 2H), 1.43 (s, 9H), 1.37-1.27 (m, 1H), 0.65 (q, J=4.3 Hz, 1H), 0.47 (td, J=7.8, 5.4 Hz, 1H).
Step 3

To tert-butyl ((1R,2R,3R,5R)-2-hydroxybicyclo[3.1.0] hexan-3-yl)carbamate 53-C (1.7 g, 7.97 mmol) and triphenylphosphine (2.7 g, 10.36 mmol) in 80 ml THF was added N,N-diisopropylethylamine (1.67 ml, 9.57 mmol) then cooled down in an ice bath. Diisopropyl azodicarboxylate, 95% (1.88 ml, 9.57 mmol) was slowly added and the mixture stirred for ~10 minutes. Diphenyl phosphoryl azide (2.06 ml, 9.57 mmol) was then added dropwise and the reaction gradually warmed to room temperature over 2 h and held at room temperature for another 3 h. It was diluted with ether and a white solid was filtered off. The organic was washed with saturated NH₄Cl, saturated NaHCO₃ and brine. After drying over sodium sulfate, and concentrating, the residue was purified by flash chromatography (0-50% ethyl acetate/Hexane) to give tert-butyl ((1R,2S,3R,5R)-2-azido-bicyclo[3.1.0]hexan-3-yl)carbamate 53-D: LCMS-ESI⁺ (m/z): [M+H]⁺ calculated for Chemical Formula: C₁₁H₁₈N₄O₂, Molecular Weight: 238.29; found: 238.98.
Step 4

To solution of tert-butyl ((1R,2S,3R,5R)-2-azidobicyclo [3.1.0] hexan-3-yl)carbamate 53-D (1.2 g, 5.036 mmol) in THF at 0° C. was added triphenylphosphine (3 g, 11.44 mmol). The reaction solution was stirred at 0° C. for 20 min, then room temperature for 20 h. To this mixture was added 20 mL H₂O and it was stirred at room temperature for 1 h then warmed to 80° C. and stirred for 30 h. After cooling to room temperature, the reaction mixture was diluted with EtOAc and washed with saturated NaHCO₃ and brine. After drying (Na₂SO₄) and concentrating, the residue was purified by flash column chromatography (0-20% methanol/dichloromethane) to give tert-butyl 41R,2S,3R,5R)-2-aminobicyclo[3.1.0]hexan-3-yl)carbamate 53-E: ¹H NMR (400 MHz, Methanol-d4) δ 3.22 (dt, J=12.0, 6.4 Hz, 1H), 3.05-2.92 (m, 2H), 2.85 (d, J=5.5 Hz, 1H), 1.57 (dd, J=12.4, 7.5 Hz, 1H), 1.36 (td, J=11.7, 4.2 Hz, 1H), 1.11 (s, 9H), 1.00 (dt, J=8.6, 4.1 Hz, 2H), 0.15 (td, J=8.2, 5.7 Hz, 1H), 0.01 (q, J=4.3 Hz, 1H). LCMS-ESI⁺ (m/z): [M+H]⁺ calculated for Chemical Formula: C₁₁H₂₀N₂O₂, Molecular Weight: 212.29; found: 212.83.
Step 5-11

Steps 5-11 were conducted in a manner similar to steps 5-11 for Compound 51 to give compound 53 (6aR,7aR,8aR, 8bS)-4-hydroxy-6-methyl-3,5-dioxo-N-(2,4,6-trifluorobenzyl)-5,6,6a,7,7a,8, 8a, 8b-octahydro-3H-cyclopropa[3,4]cyclopenta[1,2-e]pyrido[1,2-a]pyrazine-2-carboxamide: ¹H NMR (400 MHz, DMSO-d6) δ 13.22 (d, J=19.1 Hz, 1H), 10.42 (t, J=5.8 Hz, 1H), 8.59 (s, 1H), 7.28-6.97 (m, 2H), 4.64 (d, J=5.7 Hz, 1H), 4.54 (dd, J=5.9, 2.8 Hz, 2H), 3.95-3.87 (m, 1H), 3.03 (s, 3H), 2.29 (dd, J=12.3, 6.9 Hz, 1H), 2.07 (ddd, J=9.0, 5.8, 3.4 Hz, 1H), 1.68 (td, J=11.6, 4.4 Hz, 1H), 1.47 (dt, J=5.8, 3.7 Hz, 1H), 0.79-0.58 (m, 2H). 19F NMR (377 MHz, DMSO-d6) δ –75.52, –108.85-–110.57 (m), –112.47 (t, J=7.2 Hz). LCMS-ESI⁺ (m/z): [M+H]⁺ Chemical Formula: C21H18F3N3O4, Molecular Weight: 433.38; found: 434.51.

Example 54

Preparation of Compound 54

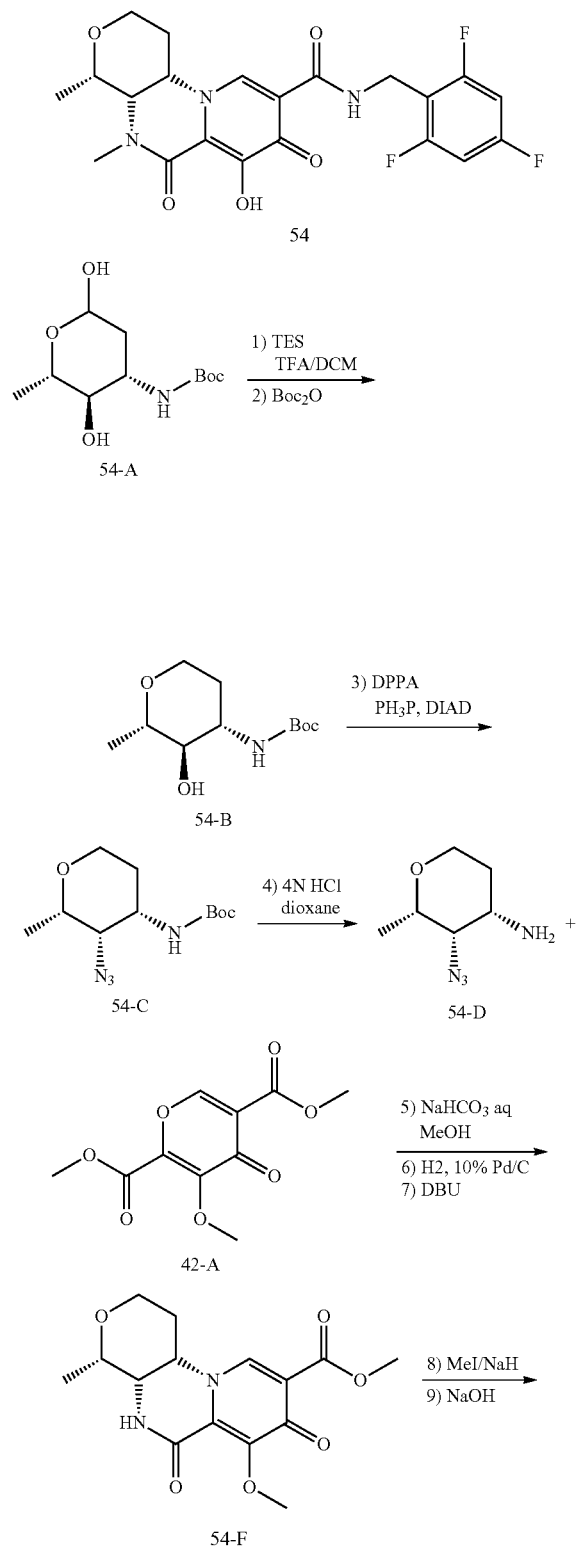

-continued

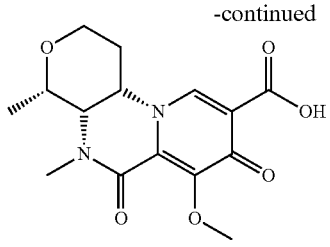

54-G

10) HATU
11) MgBr₂

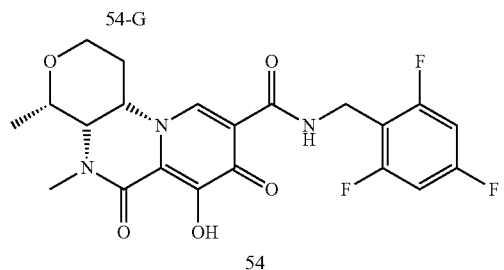

54

Step 1

Tert-butyl ((2S,3R,4S)-3,6-dihydroxy-2-methyltetrahydro-2H-pyran-4-yl)carbamate 54-A (3 g, 12.13 mmol) was dissolved in 50 mL of 30% TFA in dichloromethane. Triethylsilane (2.91 ml, 0.02 mol) in dichloromethane (35 ml) was added. It was stirred at room temperature for 1 h. The solution was diluted with 10 mL of toluene and concentrated. Trituration with hexanes gave the TFA salt of (2S,3R,4S)-4-amino-2-methyltetrahydro-2H-pyran-3-ol. This was used as is in the next step.

Step 2

TFA salt of (2S,3R,4S)-4-amino-2-methyltetrahydro-2H-pyran-3-ol was dissolved in ethyl acetate (50 mL) and saturated NaHCO3 (50 mL) (to pH>7) at room temperature. Di-tert-butyl dicarbonate 97% (13 g, 60 mmol) was added. It was stirred at room temperature overnight. Brine was added and the layers separated. The organic layer was dried (Na₂SO₄) and concentrated. The residue was purified by flash column chromatography using 0-100% ethyl acetate/hexanes as eluent to give tert-butyl ((2S,3R,4S)-3-hydroxy-2-methyltetrahydro-2H-pyran-4-yl)carbamate 54-B. $^1$H NMR (400 MHz, Chloroform-d) δ 4.60 (s, 1H), 3.92 (dd, J=11.9, 4.9, 1.6 Hz, 1H), 3.55 (d, J=12.7 Hz, 1H), 3.50-3.39 (m, 1H), 3.22 (dq, J=9.1, 6.2 Hz, 1H), 3.00 (t, J=9.1 Hz, 1H), 1.95-1.84 (m, 1H), 1.64-1.49 (m, 1H), 1.45 (s, 8H), 1.30 (d, J=6.1 Hz, 3H). No mass by LCMS.

Step 3

To tert-butyl ((2S,3R,4S)-3-hydroxy-2-methyltetrahydro-2H-pyran-4-yl)carbamate 54-B (1.09 g, 4.713 mmol) and triphenylphosphine (1.358 g, 5.184 mmol) in 100 ml THF was added N,N-diisopropylethylamine (0.985 ml, 5.655 mmol) then cooled down in an ice bath. Diisopropyl azodicarboxylate, 95% (1.113 ml, 5.655 mmol) was slowly added and the mixture stirred for ~10 minutes. Diphenyl phosphoryl azide (1.22 ml, 5.655 mmol) was then added dropwise and the reaction gradually warmed to room temperature over 2 h and maintained at room temperature for another 3 h. It was diluted with ether and filtered. The filtrate was washed with saturated NH₄Cl, saturated NaHCO₃, brine and dried over Na₂SO₄. After filtration, the filtrate was concentrated and purified by flash column chromatography (0-100% ethyl acetate/hexanes) to give tert-butyl ((2S,3S,4S)-3-azido-2-methyltetrahydro-2H-pyran-4-yl)carbamate 54-C. $^1$H NMR (400 MHz, Chloroform-d) δ 4.78 (d, J=8.0 Hz, 2H), 3.97 (ddd, J=11.8, 4.9, 1.6 Hz, 3H), 3.90-3.69 (m, 5H), 3.66 (d, J=3.3 Hz, 2H), 3.58 (qd, J=6.4, 1.4 Hz, 3H), 3.46 (td, J=12.1, 2.5 Hz, 3H), 3.26 (ddd, J=11.8, 10.9, 4.7 Hz, 1H), 2.84 (td, J=6.6, 1.3 Hz, 1H), 2.46 (dd, J=6.5, 2.1 Hz, 1H), 2.07-1.91 (m, 1H), 1.87-1.74 (m, 2H), 1.70 (td, J=12.5, 4.9 Hz, 2H), 1.63-1.51 (m, 4H), 1.45 (d, J=7.0 Hz, 34H), 1.33 (dd, J=16.2, 6.4 Hz, 11H).

Step 4

Tert-butyl ((2S,3R,4S)-3-hydroxy-2-methyltetrahydro-2H-pyran-4-yl)carbamate 54-C (830 mg, 3.24 mmol) was dissolved in dichloromethane at room temperature and treated with 4N HCl in dioxane. It was evaporated to dryness, then azeotroped with toluene twice to give the HCl salt of (2S,3S,4S)-3-azido-2-methyltetrahydro-2H-pyran-4-amine 54-D.

Step 5-11

Steps 5-11 were conducted in a manner similar to steps 5-11 for Compound 51 to give compound 54 (4S,4aS,11aS)-7-hydroxy-4,5-dimethyl-6,8-dioxo-N-(2,4,6-trifluorobenzyl)-1,2,4,4a,5,6,8,11a-octahydropyrano[3,4-e]pyrido[1,2-a]pyrazine-9-carboxamide. $^1$H NMR (400 MHz, Methanol-d4) δ 8.45 (s, 1H), 6.97-6.74 (m, 2H), 4.74-4.53 (m, 3H), 4.13-3.86 (m, 3H), 3.71 (ddd, J=12.3, 9.0, 3.5 Hz, 1H), 3.26 (s, 3H), 2.28 (ddt, J=13.7, 9.0, 4.5 Hz, 1H), 2.00 (dt, J=14.4, 4.5 Hz, 1H), 1.36 (d, J=7.0 Hz, 3H). 19F NMR (377 MHz, Methanol-d4) δ −78.26, −110.66 (ddd, J=15.3, 9.0, 6.1 Hz), −114.22 (t, J=7.1 Hz). LCMS-ESI⁺ (m/z): [M+H]⁺ Chemical Formula: C21H20F3N3O5, Molecular Weight: 451.40; found: 452.17.

Example 55

Preparation of Compound 55

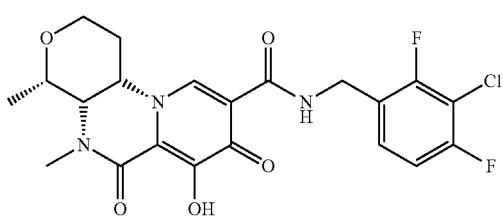

55

Compound 55 was prepared in a manner similar to compound 54 substituting (3-chloro-2,4-difluorophenyl)methanamine for 2,4,6-trifluorobenzyl amine to give (4S,4aS,11aS)-N-(3-chloro-2,4-difluorobenzyl)-7-hydroxy-4,5-dimethyl-6,8-dioxo-1,2,4,4a,5,6,8,11a-octahydropyrano[3,4-e]pyrido[1,2-a]pyrazine-9-carboxamide: $^1$H NMR (400 MHz, Methanol-d4) δ 8.47 (s, 1H), 7.37 (td, J=8.1, 5.8 Hz, 1H), 7.20-6.93 (m, 1H), 4.68 (d, J=31.9 Hz, 3H), 4.14-3.87 (m, 3H), 3.71 (ddd, J=12.2, 9.1, 3.4 Hz, 1H), 3.27 (s, 3H), 2.39-2.18 (m, 1H), 2.05-1.88 (m, 1H), 1.38 (d, J=7.0 Hz, 3H). 19F NMR (377 MHz, Methanol-d4) δ −78.25, −116.52--118.01 (m), −119.84 (d, J=7.7 Hz). LCMS-ESI⁺ (m/z): [M+H]⁺ Chemical Formula: C21H20ClF2N3O5, Molecular Weight: 467.85; found: 448.15.

Example 56

Preparation of Compound 56

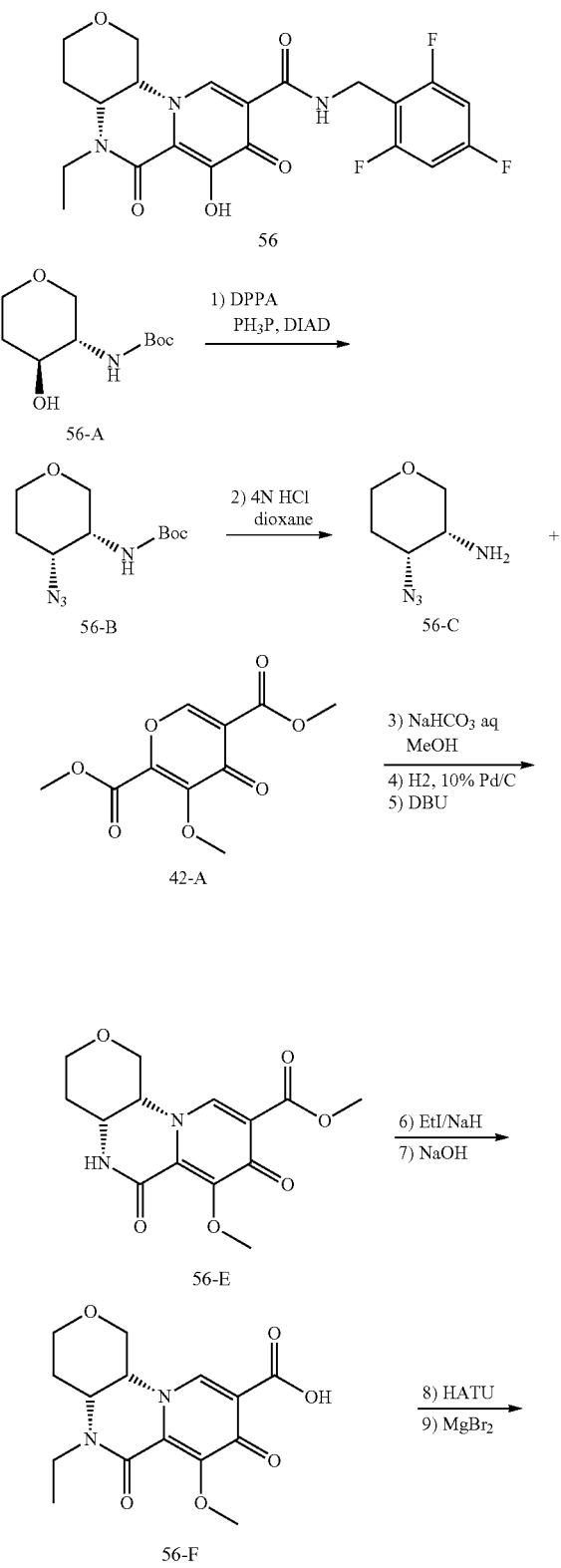

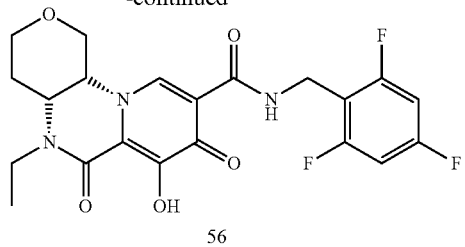

Step 1

To tert-butyl ((3S,4S)-4-hydroxytetrahydro-2H-pyran-3-yl)carbamate 56-A (3.0 g, 13.81 mmol) and triphenylphosphine (4.0 g, 15.25 mmol) in 100 ml THF was added N,N-diisopropylethylamine (3.0 ml, 17.20 mmol) then the mixture cooled down in an ice bath. Diisopropyl azodicarboxylate, 95% (3.3 ml, 16.76 mmol) was slowly added and the mixture was stirred for ~10 minutes. Diphenyl phosphoryl azide (3.6 ml, 16.76 mmol) was then added dropwise and the reaction gradually warmed to room temperature over 2 h and maintained at room temperature for another 3 h. The mixture was diluted with ether, filtered, and the filtrate was washed with saturated $NH_4Cl$, saturated $NaHCO_3$ and brine; then dried ($Na_2SO_4$) and concentrated. The residue was purified by flash column chromatography (0-100% ethyl acetate/hexanes) to give tert-butyl ((3R,4R)-4-azidotetrahydro-2H-pyran-3-yl)carbamate 56-B. $^1$H NMR (400 MHz, Chloroform-d) δ 4.87 (d, J=8.9 Hz, 1H), 3.87 (dq, J=9.8, 4.4, 4.0 Hz, 2H), 3.71 (ddd, J=11.8, 7.8, 3.9 Hz, 1H), 3.59 (dd, J=11.7, 4.3 Hz, 2H), 3.48 (dd, J=11.4, 7.5 Hz, 1H), 1.87 (dtd, J=8.7, 5.5, 3.7 Hz, 2H), 1.42 (s, 9H).

Step 2

Tert-butyl ((3R,4R)-4-azidotetrahydro-2H-pyran-3-yl)carbamate 56-B (1.72 g, 7.1 mmol) was dissolved in DCM at room temperature and treated with 4N HCl in dioxane. It was evaporated to dryness, then azeotroped with toluene twice to give the HCl salt of (3R,4R)-4-azidotetrahydro-2H-pyran-3-amine 56-C.

Steps 3-9

Steps 3-9 were performed in a manner similar to steps 5-11 for compound 51 substituting ethyl iodide for methyl iodide to give compound 56 (4aR,11aR)-5-ethyl-7-hydroxy-6,8-dioxo-N-(2,4,6-trifluorobenzyl)-1,3,4,4a,5,6,8,11a-octahydropyrano[4,3-e]pyrido[1,2-a]pyrazine-9-carboxamide: $^1$H NMR (400 MHz, Methanol-d4) δ 8.60 (s, 1H), 6.88 (t, J=8.4 Hz, 2H), 4.74 (dt, J=15.2, 2.0 Hz, 1H), 4.65 (s, 2H), 4.44 (d, J=2.8 Hz, 1H), 4.14 (dt, J=11.3, 3.9 Hz, 1H), 4.03-3.80 (m, 3H), 3.64 (td, J=11.5, 2.5 Hz, 1H), 3.39-3.32 (m, 1H), 1.99 (dd, J=14.0, 3.6 Hz, 1H), 1.71 (ddt, J=14.1, 11.0, 5.7 Hz, 1H), 1.28 (t, J=7.1 Hz, 3H). $^{19}$F NMR 19F NMR (377 MHz, Methanol-d4) −78.20, −110.71 (ddd, J=15.3, 9.0, 6.2 Hz), −114.19 (t, J=7.1 Hz). LCMS-ESI$^+$ (m/z): [M+H]$^+$ Chemical Formula: $C_{21}H_{20}F_3N_3O_5$, Molecular Weight: 451.40; found: 452.19.

Example 57

Preparation of Compound 57

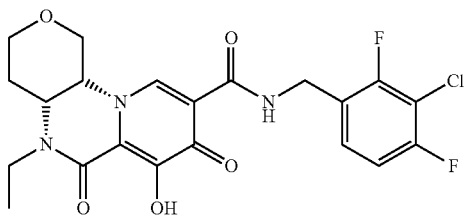

Compound 57 was prepared in a manner similar to compound 56 substituting (2,4,6-trifluorophenyl)methanamine by (3-chloro-2,4-difluorophenyl)methanamine to give compound 57 (4aR,11aR)-N-(3-chloro-2,4-difluorobenzyl)-5-ethyl-7-hydroxy-6,8-dioxo-1,3,4,4a,5,6,8,11a-octahydropyrano[4,3-e]pyrido[1,2-a]pyrazine-9-carboxamide: $^1$H NMR (400 MHz, Methanol-d4) δ 8.62 (s, 1H), 7.38 (td, J=8.4, 6.0 Hz, 1H), 7.08 (td, J=8.7, 1.9 Hz, 1H), 4.79-4.68 (m, 1H), 4.66 (s, 2H), 4.44 (d, J=3.4 Hz, 1H), 4.14 (dt, J=11.6, 4.1 Hz, 1H), 4.03-3.81 (m, 3H), 3.64 (td, J=11.5, 2.5 Hz, 1H), 3.40-3.32 (m, 1H), 2.10-1.91 (m, 1H), 1.81-1.59 (m, 1H), 1.29 (t, J=7.2 Hz, 3H). $^{19}$F NMR 19F NMR (377 MHz, Methanol-d4) δ −115.45−−118.97 (m), −119.92 (d, J=7.9 Hz). LCMS-ESI$^+$ (m/z): [M+H Chemical Formula: $C_{21}H_{20}ClF_2N_3O_5$, Molecular Weight: 467.85; found: 468.15.

Example 58

Preparation of Compound 58

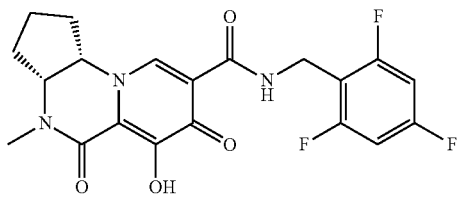

Compound 58 was prepared in a synthetic sequence similar to that previously described for compound 29, using N-Boc protected (1R,2S)-cyclopentane-1,2-diamine as a reaction partner with the previously described common pyrone 1-B. Following the referenced steps (vide supra), final purification was performed on a 4 g silica gel column eluting from 100% EtOAc to 9:1 EtOAc/MeOH to provide the final product 58.

$^1$H NMR (400 MHz, CD3OD) δ 8.43 (s, 1H), 6.88 (m, 2H), 4.67 (m, 1H), 4.64-4.55 (m, 1H), 4.44 (s, 1H), 4.11 (m, 1H), 3.12 (s, 3H), 2.34 (dq, J=14.0, 7.3 Hz, 1H), 2.14 (dt, J=7.3, 4.4 Hz, 2H), 1.96 (m, 1H), 1.91-1.76 (m, 2H).

LCMS-ESI+ (m/z): [M+H]+ calculated for $C_{20}H_{19}F_3N_3O_4$: 422.13; found: 422.2.

Example 59

Preparation of Compound 59

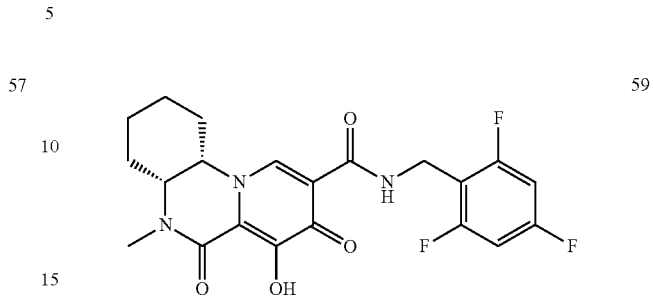

Compound 59 was prepared in a synthetic sequence similar to that previously described for compound 4 using tert-butyl ((1R,2S)-2-aminocyclohexyl) carbamate as a reaction partner with the previously described pyrone 1-B. Following a sequence similar to that described previously (vide supra), final purification was performed on a 4 g silica gel column eluting from 100% EtOAc to 9:1 EtOAc/MeOH to provide the final product 59.

$^1$H NMR (400 MHz, Chloroform-d) δ 12.62 (s, 1H), 10.44 (s, 1H), 8.41 (s, 1H), 6.66-6.61 (m, 2H), 4.65-4.60 (dd, m, 1H), 4.59 (m, 1H), 4.24 (m, 1H), 4.10 (m, 1H), 3.76 (s, 3H), 2.27 (s, 1H), 2.10 (m, 2H), 1.99 (m, 1H), 1.85 (m, 2H), 1.60-1.76 (bm, 4H), 1.22 (m, 1H). LCMS-ESI+ (m/z): [M+H]+ calculated for $C_{20}H_{19}F_3N_3O_4$: 436.2; found: 436.1.

Example 60

Preparation of Compound 60

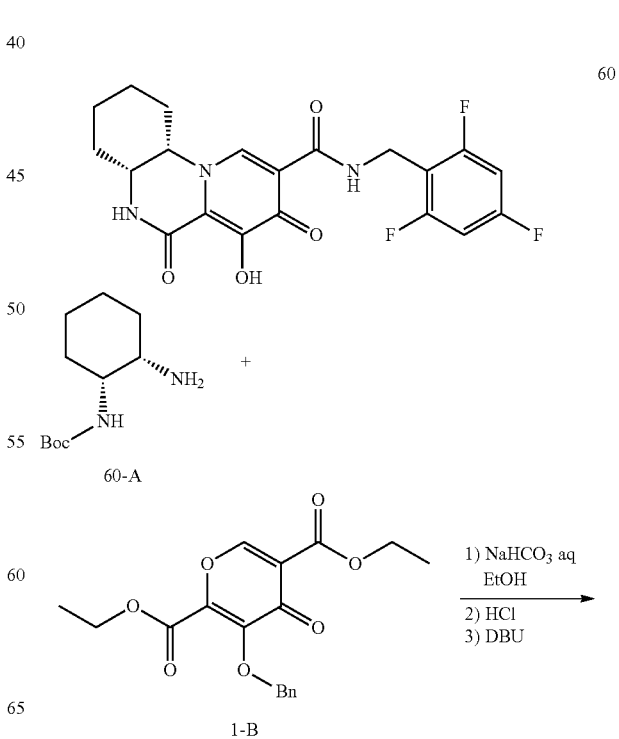

161

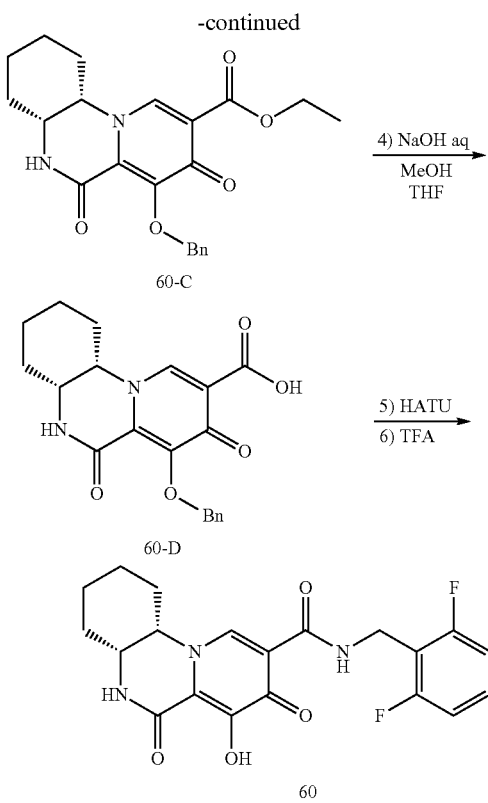

Step 1,2,3

The mixture of the pyrone 1-B (500 mg, 1.44 mmol) and tert-butyl ((1R,2S)-2-aminocyclohexyl)carbamate (60-A) (310 mg, 1.44 mmol) with sodium bicarbonate (242 mg, 2.88 mmol) in water (10 mL) and ethanol (10 mL) was stirred at room temperature for 16 h. It was concentrated and co-evaporated with acetonitrile to remove water. The crude residue was used for the next reaction as is.

The crude residue was dissolved in dichloromethane (10 mL) and treated with 4 N HCl in dioxane (6 mL). It was stirred at room temperature for 2 h and concentrated to dryness.

To the above residue was added 20 mL of anhydrous ethanol and 1,8-Diazabicyclo[5.4.0]undec-7-ene (2.0 ml, 13.5 mmol). The mixture was warmed to 60° C. for 120 min. The mixture was concentrated. The residue was purified by flash chromatography on silica gel to afford (4aR,11aS)-methyl 7-methoxy-6,8-dioxo-2,3,4,4a,5,6,8,11a-octahydro-1H-pyrido[1,2-a]quinoxaline-9-carboxylat 60-C. LCMS-ESI+ (m/z): [M+H]+ calculated for Chemical Formula: $C_{22}H_{24}N_2O_5$, Molecular Weight: 396.44; found: 397.34.

Step 4

To a mixture of the Reactant 60-C (528 mg, 1.33 mmol) in THF (10 mL) and methanol (2 mL) was added 1N NaOH (5 mL). The mixture was stirred at room temperature for about 60 min and then acidified with 2 mL of 3 N HCl and concentrated to dryness. The crude acid 60-D was used for the next reaction as is. LCMS-ESI+ (m/z): [M+H]+ calculated for Chemical Formula: $C_{20}H_{20}N_2O_5$, Molecular Weight: 368.38; found: 369.23.

Step 5, 6

Intermediate 60-D (1.33 mmol) and (2,4,6-trifluorophenyl)methanamine (429 mg, 2.66 mmol) were suspended in dichloromethane (70 mL) and treated with diisopropylethylamine (1 ml, 6.2 mmol) at room temperature. To this

162 suspension was added (dimethylamino)-N,N-dimethyl(3H-[1,2,3]triazolo[4,5-b]pyridin-3-yloxy)methaniminium hexafluorophosphate (HATU, 0.76 g, 2.0 mmol). After 0.5 h, the reaction mixture was diluted with dichloromethane, washed with 3% LiCl aq, saturated $NH_4Cl$ and 0.5N HCl. The organic layer was dried ($Na_2SO_4$), concentrated. Purification by flash chromatography gave the desired amide.

The residue from the previous step was dissolved in TFA (2 mL) at room temperature and stirred for 30 min. The mixture was concentrated and the residue was purified by flash chromatography to give 60. $^1$H NMR (400 MHz, DMSO-d6) δ 12.64 (s, 1H), 10.41 (t, J=5.8 Hz, 1H), 9.18 (s, 1H), 8.44 (s, 1H), 7.31-6.94 (m, 2H), 4.71-4.28 (m, 3H), 4.22-3.88 (m, 1H), 2.15-1.81 (m, 1H), 1.78-1.48 (m, 4H), 1.38 (dt, J=27.0, 8.4 Hz, 3H). $^{19}$F NMR (376 MHz, DMSO-d6) δ −109.35 (tt, J=9.1, 6.3 Hz), −112.48 (p, J=7.5 Hz). LCMS-ESI+(m/z): [M+H]+ Chemical Formula: $C_{20}H_{18}F_3N_3O_4$, Molecular Weight: 421.32; found: 422.31.

Example 61

Preparation of Compound 61

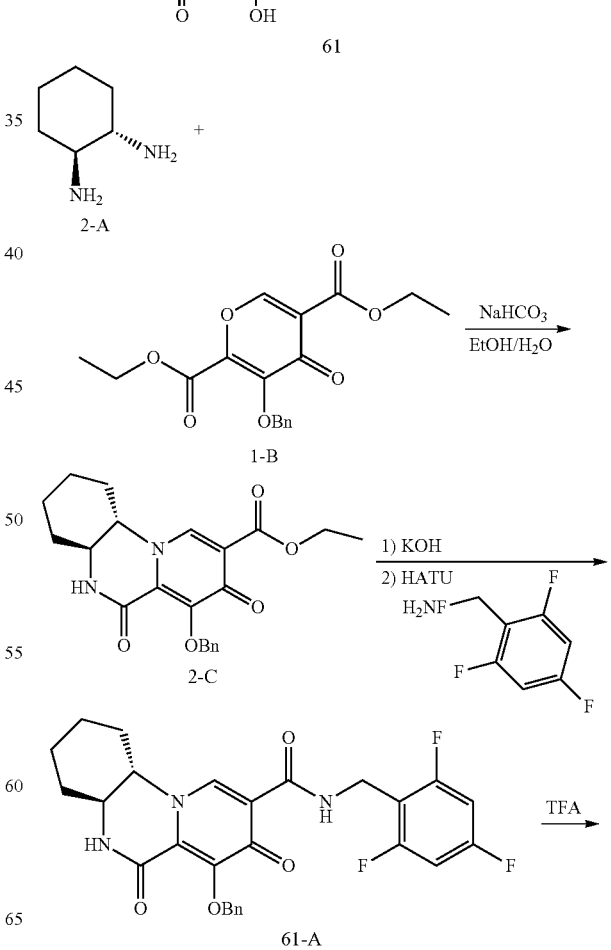

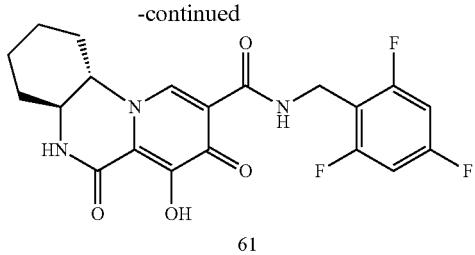

61

Step 1

A 50-mL 1-neck round bottom flask was charged with reactant 2-A (0.165 g, 1.45 mmol), 1-B (0.50 g, 1.45 mmol) and NaHCO$_3$ (0.25 g, 2.9 mmol) in ethanol (10 ml) and water (10 ml). The reaction mixture was stirred at room temperature overnight. The reaction mixture was concentrated down, re-dissolved in EtOAc (50 mL), washed with water (2×) and dried over Na$_2$SO$_4$. After concentration, the crude was purified by column chromatography on silica gel with hexane-EtOAc to obtain 2-C. LCMS-ESI+(m/z): [M+H]+; found: 397.

Step 2

A 50-mL 1-neck round bottom flask was charged with reactant 2-C (0.17 g, 0.43 mmol) in THF (5 mL) and MeOH (5 mL). 1 N KOH in water (1.3 mL) was added to the reaction solution. The reaction mixture was stirred at room temperature for 1 hour. After acidification with 1 N HCl, the solution was concentrated to remove the solvent completely and the crude acid was used for the next step without further purification. The crude acid (0.27 mmol), 2,4,6-trifluorophenyl methanamine (0.084 g, 0.52 mmol), DIPEA (0.169 g, 1.3 mmol) and HATU (0.20 g, 0.52 mmol) were stirred in DCM (10 ml) at room temperature for 1 hour. The reaction mixture was concentrated down, re-dissolved in EtOAc (50 mL), washed with saturated NaHCO$_3$ (2×), sat NH$_4$Cl and dried over Na$_2$SO$_4$. After concentration, the crude was purified by column chromatography on silica gel with hexane-EtOAc to obtain 61-A. LCMS-ESI+ (m/z): [M+H]+; found: 512.

Step 3

A 50-mL 1-neck round bottom flask was charged with reactant 61-A (0.03 g, 0.06 mmol) in TFA (2 mL). The reaction mixture was stirred at room temperature for 30 minutes. The solution was concentrated and the residue was purified by flash chromatography using 0-20% MeOH in EtOAc to afford compound 61. $^1$H NMR (400 MHz, DMSO-d6) δ 12.84 (s, 1H), 10.42 (t, J=5.6 Hz, 1H), 9.37 (s, 1H), 8.28 (s, 1H), 7.18 (t, J=8.7 Hz, 2H), 4.53 (d, J=5.7 Hz, 2H), 3.88 (d, J=11.3 Hz, 1H), 3.51 (d, J=10.9 Hz, 1H), 2.10-1.78 (m, 2H), 1.71 (d, J=11.4 Hz, 1H), 1.64-1.08 (m, 4H). $^{19}$F NMR (376 MHz, DMSO-d6) δ −109.41 (m, 1F), −112.48 (d, J=7.8 Hz, 2F). LCMS-ESI+ (m/z): [M+H]+ found: 422.

Example 62

Preparation of Compound 62

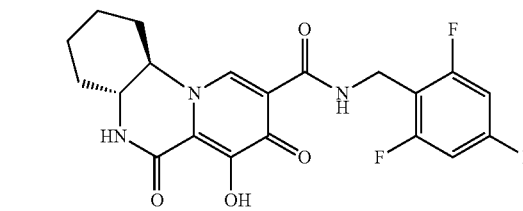

62

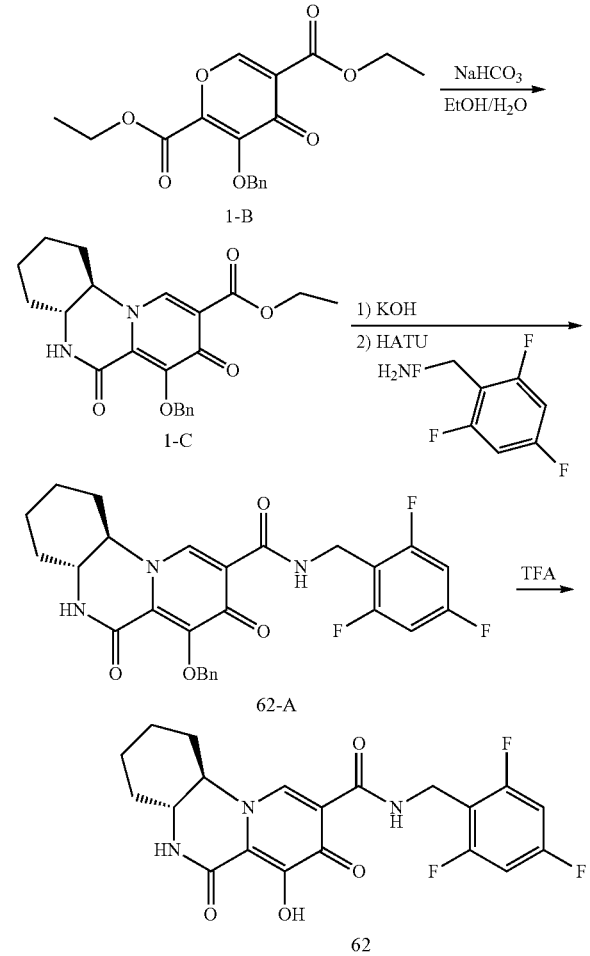

Step 1

A 50-mL 1-neck round bottom flask was charged with reactant 1-A (0.165 g, 1.45 mmol), 1-B (0.50 g, 1.45 mmol) and NaHCO$_3$ (0.25 g, 2.9 mmol) in ethanol (10 ml) and water (10 ml). The reaction mixture was stirred at room temperature overnight. The reaction mixture was concentrated down, re-dissolved in EtOAc (50 mL), washed with water (2×) and dried over Na$_2$SO$_4$. After concentration, the crude was purified by column chromatography on silica gel with hexane-EtOAc to obtain 1-C. LCMS-ESI⁺ (m/z): [M+H]⁺; found: 397.

Step 2

A 50-mL 1-neck round bottom flask was charged with reactant 1-C (0.17 g, 0.43 mmol) in THF (5 mL) and MeOH (5 mL). 1 N KOH in water (1.3 mL) was added to the reaction solution. The reaction mixture was stirred at room temperature for 1 hour. After acidification with 1 N HCl, the solution was concentrated to remove the solvent completely and the crude acid was used for next step without further purification. The crude acid (0.27 mmol), 2,4,6-trifluorophenyl methanamine (0.084 g, 0.52 mmol), DIPEA (0.169 g, 1.3 mmol) and HATU (0.20 g, 0.52 mmol) in DCM (10 ml) were stirred at room temperature for 1 hour. The reaction mixture was concentrated down, re-dissolved in EtOAc (50 mL), washed with saturated NaHCO₃ (2×), saturated NH₄Cl and dried over Na₂SO₄. After concentration, the crude was purified by column chromatography on silica gel with hexane-EtOAc to obtain 62-A. LCMS-ESI⁺ (m/z): [M+H]⁺; found: 512.

Step 3

A 50-mL 1-neck round bottom flask was charged with reactant 62-A (0.03 g, 0.06 mmol) in TFA (2 mL). The reaction mixture was stirred at room temperature for 30 minutes. The solution was concentrated and the residue was purified by flash chromatography using 0-20% MeOH in EtOAc afford compound 62. ¹H NMR (400 MHz, DMSO-d6) δ 10.41 (t, J=5.9 Hz, 1H), 9.38 (s, 1H), 8.28 (s, 1H), 7.18 (t, J=8.6 Hz, 2H), 4.53 (d, J=5.7 Hz, 2H), 3.88 (d, J=10.4 Hz, 1H), 3.48 (d, J=11.1 Hz, 1H), 1.95 (dd, J=33.6, 17.4 Hz, 2H), 1.70 (d, J=11.9 Hz, 1H), 1.60-1.14 (m, 5H). ¹⁹F NMR (376 MHz, DMSO-d6) δ −109.41 (m, 1F), −112.48 (d, J=7.8 Hz, 2F).

LCMS-ESI⁺ (m/z): [M+H]⁺ found: 422.

Example 63

Preparation of Compound 63

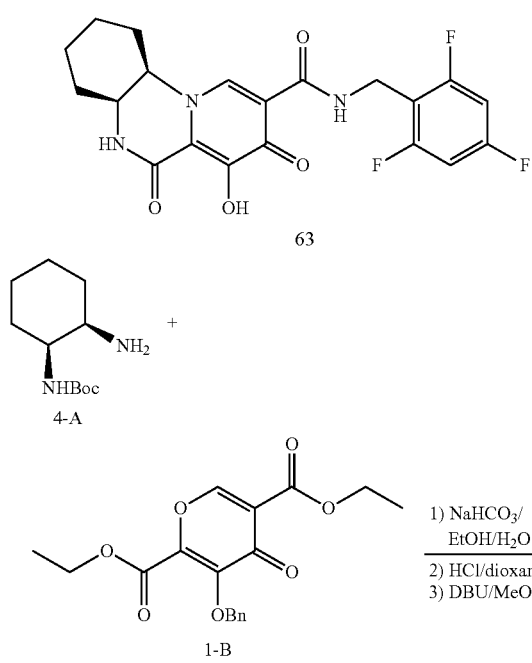

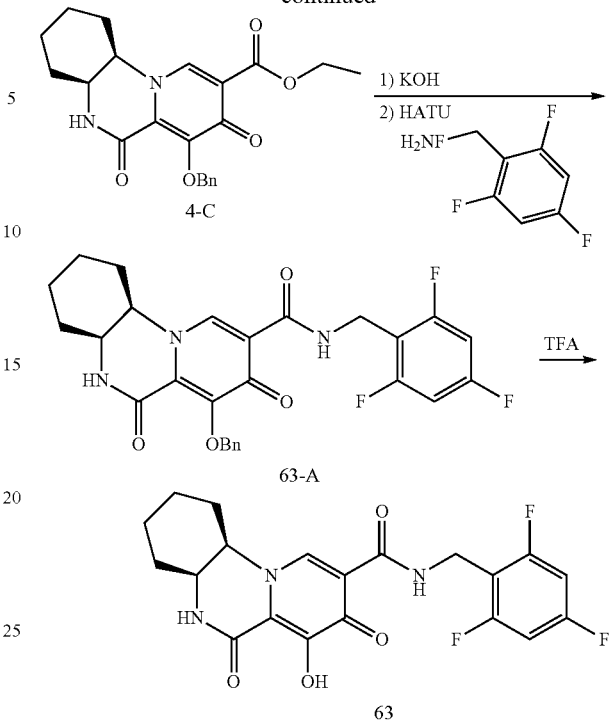

Step 1

A 50-mL 1-neck round bottom flask was charged with reactant 4-A (0.165 g, 1.45 mmol), 1-B (0.50 g, 1.45 mmol) and NaHCO₃ (0.25 g, 2.9 mmol) in ethanol (10 ml) and water (10 ml). The reaction mixture was stirred at room temperature overnight. The reaction mixture was concentrated down, re-dissolved in EtOAc (50 mL), washed with water (2×) and dried over Na₂SO₄. After concentration, the crude was purified by column chromatography on silica gel with hexane-EtOAc to obtain 4-C. LCMS-ESI⁺ (m/z): [M+H]⁺; found: 397.

Step 2

A 50-mL 1-neck round bottom flask was charged with reactant 4-C (0.17 g, 0.43 mmol) in THF (5 mL) and MeOH (5 mL). 1 N KOH in water (1.3 mL) was added to the reaction solution. The reaction mixture was stirred at room temperature for 1 hour. After acidification with 1 N HCl, the solution was concentrated to remove the solvent completely and the crude acid was used for the next step without further purification. The crude acid (0.27 mmol), 2,4,6-trifluorophenyl methanamine (0.084 g, 0.52 mmol), DIPEA (0.169 g, 1.3 mmol) and HATU (0.20 g, 0.52 mmol) in DCM (10 ml) were stirred at room temperature for 1 hour. The reaction mixture was concentrated down, re-dissolved in EtOAc (50 mL), washed with saturated NaHCO₃ (2×), saturated NH₄Cl and dried over Na₂SO₄. After concentration, the crude was purified by column chromatography on silica gel with hexane-EtOAc to obtain 63-A. LCMS-ESI⁺ (m/z): [M+H]⁺; found: 512.

Step 3

A 50-mL 1-neck round bottom flask was charged with reactant 63-A (0.03 g, 0.06 mmol) in TFA (2 mL). The reaction mixture was stirred at room temperature for 30 minutes. The solution was concentrated and the residue was purified by flash chromatography using 0-20% MeOH in EtOAc to afford compound 63. ¹H NMR (400 MHz, Chloroform-d) δ 11.70 (s, 1H), 10.65-10.18 (m, 1H), 8.27 (s, 1H), 7.26 (m, 1H), 6.90 (td, J=9.7, 6.4 Hz, 1H), 4.89 (s, 1H), 4.60 (d, J=6.0 Hz, 2H), 4.09 (dd, J=11.4, 2.6 Hz, 1H), 3.96-3.66 (m, 2H), 2.68 (s, 1H), 2.15-1.43 (m, 6H). $^{19}$F NMR (376 MHz, Chloroform-d) δ 120.53--120.85 (m, 1F), -134.68--136.79 (m, 1F), -142.26--144.11 (m, 1F). LCMS-ESI$^+$ (m/z): [M+H]$^+$ found: 422.

Example 64

Antiviral Assays in MT4 Cells

For the antiviral assay utilizing MT4 cells, 0.4 μL of 189× test concentration of 3-fold serially diluted compound in DMSO was added to 40 μL of cell growth medium (RPMI 1640, 10% FBS, 1% penicillin/streptomycin, 1% L-Glutamine, 1% HEPES) in each well of 384-well assay plates (10 concentrations) in quadruplicate.

1 mL aliquots of 2×10$^6$ MT4 cells are pre-infected for 1 and 3 hours respectively at 37° C. with 25 μL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 μL of 2000 (for MT4) cells is added to each well of the assay plates.

Assay plates were then incubated in a 37° C. incubator. After 5 days of incubation, 25 μL of 2× concentrated CellTiter-Glo™ Reagent (catalog # G7573, Promega Biosciences, Inc., Madison, Wis.) was added to each well of the assay plate. Cell lysis was carried out by incubating at room temperature for 2-3 minutes, and then chemiluminescence was read using the Envision reader (PerkinElmer).

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

Example 65

Human PXR Activation Assay

Luciferase Reporter Gene Assay.

A stably transformed tumor cell line (DPX2) was plated on 96-well microtiter plates. DPX2 cells harbor the human PXR gene (NR112) and a luciferase reporter gene linked to two promoters identified in the human CYP3A4 gene, namely XREM and PXRE. The cells were treated with six concentrations of each compound (0.15~50 μM) and incubated for 24 hours. The number of viable cells was determined and the reporter gene activity was assessed. Positive control: Rifampicin at 6 concentrations (0.1~20 μM). % E$_{max}$ relative to the maximum fold induction by 10 or 20 μM RIF was calculated for test compounds according to the following equation which adjusts for the DMSO background: % E$_{max}$=(Fold induction−1)/(Maximum fold induction by RIF−1)×100%.

Example 66

OCT2 Inhibition Assay

The dose dependent inhibition of OCT2 mediated uptake of a model substrate $^{14}$C-Tetraethylammonium (TEA) by test compounds was studied in wild-type and OCT2-transfected MDCKII cells at 7 concentrations from 0.014 μM to 10 μM.

MDCKII cells were maintained in minimal essential medium (MEM) with 1% Pen/Strep, 10% fetal bovine serum, and 0.25 mg/mL hygromycin B in an incubator set at 37° C., 90% humidity and 5% CO$_2$. 24 hours prior to assay, media containing 5 mM sodium butyrate were added to MDCKII cells in flasks, and cells were grown to 80-90% confluence. On assay day, cells were trypsinized and resuspended in Krebs-Henseleit Buffer (KHB), pH 7.4 at 5×10$^6$ million cells/mL. Cells were preincubated for 15 min in assay plate before addition of test compound or substrate.

Test compounds were serially diluted in DMSO and then spiked (2 μL) into in 0.4 mL KHB buffer containing wild-type or OCT2-transfected cells and incubated for 10 minutes. Assay was initiated with the addition of 0.1 mL of 100 μM $^{14}$C-TEA in KHB buffer (20 μM final concentration after mixing). The concentration of TEA is based on the K$_m$. After 10 minutes of incubation, the assay mixture was quenched with addition of 0.5 mL of ice-cold 1×PBS buffer. Samples were then centrifuged at 1000 rpm for 5 min and supernatants were removed. Wash steps were repeated four times with ice-cold PBS. Finally, the cell pellets were lysed with 0.2N NaOH and let sit at room temperature for at least 30 min to ensure complete lysis. Samples were then counted on liquid scintillation counter and dpm counts were used to perform the following calculations. The % inhibition was calculated as follows: % inhibition=[1−{[OCT2]$_i$−[WT]$_{ni}$}/{[OCT2]$_{ni}$−[WT]$_{ni}$}]*100 where, [OCT2]$_i$ represents the dpm count in the presence of test compound for either OCT2 cells, [OCT2]$_i$ represents the dpm count in the absence of test compound for OCT2 cells and [WT]$_{ni}$ represents the dpm count in the absence of test compound for wild type cells, respectively.

TABLE 1

| Compound | EC$_{50}$ (nM) | CC$_{50}$ (nM) | OCT2 IC$_{50}$ (nM) | PXR % inh at 15 uM (adjusted) |
|---|---|---|---|---|
| 1 | 6.429 | 27344 | | 32 |
| 2 | 3.904 | 11217 | | 46 |
| 3 | 2.957 | 11030 | | |
| 4 | 2.527 | 10536 | | 65 |
| 5 | 4.739 | 16989 | | 66 |
| 29 | 2.148 | 16714 | 216 | 49 |
| 30 | 3.25 | 10389 | | 9 |
| 58 | 3.32 | 10893 | 2493 | 25 |
| 59 | 3.424 | 11398 | 2511 | 44 |
| 31 | 2.623 | 52456 | 10000 | 1 |
| 6 | 5.019 | 21974 | | |
| 32 | 3.799 | 57143 | 10000 | 19 |
| 7 | 14.853 | 19849 | | 36 |
| 48 | 4.303 | 32281 | | 1 |
| 49 | 3.317 | 11994 | | 1 |
| 33 | 2.838 | 31116 | | 12 |
| 34 | 2.226 | 32326 | | 3 |
| 50 | 2.682 | 48439 | | 1 |
| 35 | 3.804 | 16456 | | 6 |
| 8 | 16.53 | 57143 | | 24 |
| 21 | 3.452 | 31068 | | 6 |
| 36 | 1.576 | 19678 | | 5 |
| 37 | 4.269 | 33946 | | 35 |
| 38 | 2.827 | 16566 | | 67 |
| 42 | 5.667 | 31872 | | 3 |
| 43 | 2.884 | 11301 | | 13 |
| 23 | 3.768 | 17969 | | 8 |
| 24 | 7.293 | 37521 | | 29 |
| 44 | 5.68 | 38020 | | 32 |
| 45 | 7.261 | 36670 | | 33 |
| 39 | 2.578 | 12846 | 10000 | 5 |
| 9 | 1.401 | 11311 | | 27 |
| 10 | 7.649 | 34916 | | |
| 11 | 3.685 | 8324 | | 4 |
| 40a | 1.278 | 29014 | | 4 |

TABLE 1-continued

| Compound | EC$_{50}$ (nM) | CC$_{50}$ (nM) | OCT2 IC$_{50}$ (nM) | PXR % inh at 15 uM (adjusted) |
|---|---|---|---|---|
| 40b | 1.31 | 23140 | | 22 |
| 12 | 6.261 | 36464 | 6400 | 18 |
| 13 | 10.716 | 7320.2 | | 5 |
| 25a | 4.584 | 25926 | | 20 |
| 25b | 4.37 | 26702 | 10000 | 13 |
| 26a | 5.266 | 24336 | | 15 |
| 26b | 4.935 | 30874 | | 24 |
| 51 | 5.278 | 6711.2 | | 33 |
| 46 | 2.926 | 28230 | | 8 |
| 52 | 4.953 | 2825 | | 24 |
| 14 | 2.894 | 11622 | | 26 |
| 15 | 7.923 | 14919 | | 6 |
| 16 | 2.13 | 11527 | | 7 |
| 53 | 6.044 | 13293 | | 46 |
| 27 | 1.169 | 57143 | | |
| 55 | 1.907 | 9660.9 | | 2 |
| 54 | 2.924 | 23928 | | 8 |
| 41 | 2.876 | 27440 | | 21 |
| 17 | 4.805 | 23913 | | 7 |
| 18 | 3.334 | 26931 | | 2 |
| 47 | 5.704 | 27246 | | 9 |
| 56 | 3.068 | 4486.6 | | 10 |
| 57 | 2.285 | 6454.4 | | 3 |
| 19 | 4.278 | 27825 | | 11 |
| 20 | 9.598 | 34090 | | 1 |
| 60 | 1.9 | 13773 | | 2 |
| 22 | 12.2 | 38349 | | 4 |
| 28 | 4.4 | 10811 | 10000 | 4 |
| 63 | 2.2 | 10331 | | 5 |
| 62 | 7.3 | 24246 | | 0 |
| 61 | 6.3 | 31410 | | 0 |

The data in Table 1 represents an average over time of each assay for each compound. For certain compounds, multiple assays have been conducted over the life of the project.

Example 67

Pharmacokinetic Analysis Following Oral or Intravenous Administration to Male SD Rats Pharmacokinetic analysis was performed on compounds 25b and 39 following intravenous or oral administration to rats.

The test compounds were formulated in 5% Ethanol, 55% PEG 300, and 40% water at 0.1 mg/mL for IV infusion and for oral dosing.

Each dosing group consisted of 3 male, Sprague-Dawley rats. At dosing, the animals weighed an average of 0.25 kg. The animals were fasted overnight prior to dose administration and up to 4 hr after dosing.

For the IV infusion group, the test article was administered by intravenous infusion over 30 min. The rate of infusion was adjusted according to the body weight of each animal to deliver a dose of 0.5 mg/kg. For the oral dosing group, the test article was administered by oral gavage at 5 mL/kg for a dose of 0.5 mg/kg.

For pharmacokinetic analysis of intravenously administered compounds, serial venous blood samples (approximately 0.3 mL each) were taken from each animal at 0, 0.250, 0.483, 0.583, 0.750, 1.50, 3.00, 6.00, 8.00, 12.0, 24.0, 48 and 72 hours after dosing. The blood samples were collected into Vacutainer™ tubes containing EDTA-K2 as the anti-coagulant and were immediately placed on wet ice pending centrifugation for plasma. An LC/MS/MS method was used to measure the concentration of the test compound in plasma. An aliquot of 50 µL of each plasma sample was added to a clean 96 well plate, and 200 µL of cold acetonitrile/internal standard solution (ACN)/(ISTD) was added. After protein precipitation, an aliquot of 110 µL of the supernatant was transferred to a clean 96-well plate and diluted with 300 µL of water. An aliquot of 10 µL of the above solution was injected into a ABSciex API-4000 triple quadrupole LC/MS/MS system utilizing a HyPurity C18 HPLC column (30×2.1 mm, 3µ), from Thermo-Hypersil (Part #22103-032130). An Agilent 1200 series binary pump (P/N G1312A Bin Pump) was used for elution and separation, and an HTS Pal autosampler (LEAP Technologies, Carrboro, N.C.) was used for sample injection. A API-4000 triple quadrupole mass spectrometer was utilized in multiple reaction monitoring mode (Applied Biosystems, Foster City, Calif.). Liquid chromatography was performed using two mobile phases: mobile phase A contained 0.1% formic acid and 1% isopropylamine in aqueous solution, and mobile phase B contained 0.1% formic acid and 1% isopropylamine in aqueous solution. Non-compartmental pharmacokinetic analysis was performed on the plasma concentration-time data. The resulting data are shown in the first three columns of Table 2. In Table 2, Cl refers to clearance, which characterizes the rate at which drug is removed from plasma. The lower the clearance of a drug is, the longer the elimination half-life is in the body. Vss refers to the steady state volume of distribution and indicates how well a drug is distributed into the tissues. The larger the Vss is, the longer the elimination half-life is in the body. MRT refers to mean residence time, which is a measure of the average time molecules exist in the body.

For pharmacokinetic analysis of orally administered compounds, serial venous blood samples (approximately 0.3 mL each) were taken from each animal at time points of 0, 0.25, 0.50, 1.0, 2.0, 4.0, 6.0, 8.0, 12.0 24.0, 48.0 and 72 hours after dosing. Blood samples were collected, prepared and analyzed in a similar way to the intravenous studies described above. Non-compartmental pharmacokinetic analysis was performed on the plasma concentration-time data. The resulting data is shown in Table 2. In Table 2, F (%) refers to oral bioavailability.

TABLE 2

| Rat Pharmacokinetics | | | | |
|---|---|---|---|---|
| Compound | Cl (L/h/kg) | Vss (L/kg) | MRT (h) | % F (solution) |
| 25b | 0.0013 | 0.141 | 119 | 39 |
| 39 | 0.0023 | 0.212 | 105 | 15 |
| Dolutegravir | 0.01 | 0.17 | 12.4 | 84 |

Some reference compounds were also tested in dog pharmacokinetic analysis.

Example 68

Resistance Assay

For the antiviral assay utilizing MT-2 cells, 50 µL of 2× test concentration of 3-fold serially diluted compound in culture medium with 10% FBS was added to each well of a 96-well plate (9 concentrations) in triplicate. MT-2 cells were infected with wild-type or mutant variants of HIV-1 for 3 hours using a volume of viral inoculum determined to produce 90% cell killing. Fifty microliters of infected cell suspension in culture medium with 10% FBS (~1.5×10$^4$ cells) was then added to each well containing 50 µL of serially diluted compound. The plates with HIV-infected cultures were then incubated at 37° C. for 5 days in the presence of the tested compounds. After 5 days of incubation, 100 µL of CellTiter-Glo™ Reagent (catalog # G7571, Promega Biosciences, Inc., Madison, Wis.) was added to each well. Cell lysis was carried out by incubating at room temperature for 10 min followed by a chemiluminescence read-out.

Data Analysis

The chemiluminescence readout from the 10-point antiviral dose response was analyzed directly by curve fitting with equation (I) to determine the $EC_{50}$.

$$y = -\left(\frac{M \times EC_{50}{}^n}{EC_{50}{}^n + [I]^n}\right) + \left(\frac{(M+H) \times CC_{50}{}^m}{CC_{50}{}^m + [I]^m}\right) \quad (I)$$

where y=Cell Survival, M=maximum cell survival enabled by drug protection, H=baseline cell survival without drug protection, n=Hill coefficient of the antiviral dose response, m=Hill coefficient of the cytotoxicity dose response, and [I]=inhibitor concentration.

$EC_{50}$ values (mean±standard deviation) were calculated from at least three independent experiments performed in triplicate. The fold-change in antiviral activity of tested compounds was calculated as a ratio of the mean $EC_{50}$ for each mutant virus divided by the mean $EC_{50}$ of the control WT virus. A lower fold-shift means the mutant virus shows less resistance to that compound.

Example 69

Plasma Protein Binding

Instrument and Reagents for Dialysis

Plasma protein binding was determined using a HTD96b equilibrium dialyzer with a plate base, stainless steel pressure plate and Teflon bock. 9 Teflon bars, labeled sequentially from A through I, were assembled with two stainless steel connecting rods. Membranes were placed between two Teflon bars, with the membrane placed approximately 2 mm below the top edge of the bar and the lower membrane edge overlapped the bottom of all wells. The membrane was soaked for about 20 minutes in water, about 20 minutes in ethanol (30/70 v/v) and rinsed with water three times to remove the ethanol. It was soaked in PBS for at least 30 minutes. Plasma in sodium EDTA (Bioreclamation or equivalent) was used. The Plasma (not pH-adjusted) was stored at −80° C. and thawed at room temperature before use.

Stock Solutions and Quench

The stock solution of the compounds tested was at 200 µM in DMSO. The quench solution used was 50 nM of an internal standard in 100% ACN.

Test Article Solutions in Plasma and CCM

To prepare a 2 µM solution of the compound tested in plasma, 5 µL of a 200 µM stock solution was added to 495 µL of blank plasma.

Equilibrium Dialysis Procedure—HTD 96b Dialyzer

100 µL plasma was added with 2 µM of test compound into one side of the well. 100 µL of buffer (for plasma vs. buffer) was added into another side of the well.

The 96-well plate was covered using an adhesive sealing film and incubated for 24 hours at 37° C. under slow rotation.

This procedure was replicated for each compound.

Sample Preparation for Analysis

50 µL of plasma sample was put into a 96 well plate, 50 µL of buffer was added. 50 µL of buffer was put into a 96 well plate. 50 µL of plasma was added. 300 µL of quench solution was added and the plate sealed and shaken for 15 minutes.

The material was centrifuged for 30 minutes at 3000 RPM and ~250 µL was transferred into a short plate. The samples were analyzed by LC/MS.

The resulting data is shown in the last row of Table 3 as "% Free" which corresponds to the percentage of compound not protein bound.

TABLE 3

Resistance (fold shift, mutant vs. wild type (wt) in MT2 cells) and % Free compound in plasma protein binding

| Compound | E138K/ Q148K | G140S/ Q148R | E92Q/ N155H | N155H/ Q148R | wt (nM) | % Free HP/Buffer |
|---|---|---|---|---|---|---|
| 25b | 2.3 | 1.9 | 2.2 | 2.2 | 1.4 | <0.1% |
| 39 | 1.5 | 1.8 | 2.3 | 2.8 | 0.9 | 0.67 |
| 41 | 3.5 | 2.9 | 2.1 | 1.8 | 2.0 | 5.7 |
| 33 | 5.9 | 2.5 | 0.9 | 2.2 | 2.5 | 5.6 |
| 44 | 23.8 | 5.9 | 2.3 | 17.7 | 7.8 | 6.8 |
| Dolutegravir | 8.2 | 3.7 | 1.9 | 2.5 | 1.7 | 1.0 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments have been described herein for purposes of illustration, various modifications may be made without deviating from the spirit and scope of the disclosure. Accordingly, the disclosure is not limited except as by the appended claims.

We claim:

1. A compound of Formula (Ic)

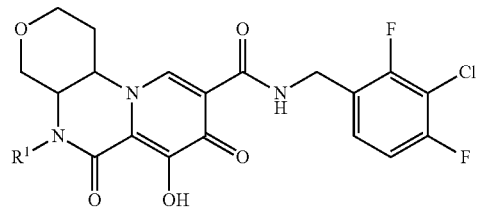

(Ic)

or a pharmaceutically acceptable salt thereof, wherein:

$R^1$ is selected from the group consisting of H, $C_{1-4}$alkyl, $C_{1-4}$haloalkyl and $C_{3-6}$cycloalkyl.

2. The compound of claim 1 having the Formula (Id)

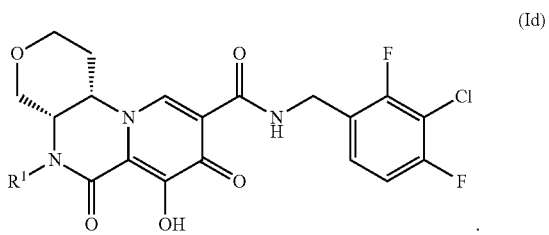

(Id)

3. A compound of Formula (Ie)

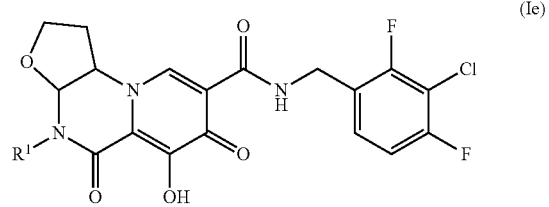

(Ie)

or a pharmaceutically acceptable salt thereof, wherein:
R$^1$ is selected from the group consisting of H, C$_{1-4}$alkyl, C$_{1-4}$haloalkyl and C$_{3-6}$cycloalkyl.

4. The compound of any one of claims 1-3, or a pharmaceutically acceptable salt thereof, wherein R$^1$ is selected from the group consisting of H, C$_{1-3}$alkyl, C$_{1-2}$haloalkyl, and C$_{3-5}$cycloalkyl.

5. The compound of any one of claims 1-3, or a pharmaceutically acceptable salt thereof, wherein R$^1$ is selected from the group consisting of hydrogen, methyl, ethyl, propyl, isopropyl, CH$_2$CF$_3$, CH$_2$CHF$_2$ and cyclopropyl.

6. The compound of any one of claims 1-3, or a pharmaceutically acceptable salt thereof, wherein R$^1$ is ethyl.

7. The compound of any of claims 1-3, or a pharmaceutically acceptable salt thereof, wherein R$^1$ is selected from the group consisting of C$_{1-4}$haloalkyl and C$_{3-6}$cycloalkyl.

8. The compound of claim 7, or a pharmaceutically acceptable salt thereof, wherein R$^1$ is selected from the group consisting of CH$_2$CF$_3$, CH$_2$CHF$_2$ and cyclopropyl.

9. A pharmaceutical composition comprising a compound of any one of claims 1-3, or pharmaceutically acceptable salt thereof, and a pharmaceutically acceptable excipient.

10. The pharmaceutical composition of claim 9 further comprising one or more additional therapeutic agents.

11. The pharmaceutical composition of claim 10 wherein the one or more additional therapeutic agents is an anti-HIV agent.

12. The pharmaceutical composition of claim 10 wherein the one or more additional therapeutic agents is selected from the group consisting of HIV protease inhibitors, HIV non-nucleoside inhibitors of reverse transcriptase, HIV nucleoside or nucleotide inhibitors of reverse transcriptase, and combinations thereof.

13. The pharmaceutical composition of claim 9, further comprising a first additional therapeutic agent selected from the group consisting of: abacavir sulfate, tenofovir, tenofovir disoproxil fumarate, tenofovir alafenamide, and tenofovir alafenamide hemifumarate and a second additional therapeutic agent selected from the group consisting of emtricitabine and lamivudine.

14. A method of treating an HIV infection in a human having or at risk of having the infection by administering to the human a therapeutically effective amount of a compound of any one of claims 1-3.

15. The method of claim 14 further comprising administering to the human a therapeutically effective amount of one or more additional therapeutic agents.

16. The method of claim 15 wherein the one or more additional therapeutic agents is an anti-HIV agent.

17. The method of claim 15 wherein the one or more additional therapeutic agents is selected from the group consisting of HIV protease inhibitors, HIV non-nucleoside inhibitors of reverse transcriptase, HIV nucleoside or nucleotide inhibitors of reverse transcriptase, and combinations thereof.

18. The method of claim 14, further comprising administering to the human a first additional therapeutic agent selected from the group consisting of: abacavir sulfate, tenofovir, tenofovir disoproxil fumarate, tenofovir alafenamide, and tenofovir alafenamide hemifumarate; and a second additional therapeutic agent selected from the group consisting of emtricitabine and lamivudine.

* * * * *